US009302120B2

(12) United States Patent
Wang et al.

(10) Patent No.: US 9,302,120 B2
(45) Date of Patent: Apr. 5, 2016

(54) SPIRO-OXINDOLE MDM2 ANTAGONISTS

(71) Applicant: The Regents of the University of Michigan, Ann Arbor, MI (US)

(72) Inventors: Shaomeng Wang, Saline, MI (US); Yujun Zhao, Ann Arbor, MI (US); Wei Sun, Yunnan (CN)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 14/170,101

(22) Filed: Jan. 31, 2014

(65) Prior Publication Data
US 2014/0148494 A1    May 29, 2014

Related U.S. Application Data

(63) Continuation of application No. 13/294,315, filed on Nov. 11, 2011, now Pat. No. 8,680,132.

(60) Provisional application No. 61/413,094, filed on Nov. 12, 2010, provisional application No. 61/451,968, filed on Mar. 11, 2011, provisional application No. 61/451,958, filed on Mar. 11, 2011, provisional application No. 61/470,992, filed on Apr. 1, 2011.

(51) Int. Cl.
| C07D 487/10 | (2006.01) |
| A61N 5/10 | (2006.01) |
| A61K 31/407 | (2006.01) |
| A61K 45/06 | (2006.01) |

(52) U.S. Cl.
CPC ............... *A61N 5/10* (2013.01); *A61K 31/407* (2013.01); *A61K 45/06* (2013.01); *C07D 487/10* (2013.01)

(58) Field of Classification Search
CPC .................................................. C07D 487/10
USPC ......................................... 548/409; 514/409
See application file for complete search history.

(56) References Cited

U.S. PATENT DOCUMENTS

| 3,219,661 | A | 11/1965 | Shavel, Jr. et al. |
| 6,617,346 | B1 | 9/2003 | Kong et al. |
| 6,734,302 | B2 | 5/2004 | Kong et al. |
| 6,916,833 | B2 | 7/2005 | Kim et al. |
| 7,060,713 | B2 | 6/2006 | Kim et al. |
| 7,083,983 | B2 | 8/2006 | Lane et al. |
| 7,125,659 | B1 | 10/2006 | Kiyoi et al. |
| 7,132,421 | B2 | 11/2006 | Fotouhi et al. |
| 7,425,638 | B2 | 9/2008 | Haley et al. |
| 7,495,007 | B2 | 2/2009 | Chen et al. |
| 7,553,833 | B2 | 6/2009 | Liu et al. |
| 7,576,082 | B2 | 8/2009 | Luk et al. |
| 7,625,895 | B2 | 12/2009 | Dominique et al. |
| 7,638,548 | B2 | 12/2009 | Liu et al. |
| 7,723,372 | B2 | 5/2010 | Liu |
| 7,737,174 | B2 | 6/2010 | Wang et al. |
| 7,759,383 | B2 | 7/2010 | Wang et al. |
| 7,776,875 | B2 | 8/2010 | Chen et al. |
| 7,834,179 | B2 | 11/2010 | Liu et al. |
| 7,928,233 | B2 | 4/2011 | Chen et al. |
| 8,053,475 | B2 | 11/2011 | Klein |
| 8,058,269 | B2 | 11/2011 | Chen et al. |
| 8,076,482 | B2 | 12/2011 | Chen et al. |
| 8,088,815 | B2 | 1/2012 | Bartkovitz et al. |
| 8,088,931 | B2 | 1/2012 | Wang et al. |
| 8,134,001 | B2 | 3/2012 | Ding et al. |
| 8,222,288 | B2 | 7/2012 | Wang et al. |
| 8,518,984 | B2 | 8/2013 | Wang et al. |
| 8,629,141 | B2 | 1/2014 | Wang et al. |
| 8,742,121 | B2 | 6/2014 | Wang et al. |
| 8,877,796 | B2 | 11/2014 | Wang et al. |
| 2002/0039790 | A1 | 4/2002 | Keplinger et al. |
| 2002/0132977 | A1 | 9/2002 | Yuan et al. |
| 2004/0171035 | A1 | 9/2004 | Huang et al. |
| 2005/0137137 | A1 | 6/2005 | Lane et al. |
| 2005/0227932 | A1 | 10/2005 | Lu et al. |
| 2005/0288287 | A1 | 12/2005 | Fotouhi et al. |
| 2006/0211718 | A1 | 9/2006 | Weissman et al. |
| 2006/0211757 | A1 | 9/2006 | Wang et al. |
| 2006/0241017 | A1 | 10/2006 | Chandran |
| 2006/0287244 | A1 | 12/2006 | Chandran |
| 2007/0249564 | A1 | 10/2007 | Erion et al. |
| 2008/0039472 | A1 | 2/2008 | Lacrampe et al. |
| 2008/0171723 | A1 | 7/2008 | Khan |
| 2008/0261917 | A1 | 10/2008 | Willems et al. |
| 2008/0280769 | A1 | 11/2008 | Doemling |
| 2009/0030181 | A1 | 1/2009 | Han et al. |
| 2009/0143364 | A1 | 6/2009 | Fotouhi et al. |

(Continued)

FOREIGN PATENT DOCUMENTS

| CN | 1410401 A | 4/2003 |
| EP | 2 298 778 A1 | 3/2011 |

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.orglwikilCancer.*
Antonchick, A.P. et al., "Highly enantioselective synthesis and cellular evaluation of spirooxindoles inspired by natural products," *Nature Chemistry* 2:735-740, Macmillan Publishers Limited (Sep. 2010; published online Jul. 11, 2010).

(Continued)

*Primary Examiner* — Shawquia Jackson
(74) *Attorney, Agent, or Firm* — Casimir Jones, SC

(57) ABSTRACT

Provided herein are compounds, compositions, and methods in the field of medicinal chemistry. The compounds and compositions provided herein relate to spiro-oxindoles which function as antagonists of the interaction between p53 and MDM2, and their use as therapeutics for the treatment of cancer and other diseases.

3 Claims, 42 Drawing Sheets

(56) References Cited

U.S. PATENT DOCUMENTS

| | | | |
|---|---|---|---|
| 2009/0149493 | A1 | 6/2009 | Lacrampe et al. |
| 2009/0227542 | A1 | 9/2009 | Khan |
| 2009/0312310 | A1 | 12/2009 | Kawato et al. |
| 2010/0048593 | A1 | 2/2010 | Weissman et al. |
| 2010/0216770 | A1 | 8/2010 | Storck et al. |
| 2011/0112052 | A1 | 5/2011 | Wang et al. |
| 2011/0201635 | A1 | 8/2011 | Liu et al. |
| 2011/0251252 | A1 | 10/2011 | Wang et al. |
| 2011/0269809 | A1 | 11/2011 | Chu et al. |
| 2012/0046306 | A1 | 2/2012 | Bartkovitz et al. |
| 2012/0071499 | A1 | 3/2012 | Chu et al. |
| 2012/0101092 | A1 | 4/2012 | Wang et al. |
| 2012/0289494 | A1 | 11/2012 | Wang et al. |
| 2013/0030173 | A1 | 1/2013 | Wang et al. |
| 2014/0378680 | A1 | 12/2014 | Wang et al. |

FOREIGN PATENT DOCUMENTS

| | | |
|---|---|---|
| GB | 1056537 | 1/1967 |
| JP | 40-23184 | 10/1965 |
| JP | 44-4986 | 2/1969 |
| RU | 2 084 449 C1 | 7/1997 |
| RU | 2186776 C2 | 10/2002 |
| WO | WO 98/00409 A1 | 1/1998 |
| WO | WO 99/12904 A1 | 3/1999 |
| WO | WO 03/051360 A1 | 6/2003 |
| WO | WO 2005/046575 A2 | 5/2005 |
| WO | WO 2005/110992 A1 | 11/2005 |
| WO | WO 2006/125784 A1 | 11/2006 |
| WO | WO 2008/106507 A2 | 9/2008 |
| WO | WO 2008/119741 A2 | 10/2008 |
| WO | WO 2008/125487 A1 | 10/2008 |
| WO | WO 2009/156735 A2 | 12/2009 |
| WO | WO 2011/067185 A1 | 6/2011 |
| WO | WO 2011/106650 A2 | 9/2011 |

OTHER PUBLICATIONS

Chen, X.-H. et al., "Organocatalytic Synthesis of Spiro[pyrrolidin-3,3'-oxindoles] with High Enantiopurity and Structural Diversity," *J. Am. Chem. Soc.* 131:13819-13825, American Chemical Society (2009).

Dudkina, A.S. and Lindsley, C.W., "Small Molecule Protein-Protein Inhibitors for the p53-MDM2 Interaction," *Current Topics in Medicinal Chemistry* 7:952-960, Bentham Science Publishers Ltd. (2007).

Galliford, C.V. and Scheidt, K.A., "Pyrrolidinyl-Spirooxindole Natural Products as Inspirations for the Development of Potential Therapeutic Agents," *Angew. Chem. Int. Ed.* 46:8748-8758, Wiley-VCH Verlag GmbH & Co. KGaA, Weinheim (2007).

Jansen, A.B.A. and Richards, C.G., "A Synthesis of Some Spiro [Indoline-3,3'-Pyrrolidines]," *Tetrahedron* 21:1327-1331, Pergamon Press Ltd. (1965).

Kang, T.-H. et al., "Pteropodine and isopteropodine positively modulate the function of rat muscarinic $M_1$ and 5-$HT_2$ receptors expressed in *Xenopus* oocyte," *Eur. J. Pharmacol.* 444:39-45, Elsevier Science B.V. (2002).

Lo, M. M.-C. et al., "A Library of Spirooxindoles Based on a Stereoselective Three-Component Coupling Reaction," *J. Am. Chem. Soc.* 126:16077-16086, American Chemical Society (2004).

Seaton, J.C. et al., "The Structure and Stereoisomerism of Three Mitragyna Alkaloids," *Can. J. Chem.* 38:1035-1042, NRC Research Press, Ottawa (1960).

Seto, M. et al., "The Synthesis of 3-Spirooxindole Derivatives. IX. The Reactions of 2-Hydroxytryptamine with Hemiacetals," *Chem. Pharm. Bull.* 24:1393-1397, Pharmaceutical Society of Japan, Tokyo (1976).

Trost, B.M. and Brennan, M.K., "Asymmetric Syntheses of Oxindole and Indole Spirocyclic Alkaloid Natural Products," *Synthesis* 18:3003-3025, Thieme Stuttgart, New York (2009).

van Tamelen, E.E. et al., "Total Synthesis of Rhyncophyllol and *dl*-Isorhyncophyllol," *J. Am. Chem. Soc.* 91:7333-7341, American Chemical Society (1969).

von Nussbaum, F. and Danishefsky, S.J., "A Rapid Total Synthesis of Spirotryprostatin B: Proof of its Relative and Absolute Stereochemistry," *Angew. Chem. Int. Ed.* 39:2175-2178, Wiley-VCH Verlag GmbH, Weinheim (2000).

Wenkert, E. et al., "3-Hydroxymethyleneoxindole and its Derivatives," *J. Am. Chem. Soc.* 81:3763-3768, American Chemical Society (1959).

Office Action mailed Jan. 9, 2013, for U.S. Appl. No. 12/945,511, filed Nov. 12, 2010, inventors: Wang, S. et al., U.S. Patent and Trademark Office, Alexandria, VA.

Notice of Allowance mailed Mar. 15, 2013, for U.S. Appl. No. 12/945,511, filed Nov. 12, 2010, inventors: Wang, S. et al., U.S. Patent and Trademark Office, Alexandria, VA.

Corrected Notice of Allowability mailed Apr. 8, 2013, for U.S. Appl. No. 12/945,511, filed Nov. 12, 2010, inventors: Wang, S. et al., U.S. Patent and Trademark Office, Alexandria, VA.

Notice of Allowance mailed Jun. 21, 2013, for U.S. Appl. No. 12/945,511, filed Nov. 12, 2010, inventors: Wang, S. et al., U.S. Patent and Trademark Office, Alexandria, VA.

Response to Rule 312 Communication mailed Jul. 24, 2013, for U.S. Appl. No. 12/945,511, filed Nov. 12, 2010, inventors: Wang, S. et al., U.S. Patent and Trademark Office, Alexandria, VA.

Office Action mailed Sep. 26, 2012, for U.S. Appl. No. 13/082,163, filed Apr. 7, 2011, inventors: Wang, S. et al., U.S. Patent and Trademark Office, Alexandria, VA.

Office Action mailed Feb. 21, 2013, for U.S. Appl. No. 13/082,163, filed Apr. 7, 2011, inventors: Wang, S. et al., U.S. Patent and Trademark Office, Alexandria, VA.

International Search Report mailed Jul. 2, 2012, for International Patent Appl. No. PCT/US2011/060300, filed Nov. 11, 2011, applicant: The Regents of the University of Michigan et al., Korean Intellectual Property Office, Daejeon Metropolitan City, Republic of Korea.

Alper, P. B. et al., "Facile, Novel Methodology for the Synthesis of Spiro[pyrrolidin3,3'-oxindoles]: Catalyzed Ring Expansion Reactions of Cyclopropanes by Aldimines," *Angew. Chem. Int. Ed.* 38:3186-3189, Wiley-VCH Verlag GmbH (1999).

Azmi, A.S. et al., "MDM2 inhibitor MI-319 in combination with cisplatin is an effective treatment for pancreatic cancer independent of p53 function," *Eur. J. Cancer* 46:1122-1131, Elsevier Ltd. (2010).

Ban, Y. and Oishi, T., "The Synthesis of 3-Spiro-oxindole Derivatives. I. Syntheses of 1-Methyl-2', 3', 10',10'α-tetrahydrospiro[indoline-3,1'(5'H)-pyrrolo[1,2-b]-isoquinoline]-2-one and its Homologs," *Chem. Pharm. Bull.* 4:441-445, Pharmaceutical Society of Japan (1963).

Barakat, K. et al., "Ensemble-based virtual screening reveals dual-inhibitors for the p53-MDM2/MDMX interactions," *Journal of Molecular Graphics & Modelling* 28:555-568, Elsevier Inc. (2010).

Baxter, E.W. and Reitz, A.B, "Reductive aminations of carbonyl compounds with borohydride and borane reducing agents. Organic reactions" (Hoboken, NJ, United States, 59, (2002) (online); Found from database ASC on STN, CA: 149-5759820 (2010).

Canner, J.A. et al., "MI-63: A novel small-molecule inhibitor targets MDM2 and induces apoptosis in embryonal and alveolar rhabdomyosarcoma cells with wild-type p53," *Br. J. Cancer* 101:774-781, Cancer Research UK (2009).

Chène, P., "Inhibiting the p53-MDM2 Interaction: An Important Target for Cancer Therapy," *Nature Reviews: Cancer* 3:102-109, Nature Publishing Group, London, UK (2003).

Cochard, F. et al., "Synthesis of Substituted 1,2,3,4-Tetrahydro-1-thiacarbazole and Spiro[pyrrolidinone-3,3'-indolinones] through a Common Intermediate Obtained by Condensation of Indolin-2-one, (Aryl)aldehydes, and Meldrum's Acid," *Eur. J. Org. Chem.* 20:3481-3490, Wiley-VCH Verlag GmbH (2002).

Cossy, J. et al., "A Convenient Route to Spiropyrrolidinyl-Oxindole Alkaloids via C-3 Substituted Ene-Pyrrolidine Carbamate Radical Cyclization," *Tetrahedron Letters* 39:2331-2332, Elsevier Science Ltd. (1998).

Cui, C-B et al., "Isolation, Structure Determination and Biological Activities of Novel Mammalian Cell Cycle Inhibitors, Spirotryprostatins A & B, Tryprostatins A & B and Related New

(56) References Cited

OTHER PUBLICATIONS

Diketopiperazine Derivatives Produced by a Fungus, *Aspergillus fumigatus*," *Symposium on the Chemistry of Natural Products* 38:49-54 (1996).

Ding, K. et al., "Structure-Based Design of Spiro-oxindoles as Potent, Specific Small-Molecule Inhibitors of the MDM2-p53 Interaction," *J. Med. Chem.* 49:3432-3435, American Chemical Society (2006).

Ding, K. et al., "Structure-Based Design of Potent Non-Peptide MDM2 Inhibitors," *J. Am. Chem. Soc.* 127:10130-10131, American Chemical Society (2005).

Ding, K. et al., "Synthesis of spirooxindoles via asymmetric 1,3-dipolar cycloaddition," *Tetrahedron Letters* 46:5949-5951, Elsevier Ltd. (2005).

Döé de Maindreville, M. and Lévy, J., "Synthèses en série indolique. VII. Synthèse et transformation chimiques de l'enchaînement tétracyclique commun aux alcaloïdes à chromophore ester anilinoacrylique," *Bulletin de la Société Chimique de France* 5-6:179-184, Societe Francaise De Chimie (1981).

Dörnyei, G. et al., "Intramolecular Mannich Reaction of 2-Oxotryptamine and Homologues with Oxo Reagents Yielding Spiro Compounds. Part II," *Collect. Czech Chem. Commun.* 67:1669-1680, Nakladatelstvi Ceskoslovenski Akademie Ved. (2002).

Edmondson, S. et al., "Total Synthesis of Spirotryprostatin A, Leading to the Discovery of Some Biologically Promising Analogs," *J. Am. Chem. Soc.* 121:2147-2155, American Chemical Society (1999).

García-Echeverría, C. et al., "Discovery of Potent Antagonists of the Interaction between Human Double Minute 2 and Tumor Suppressor p53," *J. Med. Chem.* 43:3205-3208, American Chemical Society (2000).

Giese, B. et al., Radical cyclization reactions, Organic reactions (Hoboken, NJ, United States), 48 (1996) (online); Found from database ASC on STN, CA: 149:5550940 (2010).

Grigg, R. et al., "Spiro-oxindoles via bimetallic [Pd(0)/Ag(I)] catalytic intramolecular Heck-1,3-dipolar cycloaddition cascade reactions," *Tetrahedron Letters* 43:2605-2608, Elsevier Science Ltd. (2002).

Harley-Mason, J. and Ingleby, R.F.J., "Hydroxytryptamines, Part IV. Synthesis and Reactions of 2-3'-Oxindolylethylamines," *J. Chem. Soc.* 3639-3642, Chemical Society of Great Britain, London, UK (1958).

Incze, M. et al., "Intramolecular Mannich Reaction of 2-Oxotryptamines with Acetone Yielding Spiro[indole-3,3'-pyrrolidin]-2-ones," *Collect. Czech Chem. Commun.* 64:408-416, Institute of Organic Chemistry and Biochemistry, Academy of Sciences of the Czech Republic, Prague (1999).

Jones, R.J. et al., "Inhibition of the p53 E3 Ligase HDM-2 Induces Apoptosis and DNA Damage-Independent p53 Phosphorylation in Mantle Cell Lymphoma," *Clin. Cancer Res.* 14:5416-5425, American Association of Cancer Research (2008).

Kabankin, A.S., et al., "Analysis of Structure—Hepatoprotective Activity Relationship for Indole Derivatives." *Chemical and Pharmaceutical Magazine*, 39:24-28 (2005).

Kuroda, M. et al., "Cytotoxic Alkaloids from the Barks of *Ochrosia elliptica*," *Natural Medicines* 53:272 (1999).

Kussie, P.H. et al., "Structure of the MDM2 Oncoprotein Bound to the p53 Tumor Suppressor Transactivation Domain," *Science* 274:948-953, American Association for the Advancement of Science (1996).

Leclercq, J., et al., "Screening of Cytotoxic Activities of *Strychnos* Alkaloids (Methods and Results)," *J. Ethnopharmacology* 15:305-316, Elsevier Scientific Publishers Ireland Ltd. (1986).

Lizos, D. et al., "A novel and economical route to (±)-horsfiline using an aryl iodoazide tandem radical cyclisation strategy," *Chem. Commun.* 2732-2733, The Royal Society of Chemistry (2001).

Lizos, D.E. and Murphy, J.A., "Concise synthesis of (±)-horsfiline and (±)-coerulescine by tandem cyclisation of iodoaryl alkenyl azides," *Org. Biomol. Chem.* 1:117-122, The Royal Society of Chemistry (2003).

Lu, Y. et al., "Discovery of a Nanomolar Inhibitor of the Human Murine Double Minute 2 (MDM2)-p53 Interaction through an Integrated, Virtual Database Screening Strategy," *J. Med. Chem.* 49:3759-3762, American Chemical Society (2006).

Marti, C. and Carreira, E.M., "Construction of Spiro[pyrrolidine-3,3'-oxindoles]—Recent Applications to the Synthesis of Oxindole Alkaloids." *Eur. J. Org. Chem.* 2209-2219, Wiley-VCH Verlag GmbH & Co. (2003).

Miyake, F.Y. et al., "Preparation and Synthetic Applications of 2-Halotryptophan Methyl Esters: Synthesis of Spirotryprostatin B," *Angew. Chem. Int. Ed.* 43:5357-5360, Wiley-VCH Verlag GmbH & Co. (2004).

Mohammad, R.M. et al., "An MDM2 antagonist (MI-319) restores p53 functions and increases the life span of orally treated follicular lymphoma bearing animals," *Mol. Canc.* 8:115, BioMed Central (2009).

Muhammad, I., "Investigation of Uña De Gato I. 7-Deoxyloganic acid and $^{15}N$ NMR spectropscopic studies on pentacyclic oxindole alkaloids from *Uncaria tomentosa*," *Phytochemistry* 57:781-785, Elsevier Science Ltd. (2001).

Nikolovska-Coleska, Z. et al., "Development and optimization of a binding assay for the XIAP BIR3 domain using fluorescence polarization," *Analytical Biochemistry* 332:261-273, Elsevier Inc. (2004).

Onishi T. et al., "Concise, asymmetric total synthesis of spirotryprostatin A," *Tetrahedron* 60:9503-9515, Elsevier Ltd. (2004).

Onishi, T. et al., "Concise, Asymmetric Total Synthesis of Spirotryprostatin A," *Org. Lett.* 5:3135-3137, American Chemical Society (2003).

Pellegrini, C. et al., "Synthesis of the Oxindole Alkaloid (−)-Horsfiline," *Tetrahedron: Asymmetry* 5:1979-1992, Elsevier Science Ltd. (1994).

Pellegrini, C. et al., "Total Synthesis of (+)-Elacomine and (−)-Isoelacomine, Two Hitherto Unnamed Oxindole Alkaloids from *Elaeagnus commutata*," *Helv. Chim. Acta* 79:151-168, Schweizerische Chemische Gessellschaft, Basel (1996).

Rothweiler, U. et al., "Isoquinolin-1-one Inhibitors of the MDM2-p53 Interaction," *ChemMedChem* 3:1118-1128, Wiley-VCH Verlag GmbH & Co. (2008).

Saddler, C. et al., "Comprehensive biomarker and genomic analysis identifies p53 status as the major determinant of response to MDM2 inhibitors in chronic lymphocytic leukemia," *Blood* 111:1584-1593, The American Society of Hematology (2008).

Samudio, I.J. et al., "Activation of p53 signaling by MI-63 induces apoptosis in acute myeloid leukemia cells," *Leukemia & Lymphoma* 51:911-919, Informa Healthcare USA, Inc. (2010).

Schubert, M.A. and Müller-Goymann, C.C. "Solvent injection as a new approach for manufacturing lipid nanoparticles—evaluation of the method and process parameters," *European Journal of Pharmaceutics and Biopharmaceutics* 55:125-131, Elsevier Science B.V. (2003).

Sebahar P.R. and Williams, R.M., "The Synthesis of Spirooxindole Pyrrolidines Via an Asymmetric Azomethine Ylide [1,3]-Dipolar Cycloaddition Reaction," *Heterocycles* 58:563-575, Elsevier Science (2002).

Sebahar, P.R. et al., "Asymmetric, stereocontrolled total synthesis of (+) and (−)-spirotryprostatin B via a diastereoselective azomethine ylide [1,3]-dipolar cycloaddition reaction," *Tetrahedron* 58:6311-6322, Elsevier Science Ltd. (2002).

Sebahar P.R. and Williams, R.M., "The Asymmetric Total Synthesis of (+)- and (−)-Spirotryprostatin B," *J. Am. Chem. Soc.* 122:5666-5667, American Chemical Society (2000).

Shangary, S. et al., "Reactivation of p53 by a specific MDM2 antagonist (MI-43) leads to p21-mediated cell cycle arrest and selective cell death in colon cancer," *Mol. Cancer Ther.* 7:1533-1542, American Association for Cancer Research (2008).

Shangary, S. et al., "Temporal activation of p53 by a specific MDM2 inhibitor is selectively toxic to tumors and leads to complete tumor growth inhibition," *Proc. Nat. Acad. Sci.* (*USA*) 105:3933-3938, The National Academy of Sciences of the USA (2008).

Sharma, P. et al., "Alkaloids of *Amsonia Brevifolia*," *Phytochemistry* 27:3649-3652, Pergamon Press (1988).

(56) References Cited

OTHER PUBLICATIONS

Somei, M. et al., "Preparation and a Novel Rearrangement Reaction of 1,2,3,4-tetrahydro-9-hydroxy-β-carboline, and Their Applications for the Total Synthesis of (±)-Coerulescine," *Heterocycles* 53:7-10, Elsevier Science (2000).

Sun, S.H. et al., "A small molecule that disrupts Mdm2-p53 binding activates p53, induces apoptosis and sensitizes lung cancer cells to chemotherapy," *Cancer Biology & Therapy* 7:845-852, Landes Bioscience (2008).

Usui, T. et al., "Tryprostatin A, a specific and novel inhibitor of microtubule assembly," *Biochem. J.* 333:543-548, The Biochemical Society, London (1998).

van Tamelen, E.E. et al., "Spiro[Pyrrolidine-3 : 3'-Oxindole and -2'-*Pseudo*-Indoxyl]," *Chemistry & Industry* 1145-1146, Society of Chemical Industry, London (1956).

Vassilev, L.T. et al., "In Vivo Activation of the p53 Pathway by Small-Molecule Antagonists of MDM2," *Science* 303:844-848, American Association for the Advancement of Science (2004).

Vogelstein, B. et al., "Surfing the p53 network," *Nature* 408:307-310, Nature Publishing Group (2000).

Wade, M. et al., "BH3 activation blocks Hdmx suppression of apoptosis and cooperates with Nutlin to induce cell death," *Cell Cycle* 7:1973-1982, Landes Bioscience (2008).

Wang, H. and Ganesan, A., "A Biomimetic Total Synthesis of (−)-Spirotryprostatin B and Related Studies," *J. Org. Chem.* 65:4685-4693, The American Chemical Society (2000).

Wu, K-M and Farrelly, J.G, "Regulatory perspectives of Type II prodrug development and time-dependent toxicity management: Nonclinical Pharm/Tox analysis and the role of comparative toxicology" *Toxicology* 236: 1-6, Elsevier Ireland Ltd. (2007).

Wu, X. et al., "The p53-mdm-2 autoregulatory feedback loop," *Genes & Development* 7:1126-1132, Cold Spring Harbor Laboratory Press (1993).

Yu, S. et al., "Potent and Orally Active Small-Molecule Inhibitors of the MDM2-p53 Interaction," *J. Med. Chem.* 52:7970-7973, American Chemical Society (2009).

Office Action mailed Nov. 12, 2013, for U.S. Appl. No. 13/082,163, filed Apr. 7, 2011, inventors: Wang, S. et al., U.S. Patent and Trademark Office, Alexandria, VA.

Office Action mailed Aug. 29, 2014, for U.S. Appl. No. 13/082,163, filed Apr. 7, 2011, inventors: Wang, S. et al., U.S. Patent and Trademark Office, Alexandria, VA.

Office Action mailed Apr. 3,2015, for U.S. Appl. No. 13/082,163, filed Apr. 7, 2011, inventors: Wang, S. et al., U.S. Patent and Trademark Office, Alexandria, VA.

Advisory Action mailed Jun. 11. 2015, for U.S. Appl. No. 13/082,163, filed Apr. 7, 2011, inventors: Wang, S. et al., U.S. Patent and Trademark Office, Alexandria, VA.

\* cited by examiner

SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Synthetic

```
<220> FEATURE:
<221> NAME/KEY: MISC_FEATURE
<222> LOCATION: (1)..(1)
<223> OTHER INFORMATION: The residue at this position is linked to
      5-Carboxyfluorescein
<220> FEATURE:
<221> NAME/KEY: MISC_FEATURE
<222> LOCATION: (1)..(2)
<223> OTHER INFORMATION: The residues at these positions are
      beta-alanine
<220> FEATURE:
<221> NAME/KEY: MISC_FEATURE
<222> LOCATION: (5)..(5)
<223> OTHER INFORMATION: The residue at this position is
      alpha-aminoisobutyric acid
<220> FEATURE:
<221> NAME/KEY: MISC_FEATURE
<222> LOCATION: (6)..(6)
<223> OTHER INFORMATION: The residue at this position is phosphotyrosine
<220> FEATURE:
<221> NAME/KEY: MISC_FEATURE
<222> LOCATION: (7)..(7)
<223> OTHER INFORMATION: The residue at this position is 6-Cl-LTrp
<220> FEATURE:
<221> NAME/KEY: MISC_FEATURE
<222> LOCATION: (9)..(9)
<223> OTHER INFORMATION: The residue at this position is
      1-amino-cyclopropanecarboxylic acid
<220> FEATURE:
<221> NAME/KEY: MISC_FEATURE
<222> LOCATION: (11)..(11)
<223> OTHER INFORMATION: The residue at this position is linked to NH2

<400> SEQUENCE: 1

Ala Ala Phe Met Xaa Tyr Trp Glu Xaa Leu Asn
1               5                   10
```

SPIRO-OXINDOLE MDM2 ANTAGONISTS

CROSS-REFERENCE TO RELATED APPLICATIONS

This application is a continuation of pending U.S. patent application Ser. No. 13/294,315, filed Nov. 11, 2011, now allowed, which claims the benefit of and priority to U.S. Provisional Patent Application No. 61/413,094, filed Nov. 12, 2010, U.S. Provisional Patent Application No. 61/451,968, filed Mar. 11, 2011, U.S. Provisional Patent Application No. 61/451,958, filed Mar. 11, 2011, and U.S. Provisional Patent Application No. 61/470,992, filed Apr. 1, 2011, the contents of each of which are hereby incorporated by reference in their entireties.

STATEMENT REGARDING FEDERALLY SPONSORED RESEARCH OR DEVELOPMENT

This invention was made with government support under CA121279 awarded by the National Institutes of Health. The government has certain rights in the invention.

BACKGROUND

The aggressive cancer cell phenotype is the result of a variety of genetic and epigenetic alterations leading to deregulation of intracellular signaling pathways (Ponder, *Nature* 411:336 (2001)). Cancer cells typically fail to execute an apoptotic program, and lack of appropriate apoptosis due to defects in the normal apoptosis machinery is considered a hallmark of cancer (Lowe et al., *Carcinogenesis* 21:485 (2000)). The inability of cancer cells to execute an apoptotic program due to defects in the normal apoptotic machinery is often associated with an increase in resistance to chemotherapy, radiation, or immunotherapy-induced apoptosis. Primary or acquired resistance of human cancer of different origins to current treatment protocols due to apoptosis defects is a major problem in current cancer therapy (Lowe et al., *Carcinogenesis* 21:485 (2000); Nicholson, *Nature* 407:810 (2000)). Accordingly, current and future efforts towards designing and developing new molecular target-specific anticancer therapies to improve survival and quality of life of cancer patients must include strategies that specifically target cancer cell resistance to apoptosis.

The p53 tumor suppressor plays a central role in controlling cell cycle progression, senescence, and apoptosis (Vogelstein et al., *Nature* 408:307 (2000); Goberdhan, *Cancer Cell* 7:505 (2005)). MDM2 and p53 are part of an auto-regulatory feed-back loop (Wu et al., *Genes Dev.* 7:1126 (1993)). MDM2 is transcriptionally activated by p53 and MDM2, in turn, inhibits p53 activity by at least three mechanisms (Wu et al., *Genes Dev.* 7:1126 (1993). First, MDM2 protein directly binds to the p53 transactivation domain and thereby inhibits p53-mediated transactivation. Second, MDM2 protein contains a nuclear export signal sequence, and upon binding to p53, induces the nuclear export of p53, preventing p53 from binding to the targeted DNAs. Third, MDM2 protein is an E3 ubiquitin ligase and upon binding to p53 is able to promote p53 degradation.

Although high-affinity peptide-based inhibitors of MDM2 have been successfully designed in the past (Garcia-Echeverria et al., *Med. Chem.* 43:3205 (2000)), these inhibitors are not suitable therapeutic molecules because of their poor cell permeability and in vivo bioavailability. Despite intensive efforts by the pharmaceutical industry, high throughput screening strategies have had very limited success in identifying potent, non-peptide small molecule inhibitors. Accordingly, there is a need for non-peptide, drug-like, small molecule inhibitors of the p53-MDM2 interaction.

The structural basis of the interaction p53 and MDM2 has been established by x-ray crystallography (Kussie et al., *Science* 274:948 (1996)).

Spiro-oxindole-based antagonists of the p53-MDM2 interaction are described in U.S. Pat. Nos. 7,759,383 B2 and 7,737,174 B2.

Skin cancer or melanoma is a commonly found type of cancer. Even though melanoma represents only a small fraction of the total number of cancer cases, it is responsible for many cancer deaths. According to statistics provided by the American Cancer Society, in contrast to many other types of cancers, the number of new cases of melanoma in the United States is still on the rise.

As with all cancers, it is imperative to diagnose melanoma early. About 70% of melanomas are "superficial spreading", meaning that they undergo a superficial, radial growth phase before they grow vertically and invade underlying tissue, a much more serious condition. Unfortunately, about 20% of cutaneous melanomas immediately start out with a vertical growth phase, which explains why these tumors are so dangerous. The 5-year survival rate for Stage 1 melanoma is very good. However, this drops off rapidly when cancer is allowed to progress and invade, first locally and then more distantly. Survival rate for Stage 2 disease is only 40-80%, Stage 3 10-70% and Stage 4 is almost invariably lethal within 5 years (<5-10% survives beyond 5 years) due to untreatable distant metastasis to especially lung and brain.

Melanoma originates from malignant transformation of melanocytes, the pigment producing skin cells, via atypical and dysplastic premalignant intermediate stages to locally invasive and finally metastatic melanoma. A large number of genes have been implicated to play a role in these processes. Metastatic melanoma, the usual cause of death, is notoriously resistant to conventional therapy.

SUMMARY OF THE INVENTION

The present disclosure contemplates that exposure of humans and animals to therapeutically effective amounts of drug(s) (e.g., small molecules) that increase the function(s) of p53 and p53-related proteins (e.g., p63, p73) inhibits the growth of p53 expressing cells. In some embodiments, the compounds provided herein inhibit the interaction between p53 or p53-related proteins and MDM2 or MDM2-related proteins (e.g., MDMX). Inhibiting the interaction between p53 or p53-related proteins and MDM2 or MDM2-related proteins inhibits the growth of cells. For example, inhibiting the interaction between p53 or p53-related proteins and MDM2 or MDM2-related proteins can inhibit cancer cells or supporting cells and/or renders such cells as a population more susceptible to the cell death-inducing activity of cancer therapeutic drugs or radiation therapies. In some embodiments, the inhibitors provided herein prolong the half-life of p53 by interfering with the p53-MDM2 interaction that would normally promote degradation of p53. The compounds provided herein satisfy an unmet need for the treatment of multiple cancer types, either when administered as monotherapy to induce senescence, cell growth inhibition, apoptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In some embodiments, treatment of animals (including humans) with a therapeutically effective amount of one or more compounds provided herein and an anticancer agent produces a greater anti-tumor activity and clinical benefit in such animals compared to those treated with the compound or anticancer drugs/radiation alone. Put another way, because the compounds provided herein can lower the apoptotic threshold of cells that express p53 or p53-related protein, the proportion of cells that successfully execute the apoptosis program in response to the apoptosis inducing activity of anticancer drugs/radiation will be increased when used in combination with one or more of the compounds provided herein. Alternatively, the compounds provided herein can be used to allow administration of a lower, and therefore less toxic and more tolerable, dose of an anticancer drug and/or radiation to produce the same tumor response/clinical benefit as the conventional dose of the anticancer drug/radiation alone. Since the doses for all approved anticancer drugs and radiation treatments are known, the present compounds, compositions, and methods provided herein can be used with one or more approved anticancer drugs and/or radiation treatment. Also, since the compounds provided herein may act at least in part by stimulating the pro-apoptotic and/or cell cycle-inhibiting activities of p53 and p53-related proteins, the exposure of cancer cells and supporting cells to therapeutically effective amounts of the compounds can be temporally linked to coincide with the attempts of cells to execute the apoptosis program in response to the anticancer drug or radiation therapy. Thus, in some embodiments, administering the compounds or compositions provided herein in combination with other known anticancer drugs provide especially efficacious therapeutic practices.

In other embodiments, the inhibitors of the interaction between p53 or p53-related proteins and MDM2 and MDM2-related proteins provided herein may protect normal (e.g., non-hyperproliferative) cells from the toxic effects of certain chemotherapeutic agents and radiation, possibly through the ability of the inhibitors to induce cell cycle arrest of normal cells. For example, the inhibitors provided herein may cause cell cycle arrest in cells comprising wild-type or functional p53 (and/or wild-type or functional p53-related proteins) while having no or less effect on cancer cells comprising mutated, deleted, or otherwise non- or less functional p53 (and/or mutated, deleted, or otherwise non- or less functional p53-related proteins). This differential protective effect may allow for more effective treatment of cancer by allowing the use of higher doses or longer treatments of chemotherapeutic agents or treatments without increasing the toxic side effects of such treatment when administered in combination with inhibitors provided herein.

Applicants have found that certain spiro-oxindoles provided herein display an unexpected combination of drug-like properties. The unexpected combinations include, e.g., two or more of in vitro efficacy, in vivo efficacy, in vitro liver microsome stability, desirable absorption, distribution, metabolism, and excretion (ADME) properties. For example, certain spiro-oxindoles provided herein are more resistant to metabolic degradation e.g., as measured by in vitro liver microsomal stability and/or in vivo pharmacokinetics, and/or display improved in vivo efficacy as compared to known antagonists of the p53-MDM2 interaction.

Applicants have also found that metabolically cleavable groups can be used to increase the aqueous solubility of the parent molecule. Thus, in some embodiments, the spiro-oxindoles provided herein are useful prodrugs with improved aqueous solubility relative to the parent molecule.

In some embodiments, the compounds provided herein are spiro-oxindoles having Formulae I-XXXV (see below under "Compounds"), or pharmaceutically acceptable salts, solvates, or prodrugs thereof. In some embodiments, the compounds provided herein inhibit the interaction between p53 or p53-related proteins and MDM2 or MDM2-related proteins.

In some embodiments, the compounds provided herein contain a metabolically cleavable group. In particular, in some embodiments, the compounds provided herein contain a hydroxy group of a hydroxycycloalkyl side chain that can be used to attach a metabolically cleavable group. Suitable metabolically cleavable groups include, but are not limited to, amino acid esters or phosphate esters.

In some embodiments, the compounds provided herein can be used to induce senescence, cell cycle arrest and/or apoptosis in cells containing functional p53 or p53-related proteins. Also provided herein are methods of using the compounds provided herein for sensitizing cells to additional agent(s), such as inducers of senescence, apoptosis and/or cell cycle arrest. The compounds provided herein can also be used to provide chemoprotection of normal cells through the induction of cell cycle arrest prior to treatment with chemotherapeutic agents. In one embodiment, the methods of rendering a normal cell resistant to chemotherapeutic agents or treatments comprises contacting the cell with one or more compounds provided herein. In one embodiment, methods of protecting normal cells in an animal having a hyperproliferative disease from the toxic side effects of chemotherapeutic agents or treatments, comprises administering to the animal a compound provided herein. Provided herein are methods for the treatment, amelioration, or prevention of disorders, side effects, or conditions caused by the administration of chemotherapeutic agents to normal cells comprising administering to an animal undergoing chemotherapy a compound provided herein. Examples of such disorders and conditions caused by chemotherapy include, without limitation, mucositis, stomatitis, xerostomia, gastrointestinal disorders, and alopecia.

The compounds provided herein are useful for the treatment, amelioration, or prevention of disorders, such as those responsive to induction of apoptotic cell death, e.g., disorders characterized by dysregulation of apoptosis, including hyperproliferative diseases such as cancer. In certain embodiments, the compounds can be used to treat, ameliorate, or prevent cancer that is characterized by resistance to cancer therapies (e.g., those cancer cells which are chemoresistant, radiation resistant, hormone resistant, and the like). In other embodiments, the compounds can be used to treat hyperproliferative diseases characterized by expression of functional p53 or p53-related proteins. In other embodiments, the compounds provided herein can be used to protect normal (e.g., non-hyperproliferative) cells from the toxic side effects of chemotherapeutic agents and treatments by the induction of cell cycle arrest in those cells.

In one embodiment, pharmaceutical compositions are provided. The pharmaceutical compositions can comprise one of more of the compounds provided herein and a pharmaceutically acceptable carrier.

In one embodiment, kits are provided. The kits can comprise one or more of the compounds provided herein, or a pharmaceutically acceptable salt thereof, and instructions for administering the compound to an animal. The kits may optionally contain other therapeutic agents, e.g., anticancer agents or apoptosis-modulating agents.

In one embodiment, methods of treating, preventing, or ameliorating a hyperproliferative disease, e.g., cancer, in a patient comprising pulsatile administration to the patient a therapeutically effective amount of one or more of the compounds provided herein, or pharmaceutically acceptable salts, solvates, or prodrugs thereof are provided.

In one embodiment, methods of treating, preventing, or ameliorating a hyperproliferative disease, e.g., cancer, in a patient comprising pulsatile administration to the patient a therapeutically effective amount of one or more of the compounds provided herein, or pharmaceutically acceptable salts, solvates, or prodrugs thereof, in combination with one or more additional therapeutic, e.g., anticancer, agents.

In one embodiment, kits comprising one or more of the compounds provided herein, or pharmaceutically acceptable salts, solvates, or prodrugs thereof, and instructions for administering the compound(s) to a patient having a hyperproliferative disease by pulsatile dosing are provided. The kits can optionally contain one or more additional therapeutic, e.g., anticancer, agents.

DETAILED DESCRIPTION OF THE INVENTION

Figure 1:
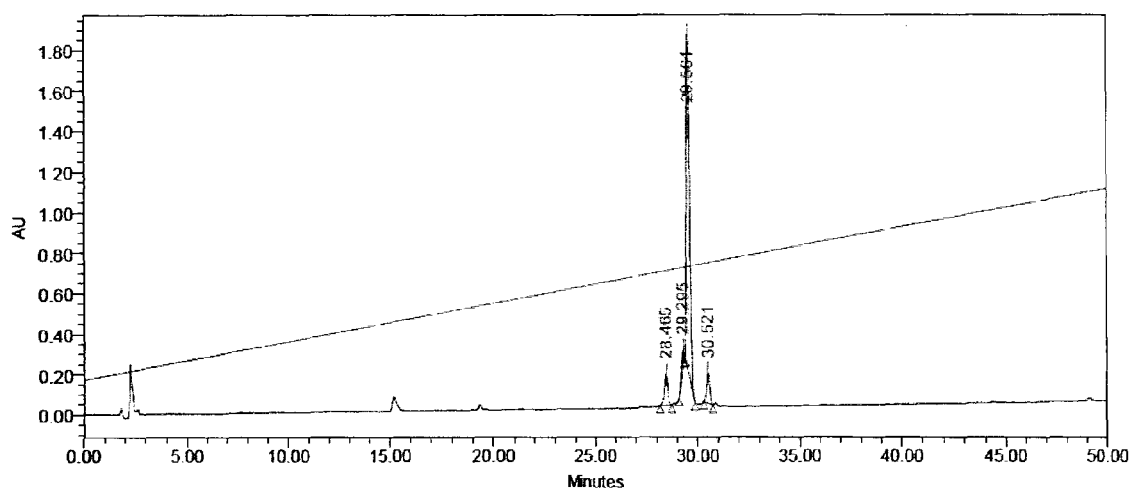
FIG. 1 is a reverse phase HPLC chromatogram of MI-519-64 after isolation by column chromatography on silica gel.

Provided herein are compounds that inhibit the interaction between p53 or p53-related proteins and MDM2 or MDM2-related proteins. By inhibiting the negative effect of MDM2 or MDM2-related proteins on p53 or p53-related proteins, these compounds sensitize cells to inducers of apoptosis and/or cell cycle arrest. In some embodiments, the compounds provided herein induce apoptosis and/or cell cycle arrest. Therefore, also provided herein are methods of sensitizing cells to inducers of apoptosis and/or cell cycle arrest and to methods of inducing apoptosis and/or cell cycle arrest in cells. In some embodiments, the methods comprise contacting the cells with one or more compounds provided herein alone or in combination with additional agent(s), e.g., an inducer of apoptosis or a cell cycle disrupter.

Also provided herein are methods of treating, ameliorating, or preventing disorders, e.g., a hyperproliferative disease, e.g., cancer, in a patient, comprising administering to the patient one or more compounds provided herein and additional agent(s), e.g., an inducer of apoptosis. Such disorders include those characterized by a dysregulation of apoptosis and those characterized by the proliferation of cells expressing functional p53 or p53-related proteins. In other embodiments, methods of protecting normal (e.g., non-hyperproliferative) cells in an animal from the toxic side effects of chemotherapeutic agents and treatments are provided. The methods comprise administering to the animal one or more compounds provided herein. Also provided herein are methods of treating preventing, or ameliorating a hyperproliferative disease, e.g., cancer, in a patient comprising administering to the patient a therapeutically effective amount of one or more of the compounds provided herein, or pharmaceutically acceptable salts, solvates, or prodrugs thereof, according to a pulsatile dosing regimen.

Also provided herein are methods of treating preventing, or ameliorating a hyperproliferative disease, e.g., cancer, in a patient comprising administering to the patient a therapeutically effective amount of one or more of the compounds provided herein, or pharmaceutically acceptable salts, solvates, or prodrugs thereof, according to a pulsatile dosing regimen in combination with one or more additional therapeutic, e.g., anticancer, agents.

Also provided herein are kits comprising one or more of the compounds provided herein, and instructions for administering the compound(s) to a patient having a hyperproliferative disease by pulsatile dosing. The kits can optionally contain one or more additional therapeutic, e.g., anticancer, agents

DEFINITIONS

The terms "pulsatile administration," "pulsatile dose administration," or "pulsatile dosing" as used herein, refer to intermittent (i.e., not continuous) administration of one or more of the compounds provided herein, or pharmaceutically acceptable salts, solvates, or prodrugs thereof, to a patient. Pulsatile dose administration regimens useful in the present disclosure encompass any discontinuous administration regimen that provides a therapeutically effective amount of the compound(s) provided herein, or pharmaceutically acceptable salts, solvates, or prodrugs thereof, to a patient in need thereof. Pulsatile dosing regimens can use equivalent, lower, or higher doses of compounds, or pharmaceutically acceptable salts, solvates, or prodrugs thereof, than would be used in continuous dosing regimens. The compounds provided herein, or pharmaceutically acceptable salts, solvates, or prodrugs thereof, can be administered as a single agent under a pulsatile dosing regimen or can be administered under a pulsatile dosing regimen in combination with one or more additional anticancer agents (where the additional anticancer agents are administered either on a continuous or a pulsatile regimen). On the day that compounds, or pharmaceutically acceptable salts, solvates, or prodrugs thereof, are scheduled to be administered to the patient, administration can occur in a single or in divided doses, e.g., once-a-day, twice-a-day, three times a day, four times a day or more. In one embodiment, compounds provided herein, or pharmaceutically acceptable salts, solvates, or prodrugs thereof, are administered once (QD) or twice (BID) on the day it is schedule to be administered. In one embodiment the compounds provided, or pharmaceutically acceptable salts, solvates, or prodrugs thereof, are administered orally to the patient according to a pulsatile dosing regimen.

In one embodiment the compounds provided herein, or pharmaceutically acceptable salts, solvates, or prodrugs thereof, are administered intravenously to the patient according to a pulsatile dosing regimen.

The therapeutic utility of drug administration can be offset by the number and severity of adverse events a patient experiences. Pulsatile dosing of compounds provided herein, or pharmaceutically acceptable salts, solvates, or prodrugs thereof, can result in a reduction in the number and/or severity of clinical adverse events coupled with a maintenance or enhancement in clinical efficacy, as compared to continuous daily dosing. The clinical benefits of pulsatile dose administration of compounds provided herein, or pharmaceutically acceptable salts, solvates, or prodrugs thereof, can be more prominent when combined with the administration of other therapeutic agents to the patient.

In one embodiment, compounds provided herein, or pharmaceutically acceptable salts, solvates, or prodrugs thereof, are administered to a patient no more frequently than one day out of every two days (e.g., administration occurs on day 1, day 3, day 5, day 7, day 9, etc.), one out of every three days (e.g., administration occurs on day 1, day 4, day 7, day 10, etc.), one out of every four days, one out of every five days, one out of every six days, one out of every seven days, one out of every eight days, one out of every nine days, one out of every ten days, one out of every two weeks, one out of every three weeks, one out of every four weeks, one out of every five weeks, or longer. The pulsatile dosing regimen can continue for one, two, three or four weeks, one, two, three or four months, one, two, three or four years or longer.

In another embodiment, compounds provided herein, or pharmaceutically acceptable salts, solvates, or prodrugs thereof, are administered to a patient one day a week, e.g., a compound of Formulae I-XXXV, or a pharmaceutically acceptable salt, solvate, or prodrug thereof, is administered to a patient on one day followed by six consecutive days wherein the compound is not administered. In another embodiment, compounds having Formulae I-XXXV, or pharmaceutically acceptable salts, solvates, or prodrugs thereof, administered to a patient one day every two weeks. In another embodiment, compounds having Formulae I-XXXV, or pharmaceutically acceptable salts, solvates, or prodrugs thereof, are administered to a patient one day every three weeks. In another embodiment, compounds having Formulae I-XXXV, or pharmaceutically acceptable salts, solvates, or prodrugs thereof, are administered to a patient one day every four weeks.

In another embodiment, compounds provided herein, or pharmaceutically acceptable salts, solvates, or prodrugs thereof, are administered to a patient on a least two consecutive days, e.g., at least three, four, five, six or seven consecutive days, followed by at least one day, at least two consecutive days, at least three consecutive days, at least four consecutive days, at least five consecutive days, at least six consecutive days, at least seven consecutive days, at least eight consecutive days, at least nine consecutive days, at least ten consecutive days, at least eleven consecutive days, at least twelve consecutive days, at least thirteen consecutive days, at least two consecutive weeks, at least three consecutive weeks, or at least four consecutive weeks or longer wherein the compound disclosed herein is not administered.

In one embodiment, compounds provided herein, or pharmaceutically acceptable salts, solvates, or prodrugs thereof, and one or more anticancer agents are administered to a patient on day 1 of an anticancer treatment cycle. Typically, the length of the treatment cycle is determined in accord with the approved dosing protocol(s) of the one or more anticancer agents that are to be administered to the patient in combination with the compounds having Formulae I-XXXV, or pharmaceutically acceptable salts, solvates, or prodrugs thereof. In one embodiment, the treatment cycle is about 14 days, about 21 days, or about 28 days. In a particular embodiment, the treatment cycle is 21 days. In one embodiment, the treatment cycle is repeated one or more times, e.g., 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, or more times.

In another embodiment, compounds provided herein, or pharmaceutically acceptable salts, solvates, or prodrugs thereof, are administered to the patient on day 1, on days 1 and 2, or on days 1, 2, and 3 of a treatment cycle and one or more anticancer agents are administered starting on day 1 of the treatment cycle in accord with the recommended dosing schedule of the anticancer agent. In one embodiment, the anticancer agent is a chemotherapeutic agent. In another embodiment, the anticancer agent is radiation therapy.

In another embodiment, compounds provided herein, or pharmaceutically acceptable salts, solvates, or prodrugs thereof, are administered via the sequential use of a combination of two or more pulsatile dosing schedules. The combination may comprise the same pulsatile dosing schedules or different pulsatile dosing schedules. The sequential use of a combination of two or more pulsatile dosing regimens may be repeated as many times as necessary to achieve or maintain a therapeutic response, e.g., from one to about fifty times, e.g., from one to about twenty times, e.g., from about one to about ten times. With every repetition any additional therapeutic agents may be the same or different from that used in the previous repetition.

In another embodiment, compounds provided herein, or pharmaceutically acceptable salts, solvates, or prodrugs thereof, are administered according to a pulsatile dosing schedule and/or sequential combination of two or more pulsatile dosing schedules followed by a waiting period. The term "waiting period," as used herein, refers to a period of time between dosing schedules when a compound disclosed herein is not administered to the patient. The waiting period may be one, two, three, four, five or six days, one, two or three weeks, one, two, three or four months, one, two, three or four years or longer. In certain embodiments, the waiting period may be one to thirty days, e.g., seven, fourteen, twenty one or thirty days, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 days. After the waiting period, the same or a different pulsatile dosing schedule and/or sequential combination of one or more pulsatile dosing schedules of a compound disclosed herein can resume. The pulsatile dosing/waiting period regimen may be repeated as many times as necessary to achieve or maintain a therapeutic response, e.g., from one to about fifty times, e.g., from one to about twenty times, e.g., from about one to about ten times. With every repetition any additional therapeutic agents may be the same or different from that used in the previous repetition.

The term "anticancer agent" as used herein, refers to any therapeutic agent (e.g., chemotherapeutic compound and/or molecular therapeutic compound), antisense therapy, radiation therapy, or surgical intervention, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgaard, Design of Prodrugs, pp. 7-9, 21-24, Elsevier, Amsterdam (1985); and Silverman, The Organic Chemistry of Drug Design and Drug Action, pp. 352-401, Academic Press, San Diego, Calif. (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate, see, e.g., US 2007/0249564 A1.

The term "metabolically cleavable group" as used herein, refers to groups which can be cleaved from the parent molecule by metabolic processes and be substituted with hydrogen. Certain compounds containing metabolically cleavable groups may be prodrugs, i.e., they are pharmacologically inactive. Certain other compounds containing metabolically cleavable groups may be antagonists of the interaction between p53 and MDM2. In such cases, these compounds may have more, less, or equivalent activity of the parent molecule. Examples of metabolically cleavable groups include those derived from amino acids (see, e.g., US 2006/0241017 A1; US 2006/0287244 A1; and WO 2005/046575 A2) or phosphorus-containing compounds (see, e.g., U.S. 2007/0249564 A1) as illustrated in Scheme 1.

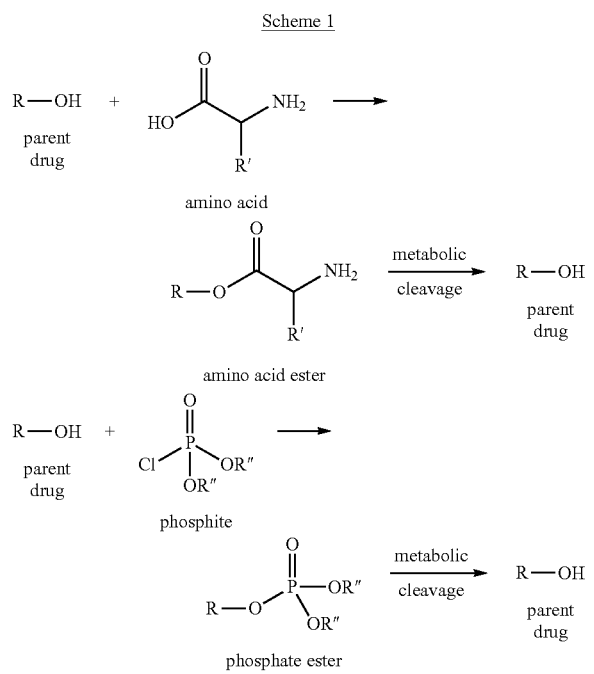

The term "pharmaceutically acceptable salt" as used herein, refers to any salt (e.g., obtained by reaction with an acid or a base) of a compound provided herein that is physiologically tolerated in the target animal (e.g., a mammal) or human. Salts of the compounds of provided herein may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds provided herein and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds provided herein compounded with a suitable cation such as $Na^+$, $NH_4^+$, and $NW_4^+$ (wherein W is a $C_{1-4}$ alkyl group), and the like. For therapeutic use, salts of the compounds provided herein are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound provided herein with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "monovalent pharmaceutically acceptable cation" as used herein refers to inorganic cations such as, but not limited to, alkaline metal ions, e.g., $Na^+$ and $K^+$, as well as organic cations such as, but not limited to, ammonium and substituted ammonium ions, e.g., $NH_4^+$, $NHMe_3^+$, $NH_2Me_2^+$, $NHMe_3^+$ and $NMe_4^+$.

The term "divalent pharmaceutically acceptable cation" as used herein refers to inorganic cations such as, but not limited to, alkaline earth metal cations, e.g., $Ca^{2+}$ and $Mg^{2+}$.

Examples of monovalent and divalent pharmaceutically acceptable cations are discussed, e.g., in Berge et al. *J. Pharm. Sci.,* 66:1-19 (1997).

The term "therapeutically effective amount," as used herein, refers to that amount of the therapeutic agent (including the compounds, pharmaceutical compositions, and compositions of matter provided herein) sufficient to result in amelioration of one or more symptoms of a disorder, or prevent advancement of a disorder, or cause regression of the disorder. For example, with respect to the treatment of cancer, in one embodiment, a therapeutically effective amount can refer to the amount of a therapeutic agent that decreases the rate of tumor growth, decreases tumor mass, decreases the number of metastases, increases time to tumor progression, increase tumor cell apoptosis, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first therapeutic agent (e.g., a compound provided herein), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second therapeutic agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least 300%, at least about 350%, at least about 400%, at least about 450%, or at least about 500% over the response in the absence of the first agent.

The term "dysregulation of apoptosis," as used herein, refers to any aberration in the ability of (e.g., predisposition) a cell to undergo cell death via apoptosis. Dysregulation of apoptosis is associated with or induced by a variety of conditions, non-limiting examples of which include, autoimmune disorders (e.g., systemic lupus erythematosus, rheumatoid arthritis, graft-versus-host disease, myasthenia gravis, or Sjögren's syndrome), chronic inflammatory conditions (e.g., psoriasis, asthma or Crohn's disease), hyperproliferative disorders (e.g., tumors, B cell lymphomas, or T cell lymphomas), viral infections (e.g., herpes, papilloma, or HIV), and other conditions such as osteoarthritis and atherosclerosis. It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

The term "functional p53," as used herein, refers to wild-type p53 expressed at normal, high, or low levels and mutant or allelic variants of p53 that retain(s) at least about 5% of the activity of wild-type p53, e.g., at least about 10%, about 20%, about 30%, about 40%, about 50%, or more of wild-type activity.

The term "p53-related protein," as used herein, refers to proteins that have at least 25% sequence homology with p53, have tumor suppressor activity, and are inhibited by interaction with MDM2 or MDM2-related proteins. Examples of p53-related proteins include, but are not limited to, p63 and p73.

The term "MDM2-related protein," as used herein, refers to proteins that have at least 25% sequence homology with MDM2, and interact with and inhibit p53 or p53-related proteins. Examples of MDM2-related proteins include, but are not limited to, MDMX and MDM4.

The term "senescence" as used herein, refers to the phenomenon whereby non-cancerous diploid cells lose the ability to divide, and characterized in part by telomeric dysfunction or shortening.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas, leukemias and the like. A neoplasm is said to be benign if it does not undergo invasion or metastasis and malignant if it does either of these. A "metastatic" cell means that the cell can invade neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, celiac sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjögren's syndrome, systemic lupus erythematosus, type 1 diabetes, ulcerative colitis, vitiligo, and the like.

The term "neoplastic disease," as used herein, refers to any abnormal growth of cells being either benign (non-cancerous) or malignant (cancerous).

The term "melanoma" as used herein refers to any form of cancer that begins in melanocytes. Melanoma includes, but is not limited to, the following subtypes: lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, and metastatic melanoma. Melanoma, as used herein also includes metastatic melanoma.

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without treatment with one or more compounds provided herein.

The terms "a" and "an" refer to one or more.

The term "apoptosis-modulating agents," as used herein, refers to agents which are involved in modulating (e.g., inhibiting, decreasing, increasing, promoting) apoptosis. Examples of apoptosis-modulating agents include proteins which comprise a death domain such as, but not limited to, Fas/CD95, TRAMP, TNF RI, DR1, DR2, DR3, DR4, DR5, DR6, FADD, and RIP. Other examples of apoptosis-modulating agents include, but are not limited to, TNFα, Fas ligand, antibodies to Fas/CD95 and other TNF family receptors, TRAIL (also known as Apo2 Ligand or Apo2L/TRAIL), antibodies to TRAIL-R1 or TRAIL-R2, Bcl-2, p53, BAX, BAD, Aid, CAD, PI3 kinase, PP1, and caspase proteins. Modulating agents broadly include agonists and antagonists of TNF family receptors and TNF family ligands. Apoptosis-modulating agents may be soluble or membrane bound (e.g. ligand or receptor). Apoptosis-modulating agents include those which are inducers of apoptosis, such as TNF or a TNF-related ligand, particularly a TRAMP ligand, a Fas/CD95 ligand, a TNFR-1 ligand, or TRAIL.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, Pa., 19th ed. 1995.

The term "alkyl" as used herein by itself or part of another group refers to a straight-chain or branched saturated aliphatic hydrocarbon having from one to eighteen carbons or the number of carbons designated (e.g., $C_1$-$C_{18}$ means 1 to 18 carbons). In one embodiment, the alkyl is a $C_1$-$C_{10}$ alkyl. In another embodiment, the alkyl is a $C_4$-$C_8$ alkyl. In another embodiment, the alkyl is a $C_1$-$C_6$ alkyl. In another embodiment, the alkyl is a $C_1$-$C_4$ alkyl. Exemplary alkyl groups include methyl, ethyl, n-propyl, isopropyl, n-butyl, sec-butyl, isobutyl, tert-butyl, n-pentyl, n-hexyl, isohexyl, n-heptyl, 4,4-dimethylpentyl, n-octyl, 2,2,4-trimethylpentyl, nonyl, decyl and the like.

The term "optionally substituted alkyl" as used herein by itself or part of another group means that the alkyl as defined above is either unsubstituted or substituted with one, two or three substituents independently selected from hydroxy (i.e., —OH), nitro (i.e., —$NO_2$), cyano (i.e., —CN), optionally substituted cycloalkyl, optionally substituted heteroaryl, optionally substituted heterocyclo, alkoxy, aryloxy, aralkyloxy, alkylthio, carboxamido or sulfonamido. In one embodiment, the optionally substituted alkyl is substituted with two substituents. In another embodiment, the optionally substituted alkyl is substituted with one substituent. In another embodiment, the substituents are selected from hydroxyl (i.e., a hydroxyalkyl), optionally substituted cycloalkyl (i.e., a (cycloalkyl)alkyl), or amino (i.e., an aminoalkyl). Exemplary optionally substituted alkyl groups include —$CH_2OCH_3$, —$CH_2CH_2NH_2$, —$CH_2CH_2NH(CH_3)$, —$CH_2CH_2CN$, —$CH_2SO_2CH_3$, hydroxymethyl, hydroxyethyl, hydroxypropyl, and the like.

The term "alkylenyl" as used herein by itself or part of another group refers to a divalent alkyl radical containing one, two, three, four, or more joined methylene groups. Exemplary alkylenyl groups include —($CH_2$)—, —($CH_2$)$_2$—, —($CH_2$)$_3$—, —($CH_2$)$_4$—, and the like.

The term "optionally substituted alkylenyl" as used herein by itself or part of another group means the alkylenyl as defined above is either unsubstituted or substituted with one, two, three, or four substituents independently selected from the group consisting of optionally substituted $C_1$-$C_6$ alkyl, optionally substituted cycloalkyl, optionally substituted aryl, and optionally substituted heteroaryl. In one embodiment, the optionally substituted $C_1$-$C_6$ alkyl is methyl. In one embodiment, the optionally substituted aryl is a phenyl optionally substituted with one or two halo groups. Exemplary optionally substituted alkylenyl groups include —CH($CH_3$)—, —C($CH_3$)$_2$—, —$CH_2CH(CH_3)$—, —$CH_2CH(CH_3)CH_2$—, —$CH_2CH(Ph)CH_2$—, —CH($CH_3$)CH($CH_3$)—, and the like.

The term "haloalkyl" as used herein by itself or part of another group refers to an alkyl as defined above having one to six halo substituents. In one embodiment, the haloalkyl has one, two or three halo substituents. Exemplary haloalkyl groups include trifluoromethyl, —$CH_2CH_2F$ and the like.

The term "hydroxyalkyl" as used herein by itself or part of another group refers to an alkyl as defined above having one hydroxy substituent. Exemplary hydroxyalkyl groups include hydroxymethyl, hydroxyethyl, hydroxypropyl, and the like.

The term "dihydroxyalkyl" as used herein by itself or part of another group refers to alkyl as defined above having two hydroxyl substituents. Exemplary dihydroxyalkyl groups include —$CH_2CH_2CCH_3(OH)CH_2OH$, —$CH_2CH_2CH(OH)CH(CH_3)OH$, —$CH_2CH(CH_2OH)_2$, —$CH_2CH_2CH(OH)C(CH_3)_2OH$—$CH_2CH_2CCH_3(OH)CH(CH_3)OH$, and the like, including stereoisomers thereof.

The term "hydroxycycloalkyl" as used herein by itself or part of another group refers to an optionally substituted cycloalkyl as defined below having a least one, e.g., one or two, hydroxy substituents. Exemplary hydroxycycloalkyl groups include:

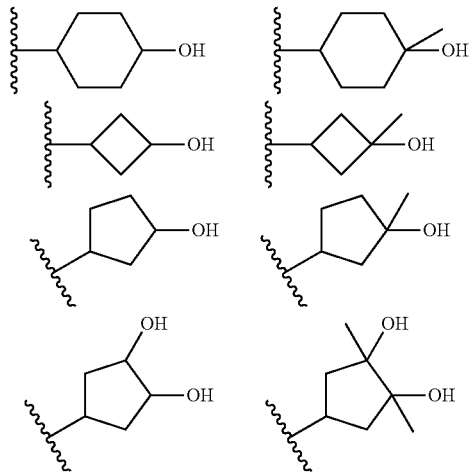

and the like, including stereoisomers thereof.

The term "optionally substituted (cycloalkyl)alkyl" as used herein by itself or part of another group refers to an optionally substituted alkyl as defined above having an optionally substituted cycloalkyl (as defined below) substituent. Exemplary optionally substituted (cycloalkyl)alkyl groups include:

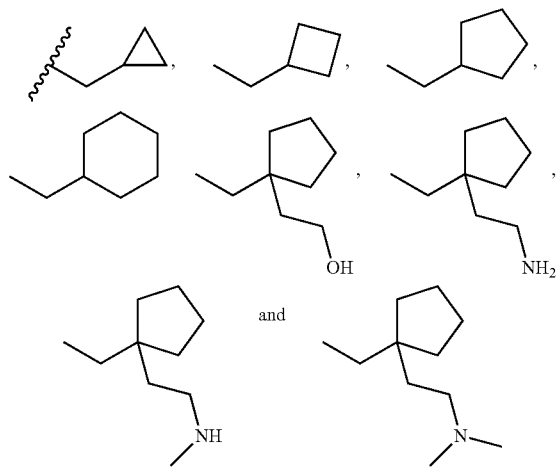

and the like, including stereoisomers thereof.

The term "aralkyl" as used herein by itself or part of another group refers to an optionally substituted alkyl as defined above having one, two or three optionally substituted aryl substituents. In one embodiment, the aralkyl has two optionally substituted aryl substituents. In another embodiment, the aralkyl has one optionally substituted aryl substituent. In another embodiment, the aralkyl is an aryl($C_1$-$C_4$ alkyl). In another embodiment, the aryl($C_1$-$C_4$ alkyl) has two optionally substituted aryl substituents. In another embodiment, the aryl($C_1$-$C_4$ alkyl) has one optionally substituted aryl substituent. Exemplary aralkyl groups include, for example, benzyl, phenylethyl, (4-fluorophenyl)ethyl, phenylpropyl, diphenylmethyl (i.e., $Ph_2CH$—), diphenylethyl ($Ph_2CHCH_2$—) and the like.

The term "cycloalkyl" as used herein by itself or part of another group refers to saturated and partially unsaturated (containing one or two double bonds) cyclic hydrocarbon groups containing one to three rings having from three to twelve carbon atoms (i.e., $C_3$-$C_{12}$ cycloalkyl) or the number of carbons designated. In one embodiment, the cycloalkyl has one ring. In another embodiment, the cycloalkyl is a $C_3$-$C_6$ cycloalkyl. Exemplary cycloalkyl groups include cyclopropyl, cyclobutyl, cyclopentyl, cyclohexyl, cycloheptyl, cyclooctyl, norbornyl, decalin, adamantyl and the like.

The term "optionally substituted cycloalkyl" as used herein by itself or part of another group means the cycloalkyl as defined above is either unsubstituted or substituted with one, two or three substituents independently selected from halo, nitro, cyano, hydroxy, amino, optionally substituted alkyl, haloalkyl, hydroxyalkyl, aminoalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. The term "optionally substituted cycloalkyl" also means the cycloalkyl as defined above may be fused to an optionally substituted aryl. Exemplary optionally substituted cycloalkyl groups include:

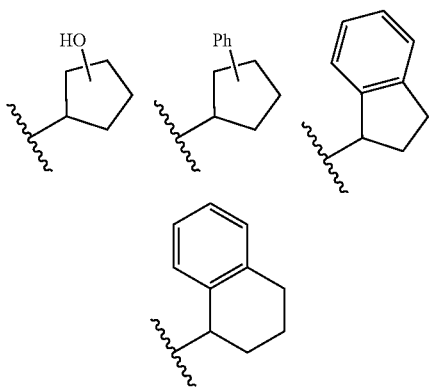

and the like.

The term "alkenyl" as used herein by itself or part of another group refers to an alkyl group as defined above containing one, two or three carbon-to-carbon double bonds. In one embodiment, the alkenyl has one carbon-to-carbon double bond. Exemplary alkenyl groups include —CH=$CH_2$, —$CH_2$CH=$CH_2$, —$CH_2CH_2$CH=$CH_2$, —$CH_2CH_2$CH=$CHCH_3$ and the like.

The term "optionally substituted alkenyl" as used herein by itself or part of another group means the alkenyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Exemplary optionally substituted alkenyl groups include —CH=CHPh, —$CH_2$CH=CHPh and the like.

The term "cycloalkenyl" as used herein by itself or part of another group refers to a cycloalkyl group as defined above containing one, two or three carbon-to-carbon double bonds. In one embodiment, the cycloalkenyl has one carbon-to-carbon double bond. Exemplary cycloalkenyl groups include cyclopentene, cyclohexene and the like.

The term "optionally substituted cycloalkenyl" as used herein by itself or part of another group means the cycloalkenyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido.

The term "alkynyl" as used herein by itself or part of another group refers to an alkyl group as defined above containing one to three carbon-to-carbon triple bonds.

In one embodiment, the alkynyl has one carbon-to-carbon triple bond. Exemplary alkynyl groups include —C≡CH, —C≡$CCH_3$, —$CH_2$C≡CH, —$CH_2CH_2$C≡CH and —$CH_2CH_2$C≡$CCH_3$.

The term "optionally substituted alkynyl" as used herein by itself or part of another group means the alkynyl as defined above is either unsubstituted or substituted with one, two or three substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. Exemplary optionally substituted alkenyl groups include —C≡CPh, —$CH_2$C≡CPh and the like.

The term "aryl" as used herein by itself or part of another group refers to monocyclic and bicyclic aromatic ring systems having from six to fourteen carbon atoms (i.e., $C_6$-$C_{14}$ aryl) such as phenyl (abbreviated as Ph), 1-naphthyl and 2-naphthyl and the like.

The term "optionally substituted aryl" as used herein by itself or part of another group means the aryl as defined above is either unsubstituted or substituted with one to five substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. In one embodiment, the optionally substituted aryl is an optionally substituted phenyl. In one embodiment, the optionally substituted phenyl has four substituents. In another embodiment, the optionally substituted phenyl has three substituents. In another embodiment, the optionally substituted phenyl has two substituents. In another embodiment, the optionally substituted phenyl has one substituent. Exemplary substituted aryl groups include 2-methylphenyl, 2-methoxyphenyl, 2-fluorophenyl, 2-chlorophenyl, 2-bromophenyl, 3-methylphenyl, 3-methoxyphenyl, 3-fluorophenyl, 3-chlorophenyl, 4-methylphenyl, 4-ethylphenyl, 4-methoxyphenyl, 4-fluorophenyl, 4-chlorophenyl, 2,6-di-fluorophenyl, 2,6-di-chlorophenyl, 2-methyl, 3-methoxyphenyl, 2-ethyl, 3-methoxyphenyl, 3,4-di-methoxyphenyl, 3,5-di-fluorophenyl 3,5-di-methylphenyl and 3,5-dimethoxy, 4-methylphenyl, 2-fluoro-3-chlorophenyl, 3-chloro-4-fluorophenyl and the like. The term optionally substituted aryl is meant to include groups having fused optionally substituted cycloalkyl and fused optionally substituted heterocyclo rings. Examples include:

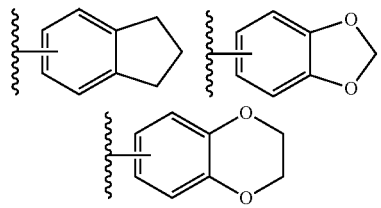

and the like.

The term "heteroaryl" as used herein by itself or part of another group refers to monocyclic and bicyclic aromatic ring systems having from five to fourteen carbon atoms (i.e., $C_5$-$C_{14}$ heteroaryl) and one, two, three or four heteroatoms independently selected from the group consisting of oxygen, nitrogen and sulfur. In one embodiment, the heteroaryl has three heteroatoms. In one embodiment, the heteroaryl has two heteroatoms. In one embodiment, the heteroaryl has one heteroatom. Exemplary heteroaryl groups include 1-pyrrolyl, 2-pyrrolyl, 3-pyrrolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, purinyl, 2-benzimidazolyl, 4-benzimidazolyl, 5-benzimidazolyl, 2-benzthiazolyl, 4-benzthiazolyl, 5-benzthiazolyl, 5-indolyl, 3-indazolyl, 4-indazolyl, 5-indazolyl, 1-isoquinolyl, 5-isoquinolyl, 2-quinoxalinyl, 5-quinoxalinyl, 2-quinolyl 3-quinolyl, 6-quinolyl and the like. The term heteroaryl is meant to include possible N-oxides. Exemplary N-oxides include pyridyl N-oxide and the like.

The term "optionally substituted heteroaryl" as used herein by itself or part of another group means the heteroaryl as defined above is either unsubstituted or substituted with one to four substituents, typically one or two substituents, independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido or sulfonamido. In one embodiment, the optionally substituted heteroaryl has one substituent. In another embodiment, the substituent is an optionally substituted aryl, aralkyl, or optionally substituted alkyl. In another embodiment, the substituent is an optionally substituted phenyl. Any available carbon or nitrogen atom may be substituted. Exemplary optionally substituted heteroaryl groups include:

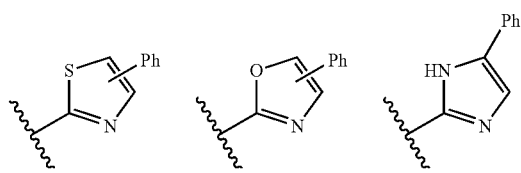

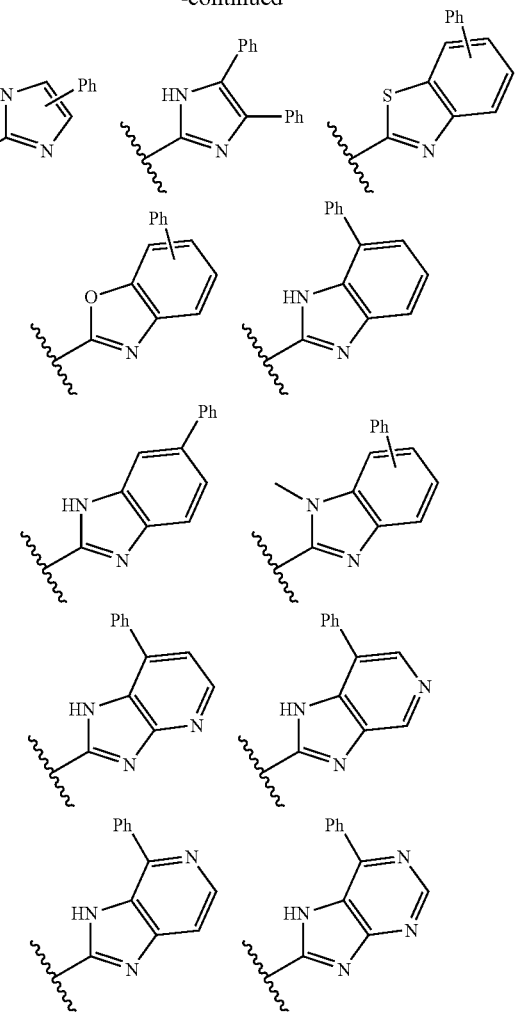

and the like.

The term "heterocyclo" as used herein by itself or part of another group refers to saturated and partially unsaturated (containing one or two double bonds) cyclic groups containing one to three rings having from two to twelve carbon atoms (i.e., $C_2$-$C_{12}$ heterocyclo) and one or two oxygen, sulfur or nitrogen atoms. The heterocyclo can be optionally linked to the rest of the molecule through a carbon or nitrogen atom. Exemplary heterocyclo groups include:

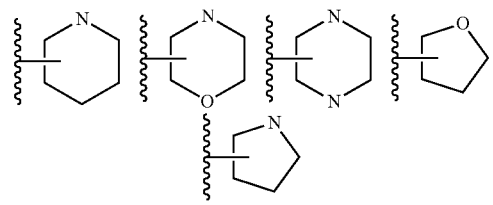

and the like.

The term "optionally substituted heterocyclo" as used herein by itself or part of another group means the heterocyclo as defined above is either unsubstituted or substituted with one to four substituents independently selected from halo, nitro, cyano, hydroxy, amino, optionally substituted alkyl, haloalkyl, hydroxyalkyl, aralkyl, optionally substituted cycloalkyl, optionally substituted alkenyl, optionally substituted alkynyl, optionally substituted aryl, optionally substituted heteroaryl, optionally substituted heterocyclo, alkoxy, aryloxy, aralkyloxy, alkylthio, carboxamido, sulfonamido, —COR$^c$, —SO$_2$R$^d$, —N(R$^e$)COR$^f$, —N(R$^e$)SO$_2$R$^g$ or —N(R$^e$)C=N(R$^h$)-amino, wherein R$^c$ is hydrogen, optionally substituted alkyl, optionally substituted aryl, or optionally substituted heteroaryl; R$^d$ is optionally substituted alkyl, optionally substituted aryl, or optionally substituted heteroaryl; R$^e$ is hydrogen, optionally substituted alkyl, optionally substituted aryl, or optionally substituted heteroaryl; R$^f$ is hydrogen, optionally substituted alkyl, optionally substituted aryl, or optionally substituted heteroaryl; R$^g$ is optionally substituted alkyl, optionally substituted aryl, or optionally substituted heteroaryl; and R$^h$ is hydrogen, —CN, optionally substituted alkyl, optionally substituted aryl, or optionally substituted heteroaryl. Substitution may occur on any available carbon or nitrogen atom. Exemplary substituted heterocyclo groups include:

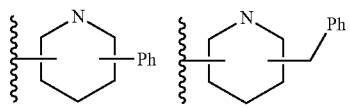

and the like. An optionally substituted heterocyclo may be fused to an aryl group to provide an optionally substituted aryl as described above.

The term "alkoxy" as used herein by itself or part of another group refers to a haloalkyl, optionally substituted alkyl, optionally substituted cycloalkyl, optionally substituted alkenyl or optionally substituted alkynyl attached to a terminal oxygen atom. Exemplary alkoxy groups include methoxy, tert-butoxy, —OCH$_2$CH=CH$_2$ and the like.

The term "aryloxy" as used herein by itself or part of another group refers to an optionally substituted aryl attached to a terminal oxygen atom. Exemplary aryloxy groups include phenoxy and the like.

The term "aralkyloxy" as used herein by itself or part of another group refers to an aralkyl attached to a terminal oxygen atom. Exemplary aralkyloxy groups include benzyloxy and the like.

The term "alkylthio" as used herein by itself or part of another group refers to a haloalkyl, aralkyl, optionally substituted alkyl, optionally substituted cycloalkyl, optionally substituted alkenyl or optionally substituted alkynyl attached to a terminal sulfur atom. Exemplary alkyl groups include —SCH$_3$ and the like.

The term "halo" or "halogen" as used herein by itself or part of another group refers to fluoro, chloro, bromo or iodo. In one embodiment, the halo is fluoro or chloro.

The term "amino" as used herein by itself or part of another group refers to a radical of formula —NR$^a$R$^b$ wherein R$^a$ and R$^b$ are independently hydrogen, haloalkyl, aralkyl, optionally substituted alkyl, optionally substituted cycloalkyl, optionally substituted heterocyclo, optionally substituted aryl or optionally substituted heteroaryl; or R$^a$ and R$^b$ taken together with the nitrogen atom to which they are attached form a four to seven membered optionally substituted heterocyclo. Exemplary amino groups include —NH$_2$, —N(H)CH$_3$, —N(CH$_3$)$_2$, N(H)CH$_2$CH$_3$, N(CH$_2$CH$_3$), —N(H)CH$_2$Ph and the like.

The term "carboxamido" as used herein by itself or part of another group refers to a radical of formula —CO-amino Exemplary carboxamido groups include —CONH$_2$, —CON(H)CH$_3$, —CON(H)Ph, —CON(H)CH$_2$CH$_2$Ph, —CON(CH$_3$)$_2$, CON(H)CHPh$_2$ and the like.

The term "sulfonamido" as used herein by itself or part of another group refers to a radical of formula —SO$_2$-amino. Exemplary sulfonamido groups include —SO$_2$NH$_2$, —SO$_2$N(H)CH$_3$, —SO$_2$N(H)Ph and the like.

The term "about," as used herein, includes the recited number ±10%. Thus, "about 10" means 9 to 11.

Certain of the compounds of the present disclosure may exist as stereoisomers, i.e., isomers that differ only in the spatial arrangement of atoms, including optical isomers and conformational isomers (or conformers). The disclosure includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

The term "substantially free of" as used herein means that the compound comprises less than about 25% of other stereoisomers, e.g., diastereomers and/or enantiomers, as established using conventional analytical methods routinely used by those of skill in the art. In some embodiments, the amount of other stereoisomers is less than about 24%, less than about 23%, less than about 22%, less than about 21%, less than about 20%, less than about 19%, less than about 18%, less than about 17%, less than about 16%, less than about 15%, less than about 14%, less than about 13%, less than about 12%, less than about 11%, less than about 10%, less than about 9%, less than about 8%, less than about 7%, less than about 6%, less than about 5%, less than about 4%, less than about 3%, less than about 2%, less than about 1%, or less than about 0.5%.

Stereoisomerically enriched compounds that contain about 95% or more of a desired stereoisomer, for example, about 96% or more, about 97% or more, about 98% or more, or about 99% or more are referred to herein as "substantially pure" or "substantially pure stereoisomers."

Stereoisomerically enriched compounds that contain about 99% or more of a desired stereoisomer are referred to herein as "pure" or "pure stereoisomers." The purity of any stereoisomerically enriched compound can be determined using conventional analytical methods such as, for example, normal phase HPLC, reverse phase HPLC, chiral HPLC, and $^1$H and $^{13}$C NMR.

Compounds

In certain embodiments, compounds of Formula I are provided:

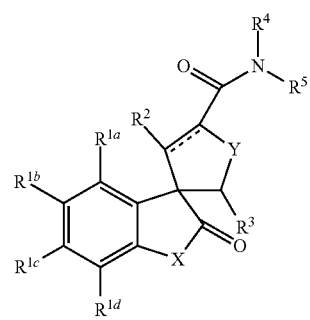

I wherein:

$R^{1a}$, $R^{1b}$, $R^{1c}$, and $R^{1d}$ are independently selected from the group consisting of hydrogen, halogen, hydroxy, amino, nitro, cyano, alkoxy, aryloxy, optionally substituted alkyl, haloalkyl, optionally substituted cycloalkyl, optionally substituted alkenyl, optionally substituted cycloalkenyl, optionally substituted aryl, optionally substituted heteroaryl, carboxamido, and sulfonamido;

$R^2$ is selected from the group consisting of optionally substituted aryl, aralkyl, and optionally substituted heteroaryl;

$R^3$ is selected from the group consisting of optionally substituted alkyl, optionally substituted (cycloalkyl)alkyl, optionally substituted cycloalkyl, optionally substituted alkenyl, optionally substituted cycloalkenyl, optionally substituted aryl, and optionally substituted heteroaryl;

$R^4$ is selected from the group consisting of hydrogen and optionally substituted alkyl;

$R^5$ is selected from the group consisting of:

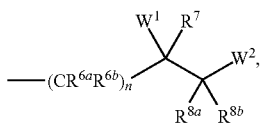

R5-1

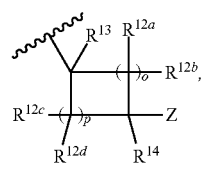

R5-2

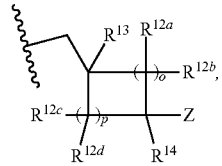

R5-2A

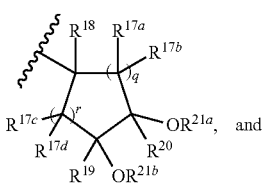

R5-3

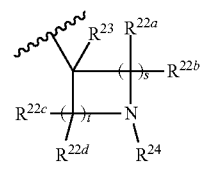

R5-4 wherein:

each $R^{6a}$ and $R^{6b}$ is independently selected from the group consisting of hydrogen and optionally substituted $C_1$-$C_6$ alkyl;

$R^7$ is selected from the group consisting of hydrogen, optionally substituted $C_1$-$C_6$ alkyl, and optionally substituted cycloalkyl;

$R^{8a}$ and $R^{8b}$ are each independently selected from the group consisting of hydrogen, optionally substituted $C_1$-$C_6$ alkyl, and optionally substituted cycloalkyl; or $R^{8a}$ and $R^{8b}$ taken together with the carbon that they are attached form a 3- to 8-membered optionally substituted cycloalkyl;

$W^1$ is selected from the group consisting of $-OR^{9a}$ and $-NR^{9b}R^{9c}$;

$R^{9a}$ is hydrogen;

$R^{9b}$ is selected from the group consisting of hydrogen, optionally substituted alkyl, optionally substituted cycloalkyl, optionally substituted aryl, optionally substituted heteroaryl, $-SO_2R^{9d}$, and $-CONR^{9e}R^{9f}$;

$R^{9c}$ is selected from the group consisting of hydrogen, optionally substituted alkyl, optionally substituted cycloalkyl, optionally substituted aryl, and optionally substituted heteroaryl; or $R^{9b}$ and $R^{9c}$ taken together with the nitrogen atom to which they are attached form a 4- to 8-membered optionally substituted heterocyclo;

$R^{9d}$ is selected from the group consisting of optionally substituted alkyl and optionally substituted cycloalkyl;

$R^{9e}$ and $R^{9f}$ are each independently selected from the group consisting of hydrogen, optionally substituted alkyl, and optionally substituted cycloalkyl; or $R^{9e}$ and $R^{9f}$ taken together with the nitrogen atom to which they are attached form a 4- to 8-membered optionally substituted heterocyclo;

$W^2$ is selected from the group consisting of $-OR^{10}$ and $-NR^{11a}R^{11b}$; with the proviso that when $W^1$ is $-OR^{9a}$ and $W^2$ is $-OR^{10}$ then at least one of $R^7$, $R^{8a}$, and $R^{8b}$ is other than hydrogen;

$R^{10}$ is hydrogen; or one of $R^{9a}$ and $R^{10}$ is hydrogen and the other is a metabolically cleavable group;

$R^{11a}$ is selected from the group consisting of hydrogen, optionally substituted alkyl, optionally substituted cycloalkyl, optionally substituted aryl, optionally substituted heteroaryl, $-SO_2R^{11c}$, and $-CONR^{11d}R^{11e}$;

$R^{11b}$ is selected from the group consisting of hydrogen, optionally substituted alkyl, optionally substituted cycloalkyl, optionally substituted aryl, and optionally substituted heteroaryl; or $R^{11a}$ and $R^{11b}$ taken together with the nitrogen atom to which they are attached form a 4- to 8-membered optionally substituted heterocyclo;

$R^{11c}$ is selected from the group consisting of optionally substituted alkyl and optionally substituted cycloalkyl;

$R^{11d}$ and $R^{11e}$ are each independently selected from the group consisting of hydrogen, optionally substituted alkyl, and optionally substituted cycloalkyl; or $R^{11d}$ and $R^{11e}$ together with the nitrogen atom to which they are attached form a 4- to 8-membered optionally substituted heterocyclo;

n is 1, 2, 3, 4, or 5;

each $R^{12a}$, $R^{12b}$, $R^{12c}$ and $R^{12d}$ is independently selected from the group consisting of hydrogen and optionally substituted $C_1$-$C_6$ alkyl;

$R^{13}$ is selected from the group consisting of hydrogen and optionally substituted $C_1$-$C_6$ alkyl;

$R^{14}$ is selected from the group consisting of hydrogen, optionally substituted $C_1$-$C_6$ alkyl, and optionally substituted cycloalkyl;

Z is selected from the group consisting of $-OR^{15}$ and $-NR^{16a}R^{16b}$; or Z and $R^{14}$ taken together form a carbonyl, i.e., a C=O, group.

$R^{15}$ is selected from the group consisting of hydrogen and metabolically cleavable group;

$R^{16a}$ is selected from the group consisting of $-SO_2R^{16c}$ and $-CONR^{16d}R^{16e}$;

$R^{16b}$ is selected from the group consisting of hydrogen and optionally substituted alkyl;

$R^{16c}$ is selected from the group consisting of optionally substituted alkyl, optionally substituted cycloalkyl, optionally substituted aryl, and optionally substituted heteroaryl;

$R^{16d}$ and $R^{16e}$ are each independently selected from the group consisting of hydrogen, optionally substituted alkyl, optionally substituted cycloalkyl, optionally substituted aryl, and optionally substituted heteroaryl; or $R^{16d}$ and $R^{16e}$ taken together with the nitrogen atom to which they are attached form a 4- to 8-membered heterocyclo;

o is 1, 2, or 3;

p is 0, 1, 2, or 3;

each $R^{17a}$, $R^{17b}$, $R^{17c}$ and $R^{17d}$ is independently selected from the group consisting of hydrogen and optionally substituted $C_1$-$C_6$ alkyl;

$R^{18}$ is selected from the group consisting of hydrogen and optionally substituted $C_1$-$C_6$ alkyl;

$R^{19}$ is selected from the group consisting of hydrogen, optionally substituted $C_1$-$C_6$ alkyl, and optionally substituted cycloalkyl;

$R^{20}$ is selected from the group consisting of hydrogen, optionally substituted $C_1$-$C_6$ alkyl, and optionally substituted cycloalkyl;

$R^{21a}$ and $R^{21b}$ are each hydrogen; or one of $R^{21a}$ and $R^{21b}$ is hydrogen and the other is metabolically cleavable group;

q is 0, 1, 2, or 3;

r is 1, 2, or 3;

each $R^{22a}$, $R^{22b}$, $R^{22c}$, and $R^{22d}$ is independently selected from the group consisting of hydrogen and optionally substituted $C_1$-$C_6$ alkyl;

$R^{23}$ is selected from the group consisting of hydrogen and optionally substituted $C_1$-$C_6$ alkyl;

$R^{24}$ is selected from the group consisting of —$SO_2R^{24a}$ and —$CONR^{24b}R^{24c}$;

$R^{24a}$ is selected from the group consisting of optionally substituted alkyl, optionally substituted cycloalkyl, optionally substituted aryl, and optionally substituted heteroaryl;

$R^{24b}$ and $R^{24c}$ are each independently selected from the group consisting of hydrogen, optionally substituted cycloalkyl, optionally substituted aryl, and optionally substituted heteroaryl; or $R^{24b}$ and $R^{24c}$ taken together with the nitrogen atom to which they are attached form a 4- to 8-membered heterocyclo;

s and t are each independently 1, 2, or 3;

X is selected from the group consisting of O, S, and NR';

Y is selected from the group consisting of O, S, and NR";

R' is selected from the group consisting of hydrogen, optionally substituted alkyl, aralkyl, and optionally substituted cycloalkyl;

R" is selected from the group consisting of hydrogen, optionally substituted alkyl, aralkyl, optionally substituted cycloalkyl, and —$COR^{31}$;

$R^{31}$ is selected from the group consisting of hydrogen and optionally substituted alkyl; and ═══ represents a single or a double bond, or a pharmaceutically acceptable salt, solvate, or prodrug thereof.

In certain embodiments, for the compounds of Formula I, ═══ represents a single bond.

In certain embodiments, the compound of Formula I is a mixture of stereoisomers, e.g., a mixture of diastereomers and/or enantiomers, e.g., a racemic mixture. In another such embodiment, the compound is a mixture of diastereomers.

In another such embodiment, the compound is a mixture of enantiomers. In particular embodiments, the compound is a single enantiomer.

In certain embodiments, $R^5$ is selected from the group consisting of R5-1 and R5-2. In particular embodiments, $R^5$ is R5-2 and Z is —OH. In particular embodiments, $R^5$ is R5-2A and Z is OH.

In certain embodiments, compounds of Formula Ia are provided:

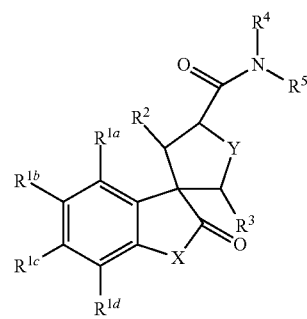

Ia wherein $R^{1a}$, $R^{1b}$, $R^{1c}$, $R^{1d}$, $R^2$, $R^3$, $R^4$, $R^5$, X, and Y have the meanings as described above for Formula I, or pharmaceutically acceptable salt, solvate, or prodrug thereof.

In certain embodiments, compounds of Formula Ib are provided:

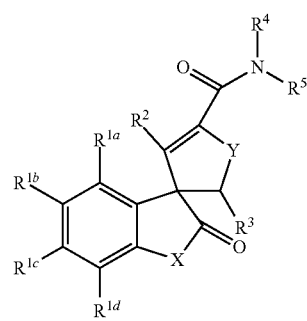

Ib wherein $R^{1a}$, $R^{1b}$, $R^{1c}$, $R^{1d}$, $R^2$, $R^3$, $R^4$, $R^5$, X, and Y have the meanings as described above for Formula I, or tautomer thereof, or a pharmaceutically acceptable salt, solvate, or prodrug thereof.

In certain embodiments, compounds of Formula II-XVII are provided:

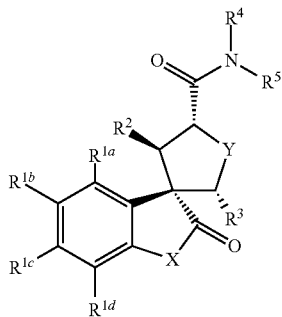

II

III
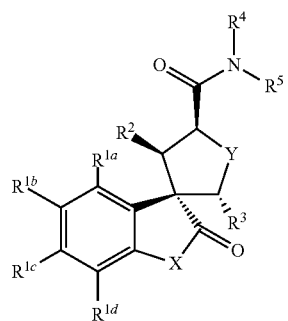
IV
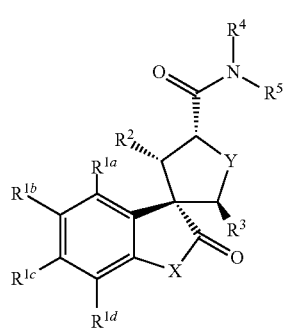
V
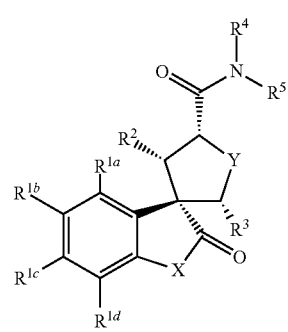
VI
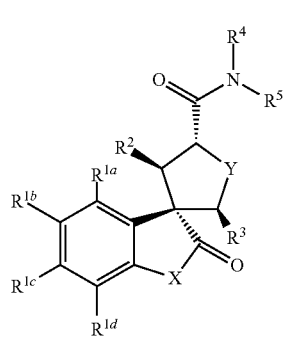
VII
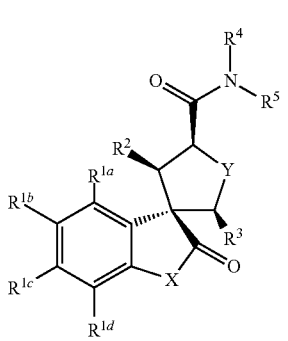
VIII
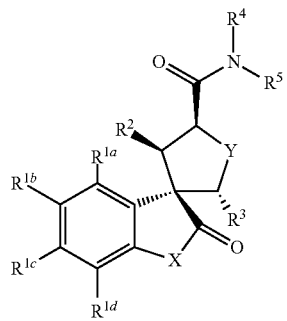
IX
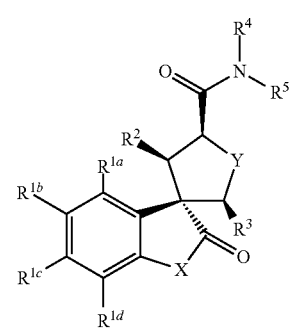
X
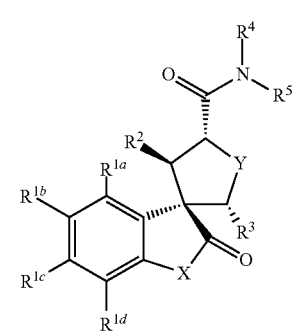
XI
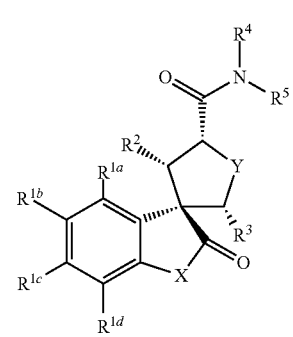
XII
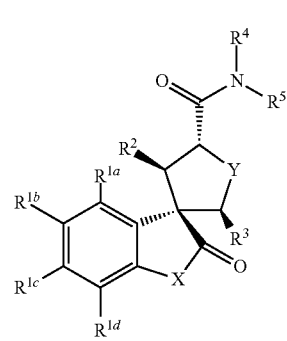

-continued

XIII
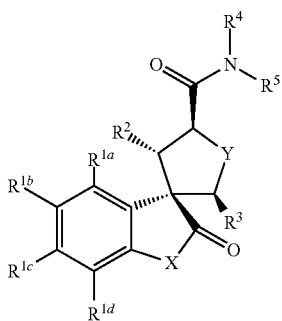

XIV
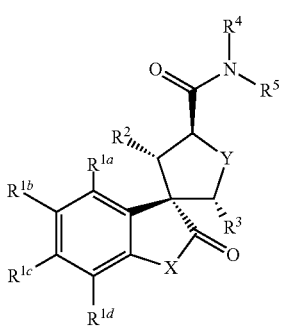

XV
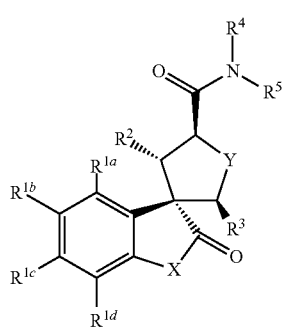

XVI
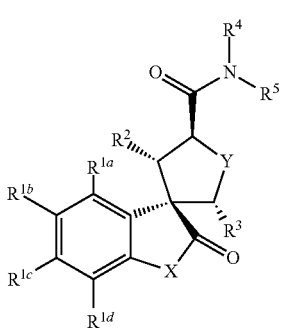

XVII
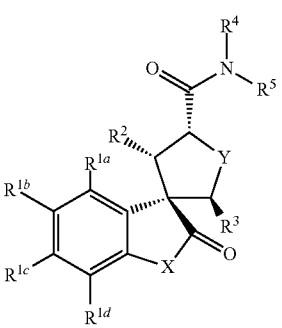

wherein $R^{1a}$, $R^{1b}$, $R^{1c}$, $R^{1d}$, $R^2$, $R^3$, $R^4$, $R^5$, X, and Y have the meanings as described above for Formula I, or a pharmaceutically acceptable salt, solvate, or prodrug thereof.

In some embodiments, compounds of Formula II are provided, wherein $R^{1a}$, $R^{1b}$, $R^{1c}$, $R^{1d}$, $R^2$, $R^3$, $R^4$, $R^5$, X, and Y have the meanings as described above in connection with Formula I, or a pharmaceutically acceptable salt, solvate, or prodrug thereof.

In some embodiments, compounds of Formula II are substantially free of one or more other stereoisomers, i.e., compounds of Formulae III-XVII. In some embodiments, compounds of Formula II are substantially pure stereoisomers. In some embodiments, compounds of Formula II are pure stereoisomers.

In some embodiments, compounds of Formula XIII are substantially free of one or more other stereoisomers. In some embodiments, compounds of Formula XIII are substantially pure stereoisomers. In some embodiments, compounds of Formula XIII are pure stereoisomers.

In some embodiments, compounds of Formula XIV are substantially free of one or more other stereoisomers. In some embodiments, compounds of Formula XIV are substantially pure stereoisomers. In some embodiments, compounds of Formula XIV are pure stereoisomers.

In some embodiments, compounds of Formula VI are provided, wherein $R^{1a}$, $R^{1b}$, $R^{1c}$, $R^{1d}$, $R^2$, $R^3$, $R^4$, $R^5$, X, and Y have the meanings as described above in connection with Formula I, or a pharmaceutically acceptable salt, solvate, or prodrug thereof.

In some embodiments, compounds of Formula VI are substantially free of one or more other stereoisomers, i.e., compounds of Formulae II-V and VII-XVII. In some embodiments, compounds of Formula VI are substantially pure stereoisomers. In some embodiments, compounds of Formulae VI are pure stereoisomers.

In some embodiments, compounds of Formula X are provided, wherein $R^{1a}$, $R^{1b}$, $R^{1c}$, $R^{1d}$, $R^2$, $R^3$, $R^4$, $R^5$, X, and Y have the meanings as described above in connection with Formula I, or a pharmaceutically acceptable salt, solvate, or prodrug thereof.

In some embodiments, compounds of Formula X are substantially free of one or more other stereoisomers, i.e., compounds of Formulae II-IX and XI-XVII. In some embodiments, compounds of Formula X are substantially pure stereoisomers. In some embodiments, compounds of Formula X are pure stereoisomers.

In some embodiments, compounds of Formula XII are provided, wherein $R^{1a}$, $R^{1b}$, $R^{1c}$, $R^{1d}$, $R^2$, $R^3$, $R^4$, $R^5$, X, and Y have the meanings as described above in connection with Formula I, or a pharmaceutically acceptable salt, solvate, or prodrug thereof.

In some embodiments, compounds of Formula XII are substantially free of one or more other stereoisomers, i.e., compounds of Formulae II-XI and XIII-XVII. In some embodiments, compounds of Formula XII are substantially pure stereoisomers. In some embodiments, compounds of XII are pure stereoisomers.

In some embodiments, compounds of Formula XII are unexpectedly more potent than compounds of Formulae II-XI and XIII-XVII. For example, as demonstrated herein, compounds of Formula XII have lower $IC_{50}$ values than compounds of Formulae II-XI and XIII-XVII against MDM2. In some embodiments, compounds of Formula XII are about 2-fold or more, e.g., about 3-fold, about 4-fold, about 5-fold, about 6-fold, about 7-fold, about 8-fold, about 9-fold, about 10-fold, about 15-fold, about 20-fold, about 25-fold, about 30-fold, about 35-fold, about 40-fold, about 45-fold, about 50-fold, or more, more potent than compounds of Formula II in fluorescence polarization-based MDM2 binding assays. In some embodiments, compounds of Formula XII are unexpectedly more efficacious than compounds of Formulae II-XI and XIII-XVII in xenograft tumor models in mice and/or in other in vivo efficacy models.

In certain embodiments, compounds of Formulae I-XVII or a pharmaceutically acceptable salt, solvate, or prodrug thereof are provided. In some embodiments, compounds of Formulae II, VI, X, and XII, or a pharmaceutically acceptable salt, solvate, or prodrug thereof are provided, wherein:

a) $R^{1a}$, $R^{1b}$, $R^{1c}$, and $R^{1d}$ are independently selected from the group consisting of hydrogen, fluoro, and chloro;
b) $R^{1a}$ and $R^{1d}$ are hydrogen; $R^{1b}$ is selected from the group consisting of hydrogen and fluoro; and $R^{1c}$ is selected from the group consisting of fluoro and chloro;
c) $R^2$ is optionally substituted phenyl;
d) $R^3$ is selected from the group consisting of optionally substituted alkyl, optionally substituted (cycloalkyl)alkyl, and optionally substituted cycloalkyl;
e) $R^4$ is hydrogen;
f) X is NH;
g) X is O;
h) X is S;
i) Y is O;
j) Y is S;
k) Y is NH; or
l) X and Y are NH;
or any combination thereof.

In certain embodiments, compounds of Formulae II, VI, X, and XII or a pharmaceutically acceptable salt, solvate, or prodrug thereof are provided, wherein $R^5$ is R5-1; $R^{6a}$ and $R^{6b}$ are hydrogen; $R^7$ is $C_1$-$C_4$ alkyl; $R^{8a}$ and $R^{8b}$ are hydrogen; W is —$OR^{10}$, $R^9$ and $R^{10}$ are hydrogen; and n is 2.

In certain embodiments, compounds of Formulae II, VI, X, and XII or a pharmaceutically acceptable salt, solvate, or prodrug thereof are provided, wherein $R^5$ is R5-1; $R^{6a}$ and $R^{6b}$ are hydrogen; $R^7$ is $C_1$-$C_4$ alkyl; $R^{8a}$ and $R^{8b}$ are hydrogen; W is —$NR^{11a}R^{11b}$, $R^9$ is hydrogen; and n is 2.

In certain embodiments, the compounds of Formulae II, VI, X, and XII or a pharmaceutically acceptable salt, solvate, or prodrug thereof are provided, wherein $R^5$ is R5-1; $R^{6a}$ and $R^{6b}$ are hydrogen; $R^7$ is $C_1$-$C_4$ alkyl; $R^{8a}$ and $R^{8b}$ are hydrogen; W is —$OR^{10}$, one of $R^9$ and $R^{10}$ is hydrogen and the other is a metabolically cleavable group; and n is 2.

In certain embodiments, compounds of Formulae II, VI, X, and XII or a pharmaceutically acceptable salt, solvate, or prodrug thereof are provided, wherein $R^5$ is R5-2; $R^{12a}$, $R^{12b}$, $R^{12c}$, and $R^{12d}$ are each hydrogen; $R^{13}$ is hydrogen; Z is —$OR^{15}$ and $R^{15}$ is hydrogen; o is 1 or 2; and p is 1 or 2.

In certain embodiments, compounds of Formulae II, VI, X, and XII or a pharmaceutically acceptable salt, solvate, or prodrug thereof are provided, wherein $R^5$ is R5-2; $R^{12a}$, $R^{12b}$, $R^{12c}$, and $R^{12d}$ are each hydrogen; $R^{13}$ is hydrogen; Z is —$NR^{16a}R^{16b}$; o is 1 or 2; and p is 1 or 2.

In certain embodiments, compounds of Formulae II, VI, X, and XII or a pharmaceutically acceptable salt, solvate, or prodrug thereof are provided, wherein $R^5$ is R5-2; $R^{12a}$, $R^{12b}$, $R^{12c}$, and $R^{12d}$ are each hydrogen; $R^{13}$ is hydrogen; Z is —$OR^{15}$ and $R^{15}$ a metabolically cleavable group; o is 1 or 2; and p is 1 or 2.

In certain embodiments, compounds of Formulae II, VI, X, and XII or a pharmaceutically acceptable salt, solvate, or prodrug thereof are provided, wherein $R^5$ is R5-3; $R^{17a}$, $R^{17b}$, $R^{17c}$, and $R^{17d}$ are each hydrogen; $R^{18}$, $R^{19}$, and $R^{20}$ are hydrogen; $R^{21a}$ and $R^{21b}$ are hydrogen; and q and r are 1.

In certain embodiments, compounds of Formulae II, VI, X, and XII or a pharmaceutically acceptable salt, solvate, or prodrug thereof are provided, wherein $R^5$ is R5-3; $R^{17a}$, $R^{17b}$, $R^{17c}$, and $R^{17d}$ are each hydrogen; $R^{18}$, $R^{19}$, and $R^{20}$ are hydrogen; one of $R^{21a}$ and $R^{21b}$ is hydrogen and the other is a metabolically cleavable group; and q and r are 1.

In certain embodiments, compounds of Formulae II, VI, X, and XII or a pharmaceutically acceptable salt, solvate, or prodrug thereof are provided, wherein $R^5$ is R5-2A.

In certain embodiments, compounds of Formulae II, VI, X, and XII or a pharmaceutically acceptable salt, solvate, or prodrug thereof are provided, wherein $R^2$ is selected from the group consisting of aralkyl and optionally substituted aryl having the Formula R2-1:

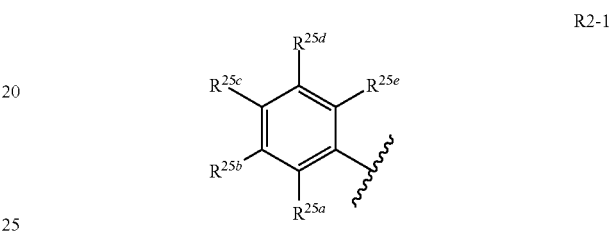

R2-1 and $R^{25a}$, $R^{25b}$, $R^{25c}$, $R^{25d}$, and $R^{25e}$ are each independently selected from the group consisting of hydrogen, halogen, hydroxy, nitro, amino, cyano, alkoxy, optionally substituted alkyl, haloalkyl, optionally substituted aryl, and optionally substituted heteroaryl. In particular embodiments, $R^{25a}$ is selected from the group consisting of hydrogen and fluoro; $R^{25b}$ is chloro; $R^{25c}$ is selected from the group consisting of hydrogen and fluoro; and $R^{25d}$ and $R^{25e}$ are hydrogen.

In certain embodiments, compounds of Formulae II, VI, X, and XII or a pharmaceutically acceptable salt, solvate, or prodrug thereof are provided, wherein $R^5$ is selected from the group consisting of:

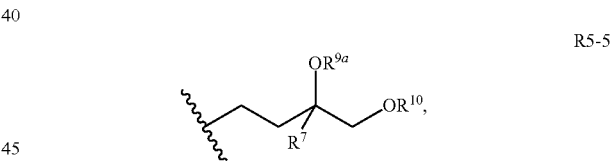

R5-5

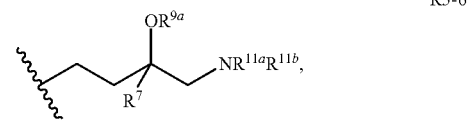

R5-6

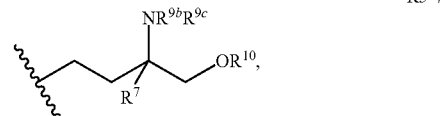

R5-7

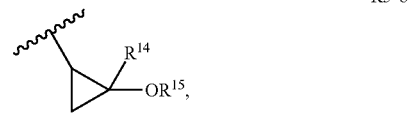

R5-8

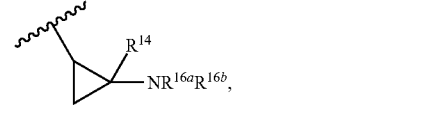

R5-9

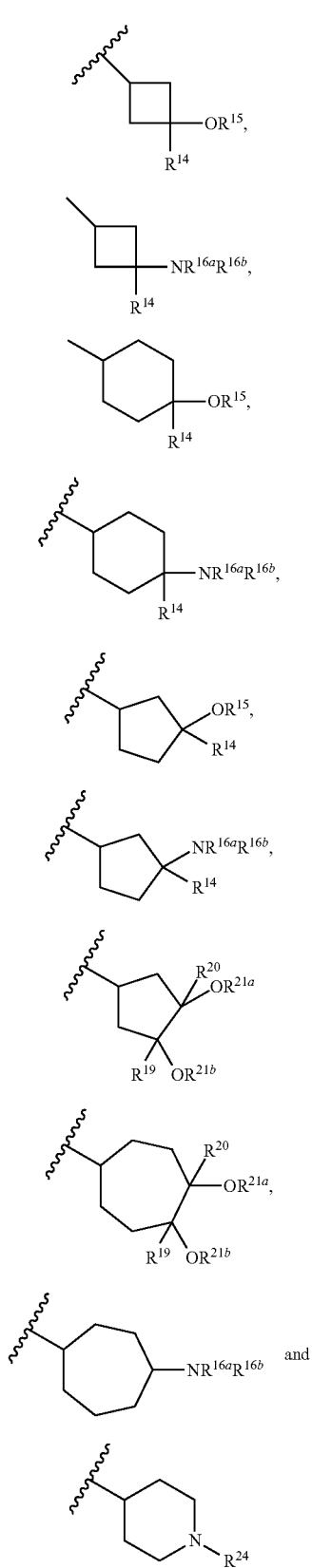

including stereoisomers, e.g., enantiomers, thereof, wherein:

$R^7$ is optionally substituted $C_1$-$C_4$ alkyl;

$R^{9a}$ and $R^{10}$ are each hydrogen; or one of $R^{9a}$ and $R^{10}$ is hydrogen and the other is a metabolically cleavable group;

$R^{9b}$ is selected from the group consisting of hydrogen, optionally substituted alkyl, optionally substituted cycloalkyl, optionally substituted aryl, optionally substituted heteroaryl, —SO$_2$R$^{9d}$, and —CONR$^{9e}$R$^{9f}$;

$R^{9c}$ is selected from the group consisting of hydrogen, optionally substituted alkyl, optionally substituted cycloalkyl, optionally substituted aryl, and optionally substituted heteroaryl; or $R^{9b}$ and $R^{9c}$ taken together with the nitrogen atom to which they are attached form a 4- to 8-membered optionally substituted heterocyclo;

$R^{9d}$ is selected from the group consisting of optionally substituted alkyl and optionally substituted cycloalkyl;

$R^{9e}$ and $R^{9f}$ are each independently selected from the group consisting of hydrogen, optionally substituted alkyl, and optionally substituted cycloalkyl; or $R^{9e}$ and $R^{9f}$ taken together with the nitrogen atom to which they are attached form a 4- to 8-membered optionally substituted heterocyclo;

$R^{11a}$ is selected from the group consisting of hydrogen, optionally substituted alkyl, optionally substituted cycloalkyl, optionally substituted aryl, optionally substituted heteroaryl, —SO$_2$R$^{11c}$, and —CONR$^{11d}$R$^{11e}$;

$R^{11b}$ is selected from the group consisting of hydrogen, optionally substituted alkyl, optionally substituted cycloalkyl, optionally substituted aryl, and optionally substituted heteroaryl; or $R^{11a}$ and $R^{11b}$ taken together with the nitrogen atom to which they are attached form a 4- to 8-membered optionally substituted heterocyclo;

$R^{11b}$ is selected from the group consisting of optionally substituted alkyl and optionally substituted cycloalkyl;

$R^{11d}$ and $R^{11e}$ are each independently selected from the group consisting of hydrogen, optionally substituted alkyl, and optionally substituted cycloalkyl; or $R^{11d}$ and $R^{11e}$ taken together with the nitrogen atom to which they are attached form a 4- to 8-membered optionally substituted heterocyclo;

$R^{14}$ is selected from the group consisting of hydrogen, $C_1$-$C_4$ alkyl, or $C_3$-$C_6$ cycloalkyl;

$R^{15}$ is hydrogen or a metabolically cleavable group;

$R^{16a}$ is selected from the group consisting of —SO$_2$R$^{16c}$ and —CONR$^{16d}$R$^{16e}$;

$R^{16b}$ is selected from the group consisting of hydrogen and optionally substituted alkyl;

$R^{16c}$ is selected from the group consisting of optionally substituted alkyl, optionally substituted cycloalkyl, optionally substituted aryl, and optionally substituted heteroaryl;

$R^{16d}$ and $R^{16e}$ are each independently selected from the group consisting of hydrogen, optionally substituted alkyl, optionally substituted cycloalkyl, optionally substituted aryl, and optionally substituted heteroaryl; or $R^{16d}$ and $R^{16e}$ taken together with the nitrogen atom to which they are attached form a 4- to 8-membered heterocyclo;

$R^{19}$ is selected from the group consisting of hydrogen, optionally substituted $C_1$-$C_6$ alkyl, and optionally substituted cycloalkyl;

$R^{20}$ is selected from the group consisting of hydrogen, optionally substituted $C_1$-$C_6$ alkyl, and optionally substituted cycloalkyl;

$R^{21a}$ and $R^{21b}$ are each hydrogen; or one of $R^{21a}$ and $R^{21b}$ is hydrogen and the other is metabolically cleavable group;

$R^{24}$ is selected from the group consisting of —$SO_2R^{24a}$ and —$CONR^{24b}R^{24c}$;

$R^{24a}$ is selected from the group consisting of optionally substituted alkyl, optionally substituted cycloalkyl, optionally substituted aryl, and optionally substituted heteroaryl; and $R^{24b}$ and $R^{24c}$ are each independently selected from the group consisting of hydrogen, optionally substituted cycloalkyl, optionally substituted aryl, and optionally substituted heteroaryl, or $R^{24b}$ and $R^{24c}$ taken together with the nitrogen atom to which they are attached form a 4- to 8-membered heterocyclo.

In certain embodiments, $R^5$ is selected from the group consisting of R5-5, R5-6, R5-10, R5-11, R5-12, R5-13, and R5-14.

In certain embodiments, $R^5$ is selected from the group consisting of R5-10 and R5-12 and $R^{14}$ is hydrogen or methyl and $R^{15}$ is hydrogen.

In certain embodiments, compounds of Formulae II, VI, X, and XII or a pharmaceutically acceptable salt, solvate, or prodrug thereof are provided, wherein $R^5$ is selected from the group consisting of:

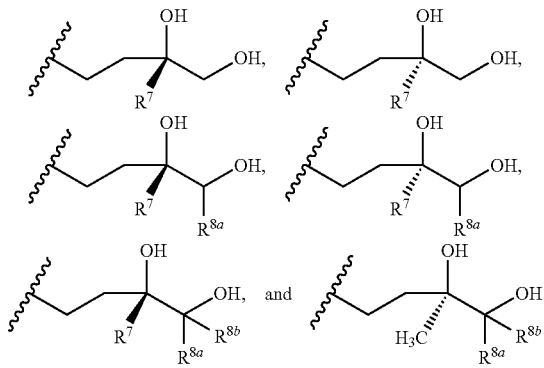

wherein:

$R^7$ is selected from the group consisting of methyl, ethyl, propyl, isopropyl, and cyclopropyl; and $R^{8a}$ and $R^{8b}$ are each independently selected from the group consisting of hydrogen, methyl, ethyl, propyl, isopropyl, and cyclopropyl.

In certain embodiments, compounds of Formulae II, VI, X, and XII or a pharmaceutically acceptable salt, solvate, or prodrug thereof are provided, wherein $R^5$ is selected from the group consisting of:

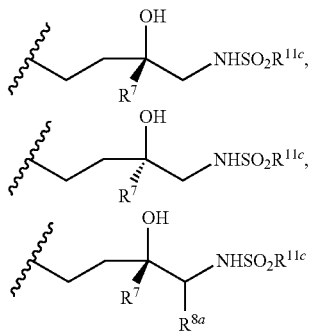

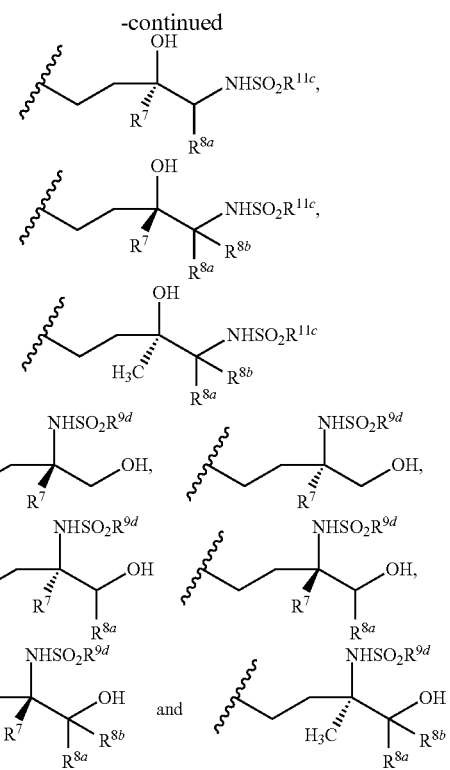

wherein:

$R^7$ is selected from the group consisting of methyl, ethyl, propyl, isopropyl, and cyclopropyl;

$R^{8a}$ and $R^{8b}$ are each independently is selected from the group consisting of hydrogen, methyl, ethyl, propyl, isopropyl, and cyclopropyl;

$R^{9d}$ is selected from the group consisting of methyl, trifluoromethyl, ethyl, propyl, isopropyl, and cyclopropyl; and $R^{11c}$ is selected from the group consisting of methyl, trifluoromethyl, ethyl, propyl, isopropyl, and cyclopropyl.

In certain embodiments, compounds of Formulae II, VI, X, and XII or a pharmaceutically acceptable salt, solvate, or prodrug thereof are provided, wherein $R^5$ is selected from the group consisting of:

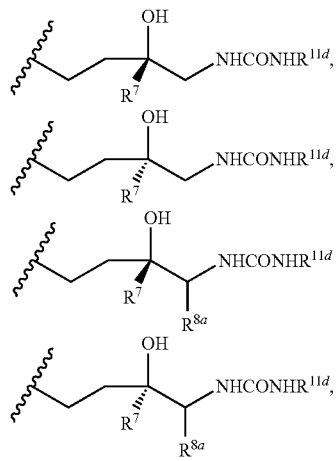

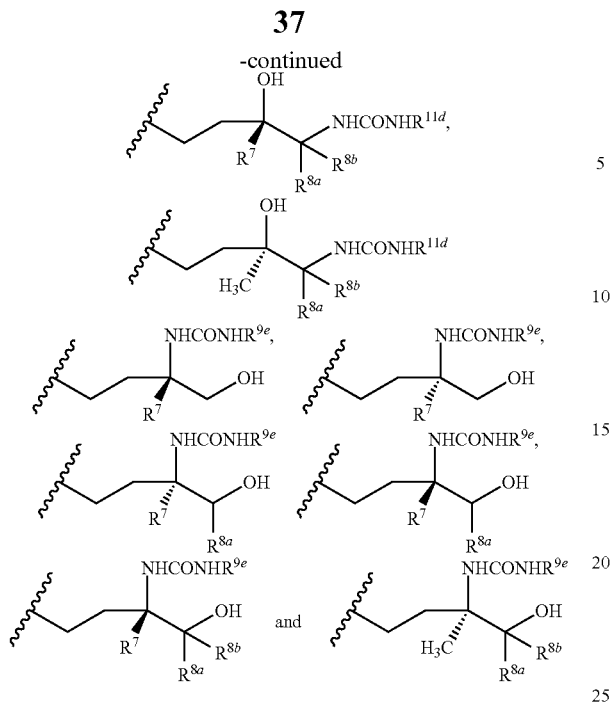

wherein:

R[7] is selected from the group consisting of methyl, ethyl, propyl, isopropyl, and cyclopropyl;

R[8a] and R[8b] are each independently is selected from the group consisting of hydrogen, methyl, ethyl, propyl, isopropyl, and cyclopropyl;

R[9e] is selected from the group consisting of methyl, trifluoromethyl, ethyl, propyl, isopropyl, and cyclopropyl; and R[11d] is selected from the group consisting of methyl, trifluoromethyl, ethyl, propyl, isopropyl, and cyclopropyl.

In certain embodiments, compounds of Formulae II, VI, X, and XII, or a pharmaceutically acceptable salt, solvate, or prodrug thereof are provided, wherein R[5] is selected from the group consisting of:

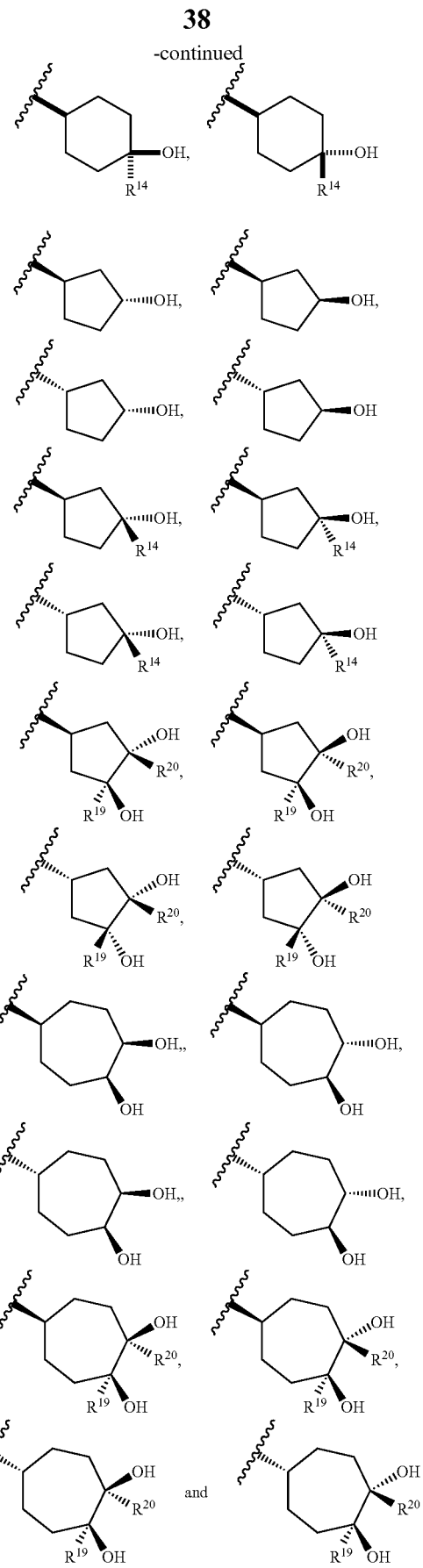

wherein:

$R^{14}$ is selected from the group consisting of methyl, ethyl, propyl, isopropyl, and cyclopropyl; and $R^{19}$ and $R^{20}$ are each independently is selected from the group consisting of hydrogen, methyl, ethyl, propyl, isopropyl, and cyclopropyl.

In certain embodiments, compounds of Formulae II, VI, X, and XII, or a pharmaceutically acceptable salt, solvate, or prodrug thereof are provided, wherein $R^5$ is selected from the group consisting of:

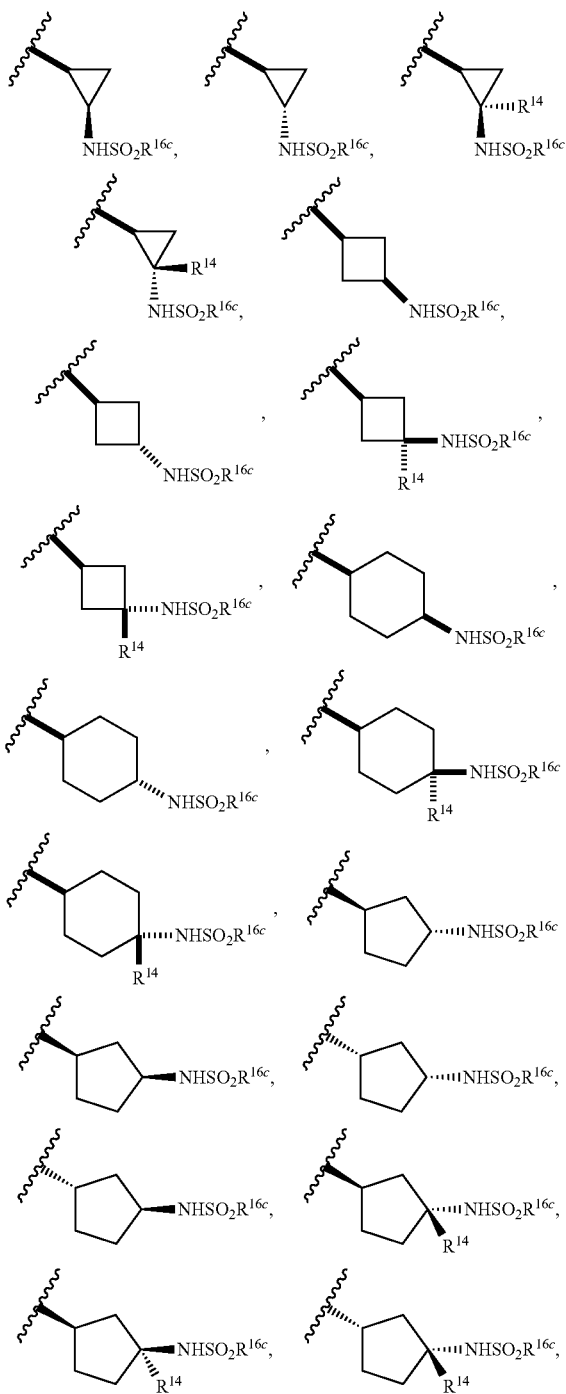

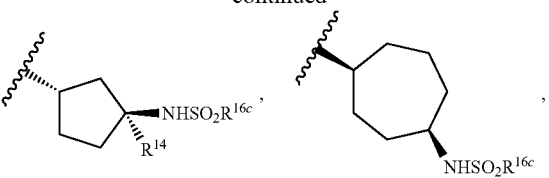

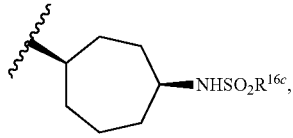

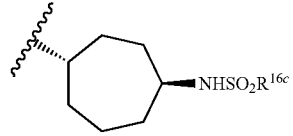

wherein:

$R^{14}$ is selected from the group consisting of methyl, ethyl, propyl, isopropyl, and cyclopropyl; and $R^{16c}$ is selected from the group consisting of methyl, trifluoromethyl, ethyl, propyl, isopropyl, and cyclopropyl.

In certain embodiments, compounds of Formulae II, VI, X, and XII, or a pharmaceutically acceptable salt, solvate, or prodrug thereof are provided, wherein $R^5$ is selected from the group consisting of:

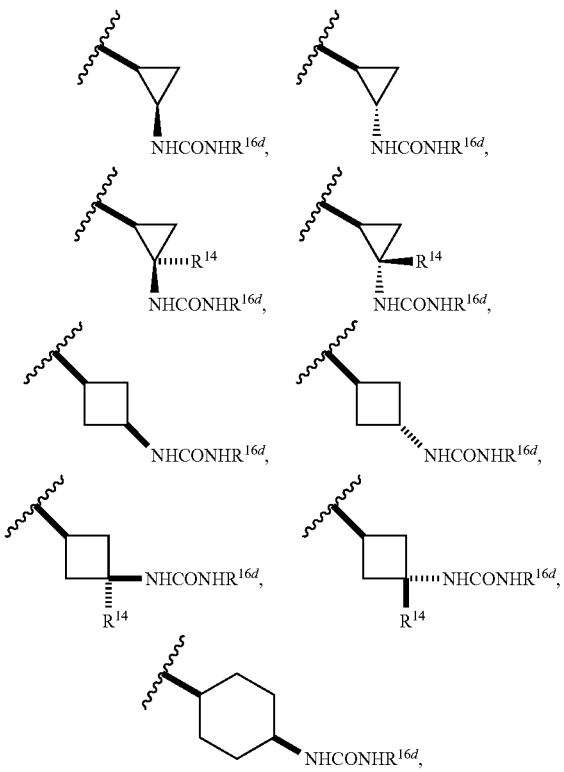

-continued

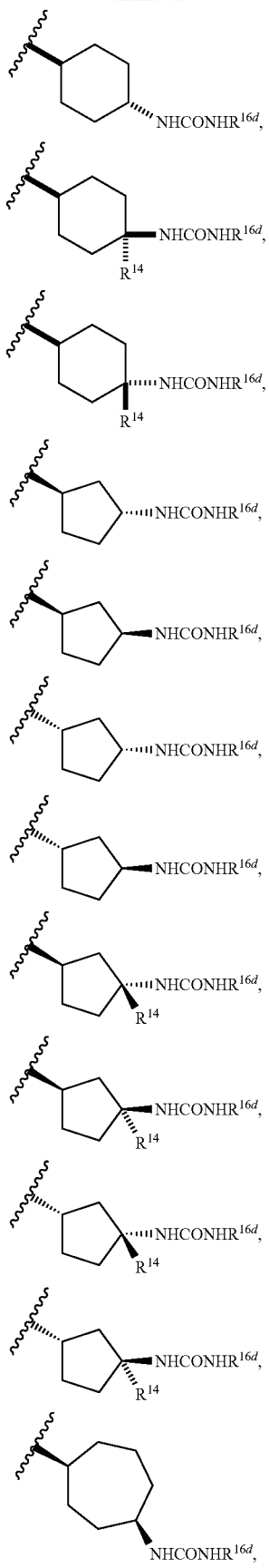

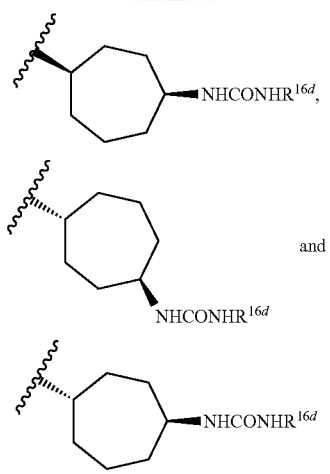

wherein:

R$^{14}$ is selected from the group consisting of methyl, ethyl, propyl, isopropyl, and cyclopropyl; and R$^{16d}$ is selected from the group consisting of methyl, trifluoromethyl, ethyl, propyl, isopropyl, and cyclopropyl.

In certain embodiments, compounds of Formulae II, VI, X, and XII, or a pharmaceutically acceptable salt, solvate, or prodrug thereof are provided, wherein R$^5$ is:

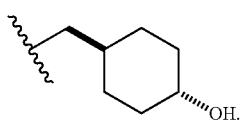 [SMILES: *C[C@H]1CC[C@H](O)CC1]

In another embodiment, compounds of Formula XVIIIa are provided:

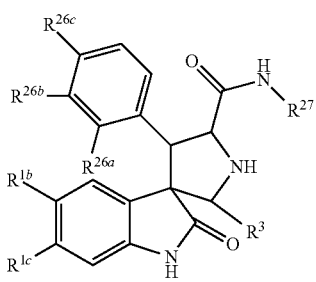

XVIIIa wherein:

R$^{1b}$ and R$^{1c}$ are independently selected from the group consisting of hydrogen, fluoro, and chloro;

R$^3$ is selected from the group consisting of optionally substituted alkyl, optionally substituted (cycloalkyl)alkyl, and, optionally substituted aryl, optionally substituted cycloalkyl;

R$^{26a}$, R$^{26b}$, and R$^{26c}$ are independently selected from the group consisting of hydrogen, fluoro, and chloro; and $R^{27}$ is selected from the group consisting of:
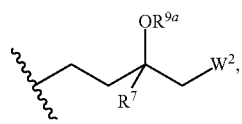 R27-1
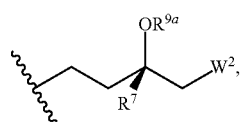 R27-2
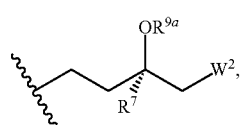 R27-3
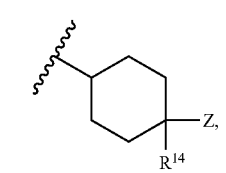 R27-4
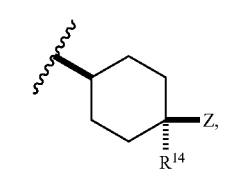 R27-5
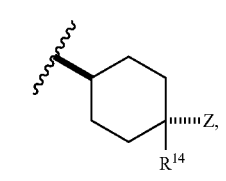 R27-6
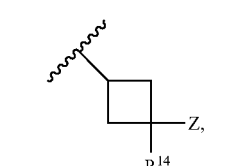 R27-7
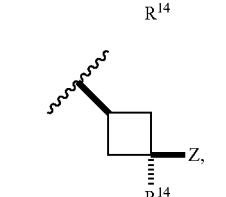 R27-8
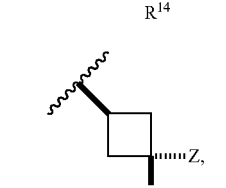 R27-9
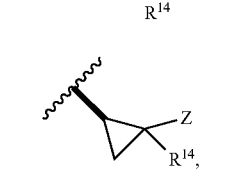 R27-10
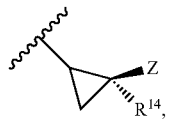 R27-11
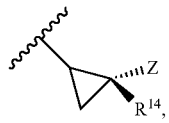 R27-12
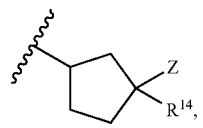 R27-13
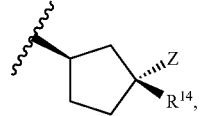 R27-14
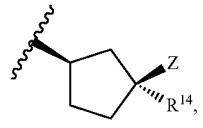 R27-15
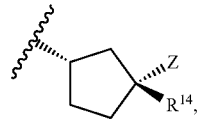 R27-16
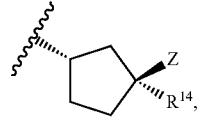 R27-17
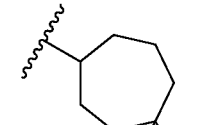 R27-18
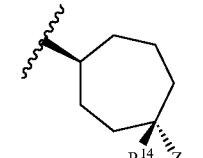 R27-19
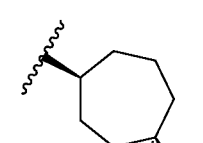 R27-20

-continued

R27-21
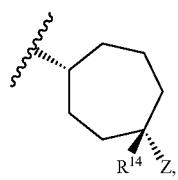

R27-22
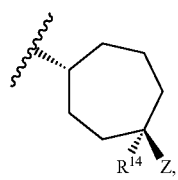

R27-23
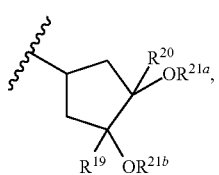

R27-24
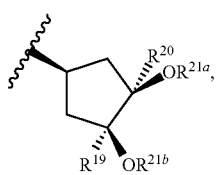

R27-25
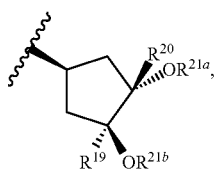

R27-26
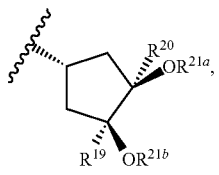

R27-27
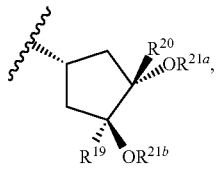

R27-28
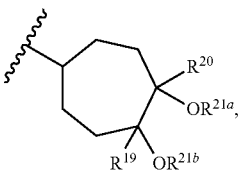

R27-29
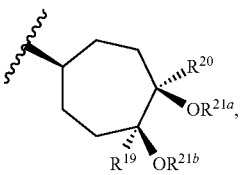

-continued

R27-30
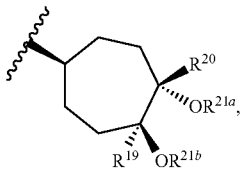

R27-31
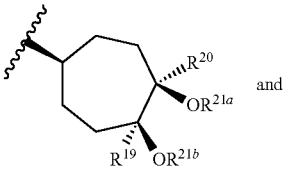
and

R27-32
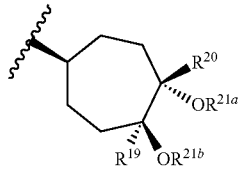

wherein:
$R^7$ is optionally substituted $C_1$-$C_4$ alkyl;
$W^2$ is selected from the group consisting of —$OR^{10}$ and —$NR^{11a}R^{11b}$;
$R^{9a}$ and $R^{10}$ are each hydrogen; or
one of $R^{9a}$ and $R^{10}$ is hydrogen and the other is a metabolically cleavable group;
$R^{11a}$ is selected from the group consisting of hydrogen, optionally substituted alkyl, optionally substituted cycloalkyl, optionally substituted aryl, optionally substituted heteroaryl, —$SO_2R^{11c}$, and —$CONR^{11d}R^{11e}$;
$R^{11b}$ is selected from the group consisting of hydrogen, optionally substituted alkyl, optionally substituted cycloalkyl, optionally substituted aryl, and optionally substituted heteroaryl; or
$R^{11a}$ and $R^{11b}$ taken together with the nitrogen atom to which they are attached form a 4- to 8-membered optionally substituted heterocyclo;
$R^{11c}$ is selected from the group consisting of optionally substituted alkyl and optionally substituted cycloalkyl;
$R^{11d}$ and $R^{11e}$ are each independently selected from the group consisting of hydrogen, optionally substituted alkyl, and optionally substituted cycloalkyl; or
$R^{11d}$ and $R^{11e}$ taken together with the nitrogen atom to which they are attached form a 4- to 8-membered optionally substituted heterocyclo;
$R^{14}$ is selected from the group consisting of hydrogen, optionally substituted $C_1$-$C_4$ alkyl, and optionally substituted cycloalkyl;
Z is selected from the group consisting of -$OR^{15}$ and —$NR^{16a}R^{16b}$;
$R^{15}$ is selected from the group consisting of hydrogen and metabolically cleavable group;
$R^{16a}$ is selected from the group consisting of —$SO_2R^{16c}$ and —$CONR^{16d}R^{16e}$;
$R^{16b}$ is selected from the group consisting of hydrogen and optionally substituted alkyl;
$R^{16c}$ is selected from the group consisting of optionally substituted alkyl, optionally substituted cycloalkyl, optionally substituted aryl, and optionally substituted heteroaryl;
$R^{16d}$ and $R^{16e}$ are each independently selected from the group consisting of hydrogen, optionally substituted alkyl, optionally substituted cycloalkyl, optionally substituted aryl, and optionally substituted heteroaryl; or $R^{16d}$ and $R^{16e}$ taken together with the nitrogen atom to which they are attached form a 4- to 8-membered heterocyclo;

$R^{19}$ is selected from the group consisting of hydrogen, optionally substituted $C_1$-$C_6$ alkyl, and optionally substituted cycloalkyl;

$R^{20}$ is selected from the group consisting of hydrogen, optionally substituted $C_1$-$C_6$ alkyl, and optionally substituted cycloalkyl;

$R^{21a}$ and $R^{21b}$ are each hydrogen; or one of $R^{21a}$ and $R^{21b}$ is hydrogen and the other is metabolically cleavable group;

or a pharmaceutically acceptable salt, solvate, or prodrug thereof.

In another embodiment, compounds of Formula XVIIIb are provided:

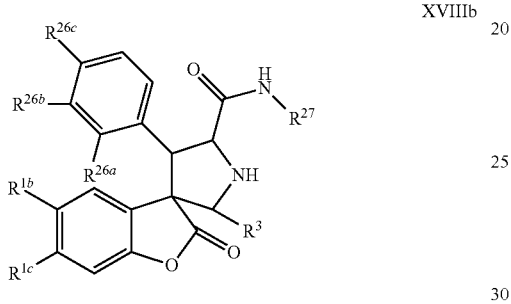

XVIIIb wherein $R^{1b}$, $R^{1b}$, $R^3$, $R^{26a}$, $R^{26b}$, $R^{26c}$, and $R^{27}$ have the meanings as described above for Formula XVIIIa, or a pharmaceutically acceptable salt, solvate, or prodrug thereof.

In another embodiment, compounds of Formula XVIIIc are provided:

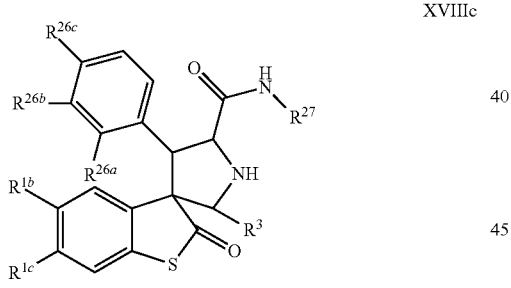

XVIIIc wherein $R^{1b}$, $R^{1b}$, $R^3$, $R^{26a}$, $R^{26b}$, $R^{26c}$, and $R^{27}$ have the meanings as described above for Formula XVIIIa, or a pharmaceutically acceptable salt, solvate, or prodrug thereof.

In certain embodiments, $R^{27}$ is selected from the group consisting of R27-2, R27-3, R27-5, R27-6, R27-8, R27-9, R27-11, R27-12, R27-14, R27-15, R27-16, R27-17, R27-19, R27-20, R27-21, R27-22, R27-24, R27-25, R27-27, R27-29, R27-30, R27-31, and R27-32. In certain embodiments, R27 is selected from the group consisting of R27-2, R27-3, R27-5, and R27-6, R27-8, R27-9, R27-14, R27-15, 827-16, and R27-17. In certain embodiments, R27 is a hydroxycycloalkyl group.

In certain embodiments, $R^{9a}$ is hydrogen; $W^2$ is OH; Z is OH; $R^7$ is $C_1$-$C_4$ alkyl, e.g., methyl, ethyl, propyl, or isopropyl, or cyclopropyl; $R^{14}$, $R^{19}$, and $R^{20}$ are each independently hydrogen, $C_1$-$C_4$ alkyl, e.g., methyl, ethyl, propyl, or isopropyl, or cyclopropyl; and $R^{21a}$ and $R^{21b}$ are each hydrogen.

In certain embodiments, $R^{9a}$ is hydrogen, $R^7$ is hydrogen, $C_1$-$C_4$ alkyl, or cyclopropyl; $W^2$ is —NHR$^{11a}$; $R^{11a}$ is $C_1$-$C_4$ alkyl, e.g., methyl, trifluoromethyl, ethyl, propyl, or isopropyl, or cyclopropyl; $R^{14}$ is hydrogen, $C_1$-$C_4$ alkyl, e.g., methyl, ethyl, propyl, or isopropyl, or cyclopropyl; Z is —NHSO$_2$R$^{16c}$ or —NHCONHR$^{16d}$; and R$^{16c}$ and R$^{16d}$ are each independently optionally substituted $C_1$-$C_4$ alkyl, e.g., methyl, trifluoromethyl, ethyl, propyl, or isopropyl, or cyclopropyl.

In certain embodiments, compounds of Formulae XIX-XXXIV are provided:

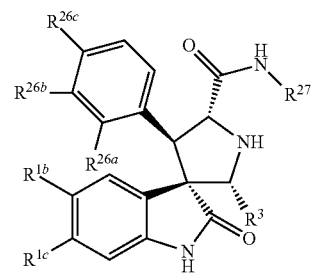

XIX

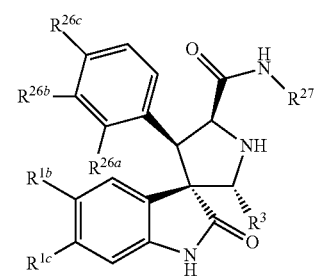

XX

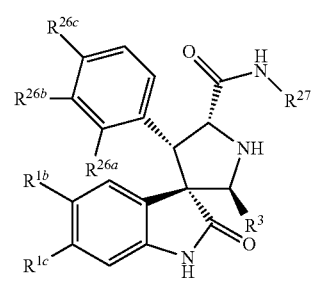

XXI

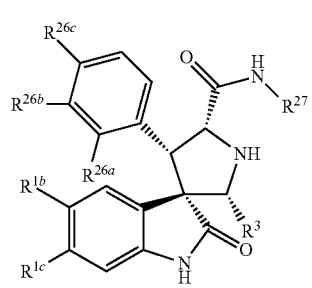

XXII

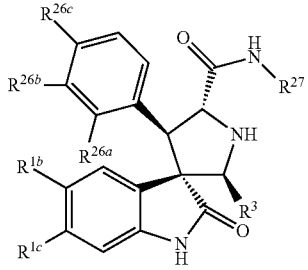

XXIII

-continued
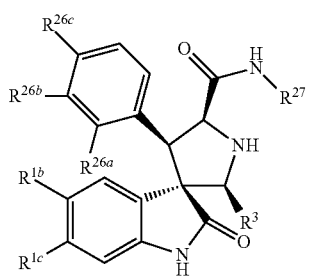
XXIV
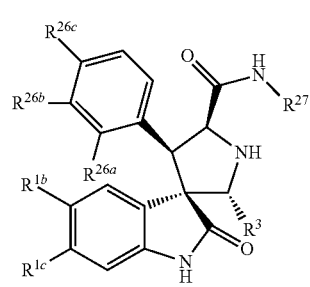
XXV
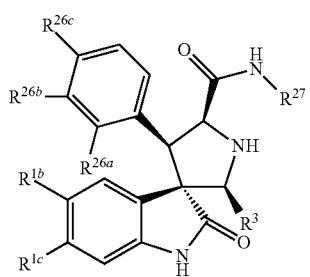
XXVI
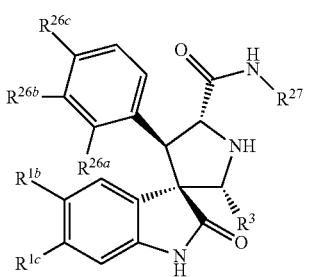
XXVII
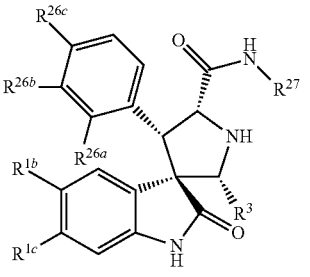
XXVIII
-continued
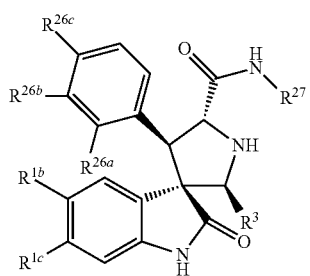
XXIX
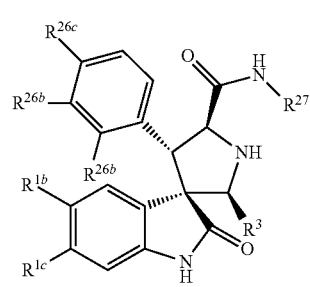
XXX
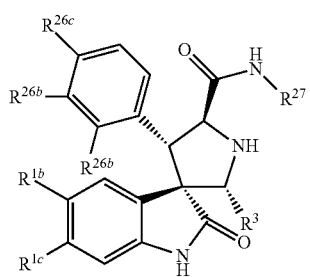
XXXI
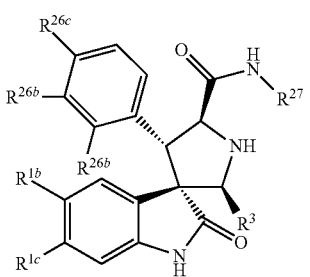
XXXII
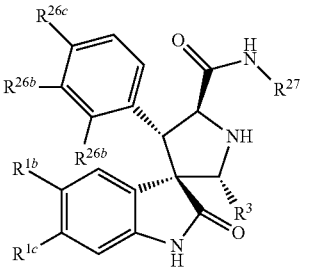
XXXIII -continued

XXXIV

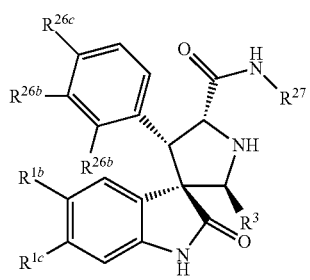

wherein $R^{1b}$, $R^{1c}$, $R^3$, $R^{26a}$, $R^{26b}$, $R^{26c}$, and $R^{27}$ have the meanings as described above in connection with Formula XVIIIa, or a pharmaceutically acceptable salt, solvate, or prodrug thereof.

In certain embodiments, compounds of Formula XIX are provided, wherein and $R^{27}$ have the meanings as described above in connection with Formula XVIIIa, or a pharmaceutically acceptable salt, solvate, or prodrug thereof.

In some embodiments, compounds of Formula XIX are substantially free of one or more other stereoisomers, i.e., compounds of Formulae XX-XXXIV. In some embodiments, compounds of Formula XIX are substantially pure stereoisomers. In some embodiments, compounds of Formula XIX are pure stereoisomers.

In certain embodiments, compounds of Formula XXIII are provided, wherein and $R^{27}$ have the meanings as described above in connection with Formula XVIIIa, or a pharmaceutically acceptable salt, solvate, or prodrug thereof.

In some embodiments, compounds of Formula XXIII are substantially free of one or more other stereoisomers, i.e., compounds of Formulae XIX-XXII and XXIV-XXXIV. In some embodiments, compounds of Formula XXIII are substantially pure stereoisomers. In some embodiments, compounds of Formula XXIII are pure stereoisomers.

In certain embodiments, compounds of Formula XXVII are provided, wherein $R^{1b}$, $R^{1c}$, $R^3$, $R^{26a}$, $R^{26b}$, $R^{26c}$, and $R^{27}$ have the meanings as described above in connection with Formula XVIIIa, or a pharmaceutically acceptable salt, solvate, or prodrug thereof.

In some embodiments, compounds of Formula XXVII are substantially free of one or more other stereoisomers, i.e., compounds of Formulae XIX-XXVI and XXVIII-XXXIV. In some embodiments, compounds of Formula XXVII are substantially pure stereoisomers. In some embodiments, compounds of Formula XXVII are pure stereoisomers.

In certain embodiments, compounds of Formula XXIX are provided, wherein $R^{1b}$, $R^{1c}$, $R^3$, $R^{26a}$, $R^{26b}$, $R^{26c}$, and $R^{27}$ have the meanings as described above in connection with Formula XVIIIa, or a pharmaceutically acceptable salt, solvate, or prodrug thereof.

In some embodiments, compounds of Formula XXIX are substantially free of one or more other stereoisomers, i.e., compounds of Formulae XIX-XXVIII and XXX-XXIV. In some embodiments, compounds of Formula XXIX are substantially pure stereoisomers. In some embodiments, compounds of Formula XXIX are pure stereoisomers.

In certain embodiments, compounds of Formulae XIX, XXIII, XXVII, and XXIX are provided, wherein $R^{27}$ is selected from the group consisting of:

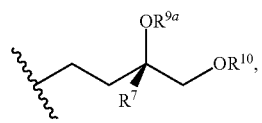

R27-33

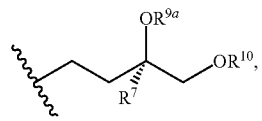

R27-34

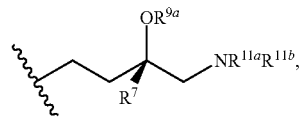

R27-35

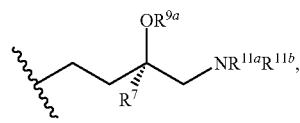

R27-36

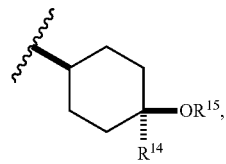

R27-37

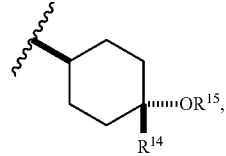

R27-38

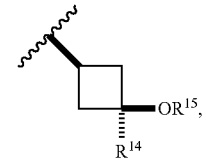

R27-39

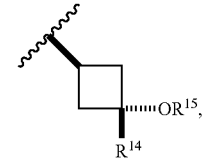

R27-40

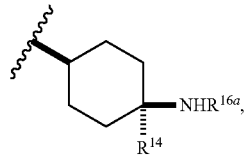

R27-41

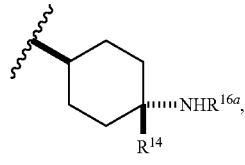

R27-42

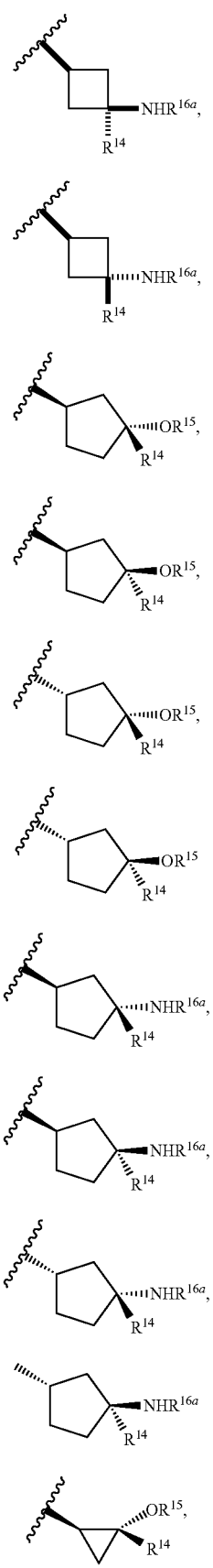

wherein:

$R^7$ is $C_1$-$C_4$ alkyl;

$R^{9a}$ and $R^{10}$ are hydrogen; or one of $R^{9a}$ and $R^{10}$ is hydrogen and the other is metabolically cleavable group;

$R^{11a}$ and $R^{11b}$ are each independently selected from the group consisting of hydrogen, optionally substituted $C_1$-$C_4$ alkyl, optionally substituted cycloalkyl, optionally substituted aryl, and optionally substituted heteroaryl; or $R^{11a}$ and $R^{11b}$ taken together with the nitrogen atom to which they are attached form a 4- to 8-membered optionally substituted heterocyclo;

$R^{14}$ is selected from the group consisting of hydrogen and $C_1$-$C_4$ alkyl;

$R^{15}$ is hydrogen or a metabolically cleavable group; and $R^{16a}$ is selected from the group consisting of —$SO_2R^{16c}$ and —$CONR^{16d}R^{16e}$;

$R^{16c}$ is selected from the group consisting of optionally substituted $C_1$-$C_4$ alkyl or cyclopropyl;

$R^{16d}$ and $R^{16e}$ are each independently selected from the group consisting of hydrogen, optionally substituted $C_1$-$C_4$ alkyl or cyclopropyl; or $R^{16d}$ and $R^{16e}$ taken together with the nitrogen atom to which they are attached form a 4- to 8-membered heterocyclo, or a pharmaceutically acceptable salt, solvate, or prodrug thereof.

In certain embodiments, compounds of Formulae XIX, XXIII, XXVII, and XXIX are provided, wherein $R^{27}$ is selected from the group consisting of:

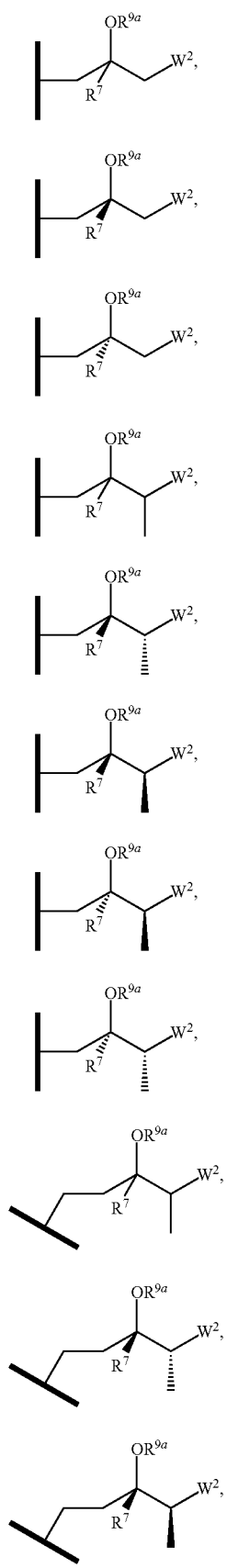
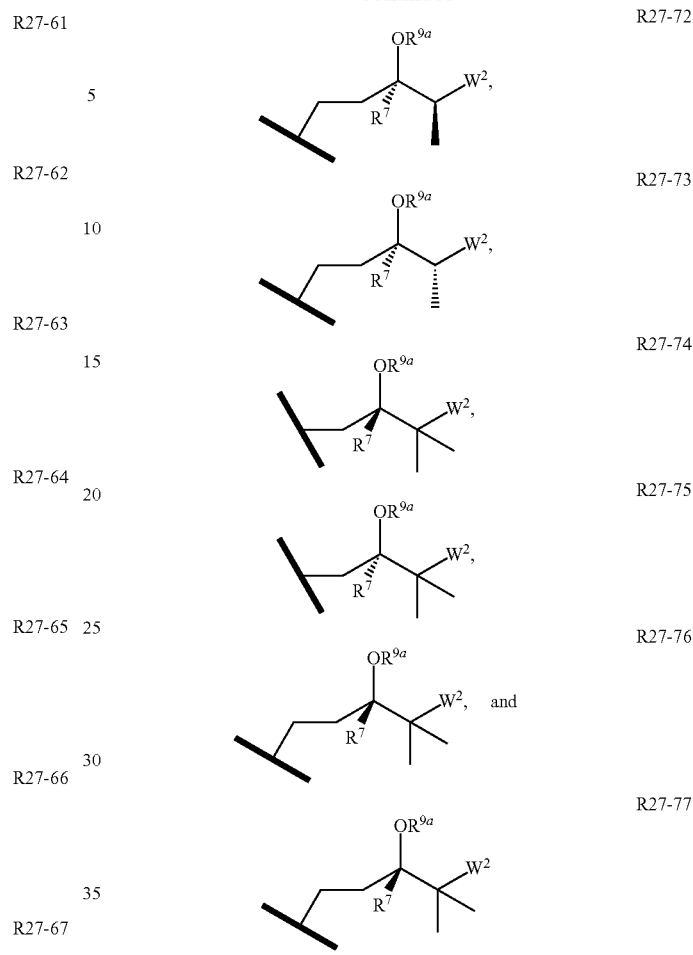

wherein:

$R^4$ is optionally substituted $C_1$-$C_4$ alkyl;

$W^2$ is selected from the group consisting of —$OR^{10}$ and —$NR^{11a}R^{11b}$;

$R^{9a}$ and $R^{10}$ are each hydrogen; or one of $R^{9a}$ and $R^{10}$ is hydrogen and the other is a metabolically cleavable group;

$R^{11a}$ is selected from the group consisting of hydrogen, optionally substituted alkyl, optionally substituted cycloalkyl, optionally substituted aryl, optionally substituted heteroaryl, —$SO_2R^{11c}$ and —$CONR^{11d}R^{11e}$;

$R^{11b}$ is selected from the group consisting of hydrogen, optionally substituted alkyl, optionally substituted cycloalkyl, optionally substituted aryl, and optionally substituted heteroaryl; or $R^{11a}$ and $R^{11b}$ taken together with the nitrogen atom to which they are attached form a 4- to 8-membered optionally substituted heterocyclo;

$R^{11c}$ is selected from the group consisting of optionally substituted alkyl and optionally substituted cycloalkyl;

$R^{11d}$ and $R^{11e}$ are each independently selected from the group consisting of hydrogen, optionally substituted alkyl, and optionally substituted cycloalkyl; or $R^{11d}$ and $R^{11e}$ taken together with the nitrogen atom to which they are attached form a 4- to 8-membered optionally substituted heterocyclo;

or a pharmaceutically acceptable salt, solvate, or prodrug thereof.

In certain embodiments, compounds of Formulae XIX, XXIII, XXVII, and XXIX are provided, wherein $R^{27}$ is selected from the group consisting of:

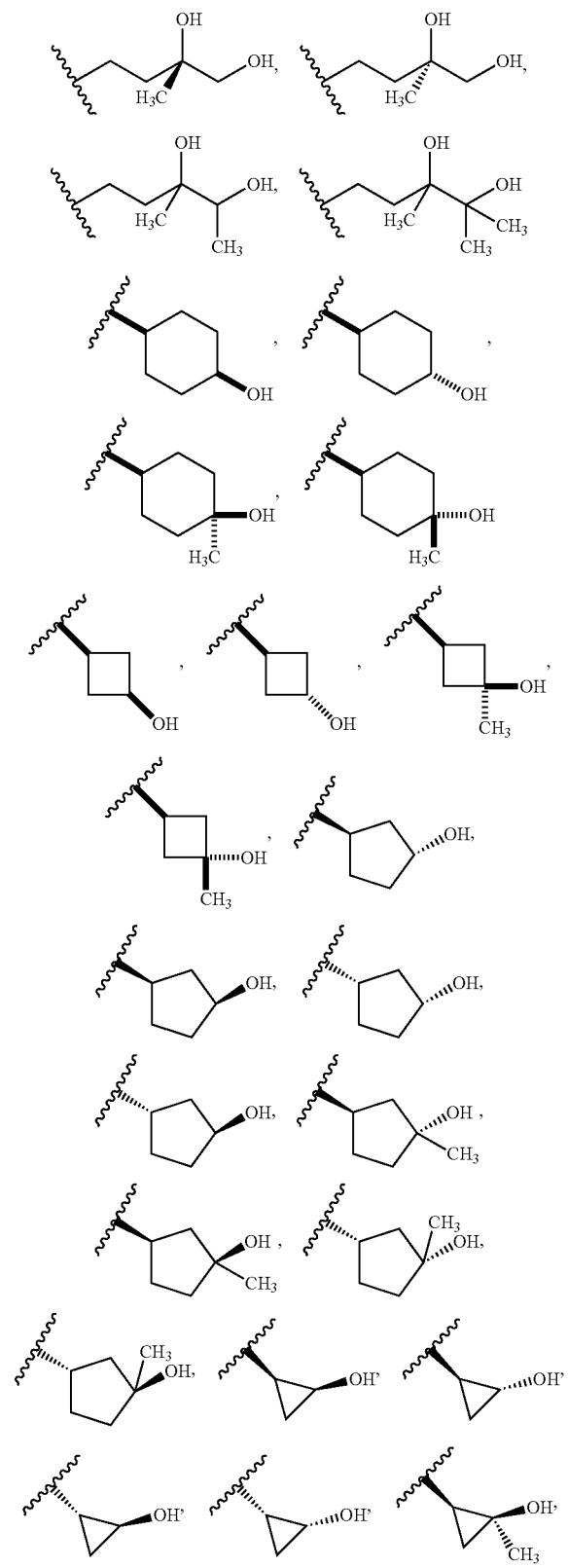

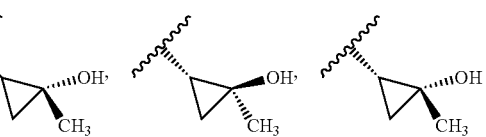

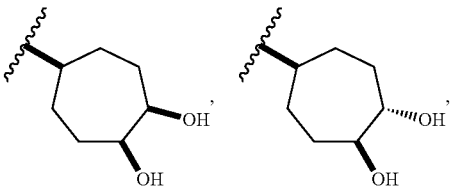

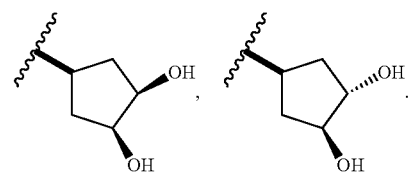

In certain embodiments, compounds of Formulae XIX, XXIII, XXVII, and XXIX are provided, wherein $R^{27}$ is selected from the group consisting of:

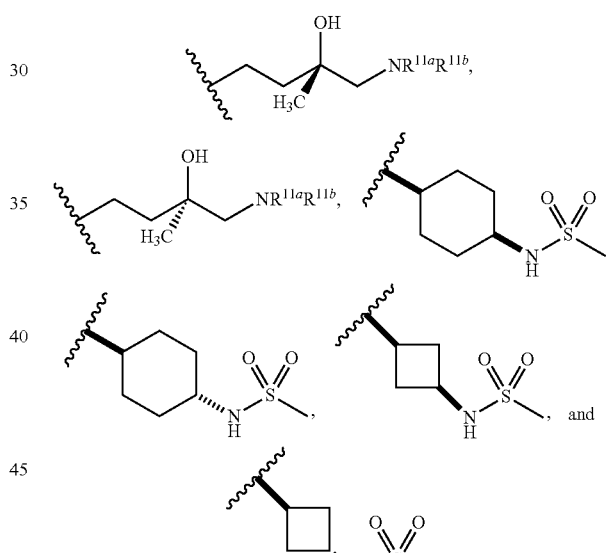

wherein $R^{11a}$ and $R^{11b}$ taken together with the nitrogen to which they are attached form a 5- or 6-membered optionally substituted heterocyclo.

In certain embodiments, compounds of Formulae XIX, XXIII, XXVII, and XXIX are provided, wherein $R^{27}$ is selected from the group consisting of:

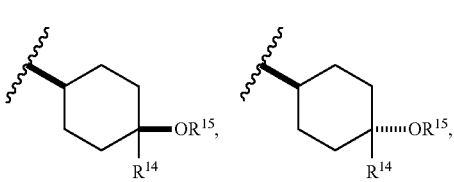

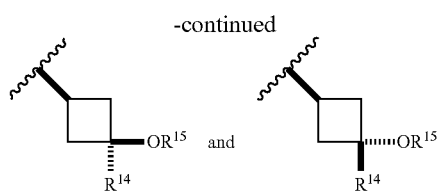

wherein:
R$^{14}$ is selected from the group consisting of hydrogen and C$_1$-C$_4$ alkyl; and
R$^{15}$ is a metabolically cleavable group.

In certain embodiments, compounds of Formulae II, VI, X, XII, XIX, XXIII, XXVII, and XXIX are provided, wherein R$^{15}$ is a metabolically cleavable group selected from the group consisting of:

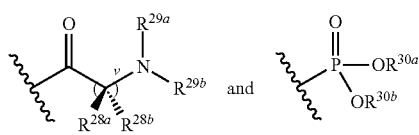

wherein:
each R$^{28a}$ and R$^{28b}$ is independently selected from the group consisting of hydrogen, optionally substituted alkyl, and aralkyl;
R$^{29a}$ and R$^{29b}$ are each selected from the group consisting of hydrogen and optionally substituted alkyl;
v is 1, 2, 3, or 4; and
R$^{30a}$ and R$^{30b}$ are each selected from the group consisting of hydrogen, optionally substituted alkyl, aralkyl, optionally substituted aryl, and monovalent pharmaceutically acceptable cation; or
taken together R$^{30a}$ and R$^{30b}$ represent a divalent pharmaceutically acceptable cation or an optionally substituted alkylenyl.

In certain embodiments, R$^{15}$ is the residue of a natural or unnatural amino acid. In other embodiments, R$^{15}$ is the residue of glycine, isoleucine alanine, leucine, asparagine, lysine, aspartic acid, methionine, cysteine, phenylalanine, glutamic acid, threonine, glutamine, tryptophan, valine, proline, serine, tyrosine, arginine, and histidine.

In certain embodiments, compounds of Formulae II, VI, X, XII, XIX, XXIII, XXVII, and XXIX are provided, wherein R$^3$ is C$_1$-C$_{10}$ alkyl.

In certain embodiments, compounds of Formulae II, VI, X, XII, XIX, XXIII, XXVII, and XXIX are provided, wherein R$^3$ is selected from the group consisting of —CH$_2$C(CH$_3$)$_3$, —CH$_2$C(CH$_3$)$_2$CH$_2$CH$_3$, —CH$_2$C(CH$_3$)$_2$CH$_2$CH$_2$CH$_3$, —CH$_2$C(CH$_3$)$_2$CH$_2$CH$_2$CH$_2$CH$_3$, —CH$_2$C(CH$_2$CH$_3$)$_2$CH$_3$, and —CH$_2$C(CH$_3$)$_2$CH$_2$—CH(CH$_3$)$_2$. In certain embodiments, R$^3$ is —CH$_2$C(CH$_3$)$_3$.

In certain embodiments, compounds of Formulae II, VI, X, XII, XIX, XXIII, XXVII, and XXIX are provided, wherein R$^3$ is optionally substituted aryl.

In certain embodiments, compounds of Formulae II, VI, X, XII, XIX, XXIII, XXVII, and XXIX are provided, wherein R$^3$ is optionally substituted phenyl.

In some embodiments, compounds of Formulae XIX, XXIII, XXVII, and XXIX are provided wherein R$^{1b}$, R$^{1c}$, R$^{26a}$, R$^{26b}$, and R$^{26c}$ are each independently selected from the group consisting of hydrogen and halogen, e.g., chloro or fluoro, or a pharmaceutically acceptable salt, solvate, or prodrug thereof.

In certain embodiments, compounds having Formulae VI, X, and XII are provided, wherein:
R$^{1a}$, R$^{1b}$, R$^{1c}$, and R$^{1d}$ are each independently selected from the group consisting of hydrogen, fluoro, and chloro;
R$^2$ is selected from the group consisting of aralkyl and:

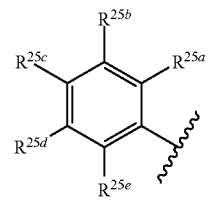

wherein:
R$^{25a}$, R$^{25b}$, R$^{25c}$, R$^{25d}$, and R$^{25e}$ are each independently selected from the group consisting of hydrogen, fluoro, and chloro;
R$^3$ is selected from the group consisting of optionally substituted C$_1$-C$_8$ alkyl and optionally substituted aryl;
R$^4$ is selected from the group consisting of hydrogen and optionally substituted C$_1$-C$_6$ alkyl;
R$^5$ is selected from the group consisting of:

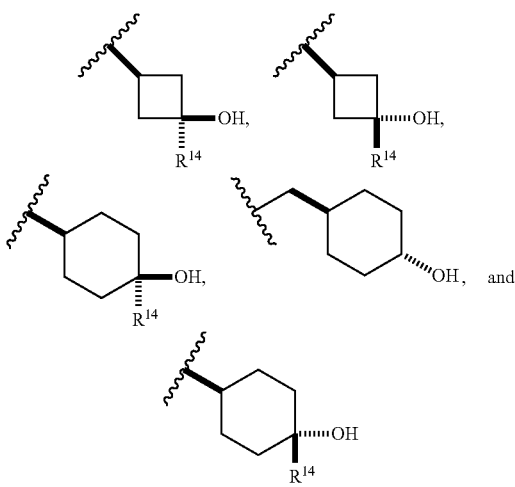

wherein:
R$^{14}$ is selected from the group consisting of hydrogen and optionally substituted C$_1$-C$_4$ alkyl;
X is selected from the group consisting of O, S, and NR';
Y is selected from the group consisting of O, S, and NR";
R' is selected from the group consisting of hydrogen and optionally substituted C$_1$-C$_4$ alkyl; and
R" is selected from the group consisting of hydrogen, optionally substituted C$_1$-C$_4$ alkyl, and —COCH$_3$,
wherein the compound is substantially free of one or more other stereoisomers,
or a pharmaceutically acceptable salt, solvate, or prodrug thereof.

In some embodiments, R$^4$ is hydrogen. In some embodiments, X is NH. In some embodiments, Y is NH. In some embodiments, R$^3$ is —CH$_2$C(CH$_3$)$_3$. In some embodiments, R$^5$ is selected from the group consisting of:

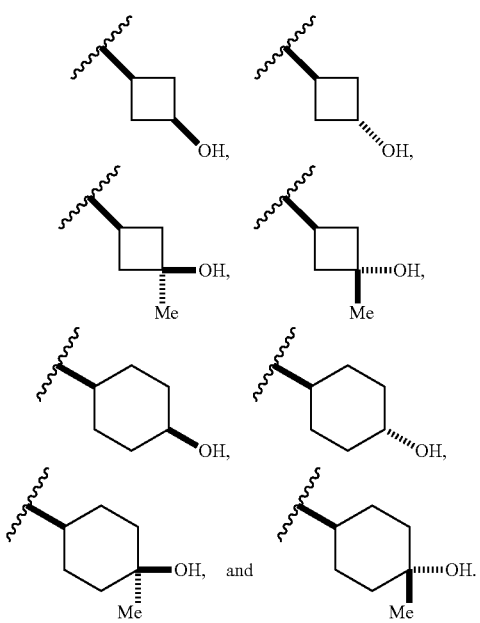

In certain embodiments, compounds having Formula XII are provided, wherein:

$R^{1a}$, $R^{1b}$, $R^{1c}$, and $R^{1d}$ are each independently selected from the group consisting of hydrogen, fluoro, and chloro;

$R^2$ is selected from the group consisting of benzyl and:

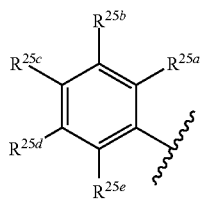

wherein:

$R^{25a}$, $R^{25b}$, $R^{25c}$, $R^{25d}$, and $R^{25e}$ are each independently selected from the group consisting of hydrogen, fluoro, and chloro;

$R^3$ is selected from the group consisting of optionally substituted $C_1$-$C_8$ alkyl and phenyl;

$R^4$ is selected from the group consisting of hydrogen and optionally substituted $C_1$-$C_6$ alkyl;

$R^5$ is selected from the group consisting of:

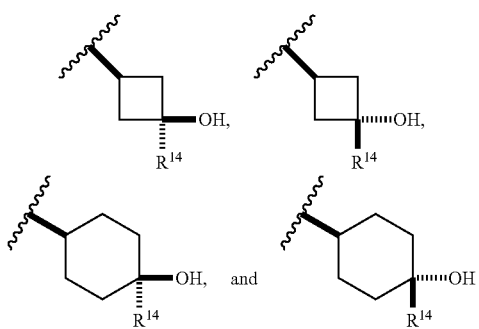

wherein:

$R^{14}$ is selected from the group consisting of hydrogen and optionally substituted $C_1$-$C_4$ alkyl;

X is selected from the group consisting of O, S, and NR';

Y is selected from the group consisting of O, S, and NR";

R' is selected from the group consisting of hydrogen and optionally substituted $C_1$-$C_4$ alkyl; and R" is selected from the group consisting of hydrogen, optionally substituted $C_1$-$C_4$ alkyl, and —COCH$_3$, wherein the compound is substantially free of one or more other stereoisomers, or a pharmaceutically acceptable salt, solvate, or prodrug thereof.

In some embodiments, $R^4$ is hydrogen. In some embodiments, X is NH. In some embodiments, Y is NH. In some embodiments, $R^3$ is —CH$_2$C(CH$_3$)$_3$. In some embodiments, $R^5$ is selected from the group consisting of:

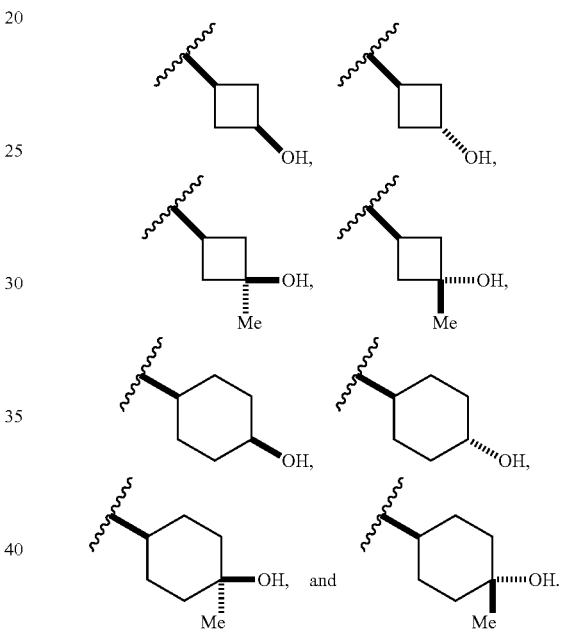

In certain embodiments, compounds having Formula XII are provided, wherein:

$R^{1a}$ is hydrogen; $R^{1b}$, $R^{1c}$, and $R^{1d}$ are each independently selected from the group consisting of hydrogen, fluoro, and chloro;

$R^2$ is:

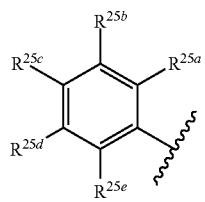

wherein:

$R^{25a}$, $R^{25b}$, $R^{25c}$, $R^{25d}$, and $R^{25e}$ are each independently selected from the group consisting of hydrogen, fluoro, and chloro;

$R^3$ is $C_4$-$C_8$ alkyl;

$R^4$ is hydrogen;

R[5] is selected from the group consisting of:

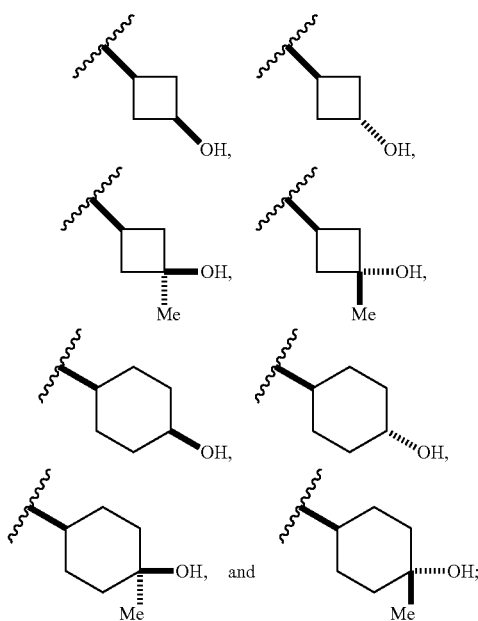

and

X and Y are NH, wherein the compound is substantially free of one or more other stereoisomers, or a pharmaceutically acceptable salt, solvate, or prodrug thereof.

In some embodiments, R[5] is selected from the group consisting of:

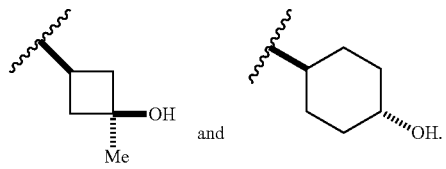 [SMILES: *[C@H]1C[C@@](C)(O)C1 ; "and" ; *[C@H]1CC[C@H](O)CC1]

In some embodiments, compounds having Formula XXXV:

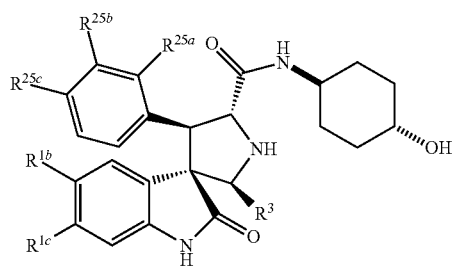

are provided, wherein:

R[1b] and R[1c] are independently selected from the group consisting of hydrogen, fluoro, and chloro;

R[3] is $C_4$-$C_8$ alkyl; and

R[25a], R[25b], and R[25c] are each independently selected from the group consisting of hydrogen, fluoro, and chloro, or a pharmaceutically acceptable salt, solvate, or prodrug thereof.

In some embodiments, compounds having Formula XXXV are substantially free of one or more other stereoisomers. In some embodiments, compounds having Formula XXXV are substantially pure stereoisomers. In some embodiments, compounds having Formula XXXV are pure stereoisomers.

In certain embodiments, compounds having the following structure:

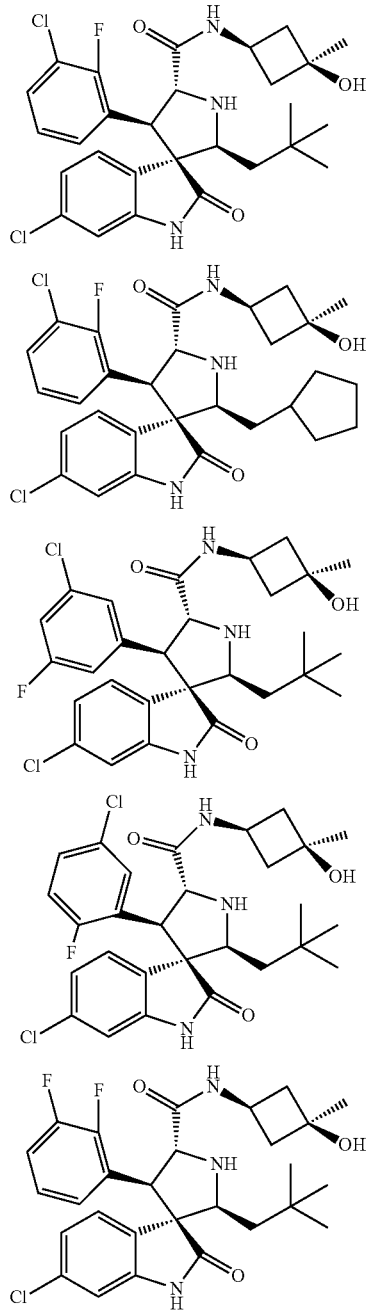

-continued
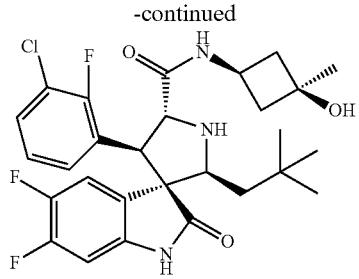
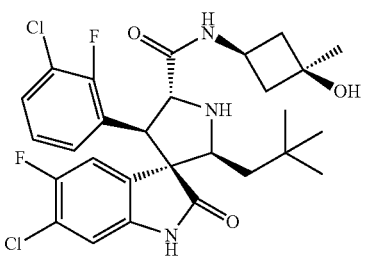
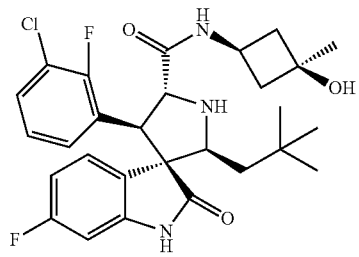
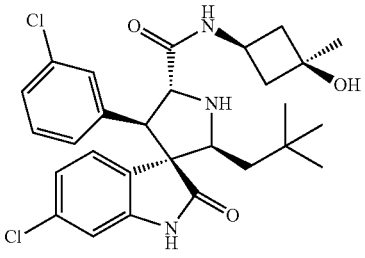
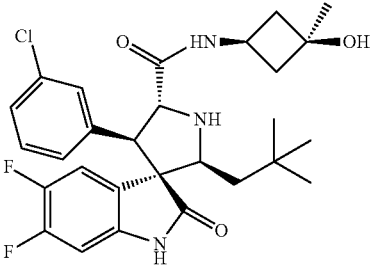
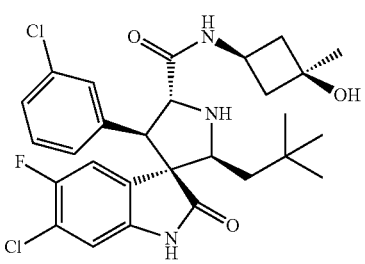
-continued
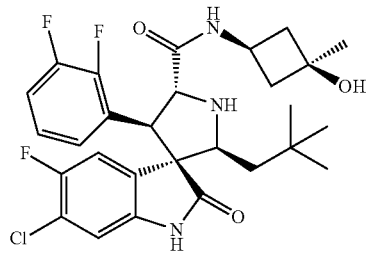
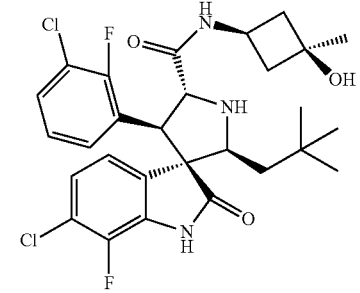
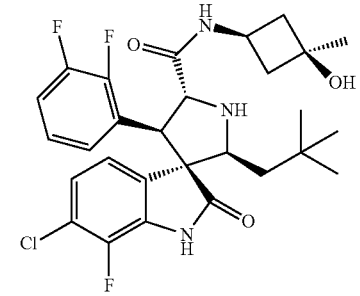
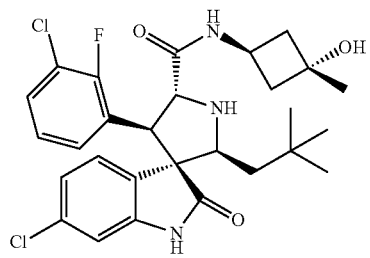
or a pharmaceutically acceptable salt or solvate thereof are provided.
In some embodiments, compounds having the following structure:
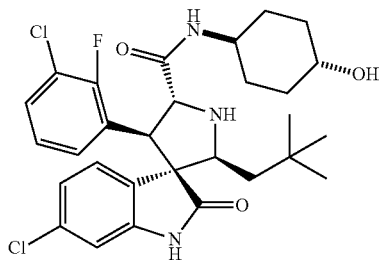

67
-continued
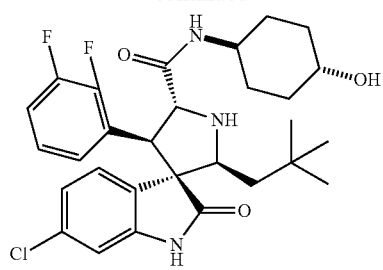
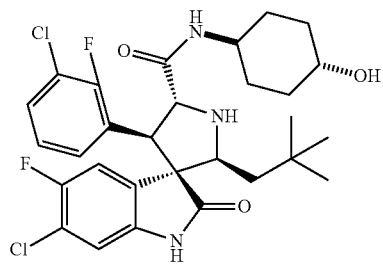
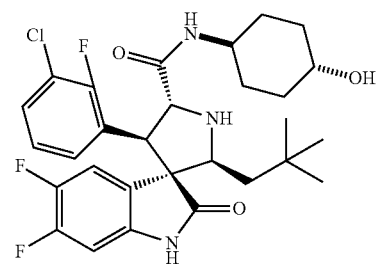
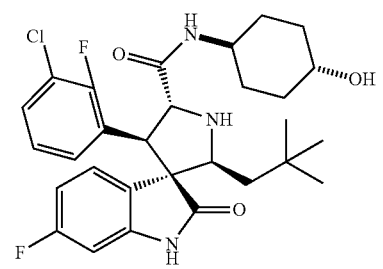
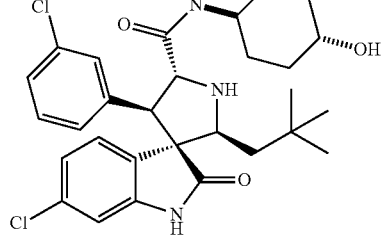
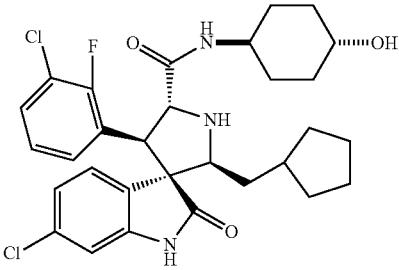
68
-continued
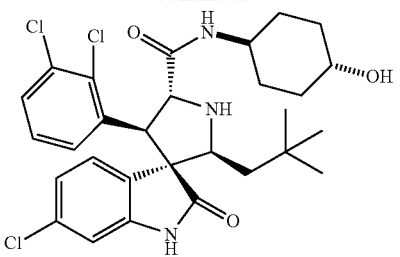
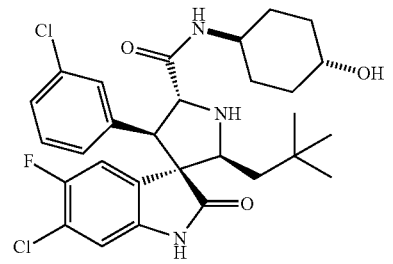
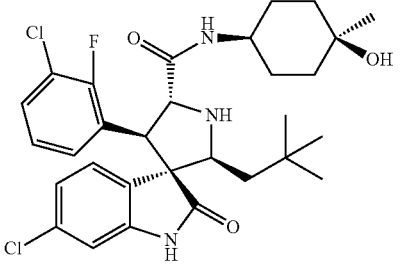
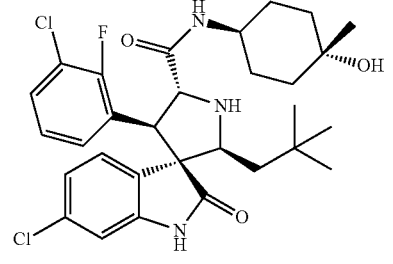
or a pharmaceutically acceptable salt or solvate thereof are provided.
In some embodiments, compounds having the following structure:
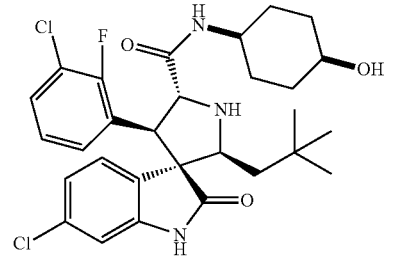

-continued
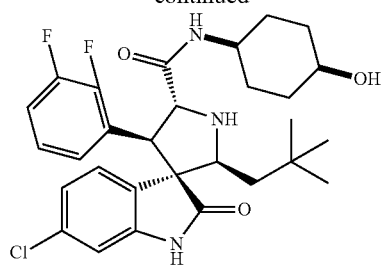
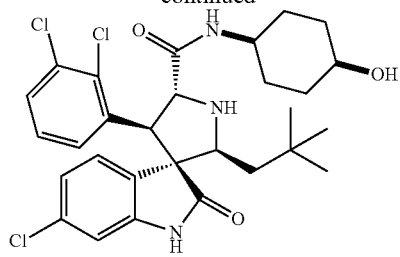
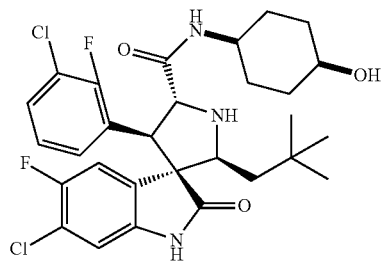
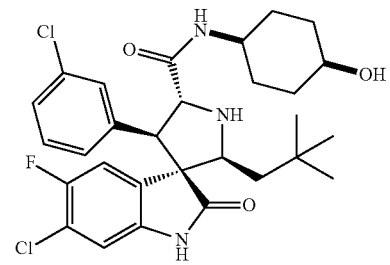
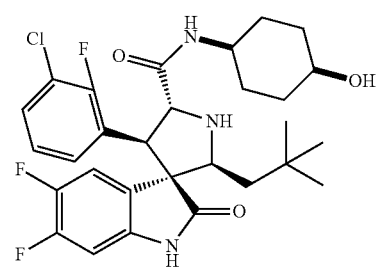
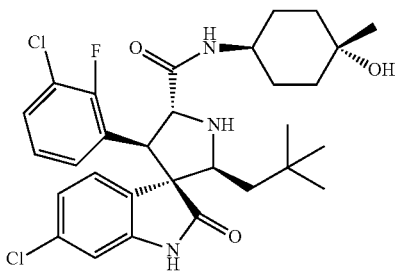
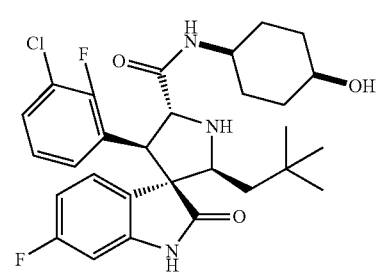
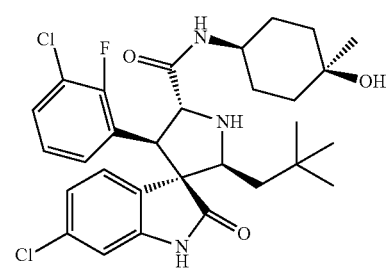
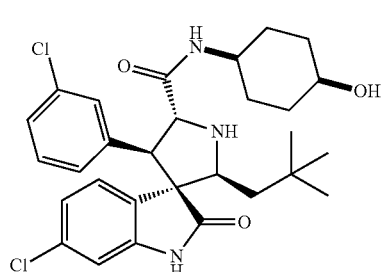
or a pharmaceutically acceptable salt or solvate thereof are provided.
In certain embodiments, compounds having the following structure:
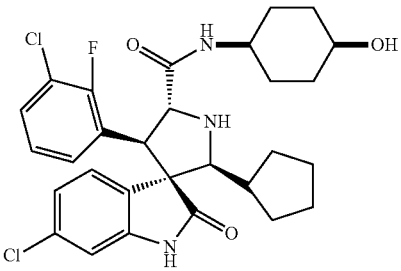
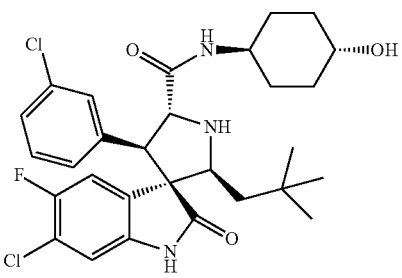

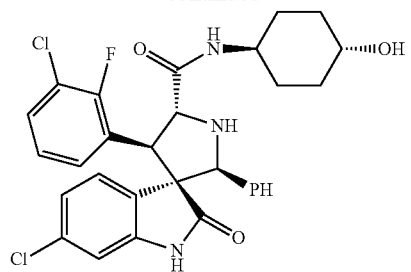
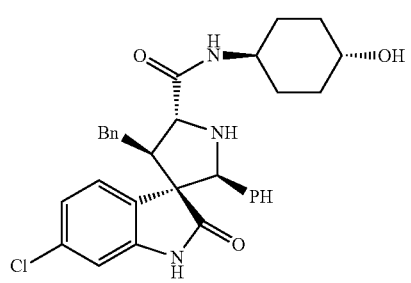
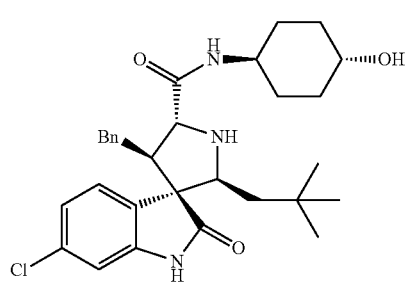
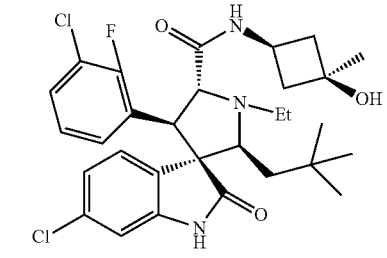
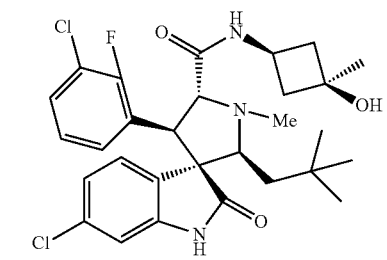
or a pharmaceutically acceptable salt or solvate thereof are provided.
In certain embodiments, compounds having the following structure:
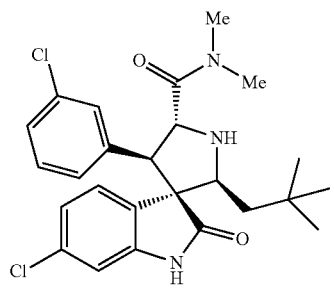
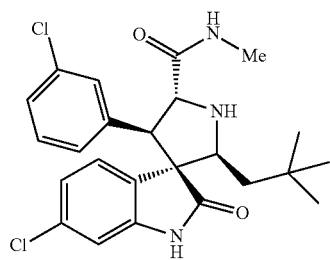
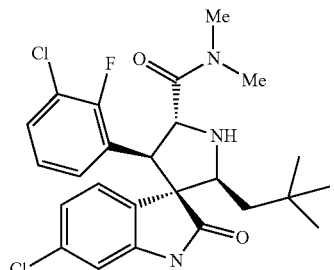
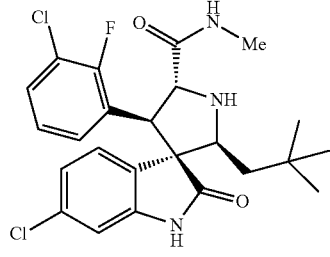
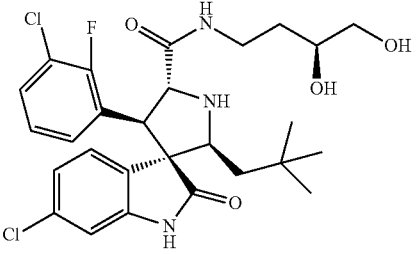
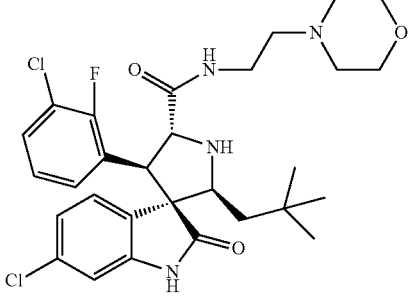

-continued
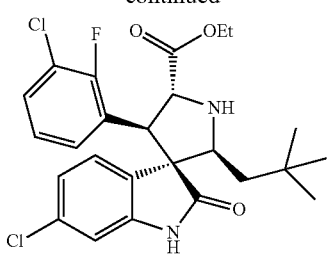
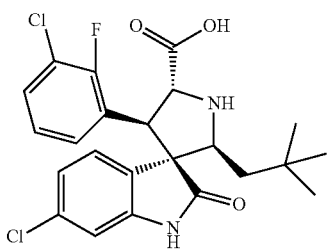
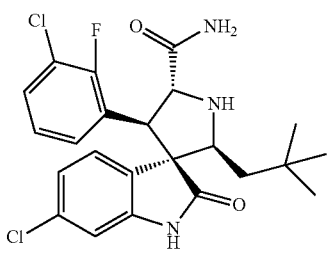
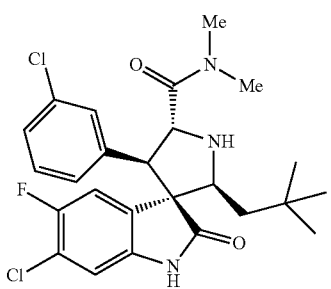
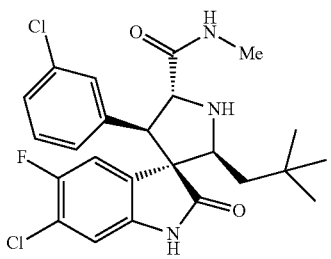
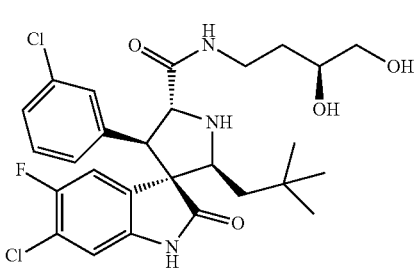
-continued
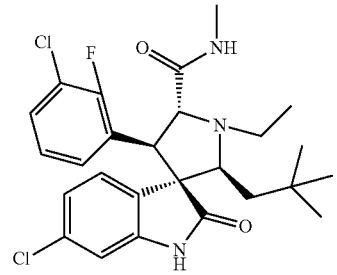
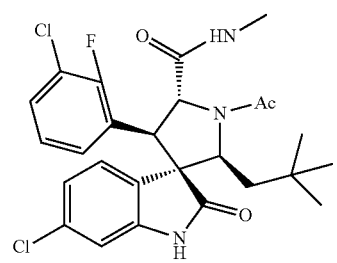
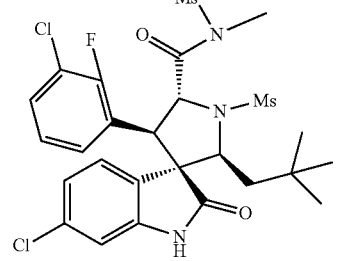
or a pharmaceutically acceptable salt or solvate thereof are provided.
In certain embodiments, compounds having the following structure:
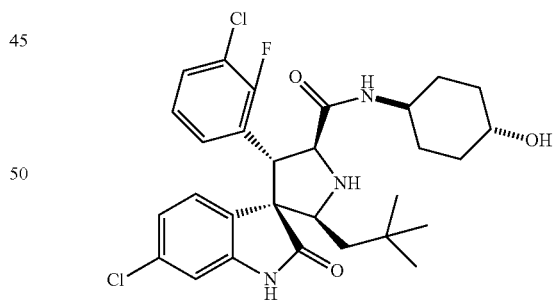
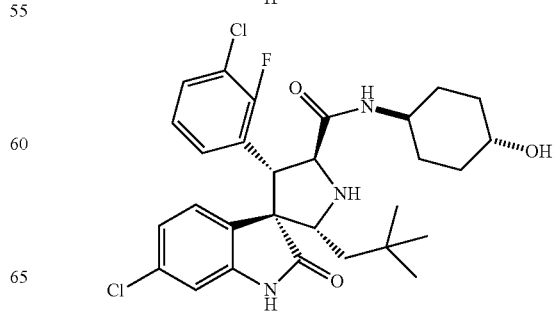

-continued

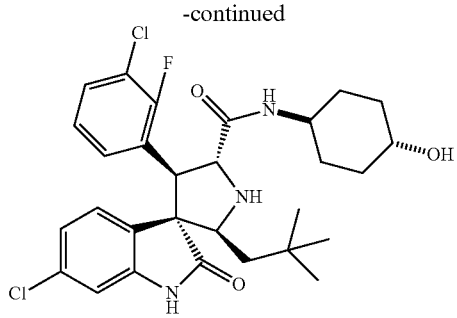

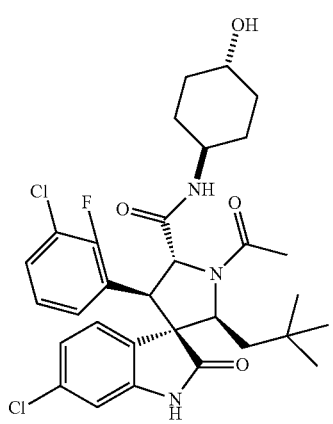

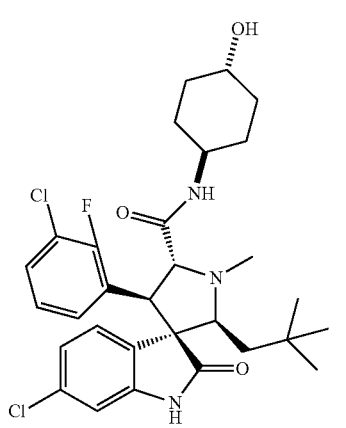

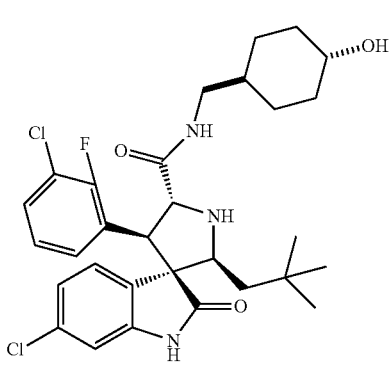

or a pharmaceutically acceptable salt or solvate thereof are provided.

In certain embodiments, compounds having the following structure:

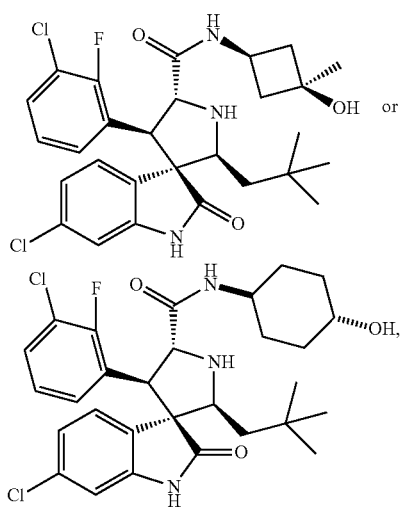

or a pharmaceutically acceptable salt or solvate thereof are provided.

In certain embodiments, compounds having the following structure:

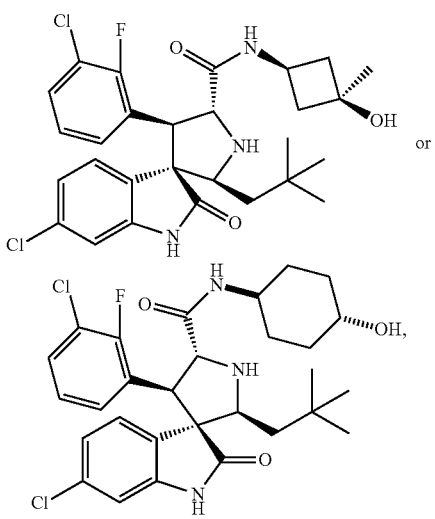

or a pharmaceutically acceptable salt or solvate thereof are provided, wherein the compound is substantially free of one or more other stereoisomers.

In certain embodiments, compounds having the following structure:

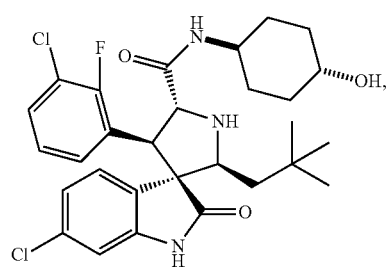 [SMILES: CC(C)(C)C[C@@H]1N[C@@H](C(=O)N[C@H]2CC[C@H](O)CC2)[C@H](c2cccc(Cl)c2F)[C@]12C(=O)Nc1cc(Cl)ccc12]

or a pharmaceutically acceptable salt or solvate thereof are provided, wherein the compound is substantially free of one or more other stereoisomers.

In certain embodiments, a compound having the following structure:

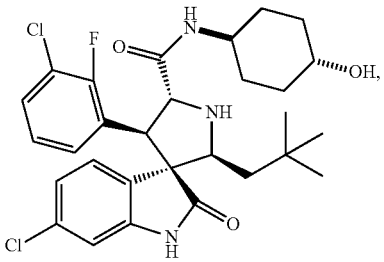 [SMILES: CC(C)(C)C[C@@H]1N[C@@H](C(=O)N[C@H]2CC[C@H](O)CC2)[C@H](c2cccc(Cl)c2F)[C@]12C(=O)Nc1cc(Cl)ccc12]

or a pharmaceutically acceptable salt or solvate thereof is provided, wherein the compound is a substantially pure stereoisomer.

In certain embodiments, a compound having the following structure:

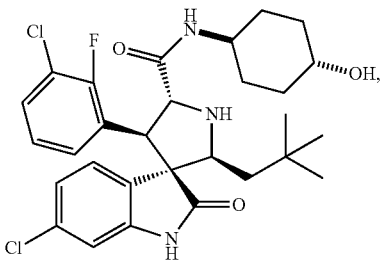 [SMILES: CC(C)(C)C[C@@H]1N[C@@H](C(=O)N[C@H]2CC[C@H](O)CC2)[C@H](c2cccc(Cl)c2F)[C@]12C(=O)Nc1cc(Cl)ccc12]

or a pharmaceutically acceptable salt or solvate thereof is provided, wherein the compound is a pure stereoisomer.

In certain embodiments, methods of preparing a compound having Formula XXXVII:

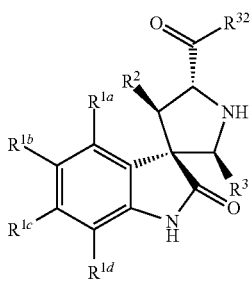

are provided, wherein:
$R^{32}$ is selected from the group consisting of —$OR^{33}$ and —$NR^{34a}R^{34b}$;
$R^{33}$ is selected from the group consisting of hydrogen, alkyl, and aralkyl;
$R^{34a}$ is selected from the group consisting of hydrogen, optionally substituted alkyl, optionally substituted cycloalkyl, aralkyl, optionally substituted aryl, and optionally substituted heteroaryl;
$R^{34b}$ is selected from the group consisting of hydrogen and alkyl;
$R^{1a}$, $R^{1b}$, $R^{2c}$, and $R^{1d}$ are each independently selected from the group consisting of hydrogen, fluoro, and chloro;

$R^2$ is selected from the group consisting of aralkyl and:

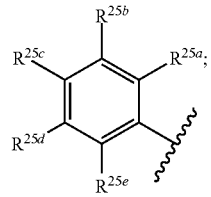

$R^{25a}$, $R^{25b}$, $R^{25c}$, $R^{25d}$, and $R^{25e}$ are each independently selected from the group consisting of hydrogen, fluoro, and chloro; and
$R^3$ is selected from the group consisting of optionally substituted $C_1$-$C_8$ alkyl and optionally substituted aryl.

In one embodiment, the method of preparing a compound having Formula XXXVII comprises allowing a compound having Formula XXXVI:

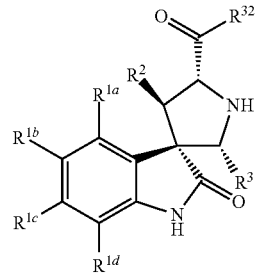

to isomerize to a compound having Formula XXXVII:

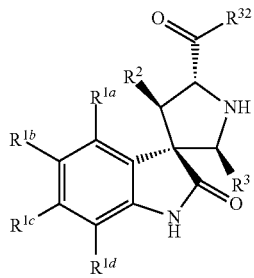

wherein $R^{1a}$, $R^{1b}$, $R^{1c}$, $R^{1d}$, $R^2$, $R^3$, and $R^{32}$ have the meanings as described above in connection with Formula XXXVII.

In one embodiment, the method of preparing a compound having
Formula XXXVII comprises dissolving a compound having Formula XXXVI:

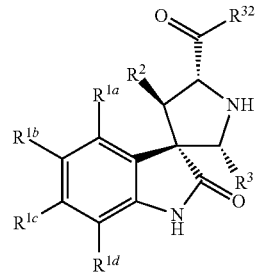

in a solvent or a mixture of solvents,
wherein $R^{1a}$, $R^{1b}$, $R^{1c}$, $R^{1d}$, $R^2$, $R^3$, and $R^{32}$ have the meanings as described above in connection with Formula XXXVII.

In one embodiment, the method of preparing a compound having Formula XXXVII comprises:

a) dissolving a compound having Formula XXXVI:

XXXVI in a solvent or a mixture of solvents; and b) allowing the compound having Formula XXXVI to isomerize to a compound having Formula XXXVII, wherein $R^{1a}$, $R^{1b}$, $R^{1c}$, $R^{1d}$, $R^2$, $R^3$, and $R^{32}$ have the meanings as described above in connection with Formula XXXVII.

In one embodiment, the method of preparing a compound having Formula XXXVII:

comprises:

a) allowing the compound having Formula XXXVI:

XXXVI to isomerize to a compound having Formula XXXVII; and b) isolating the compound having Formula XXXVII substantially free from the compound having Formula XXXVI, and one or more other stereoisomers, wherein $R^{1a}$, $R^{1b}$, $R^{1c}$, $R^{1d}$, $R^2$, $R^3$, and $R^{32}$ have the meanings as described above in connection with Formula XXXVII.

In one embodiment, the method of preparing a compound having Formula XXXVII:

comprises:

a) dissolving a compound having Formula XXXVI:

XXXVI in a solvent or a mixture of solvents;

b) allowing the compound having Formula XXXVI to isomerize to a compound having Formula XXXVII; and c) isolating the compound having Formula XXXVII substantially free from the compound having Formula XXXVI, and one or more other stereoisomers, wherein $R^{1a}$, $R^{1b}$, $R^{1c}$, $R^{1d}$, $R^2$, $R^3$, and $R^{32}$ have the meanings as described above in connection with Formula XXXVII.

In one embodiment, the solvent is selected from the group consisting of acetonitrile, methanol, ethyl acetate, and water, or a mixture thereof.

In one embodiment, the isomerization is carried out at a pH of less than 7, e.g., at a pH of about 6, about 5, about 4, about 3, about 2, or about 1. In one embodiment, the isomerization is carried out at a pH of about 7. In one embodiment, the isomerization is carried out at a pH of greater than 7, e.g., at a pH of about 8, about 9, about 10, about 11, about 12, or about 13.

In one embodiment, the isomerization is carried out in the presence of an acid, e.g., trifluoroacetic acid or acetic acid.

In one embodiment, the isomerization is carried out in the presence of a base, e.g., NaHCO$_3$.

In one embodiment, isomerization is carried out at a temperature of about 20° C. to about 100° C., e.g., at a temperature of about 25° C. to about 70° C., e.g., at a temperature of about 45° C. to about 65° C. In one embodiment the isomerization is carried out at about room temperature, e.g., at about 25° C. In one embodiment the isomerization is carried out above room temperature, e.g., at about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C.

In one embodiment, the isomerization is carried about for a period of time between about 0.5 hours and about 2 weeks, e.g., for about 1 hour, about 3 hours, about 6 hours, about 12 hours, about 1 day, about 2 days, about 3 days, about 4 days, about 5 days, about 6 days, or about 1 week. The period of time needed for isomerization to occur may depend on a variety of factors including the chemical structure of Formula XXXVI, the solvent(s), the temperature, and/or the pH.

In one embodiment, $R^{32}$ is —$OR^{33}$.

In one embodiment $R^{32}$ is —$NR^{34a}R^{34b}$.

In one embodiment, $R^{34b}$ is hydrogen and $R^{34a}$ is selected from the group consisting of alkyl, hydroxyalkyl, hydroxycycloalkyl, optionally substituted aryl, and optionally substituted heteroaryl.

In one embodiment, $R^{34b}$ is hydrogen and $R^{34a}$ is selected from the group consisting of:

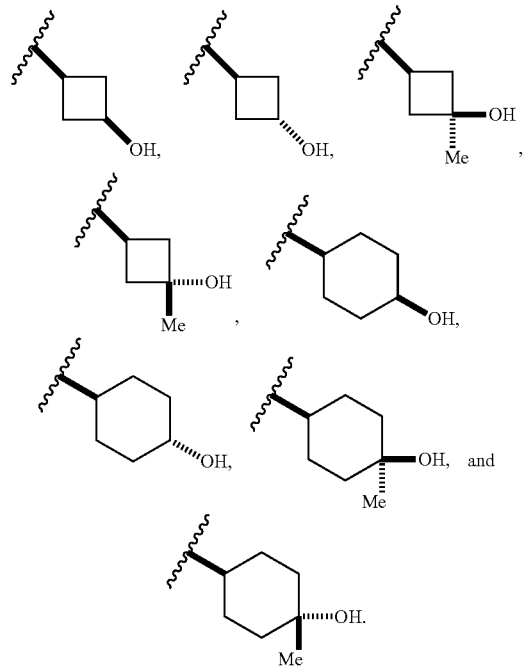

In one embodiment, the compound having Formula XXXVII is isolated as a substantially pure stereoisomer. In one embodiment, the compound having Formula XXXVII is isolated as a pure stereoisomer.

In one embodiment,
$R^{32}$ is –$NR^{34a}R^{34b}$.
$R^{34a}$ is:

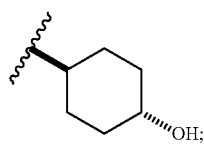 [SMILES: *[C@H]1CC[C@H](O)CC1]

$R^{34b}$ is hydrogen;
$R^2$ is:

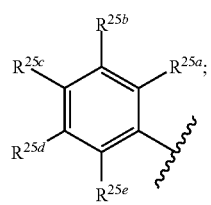

and
$R^3$ is $C_1$-$C_8$ alkyl.

In one embodiment, a method of preparing MI-77301 comprising allowing MI-773 to isomerize to MI-77301 is provided.

In one embodiment, a method of preparing MI-77301 comprising:

a) allowing MI-773 to isomerize to MI-77301; and b) isolating MI-77301 substantially free from one or more other stereoisomers, is provided.

In one embodiment, a method of preparing MI-77301 comprising:

a) dissolving MI-773 in a solvent or a mixture of solvents;

b) allowing MI-773 to isomerize to MI-77301; and c) isolating MI-77301 substantially free from one or more other stereoisomers, is provided.

The compounds and processes provided herein will be better understood in connection with the following synthetic schemes which illustrate the methods by which the compounds provided herein may be prepared. Starting materials can be obtained from commercial sources or prepared by well-established literature methods known to those of ordinary skill in the art. It will be readily apparent to one of ordinary skill in the art that the compounds defined above can be synthesized by substitution of the appropriate reagents and agents in the syntheses shown below.

Compounds of Formula Ia wherein Y is NH can be synthesized as described in Schemes 2 and 3.

Scheme 2

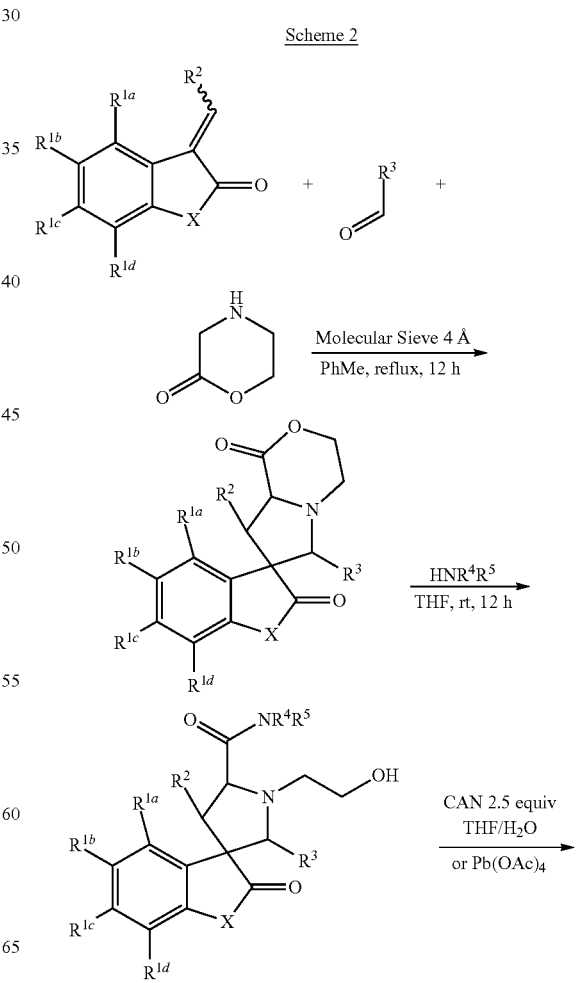

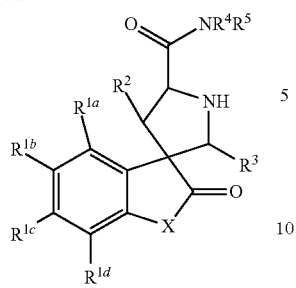

Formula Ia
(wherein Y is NH)

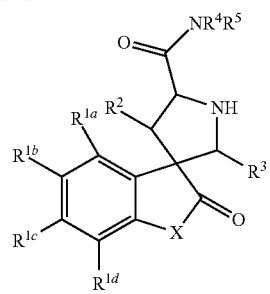

Formula Ia
(wherein Y is NH)

R = p-OMeBn—, Bn—, Me— or other alkyl group

Compounds of Formula Ia can be separated by chiral resolution methods well known in the art, e.g., chiral column chromatography, to give compounds of Formulae II-XVII. Suitable chiral columns for use in chiral resolutions include, for example, Daicel CHIRALCEL® OD-H, Daicel CHIRAKPAK® AD-H and Regis Technologies ULMO chiral columns. Other chiral resolution methods are also possible. Compounds of Formulae II-XVII can also be prepared by asymmetric synthetic methods. For example, compounds of Formula II, wherein Y is NH, can be synthesized by using a asymmetric 1,3-dipolar cycloaddition as the key step as previously described (See U.S. Pat. Nos. 7,759,383 B2 and 7,737,174 B2, and Ding et al., *J. Am. Chem. Soc.* 127:10130-10131 (2005)) (Scheme 4).

Scheme 3

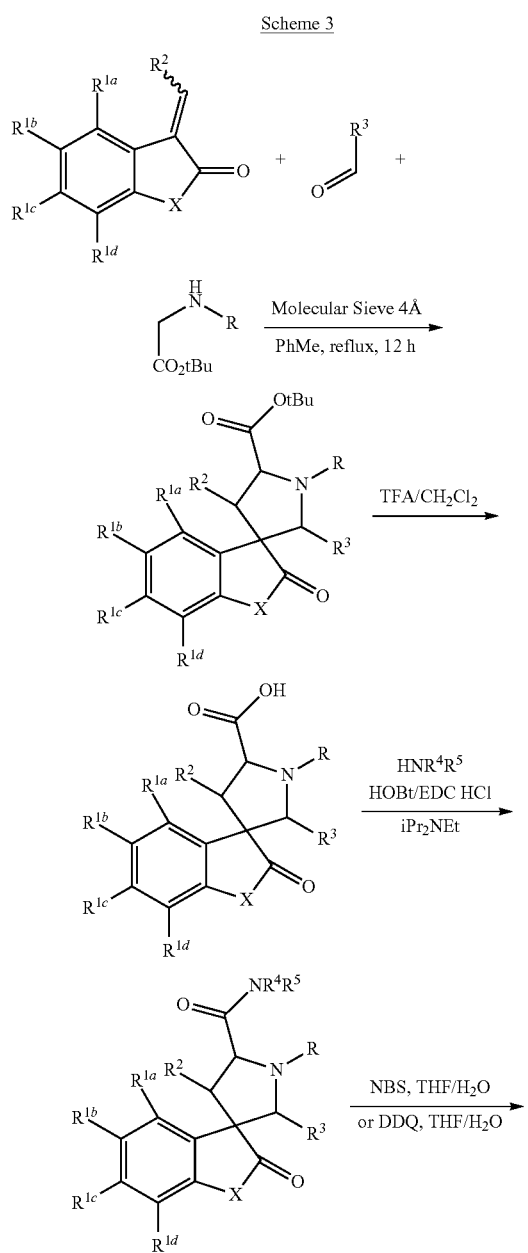

Scheme 4

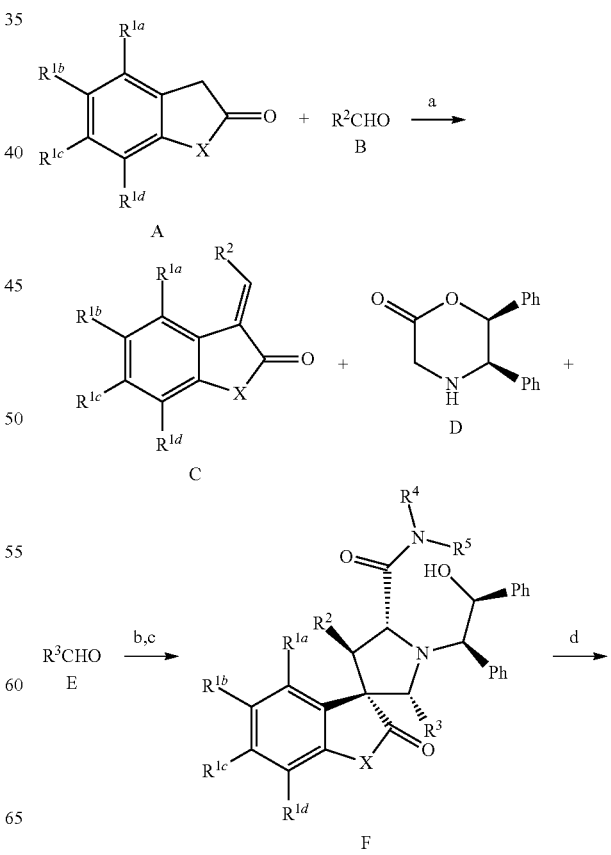

-continued

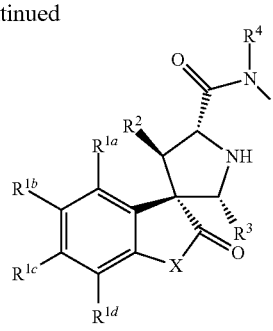

Formula II
(wherein Y = NH)

Reagents and conditions: a) CH₂Cl₂—CH₃CN, KF—Al₂O₃, microwave, or methanol, piperidine reflux; b) 4Å molecular sieves, toluene, 70° C.; c) HNR⁴R⁵, r.t.; d) Pb(OAc)₄, CH₂Cl₂—MeOH (1:1), 0° C., or ammonium cerium(IV) nitrate (CAN), CH₃CN, K₂CO₃, r.t.

Briefly, compound A reacts with aldehyde B to give C. Compound C reacts with aldehyde E and compound D to give F (a compound of Formula I wherein R″ is aralkyl). Treatment of F with Pb(OAc)₄ or CAN gives the compound of Formula II wherein Y is NH.

Compounds of Formula XII can be prepared via isomerization of compounds of Formula II. Without intending to be bound by theory, the isomerization of a compound having Formula II to a compound having Formula XII (and other isomers, including compounds having Formula VI) may involve formation of the imine intermediate shown in Scheme 5. Compounds of Formula XII may be less likely to isomerize, i.e., they may be chemically more stable, than compounds of Formula II.

Scheme 5

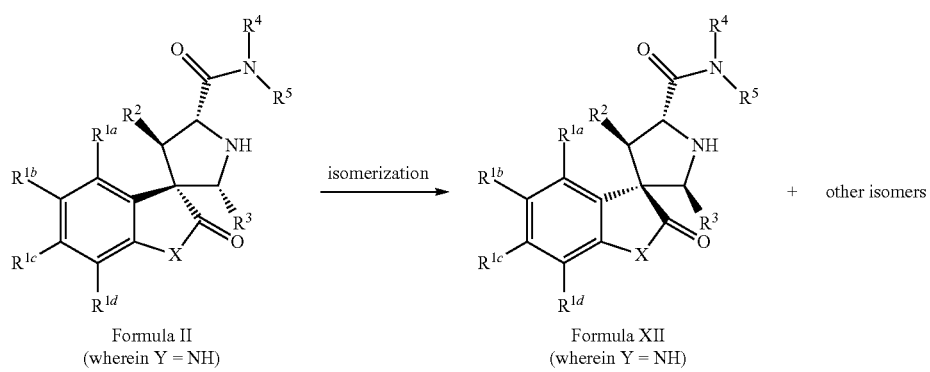

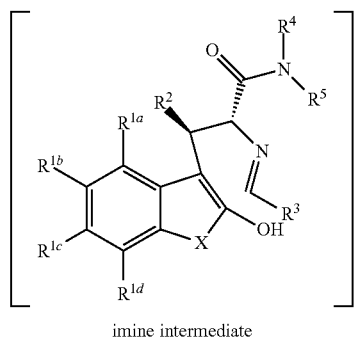

imine intermediate

Methods

In some embodiments, compounds provided herein induce cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. By inhibiting the interaction between p53 or p53-related proteins and MDM2 or MDM2-related proteins, the compounds provided herein can be used to induce apoptosis in any disorder that can be treated, ameliorated, or prevented by the induction of apoptosis. In one embodiment, the inhibitors can be used to induce apoptosis in cells comprising functional p53 or p53-related proteins.

In another embodiment, the disclosure pertains to modulating apoptosis with compounds provided herein in combination with one or more additional apoptosis-modulating agents. Examples of apoptosis-modulating agents include, but are not limited to, Fas/CD95, TRAMP, TNF R1, DR1, DR2, DR3, DR4, DR5, DR6, FADD, RIP, TNFα, Fas ligand, TRAIL, antibodies to TRAIL-R1 or TRAIL-R2, Bcl-2, p53, BAX, BAD, Aid, CAD, PI3 kinase, PP1, and caspase proteins. Other agents involved in the initiation, decision and degradation phase of apoptosis are also included. Examples of apoptosis-modulating agents include agents, the activity, presence, or change in concentration of which, can modulate apoptosis in a subject. Apoptosis-modulating agents include those which are inducers of apoptosis, such as TNF or a TNF-related ligand, particularly a TRAMP ligand, a Fas/CD95 ligand, a TNFR-1 ligand, or TRAIL.

In some embodiments, the compounds, compositions, and methods provided herein, including the methods comprising pulsatile dose administration, are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia (CLL) including B-CLL, acute myelogenous leukemia, chronic myelogenous leukemia, chronic granulocytic leukemia, acute granulocytic leukemia, hairy cell leukemia, neuroblastoma, sarcoma such as liposarcoma, malignant fibrous histiocytoma, osteosarcoma, Ewing's sarcoma, leiomyosarcoma, and rhabdomyosarcoma, Kaposi's sarcoma, polycythemia vera, essential thrombocytosis, Hodgkin's disease, non-Hodgkin's lymphoma, soft-tissue sarcomas such as lipoma, and malignant Schwannoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to other anticancer agents.

In some embodiments, the compounds, compositions, and methods provided herein, including the methods comprising pulsatile dose administration, are used to treat, ameliorate, or prevent a cancer selected from the group consisting of melanoma, lung cancer, a sarcoma, colon cancer, prostate cancer, choriocarcinoma, breast cancer, retinoblastoma, stomach carcinoma, acute myeloid leukemia, a lymphoma, multiple myeloma, and a leukemia in a patient.

In some embodiments, the compounds, compositions, and methods provided herein, including the methods comprising pulsatile dose administration, are used to treat, ameliorate, or prevent melanoma in a patient.

In some embodiments, the compounds, compositions, and methods provided herein, including the methods comprising pulsatile dose administration, are used to treat, ameliorate, or prevent liposarcoma in a patient.

In some embodiments, the compounds, compositions, and methods provided herein, including the methods comprising pulsatile dose administration, are used to treat cancers that express functional or wild type p53 or p53-related proteins. In some embodiments, the compounds, compositions, and methods provided herein are used to treat cancers that express elevated levels of MDM2 or MDM2-related proteins.

In some embodiments, the methods, compounds, and compositions provided herein, including the methods comprising pulsatile dose administration, can be used to treat a patient having a sarcoma, including, for example, liposarcoma, malignant fibrous histiocytoma, osteosarcoma, and rhabdomyosarcoma. In some embodiments, the methods, compounds, and compositions provided herein, including the methods comprising pulsatile dose administration, can be used to treat a patient having a soft tissue tumor, including, for example, Ewing's sarcoma, leiomyosarcoma, lipoma, and malignant Schwannomas. In some embodiments, the methods, compounds, and compositions provided herein, including the methods comprising pulsatile dose administration, can be used to treat a patient having lung, breast, liver, or colon cancer. In some embodiments, the methods, compounds, and compositions provided herein, including the methods comprising pulsatile dose administration, can be used to treat a patient having B-cell chronic lymphocytic leukemia and acute myeloid leukemia.

In some embodiments, infections suitable for treatment with the compounds, compositions, and methods provided herein include, but are not limited to, infections caused by viruses, bacteria, fungi, mycoplasma, prions, and the like.

In some embodiments, methods are provided, including the methods comprising pulsatile dose administration, for administering an effective amount of a compound or composition provided herein and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is an anticancer agent.

A number of suitable therapeutic or anticancer agents are contemplated for use in the methods provided herein, including the methods comprising pulsatile dose administration. Indeed, the methods provided herein can include but are not limited to, administration of numerous therapeutic agents such as: agents that induce apoptosis; polynucleotides (e.g., anti-sense, ribozymes, siRNA); polypeptides (e.g., enzymes and antibodies); biological mimetics (e.g., gossypol or BH3 mimetics); agents that bind (e.g., oligomerize or complex) with a Bcl-2 family protein such as Bax; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors; agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-κB modulators; anti-CDK compounds; HDAC inhibitors; and the like. Numerous other examples of therapeutic agents such as chemotherapeutic compounds and anticancer therapies suitable for co-administration with the disclosed compounds are known to those skilled in the art.

In certain embodiments, anticancer agents comprise agents that induce or stimulate apoptosis. Agents that induce or stimulate apoptosis include, for example, agents that interact with or modify DNA, such as by intercalating, cross-linking, alkylating, or otherwise damaging or chemically modifying DNA. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor. Additional anticancer agents include: vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods provided herein, including the methods comprising pulsatile dose administration, include one or more compounds provided herein and at least one anti-hyperproliferative or anti-neoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyl-triazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present disclosure include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present disclosure. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | |
|---|---|
| Aldesleukin | Proleukin |
| (des-alanyl-1, serine-125 human interleukin-2) | |
| Alemtuzumab | Campath |
| (IgG1κ anti CD52 antibody) | |
| Alitretinoin | Panretin |
| (9-cis-retinoic acid) | |

TABLE 1-continued

| | |
|---|---|
| Allopurinol<br>(1,5-dihydro-4 H-pyrazolo[3,4-d]pyrimidin-4-one monosodium salt) | Zyloprim |
| Altretamine<br>(N,N,N',N',N'',N''-hexamethyl-1,3,5-triazine-2,4,6-triamine) | Hexalen |
| Amifostine<br>(ethanethiol, 2-[(3-aminopropyl)amino]-, dihydrogen phosphate (ester)) | Ethyol |
| Anastrozole<br>(1,3-Benzenediacetonitrile,a,a,a',a'-tetramethyl-5-(1H-1,2,4-triazol-1-ylmethyl)) | Arimidex |
| Arsenic trioxide | Trisenox |
| Asparaginase<br>(L-asparagine amidohydrolase, type EC-2) | Elspar |
| BCG Live<br>(lyophilized preparation of an attenuated strain of *Mycobacterium bovis* (*Bacillus Calmette-Gukin* [BCG], substrain Montreal) | TICE BCG |
| bexarotene capsules<br>(4-[1-(5,6,7,8-tetrahydro-3,5,5,8,8-pentamethyl-2-napthalenyl) ethenyl] benzoic acid) | Targretin |
| bexarotene gel | Targretin |
| Bleomycin<br>(cytotoxic glycopeptide antibiotics produced by *Streptomyces verticillus*; bleomycin $A_2$ and bleomycin $B_2$) | Blenoxane |
| Capecitabine<br>(5'-deoxy-5-fluoro-N-[(pentyloxy)carbonyl]-cytidine) | Xeloda |
| Carboplatin<br>(platinum, diammine [1,1-cyclobutanedicarboxylato(2-)-0,0']-,(SP-4-2)) | Paraplatin |
| Carmustine<br>(1,3-bis(2-chloroethyl)-1-nitrosourea) | BCNU, BiCNU |
| Carmustine with Polifeprosan 20 Implant | Gliadel Wafer |
| Celecoxib<br>(as 4-[5-(4-methylphenyl)-3-(trifluoromethyl)-1H-pyrazol-1-yl] benzenesulfonamide) | Celebrex |
| Chlorambucil<br>(4-[bis(2chlorethyl)amino]benzenebutanoic acid) | Leukeran |
| Cisplatin<br>($PtCl_2H_6N_2$) | Platinol |
| Cladribine<br>(2-chloro-2'-deoxy-b-D-adenosine) | Leustatin, 2-CdA |
| Cyclophosphamide<br>(2-[bis(2-chloroethyl)amino] tetrahydro-2H-13,2-oxazaphosphorine 2-oxide monohydrate) | Cytoxan, Neosar |
| Cytarabine<br>(1-b-D-Arabinofuranosylcytosine, $C_9H_{13}N_3O_5$) | Cytosar-U |
| cytarabine liposomal | DepoCyt |
| Dacarbazine<br>(5-(3,3-dimethyl-1-triazeno)-imidazole-4-carboxamide (DTIC)) | DTIC-Dome |
| Dactinomycin, actinomycin D<br>(actinomycin produced by *Streptomyces parvullus*, $C_{62}H_{86}N_{12}O_{16}$) | Cosmegen |
| Darbepoetin alfa<br>(recombinant peptide) | Aranesp |
| daunorubicin liposomal<br>((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome |
| Daunorubicin HCl, daunomycin<br>((1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine |
| Denileukin diftitox<br>(recombinant peptide) | Ontak |
| Dexrazoxane<br>((S)-4,4'-(1-methyl-1,2-ethanediyl)bis-2,6-piperazinedione) | Zinecard |
| Docetaxel<br>((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere |
| Doxorubicin HCl<br>(8S,10S)-10-[(3-amino-2,3,6-trideoxy-a-L-lyxo-hexopyranosyl)oxy]-8-glycolyl-7,8,9,10-tetrahydro-6,8,11- | Adriamycin, Rubex |

TABLE 1-continued

| | |
|---|---|
| trihydroxy-1-methoxy-5,12-naphthacenedione hydrochloride) | |
| doxorubicin | Adriamycin PFS Intravenous injection |
| doxorubicin liposomal | Doxil |
| dromostanolone propionate (17b-Hydroxy-2a-methyl-5a-androstan-3-one propionate) | Dromostanolone |
| dromostanolone propionate | Masterone injection |
| Elliott's B Solution | Elliott's B Solution |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence |
| Epoetin alfa (recombinant peptide) | Epogen |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt |
| Etoposide phosphate (4'-Demethylepipodophyllotoxin 9-[4,6-O-(R)-ethylidene-(beta)-D-glucopyranoside], 4'-(dihydrogen phosphate)) | Etopophos |
| etoposide, VP-16 (4'-demethylepipodophyllotoxin 9-[4,6-0-(R)-ethylidene-(beta)-D-glucopyranoside]) | Vepesid |
| Exemestane (6-methylenandrosta-1,4-diene-3,17-dione) | Aromasin |
| Filgrastim (r-metHuG-CSF) | Neupogen |
| floxuridine (intraarterial) (2'-deoxy-5-fluorouridine) | FUDR |
| Fludarabine (fluorinated nucleotide analog of the antiviral agent vidarabine, 9-b-D-arabinofuranosyladenine (ara-A)) | Fludara |
| Fluorouracil, 5-FU (5-fluoro-2,4(1H,3H)-pyrimidinedione) | Adrucil |
| Fulvestrant (7-alpha-[9-(4,4,5,5,5-penta fluoropentylsulphinyl) nonyl]estra-1,3,5-(10)-triene-3,17-beta-diol) | Faslodex |
| Gemcitabine (2'-deoxy-2',2'-difluorocytidine monohydrochloride (b-isomer)) | Gemzar |
| Gemtuzumab Ozogamicin (anti-CD33 hP67.6) | Mylotarg |
| Goserelin acetate | Zoladex Implant |
| Hydroxyurea | Hydrea |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin |
| Ifosfamide (3-(2-chloroethyl)-2-[(2-chloroethyl)amino]tetrahydro-2H-1,3,2-oxazaphosphorine 2-oxide) | IFEX |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec |
| Interferon alfa-2a (recombinant peptide) | Roferon-A |
| Interferon alfa-2b (recombinant peptide) | Intron A (Lyophilized Betaseron) |
| Irinotecan HCl ((4S)-4,11-diethyl-4-hydroxy-9-[(4-piperi-dinopiperidino)carbonyloxy]-1H-pyrano[3',4': 6,7] indolizino[1,2-b] quinoline-3,14(4H,12H) dione hydrochloride trihydrate) | Camptosar |
| Letrozole (4,4'-(1H-1,2,4-Triazol-1-ylmethylene) dibenzonitrile) | Femara |

TABLE 1-continued

| | |
|---|---|
| Leucovorin<br>(L-Glutamic acid, N[4[[(2amino-5-formyll,4,5,6,7,8 -hexahydro4oxo6-pteridinyl)methyl]amino]benzoyl], calcium salt (1:1)) | Wellcovorin, Leucovorin |
| Levamisole HCl<br>((−)-(S)-2,3,5,6-tetrahydro-6-phenylimidazo [2,1-b] thiazole monohydrochloride $C_{11}H_{12}N_2S \cdot HCl$) | Ergamisol |
| Lomustine<br>(1-(2-chloro-ethyl)-3-cyclohexyl-1-nitrosourea) | CeeNU |
| Meclorethamine, nitrogen mustard<br>(2-chloro-N-(2-chloroethyl)-N-methylethanamine hydrochloride) | Mustargen |
| Megestrol acetate<br>17α(acetyloxy)-6-methylpregna-4,6-diene-3,20-dione | Megace |
| Melphalan, L-PAM<br>(4-[bis(2-chloroethyl) amino]-L-phenylalanine) | Alkeran |
| Mercaptopurine, 6-MP<br>(1,7-dihydro-6 H-purine-6-thione monohydrate) | Purinethol |
| Mesna<br>(sodium 2-mercaptoethane sulfonate) | Mesnex |
| Methotrexate<br>(N-[4-[[(2,4-diamino-6-pteridinyl)methyl]methylamino]benzoyl]-L-glutamic acid) | Methotrexate |
| Methoxsalen<br>(9-methoxy-7H-furo[3,2-g][1]-benzopyran-7-one) | Uvadex |
| Mitomycin C | Mutamycin |
| mitomycin C | Mitozytrex |
| Mitotane<br>(1,1-dichloro-2-(o-chlorophenyl)-2-(p-chlorophenyl) ethane) | Lysodren |
| Mitoxantrone<br>(1,4-dihydroxy-5,8-bis[[2-[(2-hydroxyethyl)amino]ethyl]amino]-9,10-anthracenedione dihydrochloride) | Novantrone |
| Nandrolone phenpropionate | Durabolin-50 |
| Nofetumomab | Verluma |
| Oprelvekin<br>(IL-11) | Neumega |
| Oxaliplatin<br>(cis-[(1R,2R)-1,2-cyclohexanediamine-N,N'] [oxalato(2-)-O,O'] platinum) | Eloxatin |
| Paclitaxel<br>(5β,20-Epoxy-1,2a,4,7β,10β,13a-hexahydroxytax-11-en-9-one 4,10-diacetate 2-benzoate 13-ester with (2R,3 S)-N-benzoyl-3-phenylisoserine) | TAXOL |
| Pamidronate<br>(phosphonic acid (3-amino-1-hydroxypropylidene) bis-, disodium salt, pentahydrate, (APD)) | Aredia |
| Pegademase<br>((monomethoxypolyethylene glycol succinimidyl) 11-17-adenosine deaminase) | Adagen (Pegademase Bovine) |
| Pegaspargase<br>(monomethoxypolyethylene glycol succinimidyl L-asparaginase) | Oncaspar |
| Pegfilgrastim<br>(covalent conjugate of recombinant methionyl human G-CSF (Filgrastim) and monomethoxypolyethylene glycol) | Neulasta |
| Pentostatin | Nipent |
| Pipobroman | Vercyte |
| Plicamycin, Mithramycin<br>(antibiotic produced by *Streptomyces plicatus*) | Mithracin |
| Porfimer sodium | Photofrin |
| Procarbazine<br>(N-isopropyl-μ-(2-methylhydrazino)-p-toluamide monohydrochloride) | Matulane |
| Quinacrine<br>(6-chloro-9-(1-methyl-4-diethyl-amine) butylamino-2-methoxyacridine) | Atabrine |
| Rasburicase<br>(recombinant peptide) | Elitek |
| Rituximab<br>(recombinant anti-CD20 antibody) | Rituxan |
| Sargramostim<br>(recombinant peptide) | Prokine |
| Streptozocin<br>(streptozocin 2-deoxy-2-[[[(methylnitrosoamino)carbonyl]amino]-a(and b)-D-glucopyranose and 220 mg citric acid anhydrous) | Zanosar |
| Talc<br>($Mg_3Si_4O_{10}(OH)_2$) | Sclerosol |

TABLE 1-continued

| | |
|---|---|
| Tamoxifen<br>((Z)2-[4-(1,2-diphenyl-1-butenyl) phenoxy]-N,N-<br>dimethylethanamine 2-hydroxy-1,2,3-<br>propanetricarboxylate (1:1)) | Nolvadex |
| Temozolomide<br>(3,4-dihydro-3-methyl-4-oxoimidazo[5,1-d]-as-tetrazine-8-<br>carboxamide) | Temodar |
| teniposide, VM-26<br>(4'-demethylepipodophyllotoxin9-[4,6-0-(R)-2-<br>thenylidene-(beta)-D-glucopyranoside]) | Vumon |
| Testolactone<br>(13-hydroxy-3-oxo-13,17-secoandrosta-1,4-dien-17-oic<br>acid [dgr]-lactone) | Teslac |
| Thioguanine, 6-TG<br>(2-amino-1,7-dihydro-6 H-purine-6-thione) | Thioguanine |
| Thiotepa<br>(Aziridine, 1,1',1''-phosphinothioylidynetris-, or Tris (1-<br>aziridinyl) phosphine sulfide) | Thioplex |
| Topotecan HCl<br>((S)-10-[(dimethylamino)methyl]-4-ethyl-4,9-dihydroxy-<br>1H-pyrano[3', 4': 6,7] indolizino [1,2-b] quinoline-3,14-<br>(4H,12H)-dione monohydrochloride) | Hycamtin |
| Toremifene<br>(2-(p-[(Z)-4-chloro-1,2-diphenyl-1-butenyl]-phenoxy)-N,N-<br>dimethylethylamine citrate (1:1)) | Fareston |
| Tositumomab, I 131 Tositumomab<br>(recombinant murine immunotherapeutic monoclonal IgG$_{2a}$<br>lambda anti-CD20 antibody (I 131 is a<br>radioimmunotherapeutic antibody)) | Bexxar |
| Trastuzumab<br>(recombinant monoclonal IgG$_1$ kappa anti-HER2 antibody) | Herceptin |
| Tretinoin, ATRA<br>(all-trans retinoic acid) | Vesanoid |
| Uracil Mustard | Uracil Mustard Capsules |
| Valrubicin, N-trifluoroacetyladriamycin-14-valerate<br>((2S-cis)-2-[1,2,3,4,6,11-hexahydro-2,5,12-trihydroxy-7<br>methoxy-6,11-dioxo-[[4 2,3,6-trideoxy-3-[(trifluoroacetyl)-<br>amino-α-L-lyxo-hexopyranosyl]oxyl]-2-naphthacenyl]-2-<br>oxoethyl pentanoate) | Valstar |
| Vinblastine, Leurocristine($C_{46}H_{56}N_4O_{10} \cdot H_2SO_4$) | Velban |
| Vincristine ($C_{46}H_{56}N_4O_{10} \cdot H_2SO_4$) | Oncovin |
| Vinorelbine<br>(3',4'-didehydro-4'-deoxy-C'-norvincaleukoblastine [R-<br>(R*,R*)-2,3-dihydroxybutanedioate (1:2)(salt)]) | Navelbine |
| Zoledronate, Zoledronic acid<br>((1-Hydroxy-2-imidazol-1-yl-phosphonoethyl) phosphonic<br>acid monohydrate) | Zometa |

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724,714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14. 18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, ML2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9,06-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmacological Basis of Therapeutics" tenth edition, Eds. Hardman et al., 2002.

In some embodiments, methods provided herein, including the methods comprising pulsatile dose administration, comprise administering one or more compounds provided herein with radiation therapy. The methods provided herein are not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tirapazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the methods provided herein.

Antimicrobial therapeutic agents may also be used as therapeutic agents in combination with the compounds provided herein. Any agent that can kill, inhibit, or otherwise attenuate the function of microbial organisms may be used, as well as any agent contemplated to have such activities. Antimicrobial agents include, but are not limited to, natural and synthetic antibiotics, antibodies, inhibitory proteins (e.g., defensins), antisense nucleic acids, membrane disruptive agents and the like, used alone or in combination. Indeed, any type of antibiotic may be used including, but not limited to, antibacterial agents, antiviral agents, antifungal agents, and the like.

In some embodiments of the methods provided herein, one or more compounds provided herein and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

In some embodiments, compositions provided herein comprise one or more of the compounds provided herein in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds provided herein may be administered as part of a pharmaceutical preparation or composition. In some embodiments, the pharmaceutical preparation or composition can include one or more pharmaceutically acceptable carriers, excipients, and/or auxiliaries. In some embodiments, the one or more carriers, excipients, and auxiliaries facilitate processing of the compound into a preparation or composition which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the one or more carriers, excipients, and/or auxiliaries.

The pharmaceutical compositions of provided herein may be administered to any patient which may experience the beneficial effects of the compounds provided herein. Foremost among such patients are mammals, e.g., humans, although the methods and compositions provided herein are not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations provided herein are manufactured by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries can be suitable flow-regulating agents and lubricants. Suitable auxiliaries include, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension including, for example, sodium carboxymethyl cellulose, sorbitol, and/or dextran. Optionally, the suspension may also contain stabilizers.

The topical compositions provided herein are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

In one embodiment, the present disclosure relates to methods of treating a patient with a hyperproliferative disease, e.g., cancer, the methods comprising pulsatile administration to the patient one or more compounds or compositions provided herein, or pharmaceutically acceptable salts, solvates, or prodrugs thereof.

The following examples are illustrative, but not limiting, of the compounds, compositions, and methods provided herein. Other suitable modifications and adaptations of the variety of conditions and parameters normally encountered in clinical therapy and which are obvious to those skilled in the art are within the spirit and scope of the methods, compounds, and compositions provided herein.

In certain aspects, the following embodiments are provided:

Embodiment I

A method of treating, preventing, or ameliorating cancer in a patient, wherein the method comprises pulsatile administration to the patient a therapeutically effective amount of a compound having Formula XII:

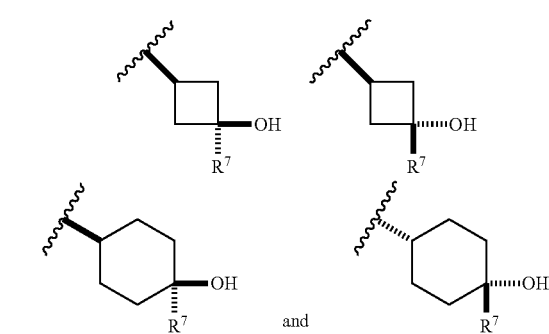

or a pharmaceutically acceptable salt thereof,
wherein:
$R^{1a}$, $R^{1b}$, $R^{1c}$, and $R^{1d}$ are each independently selected from the group consisting of hydrogen, fluoro, and chloro;
$R^2$ is:

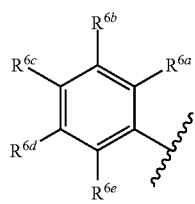

wherein:
$R^{6a}$, $R^{6b}$, $R^{6c}$, $R^{6d}$, and $R^{6e}$ are each independently selected from the group consisting of hydrogen, fluoro, and chloro;
$R^3$ is optionally substituted $C_1$-$C_8$ alkyl;
$R^4$ is selected from the group consisting of hydrogen and optionally substituted $C_1$-$C_6$ alkyl;
$R^5$ is selected from the group consisting of:

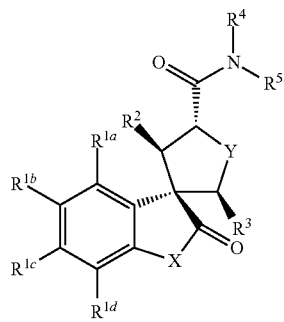

and wherein:
$R^7$ is selected from the group consisting of hydrogen and optionally substituted $C_1$-$C_4$ alkyl;
X is selected from the group consisting of O, S, and NR';
Y is selected from the group consisting of O, S, and NR";
R' is selected from the group consisting of hydrogen and optionally substituted $C_1$-$C_4$ alkyl; and
R" is selected from the group consisting of hydrogen and optionally substituted $C_1$-$C_4$ alkyl,
wherein the compound is substantially free of one or more other stereoisomers.

Embodiment II

The method of Embodiment I, wherein $R^4$ is hydrogen, or a pharmaceutically acceptable salt thereof.

Embodiment III

The method of Embodiment I, wherein X is NH, or a pharmaceutically acceptable salt thereof.

Embodiment IV

The method of Embodiment I, wherein Y is NH, or a pharmaceutically acceptable salt thereof.

Embodiment V

The method of Embodiment I, wherein $R^3$ is —$CH_2C(CH_3)_3$, or a pharmaceutically acceptable salt thereof.

Embodiment VI

The method of Embodiment I, wherein $R^5$ is selected from the group consisting of:

105

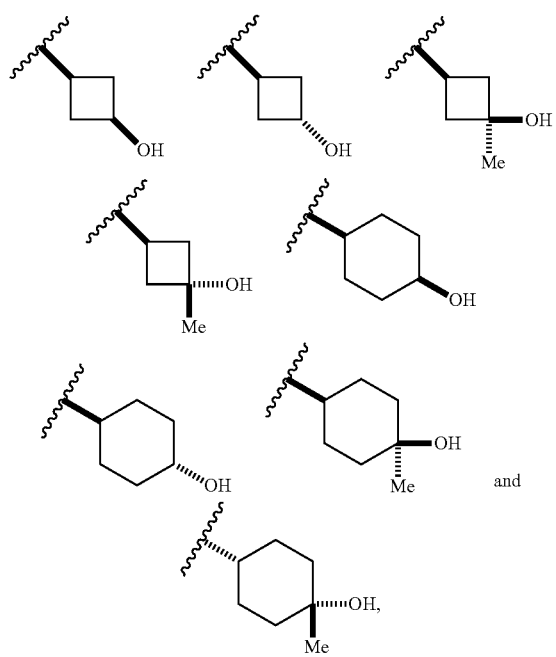

or a pharmaceutically acceptable salt thereof.

Embodiment VII

The method of Embodiment I, wherein:
$R^{1a}$ is hydrogen;
$R^{1b}$, $R^{1c}$, and $R^{1d}$ are each independently selected from the group consisting of hydrogen, fluoro, and chloro;
$R^3$ is $C_4$-$C_8$ alkyl;
$R^4$ is hydrogen;
$R^5$ is selected from the group consisting of:

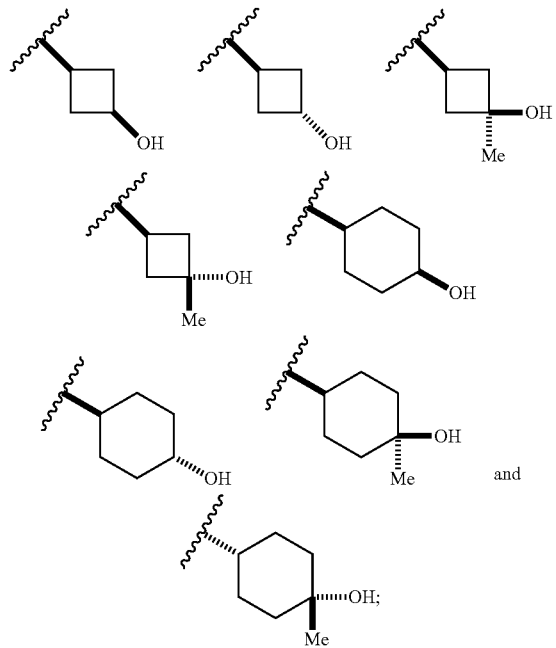

and
X and Y are NH;
or a pharmaceutically acceptable salt thereof.

106

Embodiment VIII

The method of Embodiments VI or VII, wherein $R^5$ is selected from the group consisting of:

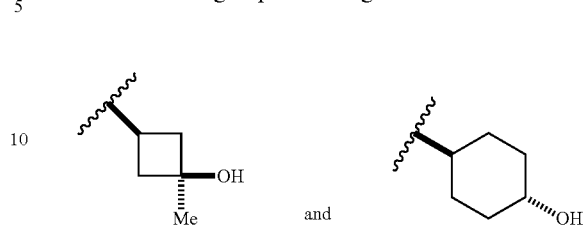

or a pharmaceutically acceptable salt thereof.

Embodiment IX

The method of Embodiment I, wherein the compound of Formula XII is selected from the group consisting of:

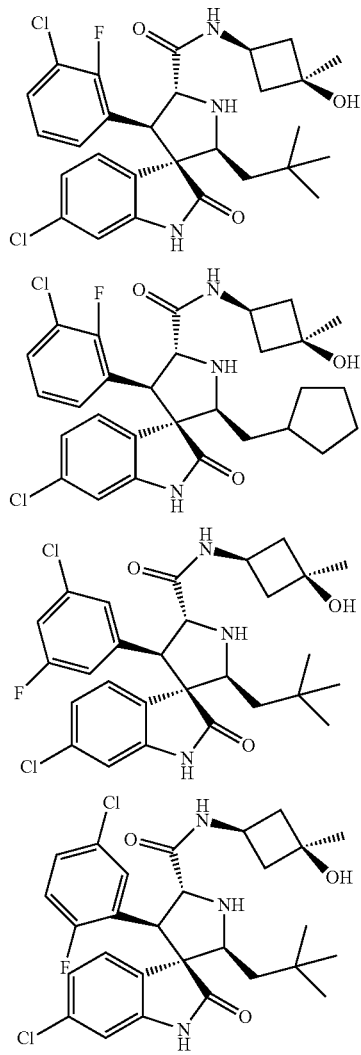

107
-continued
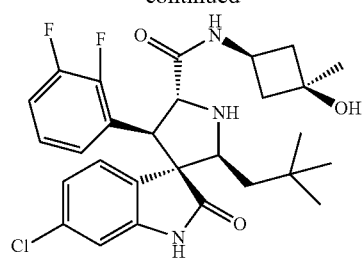
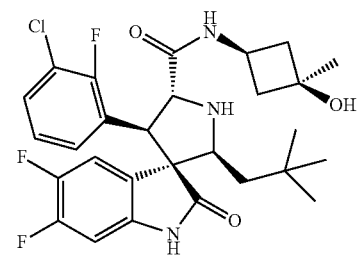
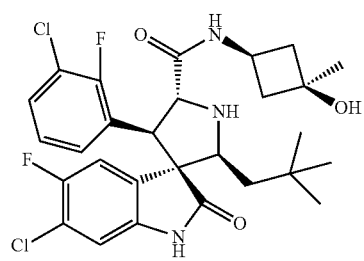
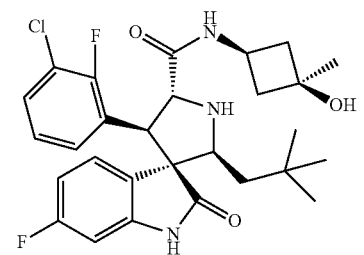
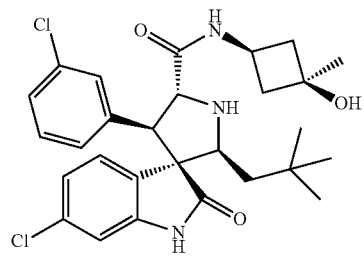
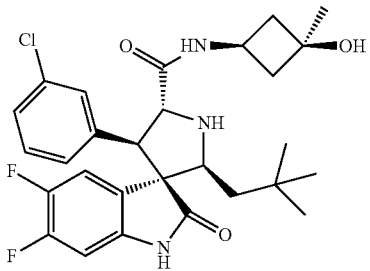
108
-continued
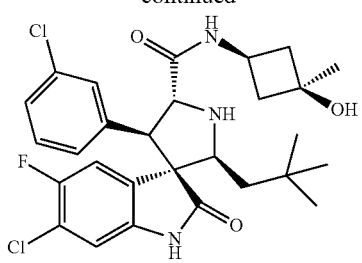
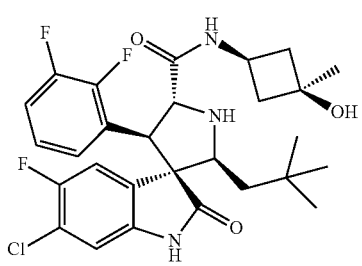
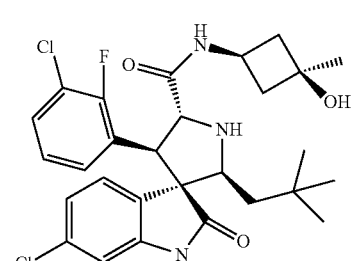
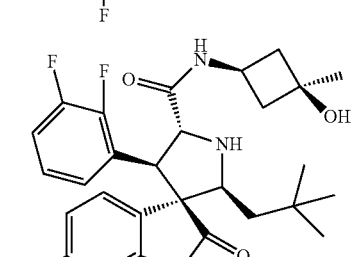
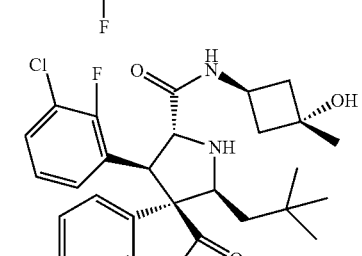
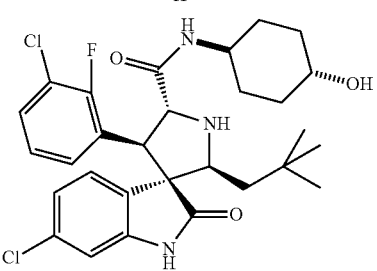

-continued
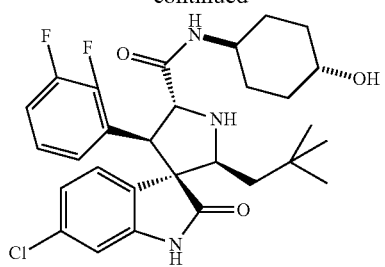
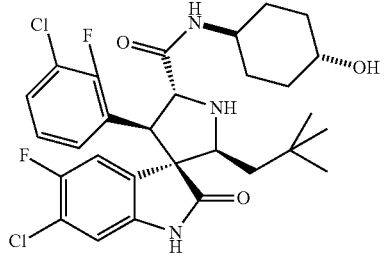
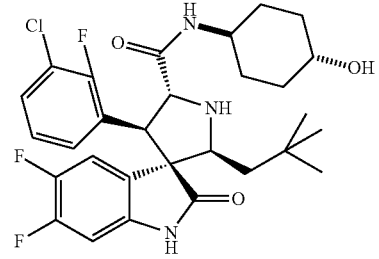
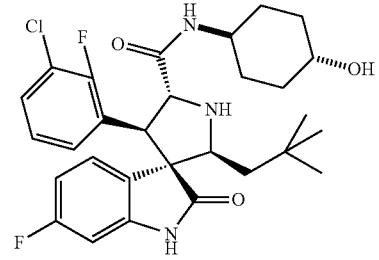
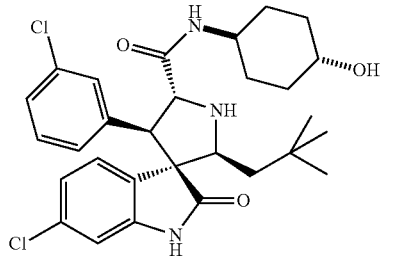
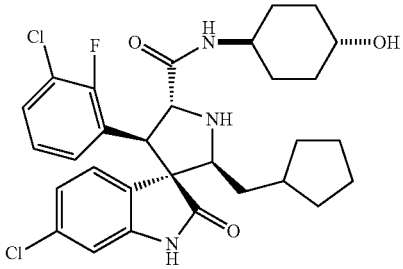
-continued
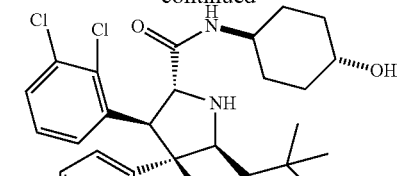
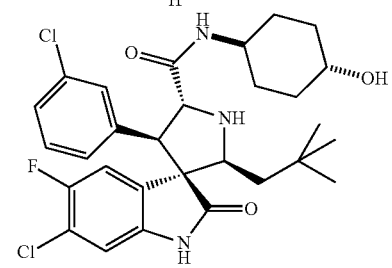
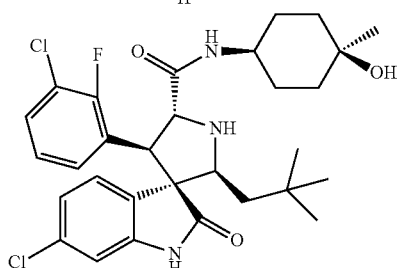
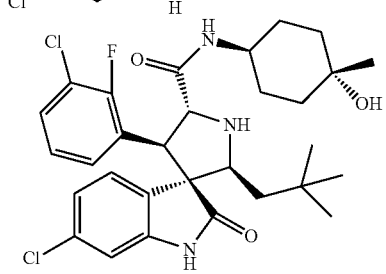
or a pharmaceutically acceptable salt thereof.
Embodiment X
The method of Embodiment I, wherein the compound of Formula XII is:
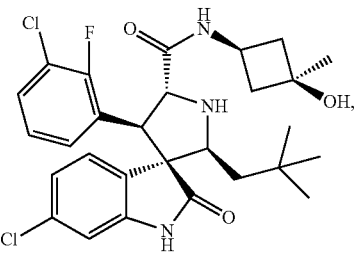 [SMILES: CC(C)(C)C[C@@H]1N[C@@H](C(=O)N[C@H]2C[C@@](C)(O)C2)[C@H](c2cccc(Cl)c2F)[C@]12C(=O)Nc1cc(Cl)ccc12]
or a pharmaceutically acceptable salt thereof.
Embodiment XI
The method of Embodiment I, wherein the compound of Formula XII is:

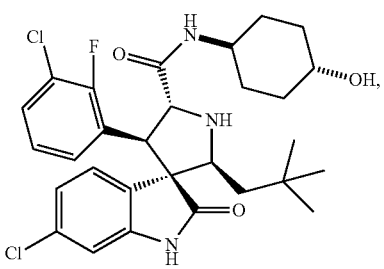

or a pharmaceutically acceptable salt thereof.

Embodiment XII

The method of any one of Embodiments IX-XI, wherein the compound is substantially free of other stereoisomers, or a pharmaceutically acceptable salt thereof.

Embodiment XIII

The method of Embodiment XII, wherein the compound is a substantially pure stereoisomer, or a pharmaceutically acceptable salt thereof.

Embodiment XIV

The method of any one of Embodiments I-XIII, wherein the compound is administered to the patient one day a week, one day every two weeks, one day every three weeks, or one day every four weeks.

Embodiment XV

The method of any one of Embodiments I-XIV, wherein cells of the hyperproliferative disease express functional p53.

Embodiment XVI

The method of any one of Embodiments I-XV, wherein the hyperproliferative disease is cancer.

Embodiment XVII

The method of Embodiment XVI, further comprising administering to the patient one or more anticancer agents.

Embodiment XVIII

The method of Embodiment XVII, wherein the anticancer agent is a chemotherapeutic agent.

Embodiment XIX

The method of Embodiment XVIII, wherein the anticancer agent is radiation therapy.

Embodiment XX

A kit comprising a compound having Formula XII:

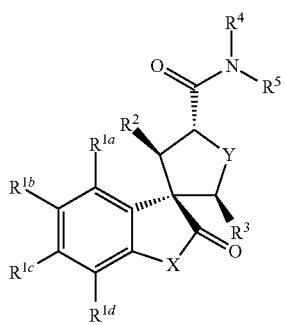

XII or a pharmaceutically acceptable salt thereof,
wherein:
$R^{1a}$, $R^{1b}$, $R^{1c}$ and $R^{1d}$ are each independently selected from the group consisting of hydrogen, fluoro, and chloro;
$R^2$ is:

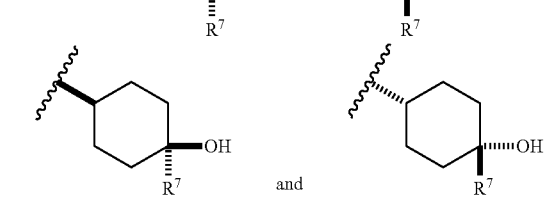

wherein:
$R^{6a}$, $R^{6b}$, $R^{6c}$, $R^{6d}$, and $R^{6e}$ are each independently selected from the group consisting of hydrogen, fluoro, and chloro;
$R^3$ is optionally substituted $C_1$-$C_8$ alkyl;
$R^4$ is selected from the group consisting of hydrogen and optionally substituted $C_1$-$C_6$ alkyl;
$R^5$ is selected from the group consisting of:

wherein:
$R^7$ is selected from the group consisting of hydrogen and optionally substituted $C_1$-$C_4$ alkyl;
X is selected from the group consisting of O, S, and NR';
Y is selected from the group consisting of O, S, and NR";
R' is selected from the group consisting of hydrogen and optionally substituted $C_1$-$C_4$ alkyl; and
R" is selected from the group consisting of hydrogen and optionally substituted $C_1$-$C_4$ alkyl, wherein the compound is substantially free of one or more other stereoisomers, and instructions for pulsatile administration of the compound to a patient having a hyperproliferative disease.

Embodiment XXI

The kit of Embodiment XX, wherein the hyperproliferative disease is cancer.

Embodiment XXII

The kit of Embodiment XXI, further comprising one or more anticancer agents.

Embodiment XXIII

The kit of Embodiment XXII, wherein the instructions direct co-administration of the compound together with the one or more anticancer agents.

In certain aspects, the following particular embodiments are provided herein:

Embodiment XXIV

A method of treating, ameliorating, or preventing melanoma in a patient comprising administering to the patient a therapeutically effective amount of a compound having Formula XII:

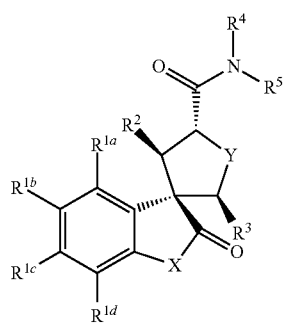

XII wherein:
$R^{1a}$, $R^{1b}$, $R^{1c}$, and $R^{1d}$ are each independently selected from the group consisting of hydrogen, fluoro, and chloro;
$R^2$ is:

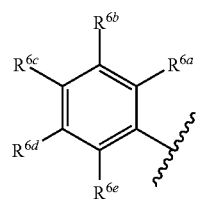

wherein:
$R^{6a}$, $R^{6b}$, $R^{6c}$, $R^{6d}$, and $R^{6e}$ are each independently selected from the group consisting of hydrogen, fluoro, and chloro;
$R^3$ is optionally substituted $C_1$-$C_8$ alkyl;
$R^4$ is selected from the group consisting of hydrogen and optionally substituted $C_1$-$C_6$ alkyl;

$R^5$ is selected from the group consisting of:

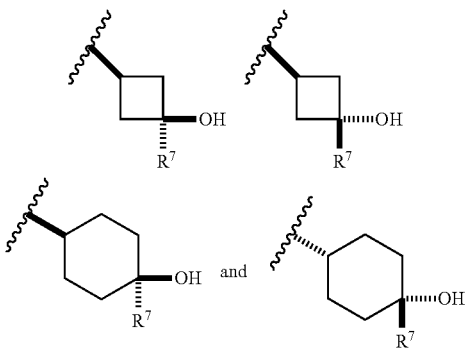

wherein:
$R^7$ is selected from the group consisting of hydrogen and optionally substituted $C_1$-$C_4$ alkyl;
X is selected from the group consisting of O, S, and NR';
Y is selected from the group consisting of O, S, and NR";
R' is selected from the group consisting of hydrogen and optionally substituted $C_1$-$C_4$ alkyl; and
R" is selected from the group consisting of hydrogen and optionally substituted $C_1$-$C_4$ alkyl,
wherein the compound is substantially free of one or more other stereoisomers,
or a pharmaceutically acceptable salt thereof.

Embodiment XXV

The method of Embodiment XXIV, further comprising administering to the patient one or more additional anticancer agents.

Embodiment XXVI

The method of Embodiment XXV, wherein the anticancer agent is a chemotherapeutic agent.

Embodiment XXVII

The method of Embodiment XXVI, wherein the anticancer agent is radiation therapy.

Embodiment XXVIII

The method of any one of Embodiments XXIV-XXVII, wherein the melanoma is characterized by resistance to conventional cancer therapy.

Embodiment XXIX

The method of any one of Embodiments XXIV-XXVIII, wherein the melanoma expresses wild-type p53 protein.

Embodiment XXX

The method of any one of Embodiments XXIV-XXIX, wherein the compound of Formula XII is:

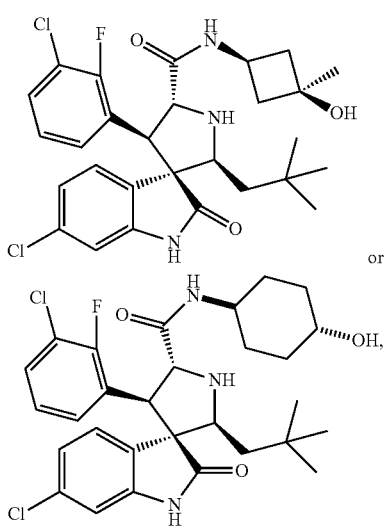

or a pharmaceutically acceptable salt thereof.

Embodiment XXXI

A kit comprising a compound having Formula XII:

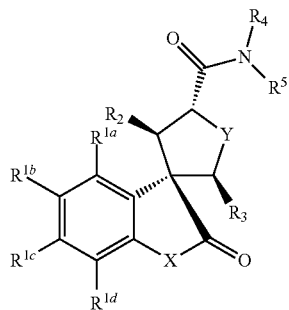

XII wherein:
$R^{1a}$, $R^{1b}$, $R^{1c}$, and $R^{1d}$ are each independently selected from the group consisting of hydrogen, fluoro, and chloro;
$R^2$ is:

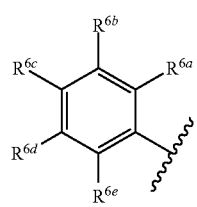

wherein:
$R^{6a}$, $R^{6b}$, $R^{6c}$, $R^{6d}$, and $R^{6e}$ are each independently selected from the group consisting of hydrogen, fluoro, and chloro;
$R^3$ is optionally substituted $C_1$-$C_8$ alkyl;
$R^4$ is selected from the group consisting of hydrogen and optionally substituted $C_1$-$C_6$ alkyl;

$R^5$ is selected from the group consisting of:

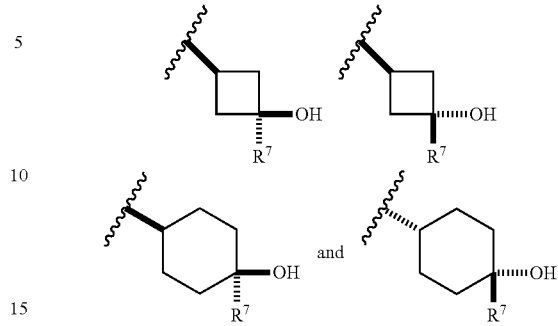

and wherein:
$R^7$ is selected from the group consisting of hydrogen and optionally substituted $C_1$-$C_4$ alkyl;
X is selected from the group consisting of O, S, and NR';
Y is selected from the group consisting of O, S, and NR'';
R' is selected from the group consisting of hydrogen and optionally substituted $C_1$-$C_4$ alkyl; and
R'' is selected from the group consisting of hydrogen and optionally substituted $C_1$-$C_4$ alkyl,
wherein the compound is substantially free of one or more other stereoisomers,
or a pharmaceutically acceptable salt thereof, and instructions for administering the compound to a patient having melanoma.

Embodiment XXXII

The kit of Embodiment XXXI, further comprising one or more additional anticancer agents.

Embodiment XXXIII

The kit of Embodiment XXXI, wherein the instructions direct co-administration of the compound together with an additional anticancer agent.

In certain aspects, the following particular embodiments are provided herein:

Embodiment XXXIV

A compound having Formulae XII:

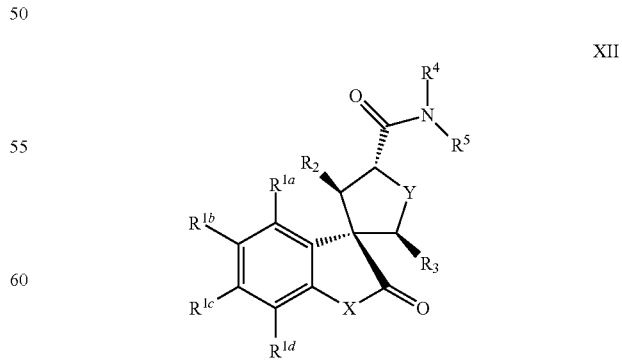

XII wherein:
$R^{1a}$, $R^{1b}$, $R^{1c}$, and $R^{1d}$ are each independently selected from the group consisting of hydrogen, fluoro, and chloro;

$R^2$ is:

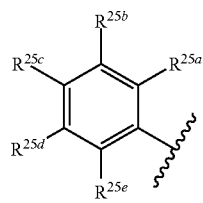

wherein:
$R^{25a}$, $R^{25b}$, $R^{25c}$, $R^{25d}$, and $R^{25e}$ are each independently selected from the group consisting of hydrogen, fluoro, and chloro;
$R^3$ is optionally substituted $C_1$-$C_8$ alkyl;
$R^4$ is selected from the group consisting of hydrogen and optionally substituted $C_1$-$C_6$ alkyl;
$R^5$ is selected from the group consisting of:

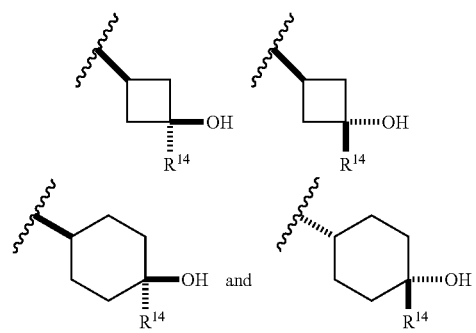

wherein:
$R^{14}$ is selected from the group consisting of hydrogen and optionally substituted $C_1$-$C_4$ alkyl;
X is selected from the group consisting of O, S, and NR';
Y is selected from the group consisting of O, S, and NR";
R' is selected from the group consisting of hydrogen and optionally substituted $C_1$-$C_4$ alkyl; and
R" is selected from the group consisting of hydrogen and optionally substituted $C_1$-$C_4$ alkyl,
wherein the compound is substantially free of one or more other stereoisomers,
or a pharmaceutically acceptable salt, solvate, or prodrug thereof.

Embodiment XXXV

The compound of Embodiment XXXIV, wherein $R^4$ is hydrogen, or a pharmaceutically acceptable salt, solvate, or prodrug thereof.

Embodiment XXXVI

The compound of Embodiment XXXIV, wherein X is NH, or a pharmaceutically acceptable salt, solvate, or prodrug thereof.

Embodiment XXXVII

The compound of Embodiment XXXIV, wherein Y is NH, or a pharmaceutically acceptable salt, solvate, or prodrug thereof.

Embodiment XXXVIII

The compound of Embodiment XXXIV, wherein $R^3$ is —$CH_2C(CH_3)_3$, or a pharmaceutically acceptable salt, solvate, or prodrug thereof.

Embodiment XXXIX

The compound of Embodiment XXXIV, wherein $R^5$ is selected from the group consisting of:

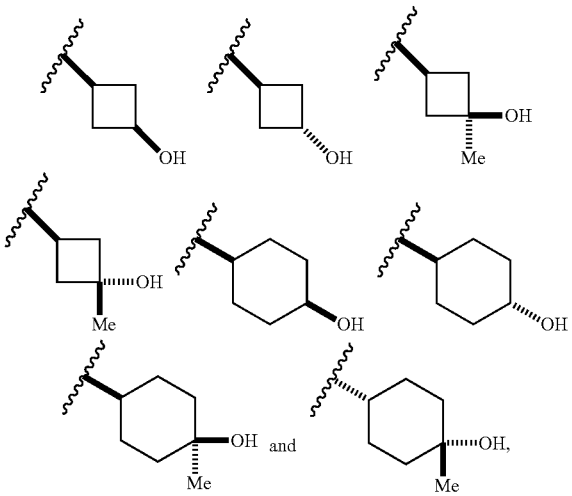

or a pharmaceutically acceptable salt, solvate, or prodrug thereof.

Embodiment XL

The compound of Embodiment XXXVIII, wherein:
$R^{1a}$ is hydrogen;
$R^{1b}$, $R^{1c}$, and $R^{1d}$ are each independently selected from the group consisting of hydrogen, fluoro, and chloro;
$R^3$ is $C_4$-$C_8$ alkyl;
$R^4$ is hydrogen;
$R^5$ is selected from the group consisting of:

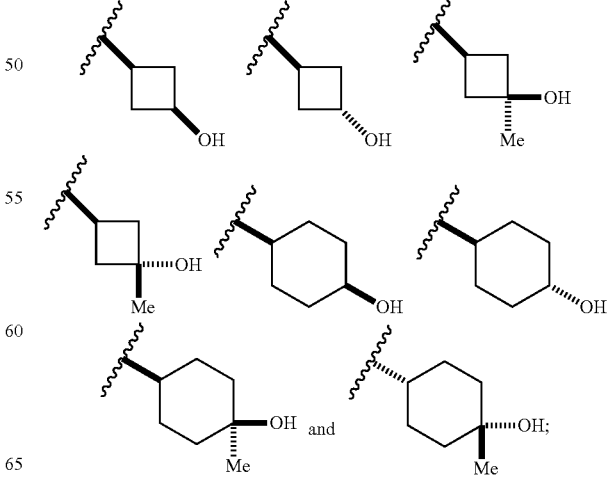

and
X and Y are NH;
or a pharmaceutically acceptable salt, solvate, or prodrug thereof.
Embodiment XLI
The compound of Embodiments XXXIX or XL, wherein $R^5$ is selected from the group consisting of:
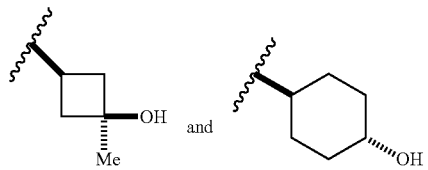 [SMILES: *[C@H]1C[C@@](C)(O)C1 ; *[C@H]1CC[C@H](O)CC1]
or a pharmaceutically acceptable salt, solvate, or prodrug thereof.
Embodiment XLII
The compound of Embodiment XXXIV selected from the group consisting of:
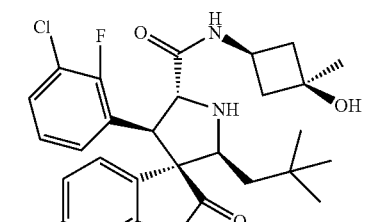
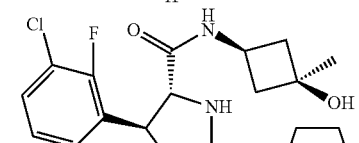
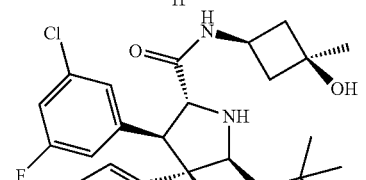
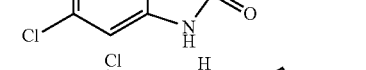
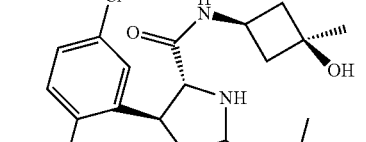
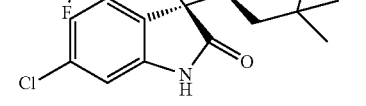
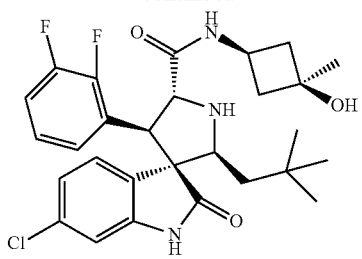
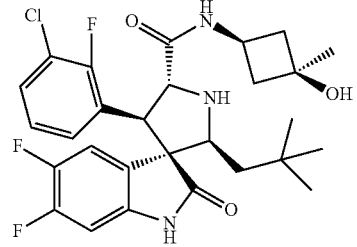
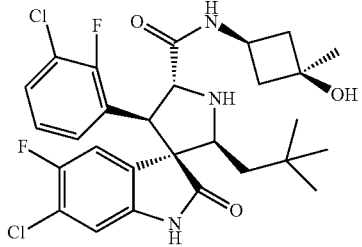
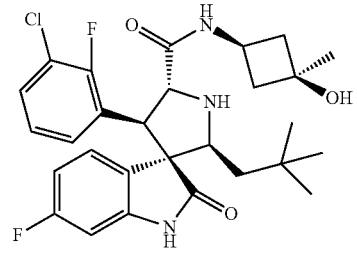
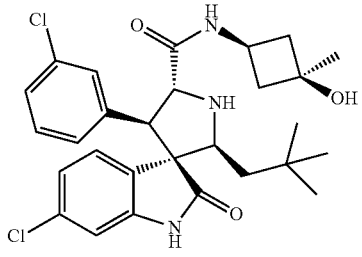
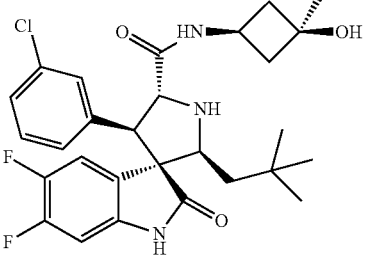

121
-continued
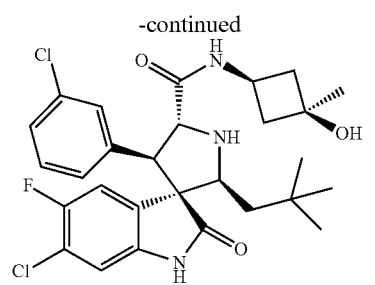
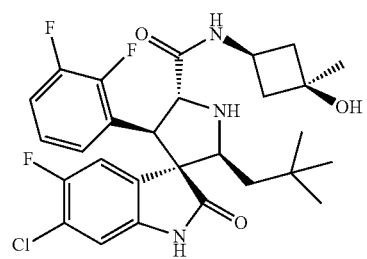
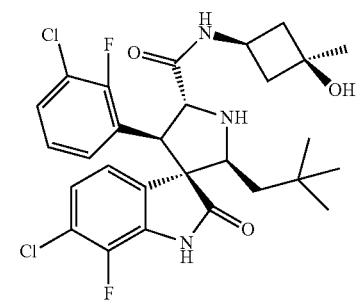
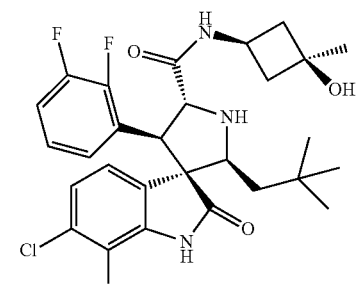
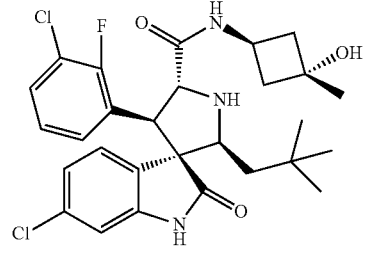
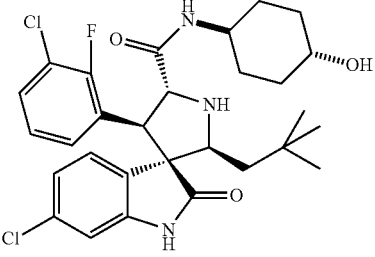
122
-continued
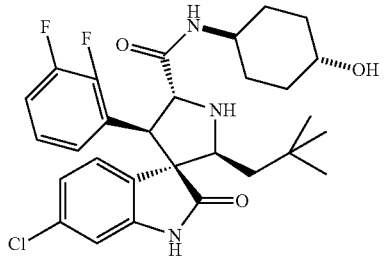
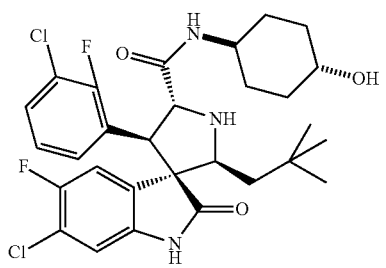
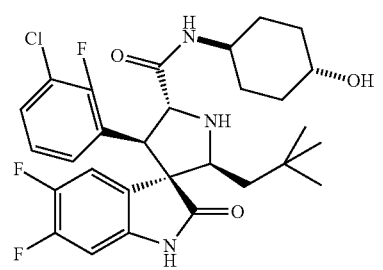
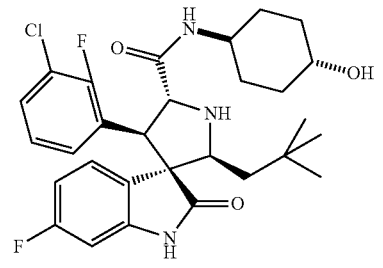
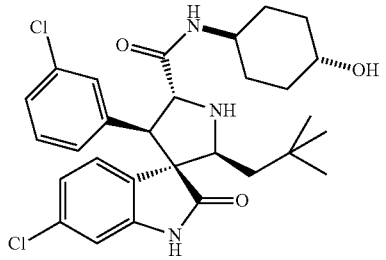
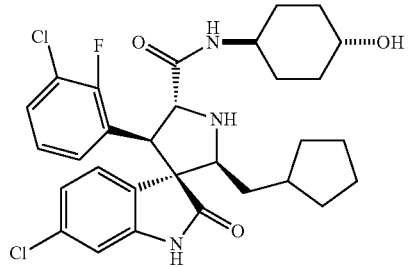

-continued

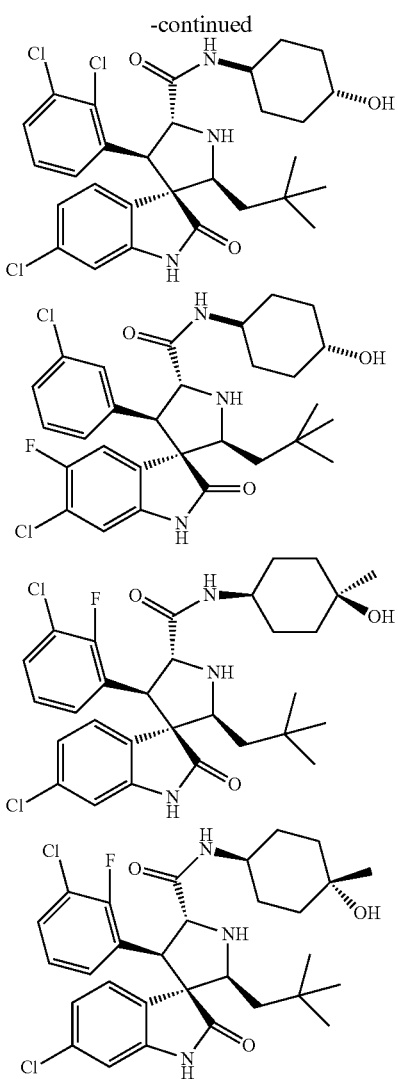

or a pharmaceutically acceptable salt, solvate, or prodrug thereof.

Embodiment XLIII

A compound having the structure:

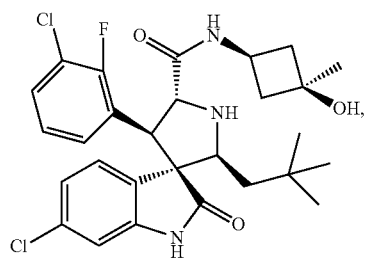 [SMILES: CC(C)(C)C[C@@H]1N[C@@H](C(=O)N[C@H]2C[C@@](C)(O)C2)[C@H](c2cccc(Cl)c2F)[C@]12C(=O)Nc1cc(Cl)ccc12]

or a pharmaceutically acceptable salt, solvate, or prodrug thereof.

Embodiment XLIV

A compound having the structure:

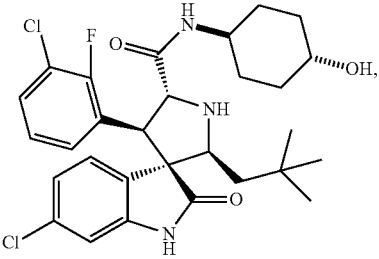 [SMILES: CC(C)(C)C[C@@H]1N[C@@H](C(=O)N[C@H]2CC[C@H](O)CC2)[C@H](c2cccc(Cl)c2F)[C@]12C(=O)Nc1cc(Cl)ccc12]

or a pharmaceutically acceptable salt, solvate, or prodrug thereof.

Embodiment XLV

The compound of any one of Embodiments XLII-XLIV, wherein the compound is substantially free of other stereoisomers, or a pharmaceutically acceptable salt, solvate, or prodrug thereof.

Embodiment XLVI

The compound of Embodiment XLV, wherein the compound is a substantially pure stereoisomer, or a pharmaceutically acceptable salt, solvate, or prodrug thereof.

Embodiment XLVII

A pharmaceutical composition comprising the compound of any one of Embodiments XXXIV-XLVI and a pharmaceutically acceptable carrier.

Embodiment XLVIII

A method of treating a patient comprising administering to the patient a therapeutically effective amount of the compound or a pharmaceutically acceptable salt thereof of any one of Embodiments XXXIV-XLVI, wherein the patient has a hyperproliferative disease.

Embodiment XLIX

A method of treating a patient comprising administering to the patient a therapeutically effective amount of the pharmaceutical composition of Embodiment XLVII, wherein the patient has a hyperproliferative disease.

Embodiment L

The method of Embodiments XLVIII or XLIX, wherein the hyperproliferative disease is cancer.

Embodiment LI

The method of claims Embodiments XLVIII or XLIX, wherein cells of the hyperproliferative disease express functional p53.

Embodiment LII

The method of Embodiment L, further comprising administering to the patient one or more anticancer agents.

Embodiment LIII

The method of Embodiment LII, wherein the anticancer agent is a chemotherapeutic agent.

Embodiment LIV

The method of Embodiment LII, wherein the anticancer agent is radiation therapy.

Embodiment LV

A method of treating a patient, wherein the patient has a hyperproliferative disorder and is being treated with an anticancer agent, comprising administering to the patient a compound or pharmaceutically acceptable salt thereof of any one of Embodiments XXXIV-XLVI.

Embodiment LVI

The method of Embodiment LV, wherein the patient is experiencing side-effects of the anticancer agent treatment selected from the group consisting of mucositis, stomatitis, xerostoma, alopecia, and gastrointestinal disorder.

Embodiment LVII

The method of Embodiment LVI, wherein cells of the hyperproliferative disorder express functional p53.

Embodiment LVIII

A kit comprising a compound of any one of Embodiments XXXIV-XLVI and instructions for administering the compound to a patient having a hyperproliferative disease.

Embodiment LIX

The kit of Embodiment LVIII, wherein the hyperproliferative disease is cancer.

Embodiment LX

The kit of Embodiment LIX, further comprising one or more anticancer agents.

Embodiment LXI

The kit of Embodiment LX, wherein the instructions direct co-administration of the compound together with the one or more anticancer agents.

Example 1

Analytical Data for Compounds

General Information

NMR spectra were recorded on a BRUKER AVANCE 250, BRUKER AVANCE 300, BRUKER AVANCE DRX-400, or BRUKER AVANCE DPX-500, or similar instrument. Unless otherwise indicated all NMR chemical shifts reported herein are denoted by the delta (δ) scale.

Liquid chromatography-mass spectrometry (denoted "LC-MS") analysis was performed using method A, method B, or method C:

Method A: WATERS UPLC-SQD apparatus; Ionization: electrospray in positive mode and/or negative mode (ES+/−); Chromatographic conditions: Column: ACQUITY BEH C18 1.7 μm-2.1×50 mm; Solvents: A: $H_2O$ (0.1% formic acid) B: $CH_3CN$ (0.1% formic acid); Column temperature: 50° C.; Flow: 1 ml/min; Gradient (2 min): from 5 to 50% of B in 0.8 min; 1.2 min: 100% of B; 1.85 min: 100% of B; 1.95:5% of B; Retention time=$t_R$ (min)

Method B: WATERS ZQ apparatus; Ionization: electrospray in positive mode and/or negative mode (ES+/−); Chromatographic conditions: Column. XBridge C18 2.5 μm-3×50 mm; Solvents: A: $H_2O$ (0.1% formic acid) B: $CH_3CN$ (0.1% formic acid); Column temperature: 70° C.; Flow: 0.9 ml/min; Gradient (7 min): from 5 to 100% of B in 5.3 min; 5.5 min: 100% of B; 6.3 min: 5% of B; Retention time=$t_R$ (min).

Method C: WATERS UPLC-SQD apparatus; Ionization: electrospray in positive mode and/or negative mode (ES+/−); Chromatographic conditions: Column. ACQUITY BEH C18 1.7 μm-2.1×50 mm; Solvents: A: $H_2O$ (0.1% formic acid) B: $CH_3CN$ (0.1% formic acid); Column temperature: 50° C.; Flow: 0.8 ml/min; Gradient (2.5 min): from 5 to 100% of B in 1.8 min; 2.4 min: 100% of B; 2.45 min: 100% of B; from 100 to 5% of B in 0.05 min; Retention time=$t_R$ (min).

Purity analysis was performed using reverse-phase HPLC using a SunFire™ C18 5 μm 4.6×150 mm column at a flow rate of 1 mL/min under the following conditions: Condition I: Gradient from 90% of solvent A (0.1% of TFA in water) and 10% of solvent B (0.1% of TFA in methanol) to 5% of solvent A and 95% of solvent B in 85 min; and Condition II: Gradient from 80% of solvent A (0.1% of TFA in water) and 20% of solvent B (0.1% of TFA in acetonitrile) to 50% of solvent A and 50% of solvent B in 30 min.

Low resolution ESI mass spectrum analysis was performed on Thermo-Scientific LCQ Fleet mass spectrometer or similar instrument.

The chemical names of the compounds provided in this example were determined with ADCLABS version 12.0.

C027—TFA Salt

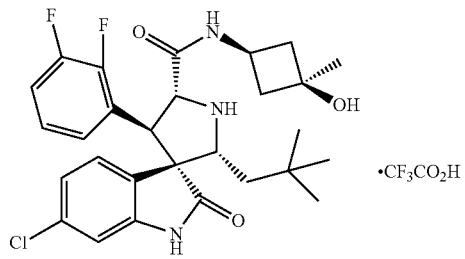 [SMILES: CC(C)(C)C[C@H]1N[C@@H](C(=O)N[C@H]2C[C@@](C)(O)C2)[C@H](c2cccc(F)c2F)[C@@]12C(=O)Nc1cc(Cl)ccc12 ; "·CF3CO2H"]

$^1$H NMR (300 MHz, MeOH-$d_4$): 7.50-7.36 (m, 1H), 7.24-7.10 (m, 2H), 6.88-6.76 (m, 3H), 5.12 (d, J=10.17 Hz, 1H), 4.49 (d, J=10.17 Hz, 1H), 4.23 (dd, J=6.83, 2.09 Hz, 1H), 3.98-3.83 (m, 1H), 2.49-2.36 (m, 1H), 2.36-2.22 (m, 1H), 2.10-1.96 (m, 2H), 1.94-1.82 (m, 1H), 1.35-1.28 (m, 1H), 1.29 (s, 3H), 0.80 (s, 9H); $^{13}$C NMR (75 MHz, MeOH-$d_4$): 108.1, 166.0, 145.4, 136.9, 127.9, 126.1 (t, $J_{C-F}$=5.6 Hz), 125.4, 123.4 118.8 (d, $J_{C-F}$=17.3 Hz), 112.0, 67.4, 64.5, 63.7, 61.6, 49.5, 45.6, 45.5, 42.4, 38.5, 30.9, 29.5, 27.6; ESI-MS calculated for $C_{28}H_{33}{}^{35}ClF_2N_3O_3$ [M+H]$^+$: 532.2179. Found: 532.42.

C029—TFA Salt

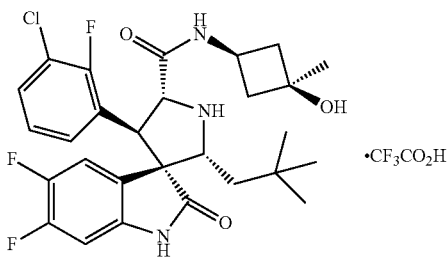 [SMILES: CC(C)(C)C[C@H]1N[C@@H](C(=O)N[C@H]2C[C@@](C)(O)C2)[C@H](c2cccc(Cl)c2F)[C@@]12C(=O)Nc1cc(F)c(F)cc12 ; "·CF3CO2H"]

¹H NMR (300 MHz, MeOH-d₄): 8.84 (d, J=6.80 Hz, 1H), 7.58 (t, J=6.80 Hz, 1H), 7.39 (t, J=7.11 Hz, 1H), 7.22 (t, J=7.80 Hz, 1H), 6.88 (dd, J=9.81, 7.80 Hz, 1H), 6.78 (d, J=10.13, 6.63 Hz, 1H), 5.11 (d, J=10.37 Hz, 1H), 4.48 (d, J=10.37 Hz, 1H), 4.21 (d, J=10.37 Hz, 1H), 4.21 (dd, J=7.32, 2.66 Hz, 1H), 3.95-3.75 (m, 1H), 2.46-2.22 (m, 2H), 2.12-1.96 (m, 2H), 1.94-1.80 (m, 1H), 1.34-1.28 (m, 1), 1.29 (s, 3H), 0.81 (s, 9H); ¹³C NMR (75 MHz, MeOH-d₄): 180.2, 169.2, 132.2, 128.7 (d, $J_{C-F}$=2.2 Hz), 126.5 (d, $J_{C-F}$=4.6 Hz), 124.7 (dd, $J_{C-F}$=33.5, 19.2 Hz), 122.6 (d, $J_{C-F}$=18.1 Hz), 101.5 (d, $J_{C-F}$=23.0 Hz), 67.4, 64.4, 63.5, 61.9, 49.8, 45.6, 45.5, 42.4, 38.6, 30.9, 29.5, 27.6; ESI-MS calculated for $C_{28}H_{32}{}^{35}ClF_3N_3O_3$ [M+H]⁺: 550.2084. Found: 550.33.

C034—TFA Salt

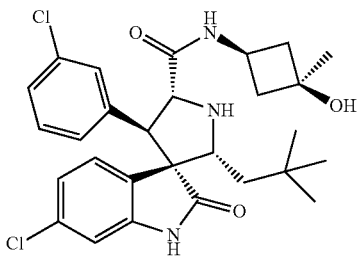

¹H NMR (300 MHz, MeOH-d₄): 7.28-7.10 (m, 5H), 6.92-6.84 (m, 1H), 6.80-6.76 (m, 1H), 5.40-5.20 (m, 1H), 5.08 (d, J=10.96 Hz, 1H), 4.40-4.20 (m, 1H), 3.90-3.60 (m, 1H), 2.50-2.30 (m, 1H), 2.30-2.15 (m, 1H), 2.15-2.00 (m, 2H), 1.90-1.75 (m, 1H), 1.57 (dd, J=15.3, 3.71 Hz, 1H), 1.25 (s, 3H), 0.79 (s, 9H); ¹³C NMR (75 MHz, MeOH-d₄): 180.0, 165.9, 144.7, 136.7, 136.6, 135.8, 131.3, 130.1, 129.8, 128.1, 128.1, 126.8, 123.5, 112.0, 67.4, 64.3, 64.0, 62.2, 57.2, 45.7, 45.6, 42.7, 38.3, 31.0, 29.6, 27.5; ESI-MS calculated for $C_{28}H_{34}{}^{35}Cl_2N_3O_3$ [M+H]⁺: 530.1977. Found: 530.50.

C031—TFA Salt

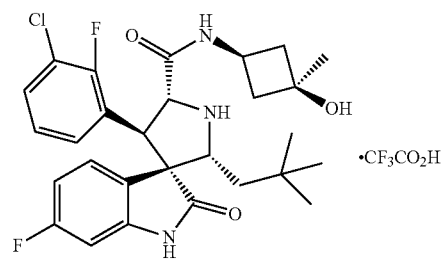 [SMILES: CC(C)(C)C[C@H]1N[C@@H](C(=O)N[C@H]2C[C@@](C)(O)C2)[C@H](c2cccc(Cl)c2F)[C@@]12C(=O)Nc1cc(F)ccc12 ; "·CF3CO2H"]

¹H NMR (300 MHz, MeOH-d₄): 7.68-7.54 (m, 1H), 7.38-7.26 (m, 1H), 7.22-7.12 (m, 1H), 6.90-6.76 (m, 1H), 6.70-6.60 (m, 1H), 6.56-6.42 (m, 1H), 5.30-5.20 (m, 1H), 4.49 (d, J=10.03 Hz, 1H), 4.25 (dd, J=71.9, 2.39 Hz, 1H), 4.00-3.82 (m, 1H), 2.50-2.21 (m, 2H), 2.18-2.00 (m, 2H), 1.98-1.82 (m, 1H), 1.40-1.30 (m, 1H), 1.28 (s, 3H), 0.79 (s, 9H); ¹³C NMR (75 MHz, MeOH-d₄): 180.6, 165.1 (d, $J_{C-F}$=246.7 Hz), 166.1, 157.7 (d, $J_{C-F}$=247.9 Hz), 145.6 (d, $J_{C-F}$=12.0 Hz), 132.0, 128.6, 128.2 (d, $J_{C-F}$=10.2 Hz), 126.3 (d, $J_{C-F}$=4.5 Hz), 125.0 (d, $J_{C-F}$=14.0 Hz), 122.4 (d, $J_{C-F}$=18.4 Hz), 122.3, 109.8 (d, $J_{C-F}$=23.2 Hz), 99.9 (d, $J_{C-F}$=27.8 Hz), 67.4, 64.5, 63.5, 61.5, 49.2, 45.6, 45.5, 42.3, 38.4, 30.9, 29.5, 27.5; ESI-MS calculated for $C_{28}H_{33}{}^{35}ClF_2N_3O_3$ [M+H]⁺: 532.2179. Found: 532.42.

C035—TFA Salt

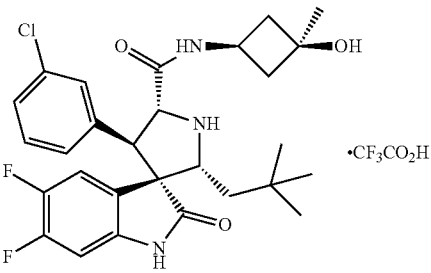 [SMILES: CC(C)(C)C[C@H]1N[C@@H](C(=O)N[C@H]2C[C@@](C)(O)C2)[C@H](c2cccc(Cl)c2)[C@@]12C(=O)Nc1cc(F)c(F)cc12 ; "·CF3CO2H"]

¹H NMR (300 MHz, MeOH-d₄): 7.40-7.00 (m, 5H), 6.80-6.40 (m, 1H), 5.60-5.00 (m, 2H), 4.60-4.20 (m, 1H), 4.00-3.80 (m, 1H), 2.60-2.40 (m, 1H), 2.40-2.20 (m, 1H), 2.20-2.00 (m, 2H), 2.00-1.80 (m, 1H), 1.70-1.50 (m, 1H), 1.28 (s, 3H), 0.83 (s, 9H); ¹³C NMR (75 MHz, MeOH-d₄): 180.0, 165.8, 160.0-145.0 (m, $2\times C_{sp2}$—F), 136.5, 135.9, 131.4, 130.0, 129.9, 128.0, 124.1 (d, $J_{C-F}$=6.3 Hz), 119.1, 116.7 (d, $J_{C-F}$=20.4 Hz), 101.4 (d, $J_{C-F}$=23.0 Hz), 67.4, 64.2, 63.8, 62.5, 57.4, 45.6, 45.5, 42.7, 38.3, 31.0, 29.5, 27.5; ESI-MS calculated for $C_{28}H_{33}{}^{35}ClF_2N_3O_3$ [M+H]⁺: 532.2179. Found: 532.42.

129
MI-519-73—TFA Salt

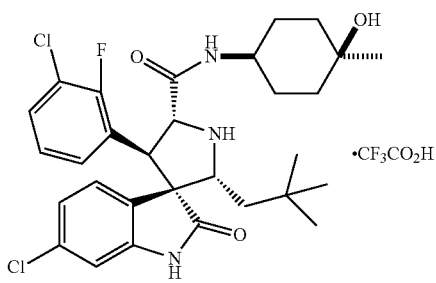

$^1$H NMR (300 MHz, MeOH-d$_4$): 7.50-7.30 (m, 2H), 7.20-7.10 (m, 1H), 6.90-6.70 (m, 3H), 5.00-4.70 (m, 1H), 4.36 (d, J=9.76 Hz, 1H), 4.05-3.96 (m, 1H), 3.70-3.50 (m, 1H), 1.94 (dd, J=14.98, 7.30 Hz, 1H), 1.80-1.00 (m, 8H), 1.16 (s, 3H), 0.90-0.70 (m, 1H), 0.80 (s, 9H); ESI-MS calculated for C$_{30}$H$_{37}$$^{35}$Cl$_2$FN$_3$O$_3$ [M+H]$^+$: 576.2196. Found: 576.58.

MI-519-74—TFA Salt

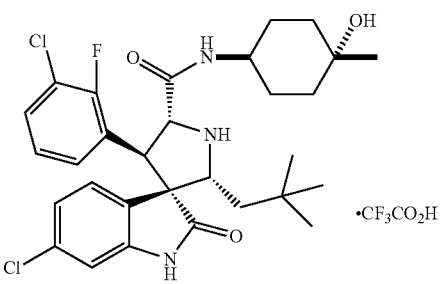

$^1$H NMR (300 MHz, MeOH-d$_4$): 7.50-7.30 (m, 2H), 7.25-7.10 (m, 1H), 6.85-6.70 (m, 3H), 5.00-4.70 (m, 1H), 4.32 (d, J=9.69 Hz, 1H), 4.10-3.95 (m, 1H), 3.85-3.70 (m, 1H), 2.00-1.80 (m, 2H), 1.75-1.20 (m, 7H), 1.13 (s, 3H), 0.95-0.75 (m, 1H), 0.81 (s, 9H); ESI-MS calculated for C$_{30}$H$_{37}$$^{35}$Cl$_2$FN$_3$O$_3$ [M+H]$^+$: 576.2196. Found: 576.58.

MI-7102—TFA Salt

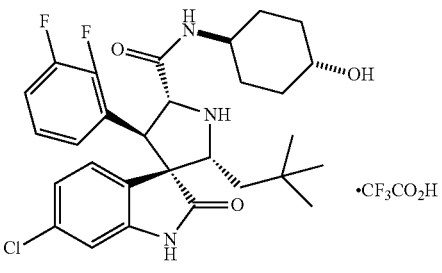

$^1$H NMR (300 MHz, MeOH-d$_4$): 7.36-7.25 (m, 1H), 7.24-7.11 (m, 2H), 6.86 (d, J=1.8 Hz, 1H), 6.80 (dd, J=1.8, 8.1 Hz, 1H), 6.72 (d, J=8.1 Hz, 1H), 4.82 (d, J=9.6 Hz, 1H), 4.36 (d, J=9.6 Hz, 1H), 4.04 (dd, J=2.4, 7.4 Hz, 1H), 3.74-3.56 (m, 1H), 3.56-3.40 (m, 1H), 2.05-1.78 (m, 5H), 1.75-1.59 (m, 1H), 1.43-1.04 (m, 5H), 0.81 (s, 9H); ESI-MS calculated for C$_{29}$H$_{35}$ClF$_2$N$_3$O$_3$ (M+H)$^+$ requires 546.23. found 546.58; HPLC (Condition I) t$_R$=50.45 min (Purity 95.4%).

130
MI-7103—TFA Salt

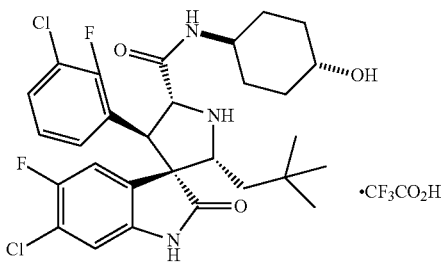

$^1$H NMR (300 MHz, MeOH-d$_4$): 8.38 (d, J=7.7 Hz, 1H), 7.54 (t, J=6.7 Hz, 1H), 7.40 (d, J=7.1 Hz, 1H), 7.20 (t, J=7.9 Hz, 1H), 6.93 (d, J=6.1 Hz, 1H), 6.86 (d, J=8.7 Hz, 1H), 4.45 (d, J=10.3 Hz, 1H), 4.13 (dd, J=2.8, 7.5 Hz, 1H), 3.77-3.55 (m, 1H), 3.55-3.42 (m, 1H), 2.09-1.71 (m, 4H), 1.70-1.56 (m, 1H), 1.4$_5$-1.$_0$2 (m, 5$_H$), 0.82 (s, 9H); ESI-MS calculated for C$_{29}$H$_{34}$Cl$_2$F$_2$N$_3$O$_3$ (M+H)$^+$ requires 580.19. found 580.67; HPLC (Condition I) t$_R$=55.01 min (Purity 88.1%).

MI-7104—TFA Salt

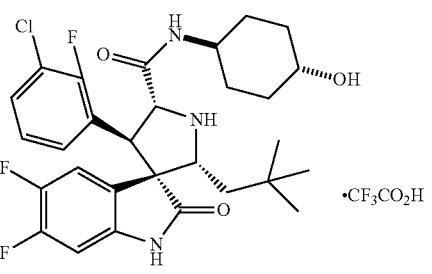

$^1$H NMR (300 MHz, MeOH-d$_4$): 7.49 (t, J=7.2 Hz, 1H), 7.45-7.38 (m, 1H), 7.22 (t, J=8.0 Hz, 1H), 6.85-6.68 (m, 2H), 4.80 (d, J=9.8 Hz, 1H), 4.36 (d, J=9.9 Hz, 1H), 4.01 (dd, J=2.4, 7.6 Hz, 1H), 3.74-3.57 (m, 1H), 3.55-3.39 (m, 1H), 2.04-1.77 (m, 4H), 1.74-1.59 (m, 1H), 1.44-1.04 (m, 5H), 0.90 (d, J=4.5 Hz, 1H), 0.82 (s, 9H); ESI-MS calculated for C$_{29}$H$_{34}$ClF$_3$N$_3$O$_3$ (M+H)$^+$ requires 564.22. found 564.58; HPLC (Condition I) t$_R$=51.76 min (Purity 86.9%).

MI-7105—TFA Salt

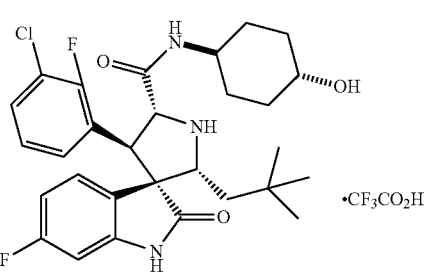

$^1$H NMR (300 MHz, MeOH-d$_4$): 7.49 (t, J=7.2 Hz, 1H), 7.45-7.38 (m, 1H), 7.22 (t, J=8.0 Hz, 1H), 6.85-6.68 (m, 2H), 4.80 (d, J=9.8 Hz, 1H), 4.36 (d, J=9.9 Hz, 1H), 4.01 (dd, J=2.4, 7.6 Hz, 1H), 3.74-3.57 (m, 1H), 3.55-3.39 (m, 1H), 2.04-1.77 (m, 4H), 1.74-1.59 (m, 1H), 1.44-1.04 (m, 5H), 0.90 (d, J=4.5 Hz, 1H), 0.82 (s, 9H); ESI-MS calculated for C$_{29}$H$_{35}$ClF$_2$N$_3$O$_3$ (M+H)$^+$ requires 546.23. found 546.58; HPLC (Condition I) t$_R$=49.20 min (Purity 99.4%).

MI-7106—TFA Salt

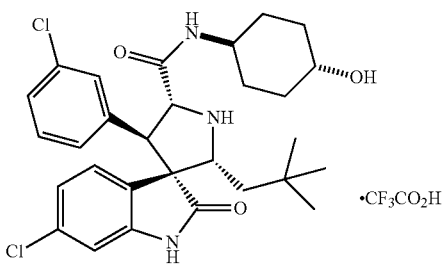

¹H NMR (300 MHz, MeOH-d₄): 8.36 (d, J=7.0 Hz, 1H), 7.59 (d, J=8.1 Hz, 1H), 7.41-7.11 (m, 4H), 7.04 (d, J=7.6 Hz, 1H), 6.78 (d, J=1.8 Hz, 1H), 5.19 (d, J=11.3 Hz, 1H), 4.44 (J=8.1 Hz, 1H), 4.07 (d, J=11.3 Hz, 1H), 3.74-3.53 (m, 1H), 3.53-3.37 (m, 1H), 2.08-1.83 (m, 3H), 1.83-1.69 (m, 1H), 1.61-1.44 (m, 1H), 1.44-1.08 (m, 4H), 1.07-0.72 (m, 1H), 0.88 (s, 9H); ESI-MS calculated for $C_{29}H_{36}Cl_2N_3O_3$ (M+H)⁺ requires 544.21. found 544.67; HPLC (Condition I) $t_R$=51.41 min (Purity 93.0%).

MI-7108—TFA Salt

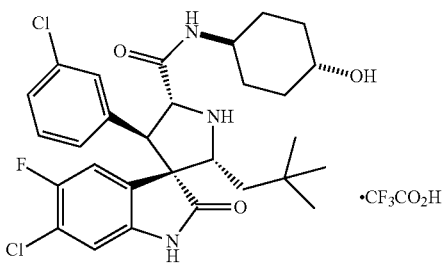

¹H NMR (300 MHz, MeOH-d₄/DMSO-d₆): 10.15 (s, 1H), 7.76 (d, J=8.2 Hz, 1H), 7.22 (s, 1H), 7.17-7.00 (m, 3H), 6.94 (d, J=7.1 Hz, 1H), 6.81 (d, J=6.0 Hz, 1H), 4.42 (d, J=8.3 Hz, 1H), 4.09 (d, J=3.0 Hz, 1H), 3.79 (d, J=8.3 Hz, 1H), 3.73-3.49 (m, 2H), 3.35 (d, J=9.5 Hz, 1H), 2.10-1.84 (m, 4H), 1.52-1.11 (m, 5H), 0.87 (s, 9H); ¹³C NMR (75 MHz, MeOH-d₄/DMSO-d₆): 177.1, 172.4, 153.6 (d, $J_{C-F}$=242.7 Hz), 138.7, 138.5 (d, $J_{C-F}$=2.4 Hz), 133.2, 129.0, 127.544, 127.541 (d, $J_{C-F}$=6.7 Hz), 126.8, 126.5, 119.7 (d, $J_{C-F}$=19.2 Hz), 111.3, 110.4 (d, $J_{C-F}$=24.1 Hz), 68.4, 66.6, 65.7, 64.0, 58.6, 46.8, 42.2, 33.26, 33.20, 30.4, 30.2, 29.7, 29.5; ESI-MS calculated for $C_{29}H_{35}Cl_2FN_3O_3$ (M+H)+ requires 562.20. found 562.67; HPLC (Condition I) $t_R$=55.08 min (Purity 96.1%); HPLC (Condition II) $t_R$=21.44 min (Purity 92.7%).

MI-7109—TFA Salt

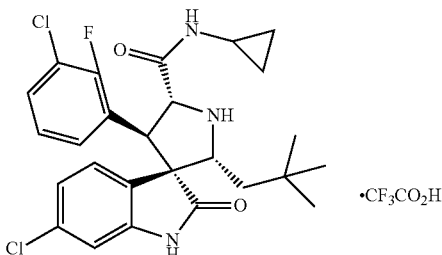

¹H NMR (300 MHz, MeOH-d₄): 7.47 (t, J=6.7 Hz, 1H), 7.42-7.33 (m, 1H), 7.18 (t, J=7.7 Hz, 1H), 6.87 (d, J=1.8 Hz, 1H), 6.78 (dd, J=1.8, 8.1 Hz, 1H), 6.70 (d, J=8.1 Hz, 1H), 4.40 (d, J=9.7 Hz, 1H), 4.11 (dd, J=2.5, 7.6 Hz, 1H), 2.77-2.65 (m, 1H), 1.99 (dd, J=7.6, 15.3 Hz, 1H), 1.24 (dd, J=2.5, 15.3 Hz, 1H), 0.92-0.62 (m, 2H), 0.81 (s, 9H), 0.56-0.30 (m, 2H); ESI-MS calculated for $C_{26}H_{29}Cl_2FN_3O_2$ (M+H)⁺ requires 504.1₆. found 504.58; HPLC (Condition I) $t_R$=53.99 min (Purity 94.4%).

B059—TFA Salt

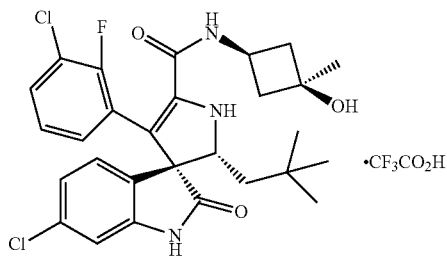 [SMILES: CC(C)(C)C[C@H]1NC(C(=O)N[C@H]2C[C@@](C)(O)C2)=C(c2cccc(Cl)c2F)[C@@]12C(=O)Nc1cc(Cl)ccc12 ; "·CF3CO2H"]

¹H NMR (300 MHz, CD₃OD): 7.45-7.34 (m, 1H), 7.26-7.12 (m, 1H), 7.04-6.93 (m, 1H), 6.90 (d, J=1.80 Hz, 1H), 6.65 (dd, J=8.08, 1.80 Hz, 1H), 4.41 (d, J=9.25 Hz, 1H), 3.96 (quint, J=8.13 Hz, 1H), 2.51-2.07 (m, 2H), 2.40-2.20 (m, 2H), 1.88 (dd, J=14.20, 9.91 Hz, 1H), 1.32 (s, 3H), 1.20-0.80 (m, 1H), 0.88 (s, 9H); ¹³C NMR (75 MHz, CD₃OD): 181.3, 172.9 (d, $J_{C-F}$=266.9 Hz), 168.6, 162.7, 145.3, 135.8, 131.7, 130.7 (d, $J_{C-F}$=38.6 Hz), 126.2 (d, $J_{C-F}$=4.5 Hz), 126.1, 123.6, 122.9, 122.7, 111.4, 78.4, 67.7, 63.4, 46.0, 45.8, 44.3, 38.0, 31.4, 30.2, 27.6; ESI-MS calculated for $C_{28}H_{31}{}^{35}Cl_2FN_3O_3$ [M+H]⁺: 546.1727. Found: 546.50.

MI-519-77—TFA Salt

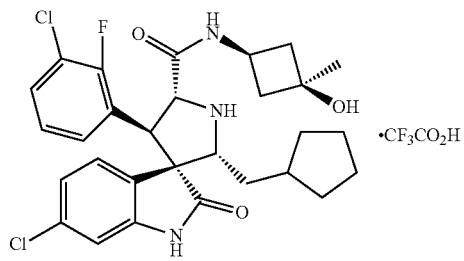 [SMILES: C[C@]1(O)C[C@@H](NC(=O)[C@@H]2N[C@H](CC3CCCC3)[C@]3(C(=O)Nc4cc(Cl)ccc43)[C@H]2c2cccc(Cl)c2F)C1 ; "·CF3CO2H"]

¹H NMR (300 MHz, CD₃OD): 7.50-7.40 (m, 1H), 7.40 (m, 1H), 7.20-7.10 (m, 1H), 6.85 (d, J=1.40 Hz, 1H), 6.84-6.72 (m, 2H), 5.00-4.80 (m, 1H), 4.45 (d, J=10.10 Hz, 1H), 4.02 (t, J=6.61 Hz, 1H), 3.90 (quintet, J=8.07 Hz, 1H), 2.50-2.25 (m, 2H), 2.10-1.82 (m, 3H), 1.81-1.31 (m, 8H), 1.30 (s, 3H), 1.10-0.91 (m, 1H), 0.91-0.81 (m 1H); ESI-MS calculated for $C_{29}H_{33}{}^{35}Cl_2FN_3O_3$ [M+H]⁺: 560.1883. Found: 560.50.

MI-519-78—TFA Salt

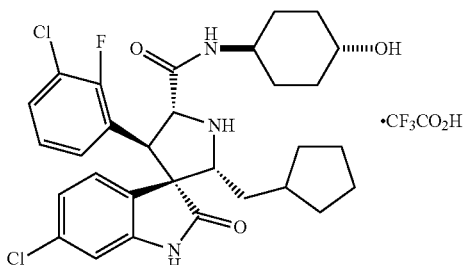

¹H NMR (300 MHz, CD₃OD): 7.45-7.31 (m, 2H), 7.20-7.11 (m, 1H), 6.86-6.82 (m, 1H), 6.81-6.78 (m, 2H), 4.90-4.80 (m, 1H), 4.45 (d, J=10.33 Hz, 1H), 4.10-3.95 (m, 1H), 3.70-3.60 (m, 1H), 3.50-3.40 (m, 1H), 2.10-1.05 (m, 17H), 1.05-0.95 (m, 1H), 0.95-0.80 (m, 1H); ESI-MS calculated for $C_{30}H_{35}{}^{35}Cl_2FN_3O_3$ [M+H]⁺: 574.2040. Found: 574.58.

MI-519-80—TFA Salt

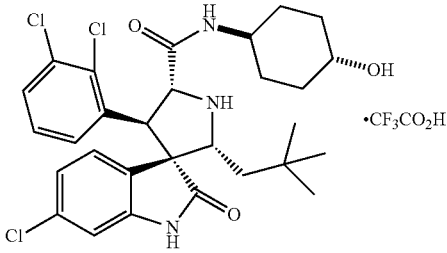

¹H NMR (300 MHz, CD₃OD): 7.80-7.72 (m, 1H), 7.50-7.38 (m, 2H), 6.87 (d, J=1.81 Hz, 1H), 6.71 (dd, J=8.16, 1.81 Hz, 1H), 6.52-6.40 (m, 1H), 4.96-4.80 (m, 1H), 4.62 (d, J=8.69 Hz, 1H), 4.10-3.95 (m, 1H), 3.70-3.55 (m, 1H), 3.50-3.45 (m, 1H), 2.00-1.80 (m, 3H), 1.80-1.60 (m, 1H), 1.40-1.00 (m, 5H), 0.95-0.85 (m, 1H), 0.80 (s, 9H); ESI-MS calculated for $C_{29}H_{35}{}^{35}Cl_3N_3O_3$ [M+H]⁺: 578.1744. Found: 578.75.

C02701—TFA Salt (2'S,3'R,4'S,5'R)-6-Chloro-4'-(2,3-difluoro-phenyl)-2'-(2,2-dimethyl-propyl)-2-oxo-1,2-dihydro-spiro[indole-3,3'-pyrrolidine]-5'-carboxylic acid (3-hydroxy-3-methyl-cyclobutyl)-amide, trifluoroacetate

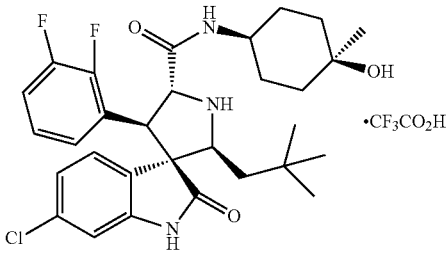

¹H NMR (300 MHz, MeOH-d₄): 8.82 (d, J=6.83 Hz, 1H), 7.65-7.55 (m, 1H), 7.45-7.30 (m, 1H), 7.20-7.05 (m, 3H), 6.80-6.75 (m, 1H), 5.40-5.10 (m, 1H), 4.61 (d, J=11.39 Hz, 1H), 4.50 (d, J=7.66 Hz, 1H), 3.95-3.80 (m, 1H), 2.45-2.30 (m, 1H), 2.30-2.15 (m, 1H), 2.05-1.80 (m, 2H), 1.80-1.60 (m, 1H), 1.27 (s, 3H), 1.20-1.08 (m, 1H), 0.86 (s, 9H); ¹³C NMR (75 MHz, MeOH-d₄): 177.8, 167.0, 160.0-148.0 (m, 2×$C_{sp2}$—F), 145.2, 137.2, 126.8, 126.5-126.0 (m), 125.0, 124.1, 123.5, 122.1 (d, $J_{C-F}$=9.74 Hz), 119.1 (d, $J_{C-F}$=17.1 Hz), 112.1, 67.3, 64.5, 64.2, 62.6, 48.5, 45.6, 45.5, 43.3, 38.3, 31.0, 29.5, 27.5; ESI-MS calculated for $C_{28}H_{33}{}^{35}ClF_2N_3O_3$ [M+H]⁺: 532.2179. Found: 532.50.

LC-MS: $t_R$ (min)=0.86; [M+H]⁺: m/z 532; [M−H]⁻: m/z 530 (method A).

¹H NMR (400 MHz, DMSO-d₆+TFA): 0.80 (s, 9H); 1.01 (d broad, J=15.2 Hz, 1H); 1.20 (s, 3H); 1.60 (m, 1H); 1.85 to 1.98 (m, 2H); 2.08 (m, 1H); 2.25 (m, 1H); 3.72 (m, 1H); 4.49 (m, 2H); 5.30 (d, J=12.1 Hz, 1H); 6.78 (d, J=2.0 Hz, 1H); 7.16 (dd, J=2.0 and 8.3 Hz, 1H); 7.23 (m, 1H); 7.42 (m, 1H); 7.48 (m, 1H); 7.74 (d, J=8.3 Hz, 1H).

C02901—TFA Salt (2'S,3'R,4'S,5'R)-4'-(3-Chloro-2-fluoro-phenyl)-2'-(2,2-dimethyl-propyl)-5,6-difluoro-2-oxo-1,2-dihydro-spiro[indole-3,3'-pyrrolidine]-5'-carboxylic acid (3-hydroxy-3-methyl-cyclobutyl)-amide, trifluoroacetate

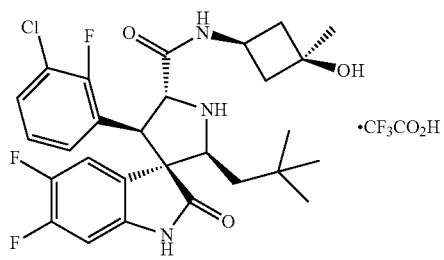 [SMILES: CC(C)(C)C[C@@H]1N[C@@H](C(=O)N[C@H]2C[C@@](C)(O)C2)[C@H](c2cccc(Cl)c2F)[C@]12C(=O)Nc1cc(F)c(F)cc12 ; "·CF3CO2H"]

¹H NMR (300 MHz, MeOH-d₄): 7.80-7.65 (m, 1H), 7.60-7.50 (m, 1H), 7.40-7.30 (m, 1H), 7.20-7.10 (m, 1H), 6.80-6.65 (m, 1H), 5.50-5.10 (m, 1H), 4.60 (d, J=11.39 Hz, 1H), 4.50 (d, J=6.96 Hz, 1H), 3.95-3.80 (m, 1H), 2.50-2.30 (m, 1H), 2.30-2.20 (m, 1H), 2.10-1.80 (m, 2H), 1.80-1.65 (m, 1H), 1.27 (s, 3H), 1.20-1.05 (m, 1H), 0.87 (s, 9H); ¹³C NMR (75 MHz, MeOH-d₄): 177.8, 167.0, 160.0-145.0 (m, 3×$C_{sp2}$—F), 132.6, 128.6, 126.6, 122.5 (d, $J_{C-F}$=18.9 Hz), 121.3 (d, $J_{C-F}$=13.0 Hz), 118.8, 115.4 (d, $J_{C-F}$=21.7 Hz), 115.1, 101.8 (d, $J_{C-F}$=23.3 Hz), 67.3, 64.6, 64.3, 62.5, 48.7, 45.6, 45.5, 43.4, 38.3, 31.0, 29.5, 27.5; ESI-MS calculated for $C_{28}H_{32}{}^{35}ClF_3N_3O_3$ [M+H]⁺: 550.2084. Found: 550.33.

LC-MS: $t_R$ (min)=0.87; [M+H]⁺: m/z 550; [M−H]⁻: m/z 548 (method A).

¹H NMR (400 MHz; DMSO-d₆+TFA): 0.80 (s, 9H); 1.01 (d, J=15.2 Hz, 1H); 1.20 (s, 3H); 1.62 (m, 1H); 1.85 to 1.98 (m, 2H); 2.08 (m, 1H); 2.26 (m, 1H); 3.73 (m, 1H); 4.52 (m, 2H); 5.28 (d, J=12.1 Hz, 1H); 6.79 (dd, J=6.7 and 10.1 Hz, 1H); 7.25 (t, J=7.8 Hz, 1H); 7.50 (m, 1H); 7.60 (m, 1H); 8.08 (m, 1H).

C03001—TFA Salt (2'S,3'R,4'S,5'R)-6-Chloro-4'-(3-chloro-2-fluoro-phenyl)-2'-(2,2-dimethyl-propyl)-5-fluoro-2-oxo-1,2-dihydro-spiro[indole-3,3'-pyrrolidine]-5'-carboxylic acid (3-hydroxy-3-methyl-cyclobutyl)-amide, trifluoroacetate

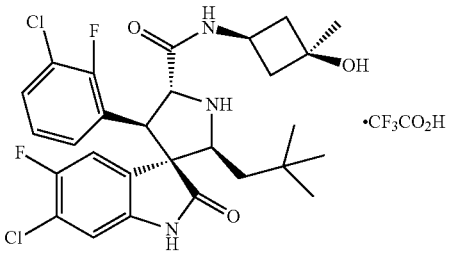 [SMILES: CC(C)(C)C[C@@H]1N[C@@H](C(=O)N[C@H]2C[C@@](C)(O)C2)[C@H](c2cccc(Cl)c2F)[C@]12C(=O)Nc1cc(Cl)c(F)cc12 ; "·CF3CO2H"]

¹H NMR (300 MHz, MeOH-d₄): 7.70 (d, J=7.30 Hz, 1H), 7.60-7.50 (m, 1H), 7.45-7.35 (m, 1H), 7.25-7.15 (m, 1H), 6.88 (d, J=6.00 Hz, 1H), 5.21 (d, J=11.35 Hz, 1H), 4.61 (d, J=11.37 Hz, 1H), 4.53 (d, J=8.19 Hz, 1H), 3.95-3.80 (m, 1H), 2.50-2.35 (m, 1H), 2.35-2.15 (m, 1H), 2.00-1.80 (m, 2H), 1.80-1.60 (m, 1H), 1.29 (s, 3H), 1.25-1.05 (m, 1H), 0.89 (s, 9H); ¹³C NMR (75 MHz, MeOH-d₄): 177.3, 166.7, 157.6 (d, $J_{C-F}$=249.5 Hz), 155.7 (d, $J_{C-F}$=243.5 Hz), 140.4 (d, $J_{C-F}$=2.8 Hz), 132.5, 128.4, 126.4 (d, $J_{C-F}$=4.9 Hz), 125.0 (d, $J_{C-F}$=7.4 Hz), 123.4 (d, $J_{C-F}$=19.5 Hz), 122.3 (d, $J_{C-F}$=18.9 Hz), 121.0 (d, $J_{C-F}$=13.0 Hz), 114.5 (d, $J_{C-F}$=25.1 Hz), 104.8, 67.1, 64.6, 64.2, 62.4, 47.3, 45.4, 45.3, 43.2, 38.2, 30.8, 29.2, 27.3; ESI-MS calculated for $C_{28}H_{32}{}^{35}Cl_2F_2N_3O_3$ [M+H]$^+$: 566.1789. Found: 566.50.

LC-MS: $t_R$ (min)=0.93; [M+H]$^+$: m/z 566 (method A).

$^1$H NMR (400 MHz, DMSO-d$_6$+TFA): 0.81 (s, 9H); 1.02 (d broad, J=15.2 Hz, 1H); 1.20 (s, 3H); 1.62 (m, 1H); 1.87 to 1.99 (m, 2H); 2.09 (m, 1H); 2.27 (m, 1H); 3.75 (m, 1H); 4.55 (m, 2H); 5.30 (d, J=12.1 Hz, 1H); 6.89 (d, J=6.3 Hz, 1H); 7.25 (t, J=7.8 Hz, 1H); 7.50 (m, 1H); 7.61 (m, 1H); 8.04 (d, J=8.9 Hz, 1H)

C031—TFA Salt

LC-MS: $t_R$ (min)=0.84; [M+H]$^+$: m/z 532; [M−H]$^−$: m/z 530 (method A).

$^1$H NMR (400 MHz, DMSO-d$_6$+TFA): 0.83 (s, 9H); 1.11 (d broad, J=15.2 Hz, 1H); 1.22 (s, 3H); 1.83 (m, 1H); 2.00 to 2.36 (m, 4H); 3.82 (m, 1H); 4.20 (dd, J=2.9 and 7.7 Hz, 1H); 4.36 (d, J=10.5 Hz, 1H); 5.00 (d, J=10.5 Hz, 1H); 6.53 to 6.74 (m, 2H); 6.94 (dd, J=5.6 and 8.8 Hz, 1H); 7.21 (t, J=8.0 Hz, 1H); 7.41 (t, J=8.0 Hz, 1H); 7.71 (t, J=8.0 Hz, 1H).

C03401—TFA Salt (2'S,3'R,4'R,5'R)-6-Chloro-4'-(3-chloro-phenyl)-2'-(2,2-dimethyl-propyl)-2-oxo-1,2-dihydro-spiro[indole-3,3'-pyrrolidine]-5'-carboxylic acid (3-hydroxy-3-methyl-cyclobutyl)-amide, trifluoroacetate

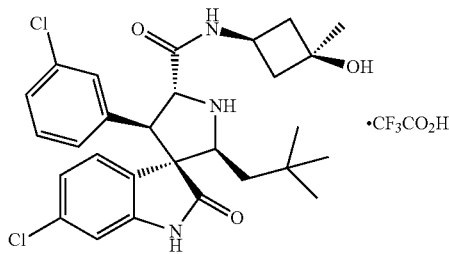 [SMILES: CC(C)(C)C[C@@H]1N[C@@H](C(=O)N[C@H]2C[C@@](C)(O)C2)[C@H](c2cccc(Cl)c2)[C@]12C(=O)Nc1cc(Cl)ccc12 ; "·CF3CO2H"]

$^1$H NMR (300 MHz, MeOH-d$_4$): 7.58 (d, J=8.07 Hz, 1H), 7.30-7.10 (m, 4H), 7.02 (d, J=7.67 Hz, 1H), 6.77 (d, J=1.54 Hz, 1H), 5.40-5.20 (m, 1H), 4.44 (d, J=7.09 Hz, 1H), 4.10 (d, J=11.25 Hz, 1H), 3.95-3.80 (m, 1H), 2.45-2.30 (m, 1H), 2.30-2.15 (m, 1H), 2.05-1.85 (m, 2H), 1.80-1.70 (m, 1H), 1.27 (s, 3H); 1.20-1.10 (m, 1H); 0.86 (s, 9H); $^{13}$C NMR (75 MHz, MeOH-d$_4$): 177.8, 167.3, 145.3, 137.1, 135.8, 134.4, 131.4, 130.4, 129.5, 128.3, 126.3, 124.2, 124.1, 112.2, 67.3, 64.9, 64.2, 62.8, 57.2, 45.7, 45.6, 43.4, 38.3, 31.0, 29.5, 27.5; ESI-MS calculated for $C_{28}H_{34}{}^{35}Cl_2N_3O_3$ [M+H]$^+$: 530.1977. Found: 530.58.

LC-MS: $t_R$ (min)=0.84; [M+H]$^+$: m/z 530; [M−H]$^−$: m/z 528 (method A).

$^1$H NMR (400 MHz, DMSO-d$_6$+TFA): 0.80 (s, 9H); 1.02 (d broad, J=15.5 Hz, 1H); 1.20 (s, 3H); 1.68 (m, 1H); 1.82 to 2.00 (m, 2H); 2.09 (m, 1H); 2.27 (m, 1H); 3.73 (m, 1H); 4.07 (d, J=11.9 Hz, 1H); 4.32 (dd, J=2.2 and 8.4 Hz, 1H); 5.29 (d, J=11.9 Hz, 1H); 6.74 (d, J=2.0 Hz, 1H); 6.98 (d, J=7.8 Hz, 1H); 7.15 to 7.35 (m, 4H); 7.78 (t, J=8.3 Hz, 1H).

C03701—TFA Salt (2'S,3'R,4'R,5'R)-6-Chloro-4'-(3-chloro-phenyl)-2'-(2,2-dimethyl-propyl)-5-fluoro-2-oxo-1,2-dihydro-spiro[indole-3,3'-pyrrolidine]-5'-carboxylic acid (3-hydroxy-3-methyl-cyclobutyl)-amide, trifluoroacetate

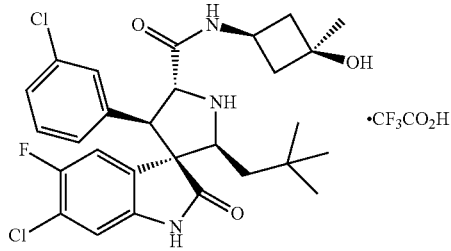 [SMILES: CC(C)(C)C[C@@H]1N[C@@H](C(=O)N[C@H]2C[C@@](C)(O)C2)[C@H](c2cccc(Cl)c2)[C@]12C(=O)Nc1cc(Cl)c(F)cc12 ; "·CF3CO2H"]

$^1$H NMR (300 MHz, MeOH-d$_4$): 9.00-8.80 (m, 1H), 7.73 (d, J=8.42 Hz, 1H), 7.40-7.20 (m, 3H), 7.15-7.05 (m, 1H), 6.89 (d, J=6.00 Hz, 1H), 5.32 (d, J=11.34 Hz, 1H), 4.52 (d, J=7.91 Hz, 1H), 4.20 (d, J=11.28 Hz, 1H), 4.00-3.80 (m, 1H), 2.50-2.35 (m, 1H), 2.35-2.20 (m, 1H), 2.20-1.90 (m, 2H), 1.90-1.80 (m, 1H), 1.31 (s, 3H), 1.30-1.15 (m, 1H), 0.91 (s, 9H); $^{13}$C NMR (75 MHz, MeOH-d$_4$): 178.8, 168.2, 157.3 (d, $J_{C-F}$=255.8 Hz), 142.1 (d, $J_{C-F}$=2.6 Hz), 137.1, 135.5, 132.8, 131.7, 130.7, 129.6, 127.2 (d, $J_{C-F}$=7.2 Hz), 124.7 (d, $J_{C-F}$=19.3 Hz), 115.5 (d, $J_{C-F}$=24.9 Hz), 114.8, 68.6, 66.6, 65.3, 64.0, 58.2, 47.0, 46.8, 44.7, 39.5, 32.2, 30.8, 28.8; ESI-MS calculated for $C_{28}H_{33}{}^{35}Cl_2FN_3O_3$ [M+H]$^+$: 548.1883. Found: 548.42.

LC-MS: $t_R$ (min)=0.87; [M+H]$^+$: m/z 548; [M−H]$^−$: m/z 546 (method A).

$^1$H NMR (400 MHz, DMSO-d$_6$): 0.70 to 2.23 (m, 18H); 3.68 to 5.10 (m, 4H); 6.78 to 8.03 (m, 6H).

C04801—TFA Salt (2'S,3'R,4'S,5'R)-6-Chloro-4'-(2,3-difluoro-phenyl)-2'-(2,2-dimethyl-propyl)-5-fluoro-2-oxo-1,2-dihydro-spiro[indole-3,3'-pyrrolidine]-5'-carboxylic acid (3-hydroxy-3-methyl-cyclobutyl)-amide, trifluoroacetate

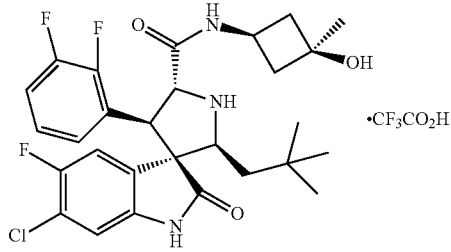 [SMILES: CC(C)(C)C[C@@H]1N[C@@H](C(=O)N[C@H]2C[C@@](C)(O)C2)[C@H](c2cccc(F)c2F)[C@]12C(=O)Nc1cc(Cl)c(F)cc12 ; "·CF3CO2H"]

$^1$H NMR (300 MHz, MeOH-d$_4$): 9.00-8.80 (m, 1H), 7.70 (d, J=8.35 Hz, 1H), 7.50-7.35 (m, 1H), 7.30-7.10 (m, 2H), 6.88 (d, J=6.88 Hz, 1H), 5.30 (d, J=11.32 Hz, 1H), 4.66 (d, J=11.33 Hz, 1H), 4.56 (d, J=7.43 Hz, 1H), 4.00-3.80 (m, 1H), 2.50-2.35 (m, 1H), 2.35-2.20 (m, 1H), 2.10-1.90 (m, 2H), 1.80-1.70 (m, 1H), 1.30 (s, 3H), 1.16 (d, J=15.34 Hz, 1H), 0.90 (s, 9H); $^{13}$C NMR (75 MHz, MeOH-d$_4$): 177.5, 166.9, 160-145 (m, 2×$C_{sp2}$—F), 155.9 (d, $J_{C-F}$=243.4 Hz), 140.7 (d, $J_{C-F}$=2.69 Hz, 1H), 126.5-126.1 (m), 125.6 (d, $J_{C-F}$=7.6 Hz), 125.0 (d, $J_{C-F}$=3.4 Hz), 123.6 (d, $J_{C-F}$=19.5 Hz), 122.0 (d, $J_{C-F}$=9.8 Hz), 119.1 (d, $J_{C-F}$=17.1 Hz), 114.7 (d, $J_{C-F}$=25.0 Hz), 113.4, 67.3, 64.7, 64.3, 62.5, 48.2, 45.6, 45.6, 43.4, 38.3, 31.0, 29.5, 27.5; ESI-MS calculated for $C_{28}H_{32}{}^{35}ClF_3N_3O_3$ [M+H]⁺: 550.2084. Found: 550.42.

LC-MS: $t_R$ (min)=0.89; [M+H]⁺: m/z 550; [M−H]⁻: m/z 548 (method A)

¹H NMR (400 MHz, DMSO-d₆+TFA): 0.81 (s, 9H); 1.02 (d broad, J=15.5 Hz, 1H); 1.20 (s, 3H); 1.62 (m, 1H); 1.87 to 1.98 (m, 2H); 2.09 (m, 1H); 2.26 (m, 1H); 3.73 (m, 1H); 4.56 (m, 2H); 5.29 (d, J=12.4 Hz, 1H); 6.89 (d, J=6.2 Hz, 1H); 7.20 to 7.49 (m, 3H); 8.06 (d, J=9.3 Hz, 1H).

MI-710201—TFA Salt (2'S,3'R,4'S,5'R)-6-Chloro-4'-(2,3-difluoro-phenyl)-2'-(2,2-dimethyl-propyl)-2-oxo-1,2-dihydro-spiro[indole-3,3'-pyrrolidine]-5'-carboxylic acid (4-hydroxy-cyclohexyl)-amide, trifluoroacetate

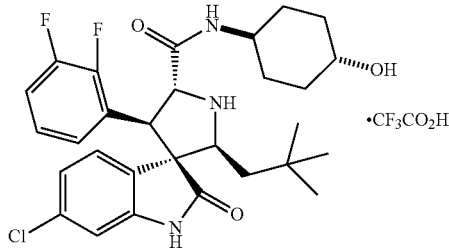

¹H NMR (300 MHz, MeOH-d₄): 7.57 (d, J=8.0 Hz, 1H), 7.50-7.36 (m, 1H), 7.27-7.07 (m, 3H), 6.79 (s, 1H), 5.11 (d, J=11.1 Hz, 1H), 4.55 (d, J=11.0 Hz, 1H), 4.39 (d, J=7.7 Hz, 1H), 3.71-3.52 (m, 1H), 3.52-3.37 (m, 1H), 3.21 (dd, J=7.4, 14.5 Hz, 1H), 1.92 (d, J=9.6 Hz, 1H), 1.86-1.70 (m, 2H), 1.58 (d, J=11.8 Hz, 1H), 1.43-1.18 (m, 4H), 1.12 (d, J=15.5 Hz, 1H), 0.99 (d, J=13.0 Hz, 1H), 0.88 (s, 9H); ESI-MS calculated for $C_{29}H_{35}ClF_2N_3O_3$ (M+H)⁺ requires 546.23. found 546.58; HPLC (Condition I) $t_R$=52.15 min (Purity 98.8%).

LC-MS: $t_R$ (min)=0.84; [M+H]⁺: m/z 546; [M−H]⁻: m/z 544 (method A).

¹H NMR (400 MHz; DMSO-d₆): mixture of isomers: 0.80 (s, 9H); 0.84 to 1.30 (m, 5H); 1.41 to 1.87 (m, 5H); 3.43 to 3.54 (m, 2H); 4.03 (m broad, 1H); 4.36 (d broad, J=10.3 Hz, 2H); 4.83 (m broad, 1H); 6.72 (d, J=2.0 Hz, 1H); 7.10 (dd, J=2.0 and 8.3 Hz, 1H); 7.14 (m, 1H); 7.24 (m, 1H); 7.40 (m, 1H); 7.58 (d, J=8.3 Hz, 1H); 7.97 (m broad, 1H); 10.56 (m broad, 1H).

MI-710401—TFA Salt (2'S,3'R,4'S,5'R)-4'-(3-Chloro-2-fluoro-phenyl)-2'-(2,2-dimethyl-propyl)-5,6-difluoro-2-oxo-1,2-dihydro-spiro[indole-3,3'-pyrrolidine]-5'-carboxylic acid (4-hydroxy-cyclohexyl)-amide, trifluoroacetate

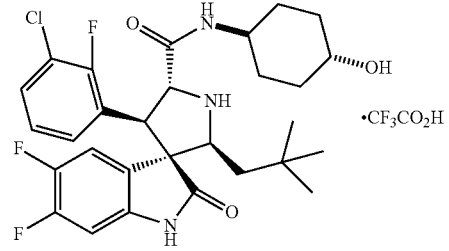

¹H NMR (300 MHz, MeOH-d₄): 7.67 (t, J=8.6 Hz, 1H), 7.57 (t, J=6.8 Hz, 1H), 7.38 (t, J=6.8 Hz, 1H), 7.15 (t, J=7.8 Hz, 1H), 6.71 (dd, J=6.6, 10.1 Hz, 1H), 5.01 (d, J=10.8 Hz, 1H), 4.52 (d, J=10.8 Hz, 1H), 4.40-4.21 (m, 1H), 3.74-3.56 (m, 1H), 3.56-3.40 (m, 1H), 2.08-1.87 (m, 2H), 1.87-1.68 (m, 2H), 1.68-1.53 (m, 1H), 1.45-1.18 (m, 3H), 1.17-0.97 (m, 2H), 0.89 (s, 9H); ESI-MS calculated for $C_{29}H_{34}ClF_3N_3O_3$ (M+H)⁺ requires 564.22. found 564.58; HPLC (Condition I) $t_R$=52.15 min (Purity 98.8%).

LC-MS: $t_R$ (min)=0.84; [M+H]⁺: m/z 564; [M−H]⁻: m/z 562 (method A)

¹H NMR (400 MHz; DMSO-d₆+TFA): 0.81 (s, 9H); 0.81 to 1.98 (m, 10H); 3.35 (m, 1H); 3.52 (m, 1H); 4.53 (d, J=12.2 Hz, 1H); 4.59 (dd, J=2.3 and 8.7 Hz, 1H); 5.33 (d, J=12.2 Hz, 1H); 6.78 (dd, J=6.8 and 10.3 Hz, 1H); 7.21 (t, J=9.0 Hz, 1H); 7.48 (m, 1H); 7.66 (m, 1H); 8.00 (m, 1H).

MI-710501—TFA Salt (2'S,3'R,4'S,5'R)-4'-(3-Chloro-2-fluoro-phenyl)-2'-(2,2-dimethyl-propyl)-6-fluoro-2-oxo-1,2-dihydro-spiro[indole-3,3'-pyrrolidine]-5'-carboxylic acid (4-hydroxy-cyclohexyl)-amide, trifluoroacetate

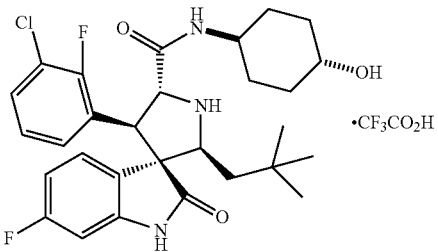

¹H NMR (300 MHz, MeOH-d₄): 7.66-7.53 (m, 1H), 7.44-7.33 (m, 1H), 7.22-7.09 (m, 1H), 6.93-6.79 (m, 1H), 6.59-6.51 (m, 1H), 5.40-5.31 (m, 1H), 4.63-4.48 (m, 1H), 4.41-4.30 (m, 1H), 2.41-2.20 (m, 2H), 2.15-1.97 (m, 2H), 1.95-1.85 (m, 1H), 1.85-1.71 (m, 1H), 1.71-1.47 (m, 3H), 1.19-1.07 (m, 1H), 0.88 (s, 9H); ESI-MS calculated for $C_{29}H_{34}ClF_3N_3O_3$ (M+H)⁺ requires 546.23. found 546.58; HPLC (Condition I) $t_R$=52.05 min (Purity 98.8%); HPLC (Condition II) $t_R$=19.26 min (Purity 100%).

LC-MS: $t_R$ (min)=0.80; [M+H]⁺: m/z 546; [M−H]⁻: m/z 544 (method A).

¹H NMR (400 MHz; DMSO-d₆+TFA): 0.81 (s, 9H); 0.81 to 1.99 (m, 10H); 3.35 (m, 1H); 3.52 (m, 1H); 4.47 (d, J=12.0 Hz, 1H); 4.53 (d broad, J=8.3 Hz, 1H); 5.37 (d, J=12.0 Hz, 1H); 6.58 (dd, J=2.6 and 9.1 Hz, 1H); 6.91 (m, 1H); 7.21 (t, J=9.0 Hz, 1H); 7.45 (m, 1H); 7.62 to 7.72 (m, 2H).

MI-710601—TFA Salt (2'S,3'R,4'R,5'R)-6-Chloro-4'-(3-chloro-phenyl)-2'-(2,2-dimethyl-propyl)-2-oxo-1,2-dihydro-spiro[indole-3,3'-pyrrolidine]-5'-carboxylic acid (4-hydroxy-cyclohexyl)-amide, trifluoroacetate

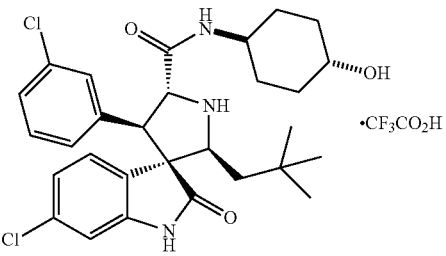

LC-MS: $t_R$ (min)=0.82; [M+H]$^+$: m/z 544; [M−H]$^−$: m/z 542 (method A).

$^1$H NMR (400 MHz; DMSO-d$_6$+TFA): 0.80 (s, 9H); 0.83 to 1.96 (m, 10H); 3.34 (m, 1H); 3.50 (m, 1H); 4.02 (d, J=12.1 Hz, 1H); 4.48 (d broad, J=8.5 Hz, 1H); 5.32 (d, J=12.1 Hz, 1H); 6.75 (dd, J=1.9 and 8.3 Hz, 1H); 6.98 (d, J=7.8 Hz, 1H); 7.18 to 7.32 (m, 4H); 7.74 (d, J=8.3 Hz, 1H).

MI-710801

(2'S,3'R,4'R,5'R)-6-Chloro-4'-(3-chloro-phenyl)-2'-(2,2-dimethyl-propyl)-5-fluoro-2-oxo-1,2-dihydro-spiro[indole-3,3'-pyrrolidine]-5'-carboxylic acid (4-hydroxy-cyclohexyl)-amide

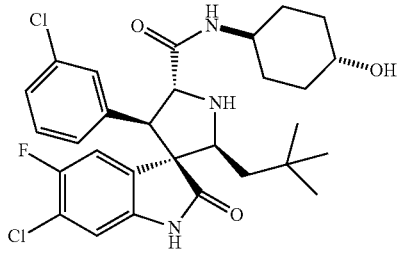

LC-MS: $t_R$ (min)=0.85; [M+H]$^+$: m/z 562; [M−H]$^−$: m/z 560 (method A).

$^1$H NMR (400 MHz; DMSO-d$_6$): 0.78 (m, 1H); 0.81 (s, 9H); 1.08 to 1.33 (m, 5H); 1.70 to 1.90 (m, 4H); 3.25 (m, 1H); 3.35 to 3.58 (m, 3H); 3.92 (d, J=9.2 Hz, 1H); 4.43 (t, J=9.2 Hz, 1H); 4.49 (d, J=4.8 Hz, 1H); 6.79 (d, J=6.4 Hz, 1H); 6.92 (d, J=7.8 Hz, 1H); 7.09 to 7.21 (m, 3H); 7.75 (d, J=8.5 Hz, 1H); 7.83 (d, J=9.3 Hz, 1H); 10.38 (s broad, 1H).

MI-710901—TFA Salt (2'S,3'R,4'S,5'R)-6-Chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid cyclopropylamide, trifluoroacetate

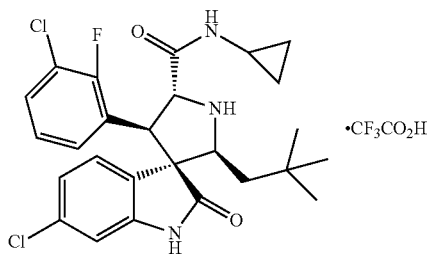 [SMILES: CC(C)(C)C[C@@H]1N[C@@H](C(=O)NC2CC2)[C@H](c2cccc(Cl)c2F)[C@]12C(=O)Nc1cc(Cl)ccc12 ; "·CF3CO2H"]

$^1$H NMR (300 MHz, MeOH-d$_4$): 7.61 (d, J=8.1 Hz, 1H), 7.53 (t, J=6.7 Hz, 1H), 7.40 (t, J=7.0 Hz, 1H), 7.21-7.08 (m, 2H), 6.79 (d, J=1.6 Hz, 1H), 5.14 (d, J=11.3 Hz, 1H), 4.60 (d, J=11.3 Hz, 1H), 4.48 (d, J=7.0 Hz, 1H), 2.78-2.58 (m, 1H), 1.86 (dd, J=8.4, 15.4 Hz, 1H), 1.13 (d, J=15.4 Hz, 1H), 0.88 (s, 9H), 0.78-0.60 (m, 2H), 0.47-0.16 (m, 2H); $^{13}$C NMR (75 MHz, MeOH-d$_4$): 177.9, 169.5, 157.8 (d, $J_{C-F}$=249.4 Hz), 145.2, 137.2, 132.6, 128.7, 126.8 (d, $J_{C-F}$=1.6 Hz), 126.6 (d, $J_{C-F}$=4.9 Hz), 124.2, 123.6, 122.5 (d, $J_{C-F}$=18.8 Hz), 121.8 (d, $J_{C-F}$=13.1 Hz), 64.7, 64.4, 62.9, 43.5, 31.0, 29.6, 23.9, 6.7, 6.5; ESI-MS calculated for $C_{26}H_{29}Cl_2FN_3O_2$ (M+H)$^+$ requires 504.16. found 504.58; HPLC (Condition I) $t_R$=58.22 min (Purity 99.6%).

LC-MS: $t_R$ (min)=0.98; [M+H]$^+$: m/z 504; [M−H]$^−$: m/z 502 (method A)

$^1$H NMR (400 MHz; DMSO-d$_6$+TFA): 0.15 (m, 1H); 0.35 (m, 1H); 0.54 to 0.70 (m, 2H); 0.81 (s, 9H); 1.01 (d, J=15.2 Hz, 1H); 1.91 (dd, J=8.4 and 15.2 Hz, 1H); 2.66 (m, 1H); 4.52 (m, 2H); 5.27 (d, J=12.0 Hz, 1H); 6.79 (d, J=2.0 Hz, 1H); 7.18 (dd, J=2.0 and 8.3 Hz, 1H); 7.23 (d, J=8.1 Hz, 1H); 7.48 (m, 1H); 7.59 (m, 1H); 7.74 (d, J=8.3 Hz, 1H).

C08301—TFA Salt

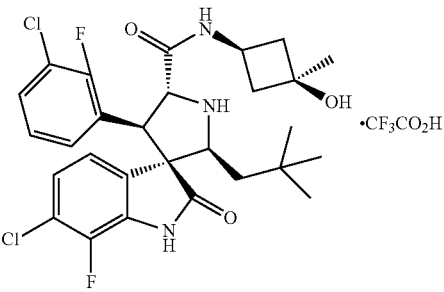 [SMILES: CC(C)(C)C[C@@H]1N[C@@H](C(=O)N[C@H]2C[C@@](C)(O)C2)[C@H](c2cccc(Cl)c2F)[C@]12C(=O)Nc1c2ccc(Cl)c1F ; "·CF3CO2H"]

$^1$H NMR (300 MHz, MeOH-d$_4$): 7.64-7.54 (m, 1H), 7.20-7.46 (m, 1H), 7.46-7.38 (m, 1H), 7.28-7.14 (m, 2H), 5.26 (d, J=11.34 Hz, 1H), 4.65 (d, J=11.43 Hz, 1H), 4.55 (dd, J=8.28, 1.59 Hz, 1H), 3.95-3.80 (m, 1H), 2.46-2.33 (m, 1H), 2.30-2.20 (m, 1H), 2.40-1.84 (m, 2H), 1.76-1.64 (m, 1H), 1.29 (s, 3H), 1.17 (dd, J=15.40, 1.5 Hz, 1H), 0.88 (s, 9H); $^{13}$C NMR (75 MHz, MeOH-d$_4$): 177.4, 166.9, 157.8 (d, $J_{C-F}$=249.9 Hz), 144.3 (d, $J_{C-F}$=248.0 Hz), 132.8, 132.5 (d, $J_{C-F}$=12.3 Hz), 128.6, 126.7 (d, $J_{C-F}$=4.87 Hz), 126.3 (d, $J_{C-F}$=3.32 Hz), 125.6, 123.9 (d, $J_{C-F}$=14.3 Hz), 122.6 (d, $J_{C-F}$=18.9 Hz), 122.1, 121.3 (d, $J_{C-F}$=13.1 Hz), 67.2, 64.7, 64.5, 62.6, 48.9, 45.6, 45.5, 43.4, 38.3, 31.0, 29.5, 27.5; ESI-MS calculated for $C_{28}H_{32}{}^{35}Cl_2F_2N_3O_3$ [M+H]$^+$: 566.18. Found: 566.50.

C08601—TFA Salt

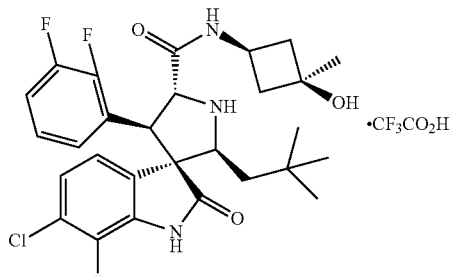

$^1$H NMR (300 MHz, MeOH-d$_4$): 8.83 (d, J=6.98 Hz, 1H), 7.54-7.38 (m, 2H), 7.30-7.14 (m, 3H), 5.26 (d, J=11.37 Hz, 1H), 4.64 (d, J=11.37 Hz, 1H), 4.56 (dd, J=8.35, 1.27 Hz, 1H), 3.95-3.80 (m, 1H), 2.48-2.34 (m, 1H), 2.30-2.20 (m, 1H), 2.08-1.86 (m, 2H), 1.80-1.64 (m, 1H), 1.30 (s, 3H), 1.18 (d, J=14.37 Hz, 1H), 0.90 (s, 9H); $^{13}$C NMR (75 MHz, MeOH-d$_4$): 177.4, 166.9, 133.9, 132.4, 130.1, 126.35 (dd, $J_{C-F}$=9.43, 2.72 Hz), 125.5, 125.0 (d, $J_{C-F}$=3.72 Hz), 124.0 (d, $J_{C-F}$=14.4 Hz), 122.1 (d, $J_{C-F}$=3.13 Hz), 121.9 (d, $J_{C-F}$=9.77 Hz), 119.3 (d, $J_{C-F}$=17.1 Hz), 119.9, 115.1, 67.3, 64.8, 64.7, 64.5, 62.6, 45.6, 45.5, 43.4, 38.4, 31.0, 29.5, 27.5; ESI-MS calculated for $C_{28}H_{32}{}^{35}ClF_3N_3O_3$ [M+H]$^+$: 550.20. Found: 550.35.

C09101—TFA Salt

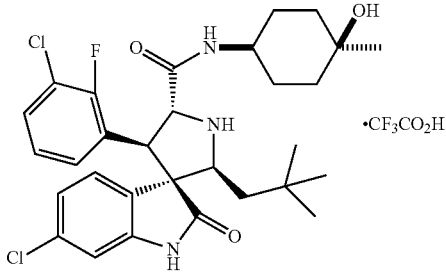

$^1$H NMR (300 MHz, MeOH-d$_4$): 8.43 (d, J=7.73 Hz, 1H), 7.66-7.54 (m, 2H), 7.39 (t, J=7.31 Hz, 1H), 7.24-7.10 (m, 2H), 6.82 (d, J=1.43 Hz, 1H), 5.26 (d, J=12.22 Hz, 1H), 4.61 (d, J=11.38 Hz, 1H), 4.53 (d, J=7.73 Hz, 1H), 3.57-3.54 (m, 1H), 1.93 (dd, J=15.41, 8.26 Hz, 1H), 1.80-1.10 (m, 9H), 1.16 (s, 3H), 0.89 (s, 9H); $^{13}$C NMR (75 MHz, MeOH-d$_4$): 177.6, 166.6, 157.7 (d, $J_{C-F}$=249.6 Hz), 144.9, 137.0, 132.4, 128.6, 126.5, 126.4 (d, $J_{C-F}$=4.9 Hz), 124.0, 123.3, 122.3 (d, $J_{C-F}$=19.2 Hz), 121.3 (d, $J_{C-F}$=13.0 Hz), 118.7, 114.9, 112.0, 68.7, 64.4, 64.0, 62.8, 50.2, 48.9, 43.2, 37.9, 37.8, 30.9, 30.8, 29.4, 28.5, 28.3; ESI-MS calculated for $C_{30}H_{32}{}^{35}Cl_2FN_3O_3$ [M+H]$^+$: 576.21. Found: 576.58.

C09601—TFA Salt

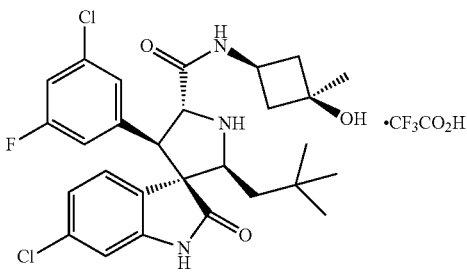 [SMILES: CC(C)(C)C[C@@H]1N[C@@H](C(=O)N[C@H]2C[C@@](C)(O)C2)[C@H](c2cc(F)cc(Cl)c2)[C@]12C(=O)Nc1cc(Cl)ccc12 ; "·CF3CO2H"]

$^1$H NMR (300 MHz, MeOH-d$_4$): 8.84 (d, J=6.87 Hz, 1H), 7.62 (d, J=8.10 Hz, 1H), 7.19 (dd, J=8.10, 1.79 Hz, 1H), 7.15 (dt, J=8.42, 1.87 Hz, 1H), 7.01 (s, 1H), 6.94 (d, J=9.62, 1.30 Hz, 1H), 6.83 (d, J=1.69 Hz, 1H), 5.21 (d, J=11.25 Hz, 1H), 4.45 (dd, J=8.21, 1.56 Hz, 1H), 4.15 (d, J=11.25 Hz, 1H), 4.00-3.82 (m, 1H), 2.50-2.36 (m, 1H), 2.36-2.22 (m, 1H), 2.10-1.98 (m, 1H) 1.91 (dd, J=15.44, 8.30 Hz, 1H), 1.84-1.72 (m, 1H), 1.31 (s, 3H), 1.16 (dd, J=15.44, 1.47 Hz, 1H), 0.90 (s, 9H); $^{13}$C NMR (75 MHz, MeOH-d$_4$): 177.7, 167.0, 164.0 (d, $J_{C-F}$=249.6 Hz), 145.3, 137.3, 136.6 (d, $J_{C-F}$=20.6H), 136.6, 126.4, 126.1 (d, $J_{C-F}$=2.91 Hz), 124.3, 123.8, 117.9 (d, $J_{C-F}$=25.0 Hz), 115.4 (d, J=23.0 Hz), 112.3, 67.3, 64.8, 64.3, 62.7, 56.7, 45.7, 45.6, 43.3, 38.4, 31.0, 29.6, 27.6; ESI-MS calculated for $C_{28}H_{33}{}^{35}Cl_2FN_3O_3$ [M+H]$^+$: 548.18. Found: 548.67.

C09701—TFA Salt

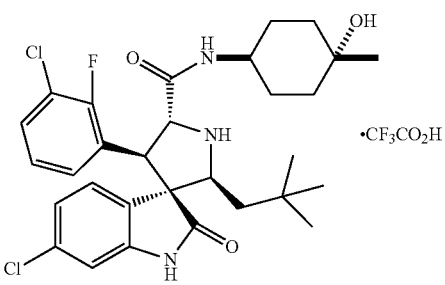

$^1$H NMR (300 MHz, MeOH-d$_4$): 8.21 (d, J=6.81 Hz, 1H), 7.68-7.54 (m, 2H), 7.39 (td, J=7.60, 1.36 Hz, 1H), 7.18 (t, J=8.09 Hz, 1H), 7.13 (dd, J=7.97, 1.92 Hz, 1H), 6.79 (d, J=1.66 Hz, 1H), 5.30 (d, J=11.51 Hz, 1H), 4.56 (d, J=11.84 Hz, 1H), 4.52 (d, J=8.26 Hz, 1H), 3.86-3.70 (m, 1H), 2.00-1.80 (m, 2H), 1.65-1.05 (m, 8H), 1.04 (s, 3H), 0.87 (s, 9H); $^{13}$C NMR (75 MHz, MeOH-d$_4$): 177.8, 167.2, 145.1, 137.2, 132.7, 128.8, 126.7 (d, $J_{C-F}$=3.6 Hz), 126.6, 124.2, 123.4, 122.6 (d, $J_{C-F}$=18.7 Hz), 121.7 (d, $J_{C-F}$=12.5 Hz), 112.1, 69.7, 64.6, 64.2, 62.9, 49.2, 43.4, 36.8, 36.4, 31.0, 29.5, 28.3, 28.3; ESI-MS calculated for $C_{30}H_{32}{}^{35}Cl_2FN_3O_3$ [M+H]$^+$: 576.21. Found: 576.67.

C11701—TFA Salt

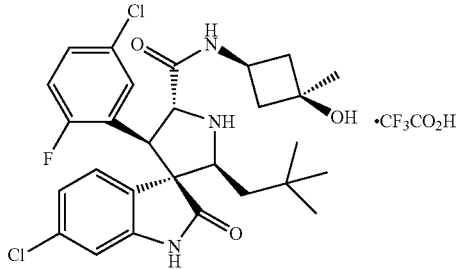 [SMILES: CC(C)(C)C[C@@H]1N[C@@H](C(=O)N[C@H]2C[C@@](C)(O)C2)[C@H](c2cc(Cl)ccc2F)[C@]12C(=O)Nc1cc(Cl)ccc12 ; "·CF3CO2H"]

$^1$H NMR (300 MHz, MeOH-d$_4$): 8.83 (d, J=6.61 Hz, 1H), 7.64 (dd, J=6.06, 2.50 Hz, 1H), 7.59 (d, J=8.11 Hz, 1H), 7.36-7.22 (m, 1H), 7.11 (dd, J=8.09, 1.76 Hz, 1H), 7.00-6.82 (m, 1H), 1.72 (d, J=1.72 Hz, 1H), 5.13 (d, J=11.21 Hz, 1H), 4.58 (d, J=11.21 Hz, 1H), 4.51 (dd, J=8.23, 1.66 Hz, 1H), 3.98-3.80 (m, 1H), 2.44-2.32 (m, 1H), 2.32-2.20 (m, 1H), 2.10-1.94 (m, 1H), 1.88 (dd, J=15.38, 8.24 Hz, 1H), 1.80-1.68 (m, 1H), 1.29 (s, 3H), 1.14 (dd, J=15.38, 1.45 Hz, 1H), 0.89 (s, 9H); $^{13}$C NMR (75 MHz, MeOH-d$_4$): 177.9, 167.1, 161.1 (d, $J_{C-F}$=243.6 Hz), 145.2, 137.3, 136.9, 132.1 (d, $J_{C-F}$=9.0 Hz), 131.2 (d, $J_{C-F}$=3.60 Hz), 130.0 (d, $J_{C-F}$=2.22 Hz), 127.0, 123.8 (d, $J_{C-F}$=57.7 Hz), 121.6 (d, $J_{C-F}$=14.8 Hz), 118.5 (d, $J_{C-F}$=25.4 Hz), 112.1, 67.4, 64.5, 64.4, 62.7, 48.4, 45.7, 45.5, 43.3, 38.4, 31.0, 29.6, 27.6; ESI-MS calculated for $C_{28}H_{33}{}^{35}Cl_2FN_3O_3$ [M+H]$^+$: 548.19. Found: 548.67.

C29701—TFA Salt

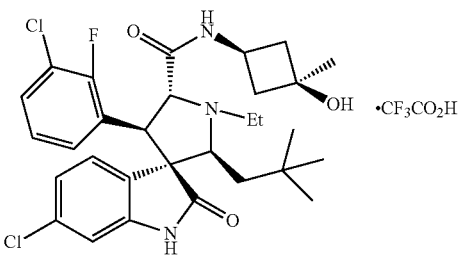 [SMILES: CCN1[C@@H](CC(C)(C)C)[C@@]2(C(=O)Nc3cc(Cl)ccc32)[C@@H](c2cccc(Cl)c2F)[C@@H]1C(=O)N[C@H]1C[C@@](C)(O)C1 ; "·CF3CO2H"]

$^1$H NMR (MeOH-d$_4$): 7.66 (d, J=8.47 Hz, 1H), 7.56 (t, J=6.87 Hz, 1H), 7.43 (td, J=7.60, 1.47 Hz, 1H), 7.22 (d, J=7.79 Hz, 1H), 7.16 (dd, J=8.17, 1.89 Hz, 1H), 6.81 (d, J=1.80 Hz, 1H), 5.17 (d, J=11.92 Hz, 1H), 4.68-4.58 (m, 2H), 3.91-3.78 (m, 1H), 3.78-3.66 (m, 2H), 2.44-2.32 (m, 1H), 2.26-2.10 (m, 2H), 1.98-1.88 (m, 1H), 1.64-1.52 (m, 1H), 1.43 (t, J=7.15 Hz, 1H), 1.33-1.25 (m, 1H), 1.29 (s, 3H), 0.81 (s, 3H); ESI-MS: Calculated for $C_{30}H_{37}Cl_2FN_3O_3$ [M+H]$^+$= 576.22. Found: 576.92.

C30201—TFA Salt

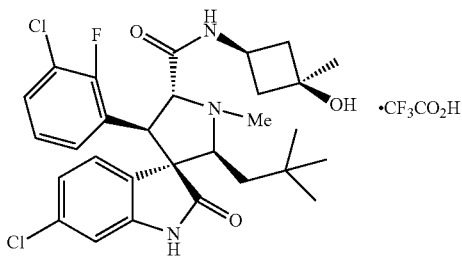 [SMILES: CN1[C@@H](CC(C)(C)C)[C@@]2(C(=O)Nc3cc(Cl)ccc32)[C@@H](c2cccc(Cl)c2F)[C@@H]1C(=O)N[C@H]1C[C@@](C)(O)C1 ; "·CF3CO2H"]

$^1$H NMR (MeOH-d$_4$): 7.68 (dd, J=8.16, 1.47 Hz, 1H), 7.48 (t, J=7.09 Hz, 1H), 7.39 (td, J=7.30, 1.29 Hz, 1H), 7.20-7.08 (m, 2H), 6.79 (d, J=1.79 Hz, 1H), 5.19 (d, J=11.56 Hz, 1H), 4.83 (d, J=11.56 Hz, 1H), 4.51 (t, J=3.96 Hz, 1H), 3.94-3.78 (m, 1H), 3.12 (s, 3H), 2.50-2.36 (m, 1H), 2.32-2.20 (m, 1H), 2.10-1.92 (m, 2H), 1.73 (dd, J=10.67, 9.23 Hz, 1H), 1.40-1.25 (m, 1H), 1.29 (s, 3H), 0.75 (s, 9H); ESI-MS: Calculated for $C_{29}H_{35}Cl_2FN_3O_3$ [M+H]$^+$=562.20. Found: 562.58.

Example 2

Fluorescence-Polarization MDM2 Binding Assay

The binding affinity of the MDM2 inhibitors was determined using an optimized, sensitive and quantitative fluorescence polarization-based (FP-based) binding assay using a recombinant human His-tagged MDM2 protein (residues 1-118) and a fluorescently tagged p53-based peptide.

The design of the fluorescence probe was based upon a previously reported high-affinity p53-based peptidomimetic compound (5-FAM-βAla-βAla-Phe-Met-Aib-pTyr-(6-Cl-LTrp)-Glu-Ac3c-Leu-Asn-NH$_2$ (SEQ ID NO: 1)) (García-Echeverría et al., *J. Med. Chem.* 43: 3205-3208 (2000)). This tagged peptide is called PMDM6-F. The K$_d$ value of PMDM6-F with the recombinant MDM2 protein was determined from the saturation curve. MDM2 protein was serially double diluted in a Dynex 96-well, black, round-bottom plate, and the PMDM6-F peptide was added at 1 nM concentration. The assay was performed in the buffer: 100 mM potassium phosphate, pH 7.5; 100 µg/mL bovine gamma globulin; 0.02% sodium azide, 0.01% Triton X-100) and the polarization values were measured after 3 h of incubation using an ULTRA READER (Tecan U.S. Inc., Research Triangle Park, N.C.). The IC$_{50}$ value was obtained by fitting the mP values in a sigmoidal dose-response curve (variable slope) with a non-linear regression, and was determined to be 1.40 nM±0.25. The K$_d$ value was calculated using the equation: K$_d$ value =IC$_{50}$–L0/2. L0 is the total concentration of the fluorescent ligand; L0/2 is the total concentration of the fluorescent ligand divided by 2. Since PMDM6-F was used at a final concentration of 1 nM, L0/2 was 0.5 nM.

Dose-dependent, competitive binding experiments were performed with serial dilutions of a tested compound in DMSO. A 5 µL sample of the tested compound and pre-incubated MDM2 protein (10 nM) and PMDM6-F peptide (1 nM) in the assay buffer (100 mM potassium phosphate, pH 7.5; 100 µg/mL bovine gamma globulin; 0.02% sodium azide, 0.01% Triton X-100), were added in a Dynex 96-well, black, round-bottom plate to produce a final volume of 125 µL. For each assay, the controls included the MDM2 protein and PMDM6-F (equivalent to 0% inhibition), PMDM6-F peptide alone (equivalent to 100% inhibition). The polarization values were measured after 3 h of incubation. The IC$_{50}$ values, i.e. the inhibitor concentration at which 50% of bound peptide is displaced, were determined from a plot using non-linear least-squares analysis. Curve fitting was performed using GRAPHPAD PRISM software (GraphPad Software, Inc., San Diego, Calif.).

In the alternative, fluorescence polarization values were measured using the Infinite M-1000 plate reader (Tecan U.S., Research Triangle Park, N.C.) in Microfluor 2 96-well, black, round-bottom plates (Thermo Scientific). In the saturation experiments, 1 nM of PMDM6-F and increasing concentrations of proteins were added to each well to a final volume of 125 µl in the assay buffer (100 mM potassium phosphate, pH 7.5, 100 µg/ml bovine γ-globulin, 0.02% sodium azide (Invitrogen), with 0.01% Triton X-100 and 4% DMSO). Plates were mixed and incubated at room temperature for 30 minutes with gentle shaking to assure equilibrium. The polarization values in millipolarization units (mP) were measured at an excitation wavelength of 485 nm and an emission wavelength of 530 nm. Equilibrium dissociation constants (K$_d$) were then calculated by fitting the sigmoidal dose-dependent FP increases as a function of protein concentrations using Graphpad Prism 5.0 software (Graphpad Software, San Diego, Calif.).

K$_i$ values of tested compounds were determined in a dose-dependent competitive binding experiment. Mixtures of 5 µl of the tested compound in different concentrations in DMSO and 120 µl of preincubated protein/fluorescent probe complex with fixed concentrations in the assay buffer (100 mM potassium phosphate, pH 7.5, 100 µg/ml bovine γ-globulin, 0.02% sodium azide, with 0.01% Triton X-100) were added into assay plates and incubated at room temperature for 30 minutes with gentle shaking. Final concentrations of the protein and fluorescent probe in the competitive assays were 10 nM and 1 nM, respectively, and final DMSO concentration is 4%. Negative controls containing protein/fluorescent probe complex only (equivalent to 0% inhibition), and positive controls containing free fluorescent probe only (equivalent to 100% inhibition), were included in each assay plate. FP values were measured as described above. IC$_{50}$ values were determined by nonlinear regression fitting of the sigmoidal dose-dependent FP decreases as a function of total compound concentrations using Graphpad Prism 5.0 software (Graphpad Software, San Diego, Calif.). $K_i$ values of tested compounds to the MDM2 protein were calculated using the measured $IC_{50}$ values, the $K_d$ value of the fluorescent probe to the protein, and the concentrations of the protein and fluorescent probe in the competitive assays (Nikolovska-Coleska et al., *Anal. Biochem.* 332:261-73 (2004)).

Compounds shown in Table 2A as the free base were tested either as the free base or as the $CF_3CO_2H$ (TFA) or HCl salt. In general, comparable assay responses are expected between the free base and salt form of a compound (See, e.g., MI-77301 (free base) and MI-77301 (TFA salt)).

Binding Kinetics of Different Isomers in Binding Media

Aliquots of freshly prepared DMSO stock solutions of compounds were diluted in FP binding assay buffer to prepare the aqueous compound incubation solutions in which compound isomerization was taking place. Final compound concentration in the incubation solution was 25 µM, and 5% of DMSO was present to enhance the solubility. These solutions were stored at room temperature for the whole time range of the experiment. 80 µL of aliquots of compound solutions were mixed with 20 µL of freshly prepared MDM2/PMDM6-F mixture in the assay plates at different time points. Final concentrations of the protein, fluorescent probe, and DMSO are same as those in the competitive assays described above. Negative and positive controls were included in each assay plate as well. Following 15 minutes of incubation at room temperature with gentle shaking, mP values were measured and $IC_{50}$ values were determined as described above (Table 2B). Due to the plate preparation and incubation time required before measurement, it should be noticed that all $IC_{50}$ values presented below are values actually obtained 20 minutes after the labeled incubation time.

Example 3

Fluorescence-Polarization MDM2 Binding Assay

The binding affinity of the MDM2 inhibitors was optionally determined using a fluorescence polarization-based (FP-based) binding assay using a recombinant human MDM2 protein (residues 5-109) and PMDM6-F as follows:

MDM2 protein was serially diluted with a step of 1.8 in a Costar 96-well, black, non binding surface reference 3686 plate, and the PMDM6-F peptide was added at 5 nM concentration. The assay was performed in the buffer: 100 mM potassium phosphate, pH 7.5; 100 µg/mL bovine gamma globulin, 0.01% Triton X-100) and the anisotropy values were measured at equilibrium using a Fusion reader (Packard). The fraction of ligand bound, $F_{SB}$, was calculated using the following equation $F_{SB}=(Aobs-AF)/[(Ab-Aobs)Q+Aobs-AF]$ (ref) where Aobs=anisotropy observed, Ab=anisotropy when all p53 is bound, AF=anisotropy when p53 is free, Q=ratio Fluorescence intensity Bound/fluorescence intensity Free (*Biochemistry* 43:16056-16066 (2004)). KD was determined, using the Langmuir equation applied to fluorescence polarization, to be 1.8 nM.

Dose-dependent, competitive binding experiments were performed with serial dilutions of a tested compound in DMSO. A 5 µL sample of the tested compound and PMDM6-F peptide (5 nM) and MDM2 protein (6 or 8 nM) in the assay buffer (100 mM potassium phosphate, pH 7.5; 100 µg/mL bovine gamma globulin, 0.01% Triton X-100), were added in Costar 96-well, black, non binding surface reference 3686 to produce a final volume of 125 µL. For each assay, the controls included the MDM2 protein and PMDM6-F (equivalent to 0% inhibition), PMDM6-F peptide alone (equivalent to 100% inhibition). The polarization values were measured at equilibrium. The $IC_{50}$ values, i.e. the inhibitor concentration at which 50% of bound peptide is displaced, were determined from a plot using the 4-parameter logistic model (Ratkowsky and Reedy, Biometrics 42(3):575-82 (1986)). The adjustment was obtained by non-linear regression using the Marquardt algorithm in Xlfit software (Table 3).

TABLE 3

| Compound | $IC_{50}$ (biot MDM2) | $IC_{50}$ (without Tag) |
|---|---|---|
| MI-710201 | 308.32 nM | 272.83 nM |
| MI-710501 | 309.08 nM | 260.40 nM |
| MI-710601 | 157.86 nM | 137.94 nM |
| MI-710801 | 289.62 nM | 256.02 nM |
| MI-710901 | 224.96 nM | 184.74 nM |
| C02701 | 149.49 nM | 111.52 nM |
| C02901 | 159.97 nM | 121.90 nM |
| C03001 | 120.23 nM | 89.59 nM |
| C031 | 3339.44 nM | 2742.86 nM |
| C03401 | 107.66 nM | 85.61 nM |
| C03701 | 270.09 nM | 220.41 nM |
| C04801 | 473.01 nM | 388.72 nM |

Example 4

Cell Growth Assay

Isogenic HCT-116 colon cancer cell lines were a kind gift from Prof. Bert Vogelstein (Johns Hopkins, Baltimore, Md.) and were maintained in McCoy's 5A medium containing 10% FBS. All other cell lines were obtained from ATCC (Manassas, Va.) and were maintained in RPMI-1640 medium containing 10% FBS.

Figure 24:
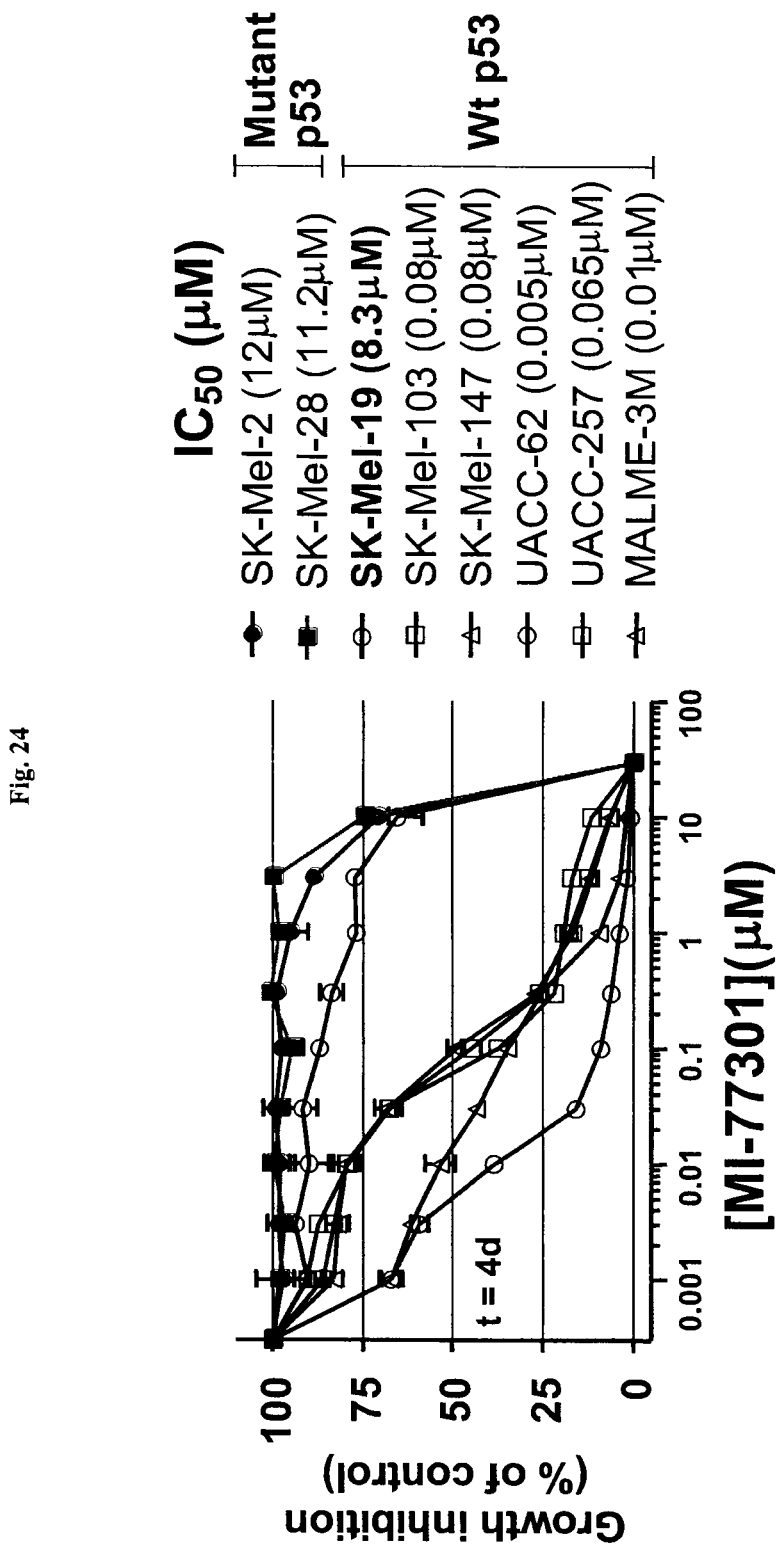
FIG. 24 is a line graph showing the cell growth inhibition activity of MI-77301 in melanoma cell lines.

Cells were seeded in 96-well flat bottom cell culture plates at a density of $2-3\times10^3$ cells/well with compounds and incubated for 4 days. The rate of cell growth inhibition after treatment with increasing concentrations of the tested compounds was determined by WST-8 (2-(2-methoxy-4-nitrophenyl)-3-(4-nitrophenyl)-5-(2,4-disulfophenyl)-2H-tetrazolium monosodium salt (Dojindo Molecular Technologies Inc., Gaithersburg, Md.). WST-8 was added at a final concentration of 10% to each well, and then the plates were incubated at 37° C. for 2-3 hrs. The absorbance of the samples was measured at 450 nm using a TECAN ULTRA Reader. The concentration of the compounds that inhibited cell growth by 50% ($IC_{50}$) was calculated by comparing absorbance in the untreated cells and the cells treated with the compounds using the GraphPad Prism software (GraphPad Software, La Jolla, Calif. 92037, USA). The results of this assay are presented in Tables 2A and 2C. Under conditions used in this assay, it is possible that a compound having Formula II isomerizes to a compound having Formula XII and other isomers (e.g., MI-773 isomerizes to MI-77301; MI-519-64 isomerizes to MI-519-6401). The results of this assay for MI-77301 in a variety of melanoma cell lines (Fernandez, Y., et al., *Cancer Res.* 65:6294-6304 and references cited therein) is presented in FIG. 24.

Example 5

Cell Death Assay

Figure 11:
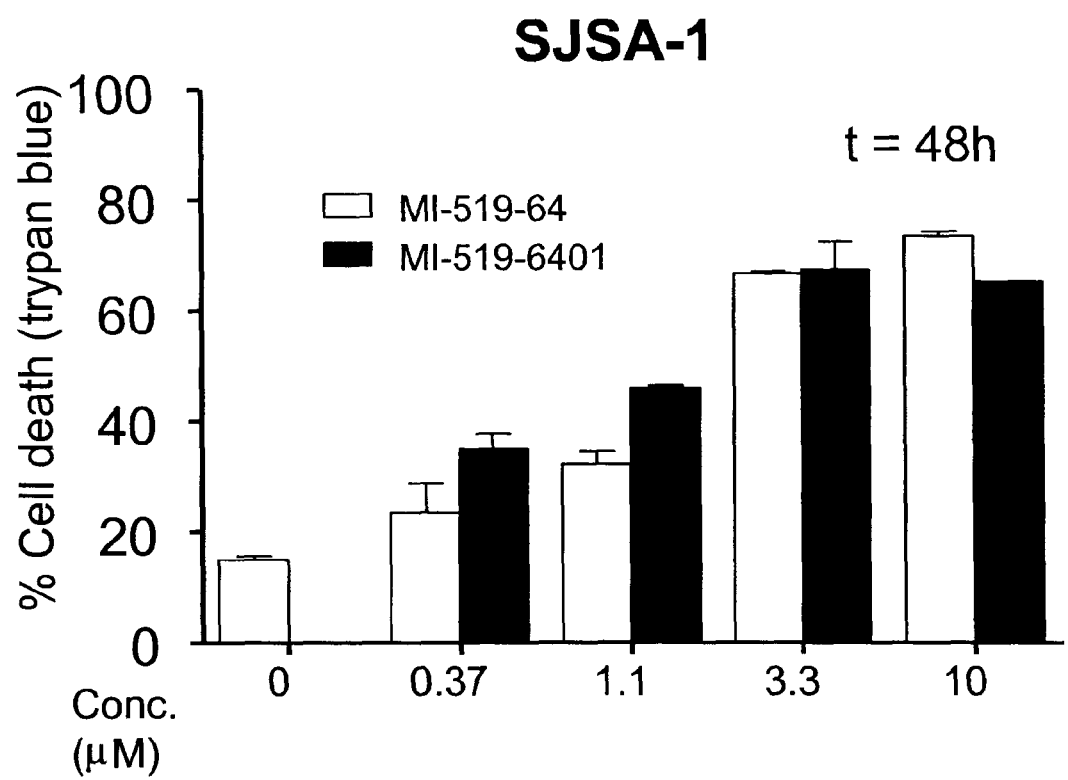
FIG. 11 is a bar graph showing cell death induced by MI-519-64 and MI-519-6401 in the SJSA-1 cell line.
Figure 12:
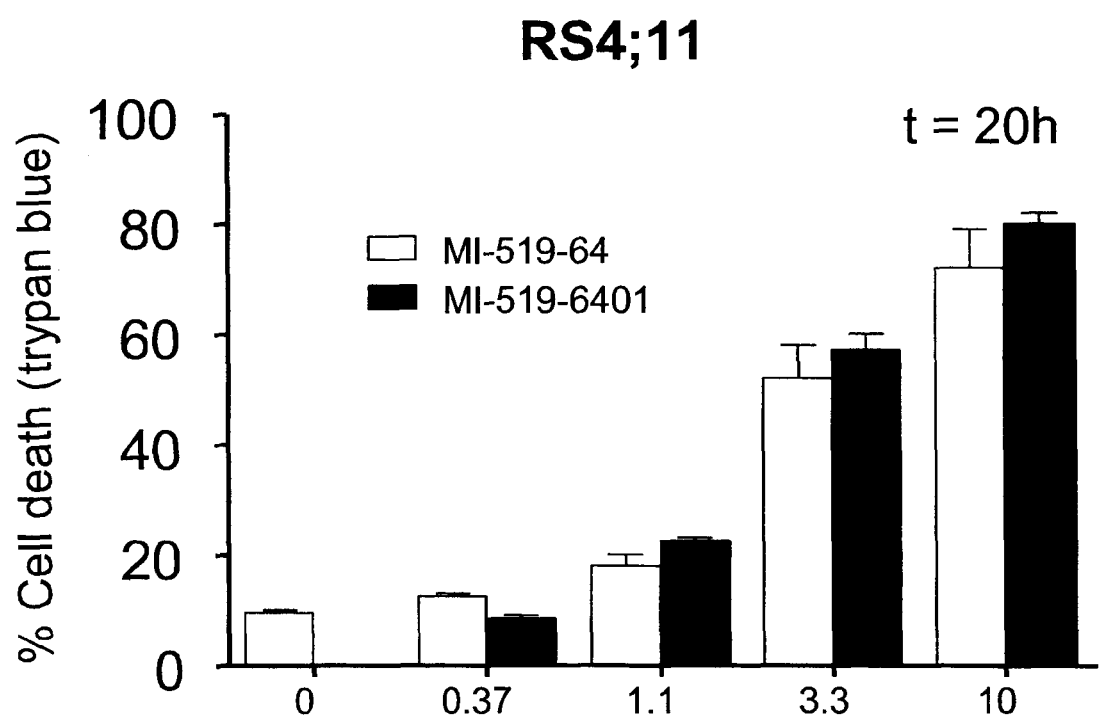
FIG. 12 is a bar graph showing cell death induced by MI-519-64 and MI-519-6401 in the RS4; 11 (human acute lymphoblastic leukemia (ALL)) cell line.
Figure 13:
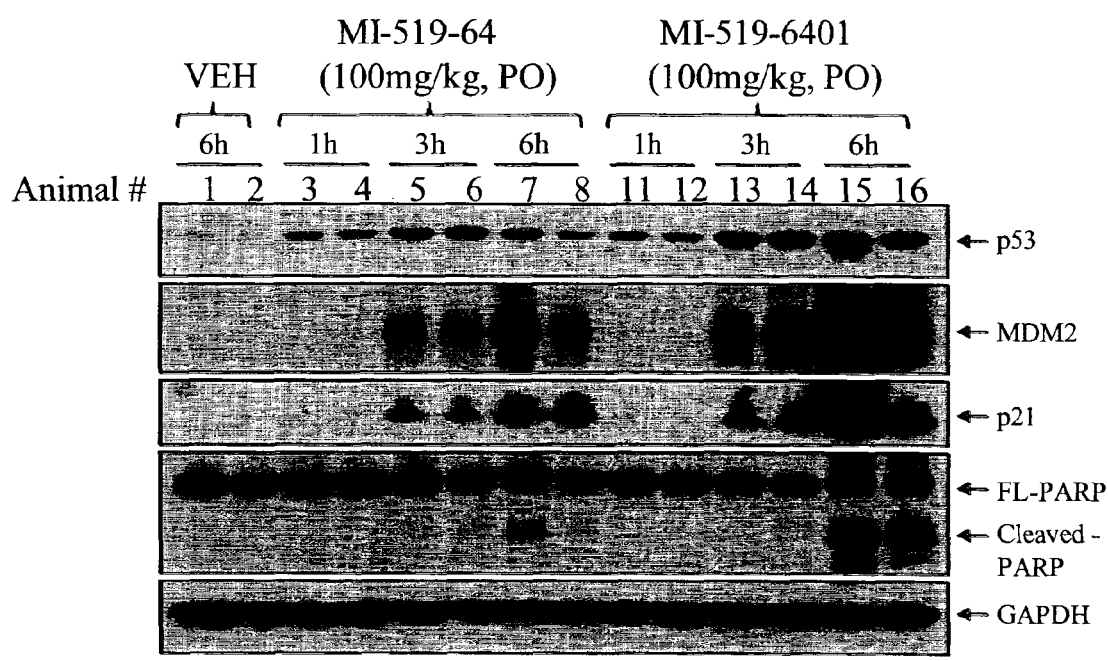
FIG. 13 is an illustration showing western blot analysis of in vivo activation of p53 and PARP cleavage induced by MI-519-64 and MI-519-6401 in SJSA-1 tumors in mice.
Figure 14:
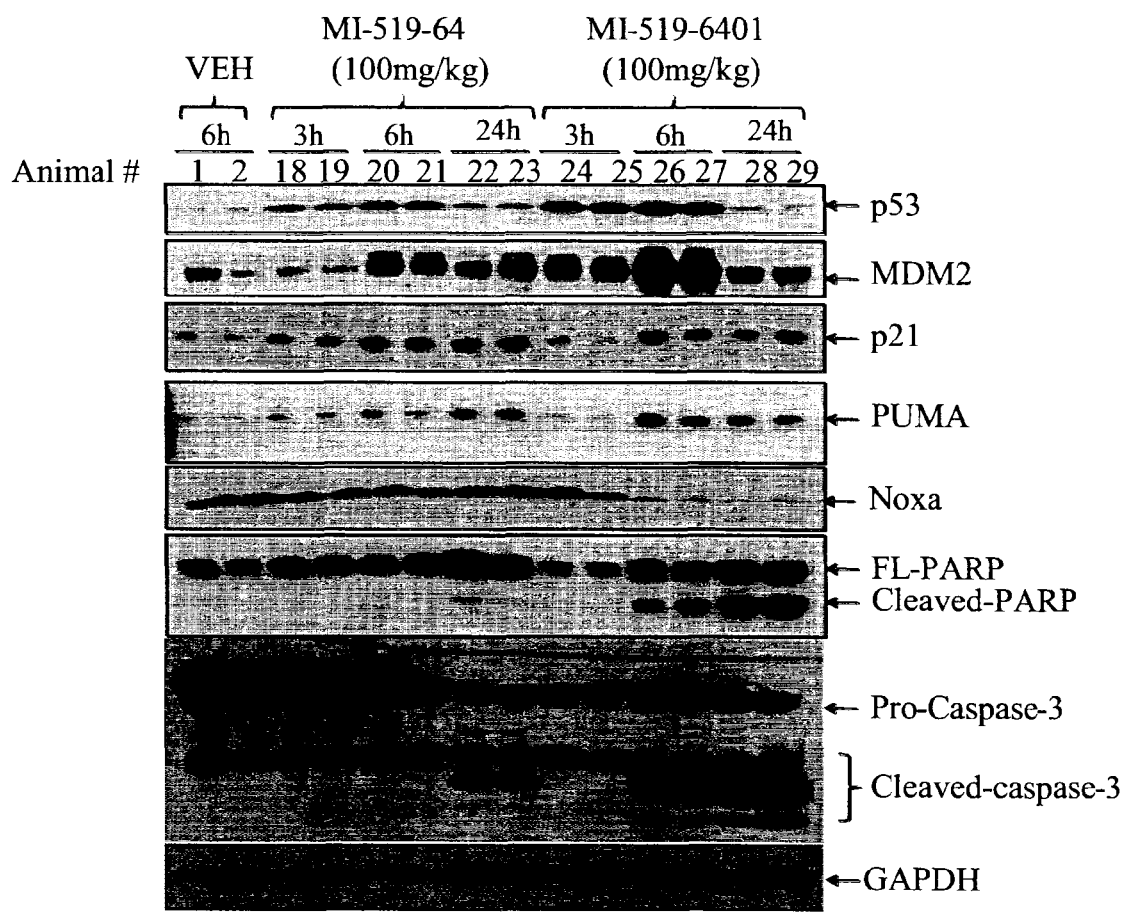
FIG. 14 is an illustration showing western blot analysis of in vivo activation of p53 and PARP cleavage induced by MI-519-64 and MI-519-6401 in RS4; 11 tumors in mice.
Figure 15:
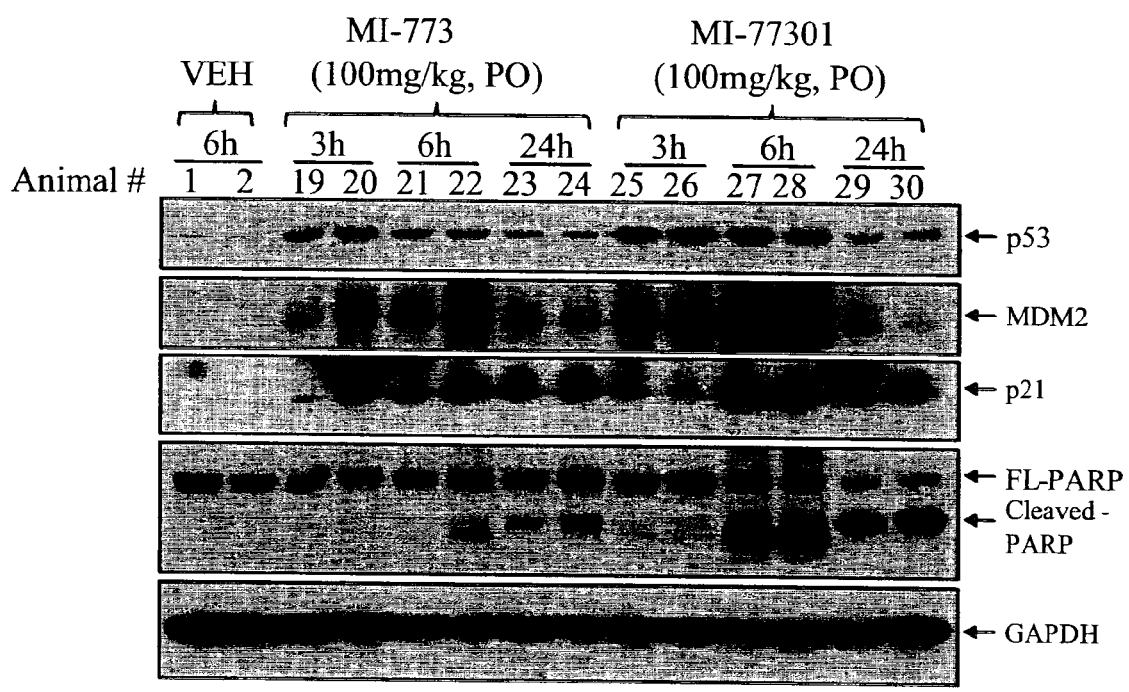
FIG. 15 is an illustration showing western blot analysis of in vivo activation of p53 and PARP cleavage induced by MI-773 and MI-77301 in SJSA-1 tumors in mice.
Figure 16:
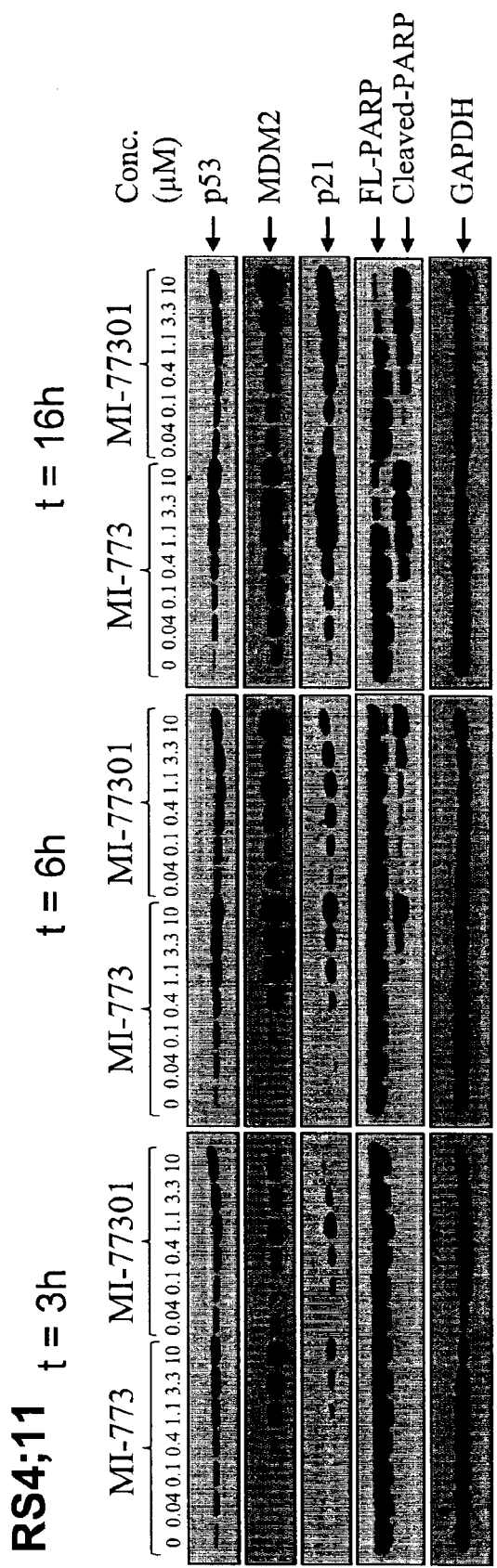
FIG. 16 is an illustration showing three western blot analyses of p53 activation and apoptosis induced by MI-773 and MI-77301 in the RS4; 11 cell line.
Figure 17:
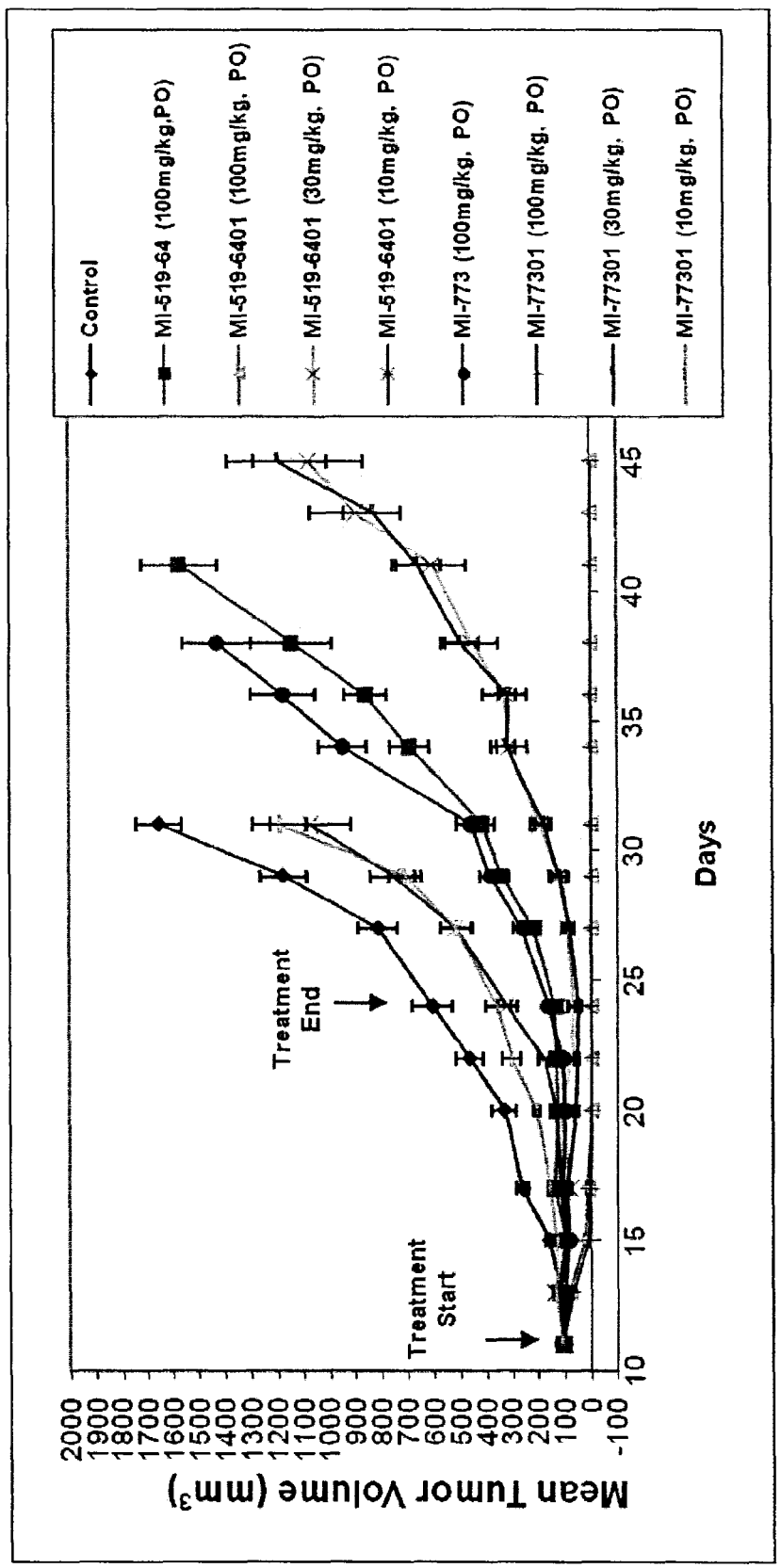
FIG. 17 is a line graph showing in vivo antitumor activity of MI-519-64, MI-519-6401, MI-773, and MI-77301 in the SJSA-1 osteosarcoma xenograft model in mice.

Cell death assays were performed using trypan blue staining. Cells were treated in the presence and absence of indicated compounds. Both the floating and adherent cells were stained with trypan blue. Cells that stained blue or the morphologically unhealthy cells were scored as dead cells. At least 100 cells were counted in each of three separate areas under microscope. As shown in FIGS. 11 and 12, MDM2 inhibitors provided herein induce cell death in SJSA-1 and RS4; 11 cancer cells with wild-type p53.

TABLE 2A

| | | IC$_{50}$ (μM, unless otherwise indicated) | | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p53—/—) | PC-3 (deleted p53) |
| MI-219 | | 180 nM | | | | | |
| MI-21901 | | 104 nM | | | | | |
| MI-519-64 | | 41.4 ± 2.6 nM | 0.27[1] | 0.18[1] | 0.50[1] | 13.69[1] | 6.1[1] |
| MI-519-65 | | <1 | <3 | <3 | <3 | >10 | NT |

TABLE 2A-continued

| | | IC$_{50}$ (μM, unless otherwise indicated) | | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p53—/—) | PC-3 (deleted p53) |
| MI-773 | | 62.1 ± 17.8 nM | 0.061 | 0.058 | 0.085 | 13.3 | 14.7 |
| MI-786 | | <1 | 0.8 | 0.5 | 1.2 | NT | 14.4 |
| C027 | | 0.167 | <3 | <3 | <3 | >10 | >10 |
| C029 | | 0.176 | <3 | <3 | <3 | >5 | >5 |
| C031 | | <5 | <3 | <3 | <3 | >10 | >10 |

TABLE 2A-continued

| | | IC$_{50}$ (μM, unless otherwise indicated) | | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p53—/—) | PC-3 (deleted p53) |
| C034 | | 0.048 | <3 | <3 | <3 | >10 | >10 |
| C035 | | <3 | <5 | <5 | <5 | >10 | >10 |
| C086 | | 0.402 | | | | | |
| MI-7102 | | 175 ± 19 nM | 0.42 | 0.20 | 0.25 | 26.8 | 19.1 |
| MI-7104 | | 169 ± 30 nM | 0.9 | 0.37 | 0.49 | 16.6 | 16.5 |

TABLE 2A-continued

| | | IC$_{50}$ (μM, unless otherwise indicated) | | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p53—/—) | PC-3 (deleted p53) |
| MI-7105 | | 520 ± 190 nM | 0.26 | 0.28 | 0.18 | 18.7 | 21.3 |
| MI-791 | | <3 | <3 | <3 | <3 | >10 | >10 |
| MI-519-6401 | | 5.6 ± 1.7 nM | 0.40 ± 0.24[1] | 0.102 ± 0.052[1] | 0.33 ± 0.012[1] | 12.2 ± 0.8[1] | 10.51 ± 3.32[1] |
| MI-77301 (free amine) | | 8.2 ± 3.0 nM | 0.058 ± 0.023[1] | 0.033 ± 0.01[1] | 0.054 ± 0.008[1] | 9.1 ± 1.7[1] | 8.45 ± 0.35[1] |
| MI-77301 (TFA salt) | | 13.3 ± 2.6 nM | 0.083; 0.075[1] | 0.048 ± 0.014[1] | 0.086 ± 0.016[1] | 12.9 ± 2.8[1] | 13.0 ± 3.0[1] |

TABLE 2A-continued

| | | IC$_{50}$ (μM, unless otherwise indicated) | | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p53—/—) | PC-3 (deleted p53) |
| MI-77302 (TFA salt) | | | | | | | |
| C02701 | | 0.027 | 0.2 | 0.2 | 0.3 | 13.2 | 12.9 |
| C02901 | | 0.035 | 0.5 | 0.6 | 0.2 | 16.4 | 15.6 |
| C03001 | | <0.1 | 0.2 | 0.2 | 0.1 | 14.2 | 29.8 |
| C03401 | | 0.018 | 0.3 | 0.6 | 0.3 | 17.3 | 17.4 |

TABLE 2A-continued

| | | IC$_{50}$ (μM, unless otherwise indicated) | | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p53—/—) | PC-3 (deleted p53) |
| C03701 | | 0.061 | 0.7 | 0.2 | 0.4 | 21.0 | 26.7 |
| C08301 | | <0.1 | 0.2 | | 0.3 | | 10.1 |
| C08601 | | 0.162 | | | | | |
| C09101 | | 0.008 | | | | | |
| C09601 | | 0.012 | | | | | |

TABLE 2A-continued

| | | IC$_{50}$ (μM, unless otherwise indicated) | | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p53—/—) | PC-3 (deleted p53) |
| MI-710201 | | 61.7 ± 5.1 nM | 0.57 | 0.25 | 0.3 | 27.6 | 19.3 |
| MI-710301 | | 35.4 | 0.13 | 0.92 | 0.10 | 11.9 | 12.50 |
| MI-710401 | | 70.2 ± 14.1 nM | 0.90 | 0.37 | 0.49 | 16.6 | 16.5 |
| MI-710601 | | 20.1 ± 5.0 nM | 0.38 | 0.26 | 0.21 | 11.5 | 18.4 |
| MI-710801 | | 32.0 ± 5.9 nM | | | | | |

TABLE 2A-continued

| | | IC$_{50}$ (μM, unless otherwise indicated) | | | | | |
|---|---|---|---|---|---|---|---|
| Example | Chemical Structure | MDM2 | SJSA-1 (p53 wild-type) | HCT-116 (p53 wild-type) | LNCAP (p53 wild-type) | HCT-116 (p53—/—) | PC-3 (deleted p53) |
| C09701 | | 0.011 | 0.1 | 0.1 | 0.2 | 10.6 | 11.1 |
| C11701 | | 0.159 | | 1.4 | 1.5 | 21.8 | 19.6 |
| CB061-Isomer B | | <0.1 | | | | | |
| CB087-Isomer B | | <0.5 | | | | | |
| CB083-Isomer B | | >5 | | | | | |

TABLE 2A-continued

| | | | SJSA-1 | HCT-116 | LNCAP | | PC-3 |
| | | | (p53 wild- | (p53 wild- | (p53 wild- | HCT-116 | (deleted |
| Example | Chemical Structure | MDM2 | type) | type) | type) | (p53—/—) | p53) |
| --- | --- | --- | --- | --- | --- | --- | --- |
| CB084-Isomer B | 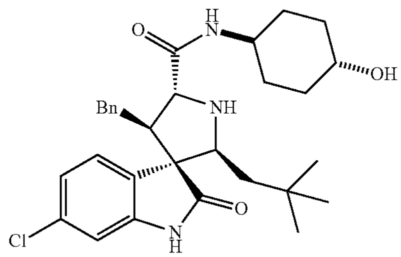 | >5 | | | | | |
| C29701 | 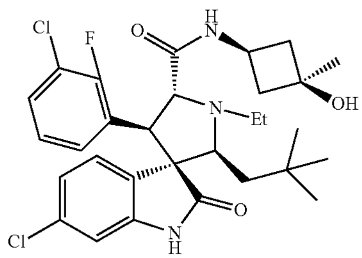 [SMILES: CCN1[C@@H](CC(C)(C)C)[C@@]2(C(=O)Nc3cc(Cl)ccc32)[C@@H](c2cccc(Cl)c2F)[C@@H]1C(=O)N[C@H]1C[C@@](C)(O)C1] | <0.1 | | | | | |
| C30201 | 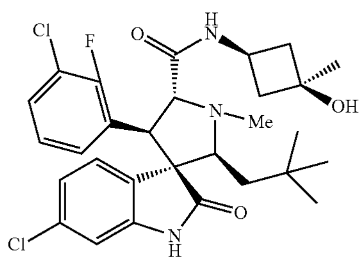 [SMILES: CN1[C@@H](CC(C)(C)C)[C@@]2(C(=O)Nc3cc(Cl)ccc32)[C@@H](c2cccc(Cl)c2F)[C@@H]1C(=O)N[C@H]1C[C@@](C)(O)C1] | <0.1 | | | | | |

[1] Four day treatment.

TABLE 2B

| Time | $IC_{50}$ values (nM) to human MDM2 protein in FP assay | | | |
| --- | --- | --- | --- | --- |
| (hours) | MI-773 | MI-77301 | MI-519-64 | MI-519-6401 |
| 0.1 | 79.9 | 11.3 | 77.2 | 6.5 |
| 3.0 | 74.3 | 11.2 | 54.0 | 7.0 |
| 7.0 | 65.2 | 12.3 | 46.2 | 8.8 |
| 24.0 | 57.7 | 15.1 | 43.4 | 8.9 |
| 32.0 | 49.2 | 10.6 | 42.7 | 8.3 |
| 48.0 | 46.6 | 14.5 | 34.8 | 8.8 |
| 72.0 | 33.3 | 12.8 | 27.9 | 9.6 |

TABLE 2C

| Example | RS4; 11 (p53 wt) $IC_{50}$ (μM) |
| --- | --- |
| MI-519-6401 | 0.13 ± 0.02[1] |
| MI-773(TFA salt) | 0.13[1] |
| MI-77301(free amine) | 0.102; 0.081[1] |
| MI-77301(TFA salt) | 0.059 ± 0.025[1] |
| MI-7102 | 0.46 |
| MI-710201 | 0.54 |
| MI-710301 | 0.16 |
| MI-7104 | 0.52 |
| MI-710401 | 0.66 |
| MI-7105 | 0.37 |
| MI-710601 | 0.13 |

[1] Four day treatment.

Example 6

Western Blotting

For Western blot analysis, cells were lyzed in ice-cold RIPA buffer: 20 mM Tris-HCl (pH 7.5), 150 mM NaCl, 1 mM EDTA, 1 mM EGTA, 1% sodium deoxycholate, 2.5 mM sodium pyrophosphate, 1 mM b-glycerophosphate, 1 mM sodium orthovanadate and 1 μg/ml leupeptin. The proteins in the whole cell lysates were detected by Western blot analysis using the following antibodies: anti-p53 (clone DO-1), anti-MDM2 (clone SMP-14), anti-p21 (clone SX118), anti-β-actin (clone AC-40) and glyceraldehyde-3-phosphate dehydrogenase (GAPDH; HRP conjugated). As shown in FIGS. 8, 9, and 13-16, MDM2 inhibitors provided herein are active in this assay.

Figure 25:
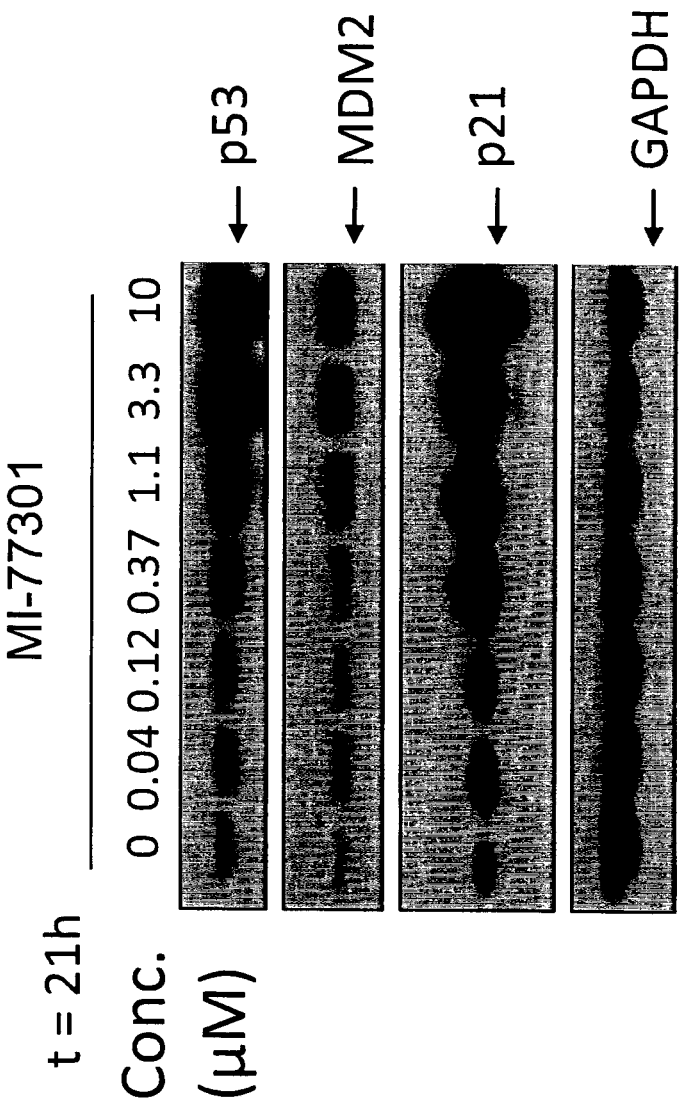
FIG. 25 is an illustration showing western blot analysis of p53 activation induced by MI-77301 in SK-Mel-103 (human melanoma) cells.
Figure 26:
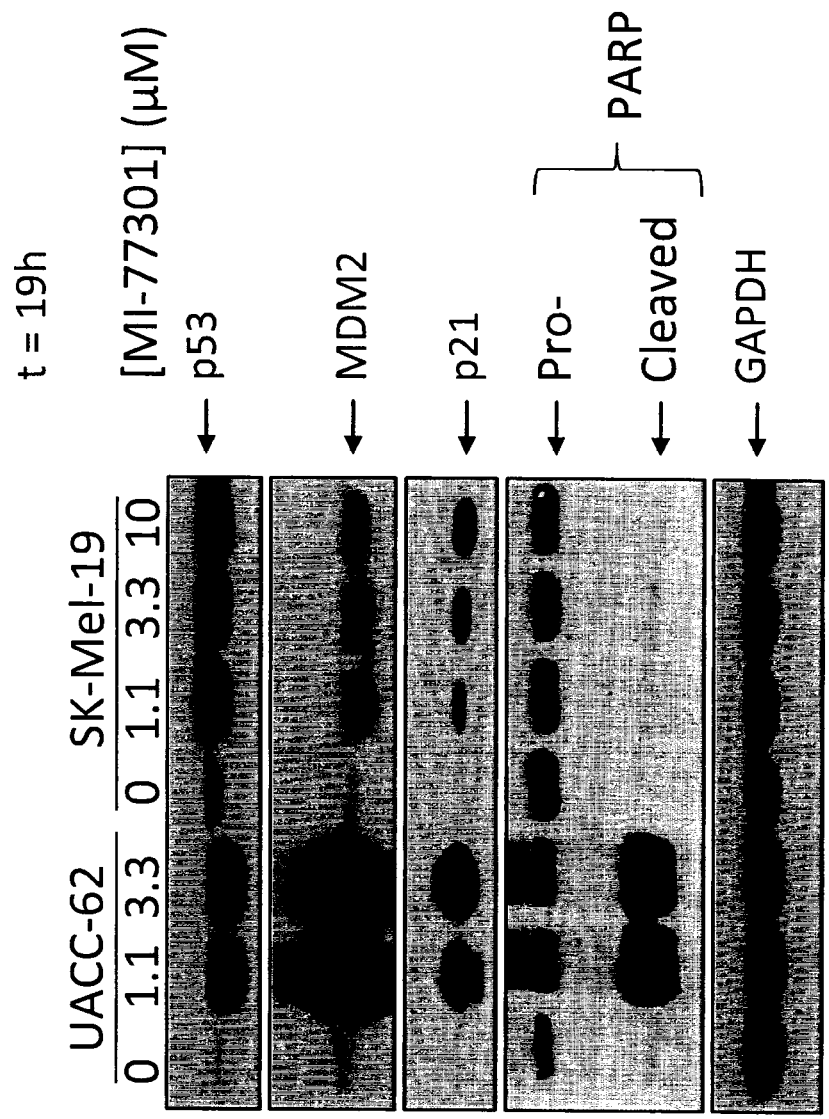
FIG. 26 is an illustration showing western blot analysis of p53 activation induced by MI-77301 in UACC-62 (p53 wt melanoma) and SK-Mel-19 (human melanoma) cells.
Figure 28:
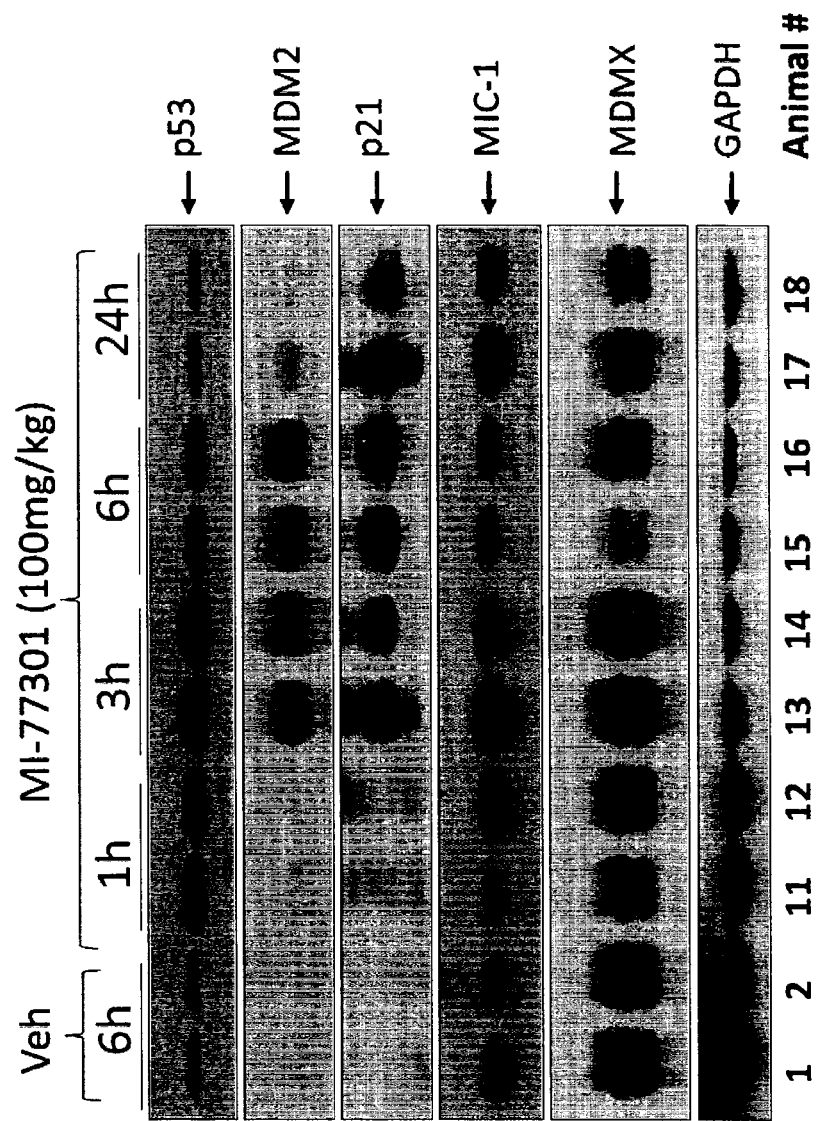
FIG. 28 is an illustration showing western blot analysis of in vivo activation of p53 induced by MI-773001 in SK-Mel-103 melanoma xenografts in mice.

PARP cleavage was used as a biochemical marker of apoptosis. During apoptosis, caspases cleave Poly (ADP-ribose)

polymerase (PARP). Rabbit anti-PARP (Cell Signaling Cat #9542), used in the experiment, detects cleavage of full length (116 kD) Poly (ADP-ribose) polymerase (PARP) and larger (89 kD) cleaved fragment of PARP. A total of $2\times10^6$ adherent cells were treated in the presence or absence of MI-77301 and incubated at 37° C. for 19 hr. Cells were harvested using 0.05% trypsin-EDTA (Invitrogen), washed in PBS and lysed on ice for 15 min using RIPA buffer (Sigma), supplemented with protease inhibitor cocktail (Roche). Clarified cell lysate was obtained by centrifuging the lysed cells at 13000×g at 4° C. for 15 min. Protein in the cell lysate was estimated using commercially available Bio-Rad protein assay dye. A total of 25 µg protein was loaded on a 4-20% SDS-PAGE gel, electrophoresed, and transferred to a PVDF membrane for 3 hours at 40 V. Membrane was blocked in TBST (20 mM Tris, 0.5 M NaCl, 0.1% Tween-20, pH 7.5) containing 5% dry milk (Bio-Rad) for 1 hr at room temperature. Primary antibody diluted in TBST, containing 5% dry milk, was applied to the membrane overnight in cold room at 4° C. on an orbital shaker. Membrane was washed in TBST, incubated for 1 hr at room temperature with either an anti-rabbit secondary antibody (Immunopure goat anti-rabbit antibody, Thermo Scientific) or an anti-mouse antibody (Pierce goat anti-mouse antibody, Thermo Scientific), diluted 1:2000 in TBST. Membrane was washed in TBST and developed using SuperSignal West Pico reagent (Thermo Scientific). Glyceraldehyde-3-phosphate dehydrogenase (GAPDH) antibody conjugated to HRP (Santa Cruz) was used as a loading control for proteins. Western blot analyses for MI-77301 are provided in FIGS. 25, 26, and 28.

Example 7

In Vivo Efficacy Studies Using SJSA-1 and 22Rv1 Xenograft Models

SJSA-1 (osteosarcoma) tumor cells were harvested with Trypsin (0.05%)-EDTA (0.53 mM) (GIBCO™, Invitrogen Corp.), growth medium added and cells placed on ice. A cell sample was mixed 1:1 with Trypan Blue (GIBCO™ Invitrogen Corp.) and counted on a hemocytometer to determine the number of live/dead cells. Cells were washed once with 1×PBS (GIBCO™, Invitrogen Corp.) and resuspended in PBS. For Matrigel injections, after washing in PBS, cells are resuspended in an ice cold mixture of 1:1 PBS and Matrigel (BD Biosciences, Invitrogen Corp.) for a final Matrigel protein concentration of 5 mg/ml. SJSA-1 tumors were inoculated into C.B-17 SCID mice at $5\times10^6$ cells in 0.1 ml with Matrigel. Cells were injected s.c. into the flank region of each mouse using a 27 gauge needle.

Figure 18:
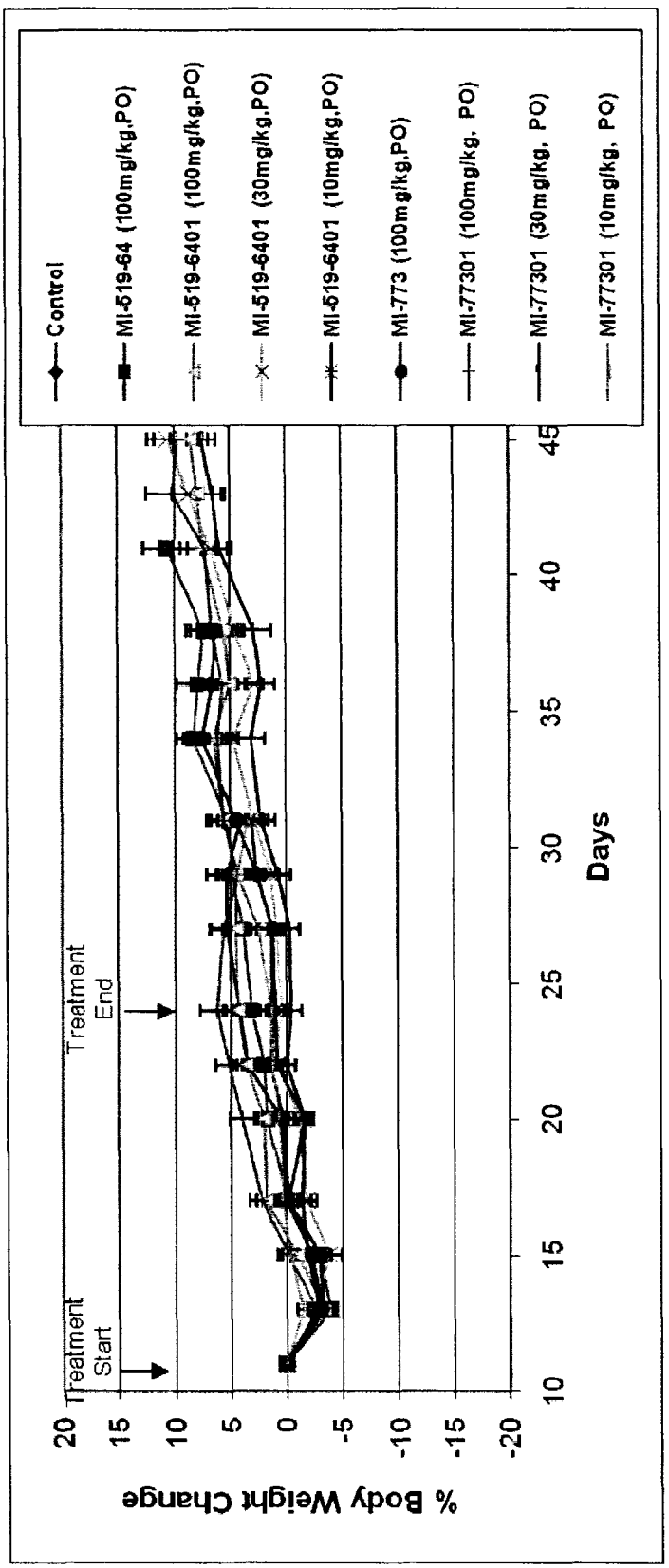
FIG. 18 is a line graph showing the animal weight following administration of MI-519-64, MI-519-6401, MI-773, and MI-77301 in mice.
Figure 21:
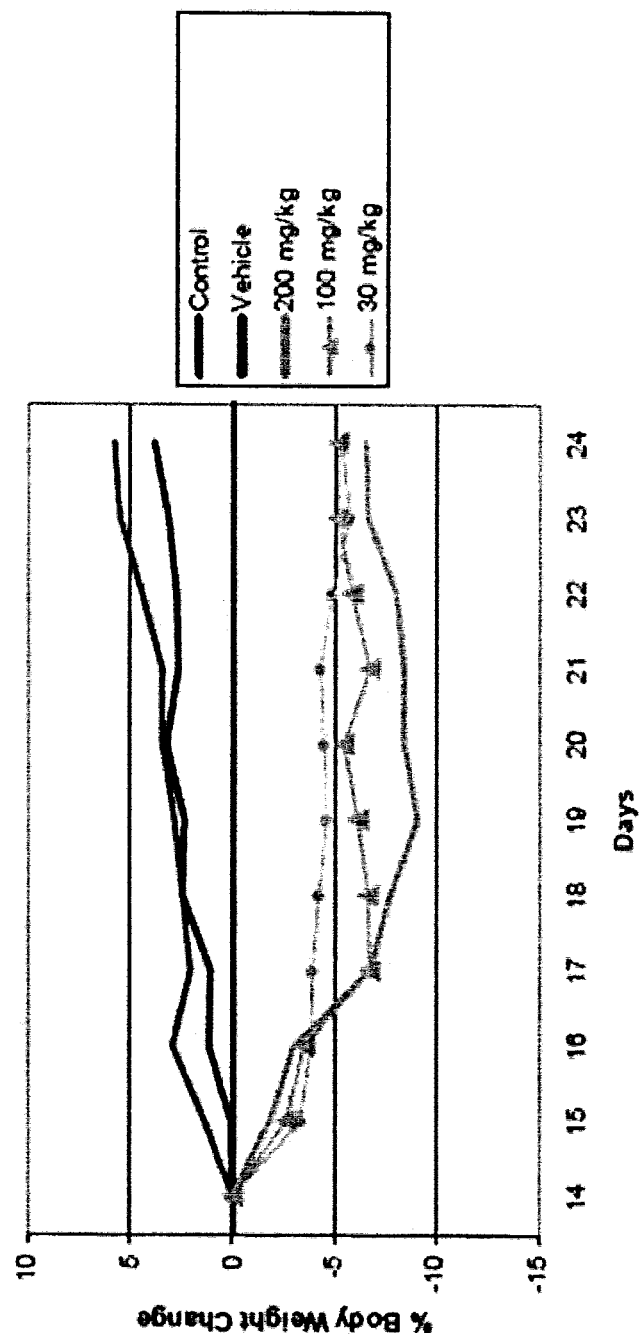
FIG. 21 is a line graph showing the animal weight following administration of MI-77301 in mice (Cpd-B=MI-77301).
Figure 22:
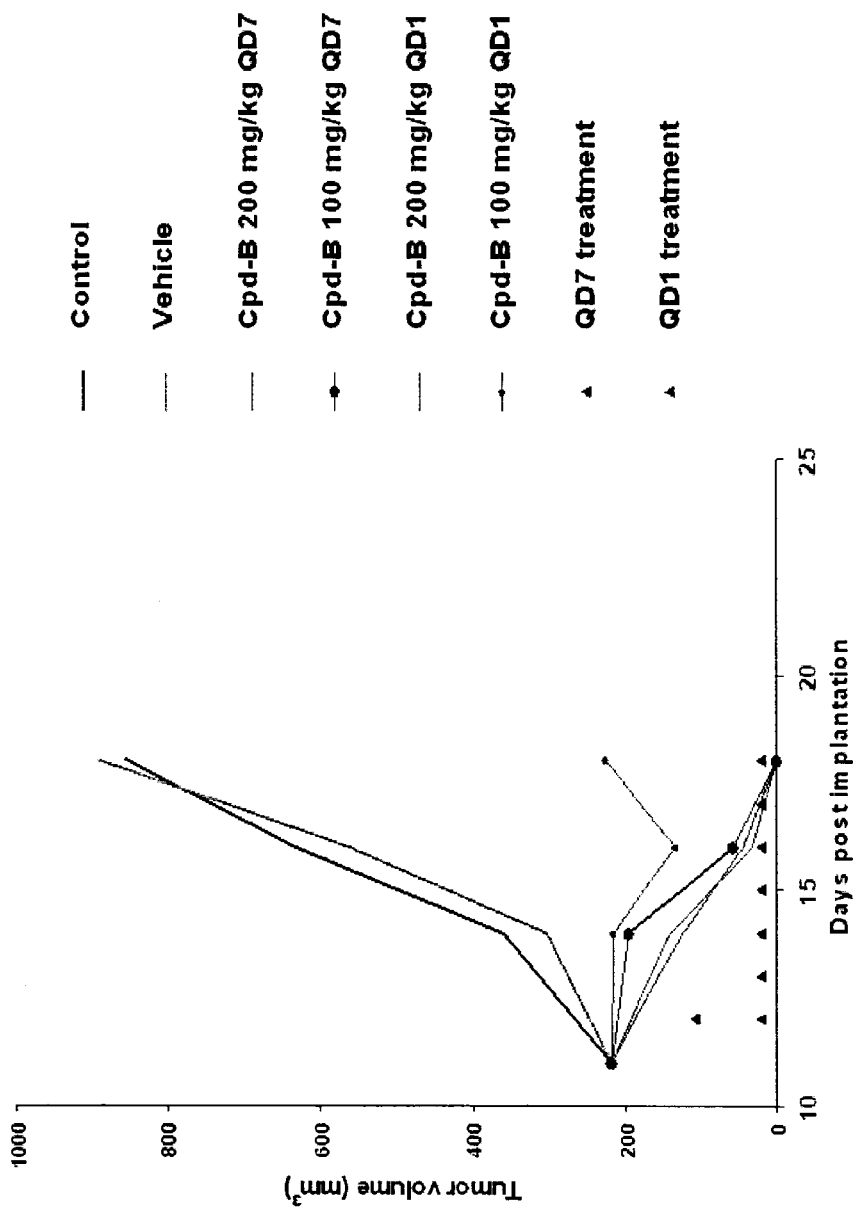
FIG. 22 is a line graph showing in vivo antitumor activity in the SJSA-1 osteosarcoma xenograft model in mice (Cpd-B=MI-77301).
Figure 23:
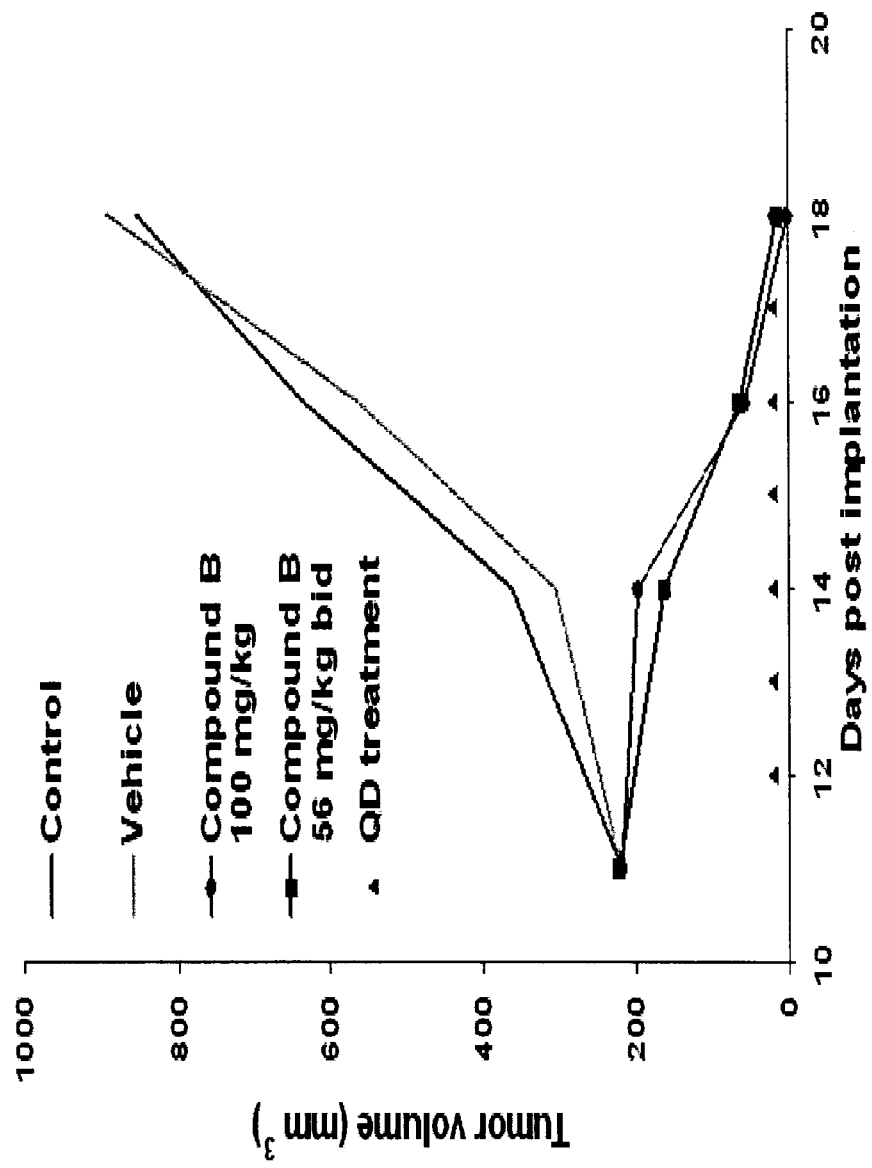
FIG. 23 is a line graph showing in vivo antitumor activity of MI-77301 in the SJSA-1 osteosarcoma xenograft model in mice (Cpd-B=MI-77301).

The size of tumors growing in the mice was measured in two dimensions using calipers. Tumor volume $(mm^3)=(A\times B^2)/2$ where A and B are the tumor length and width (in mm), respectively. During treatment, tumor volume and body weight was measured three times a week. After the treatment was stopped, tumor volume (FIGS. 17, 20, 22, and 23) and body weight (FIGS. 18 and 21) was measured at least once a week. Mice were kept for an additional 60 days for further observation of tumor growth and toxicity. As shown in FIG. 22, a single 200 mg/kg dose of MI-77301 (QD1 treatment) shows comparable efficacy to a continuous dosing regimen (QD7 treatment).

Before treatment began, tumors were allowed to grow to 60-140 $mm^3$ in volume, at which point the blood vessel supplies to the tumor should have been established. Mice with tumors within acceptable size range were randomized into treatment groups of 8 mice for experimental compounds and 10 mice for the Control group. Experimental compounds were given orally, once per day for 2-3 weeks. The Control group received vehicle alone (10% PEG 400:3% Cremophor: 87% PBS). Other suitable vehicles for in vivo administration of the compounds provided herein include, without limitation, 98% PEG 200:2% polysorbate 80; 98% PEG 200:2% TPGS; and 0.5% polysorbate 80:0.6% methyl cellulose: 98.9% water.

Figure 19:
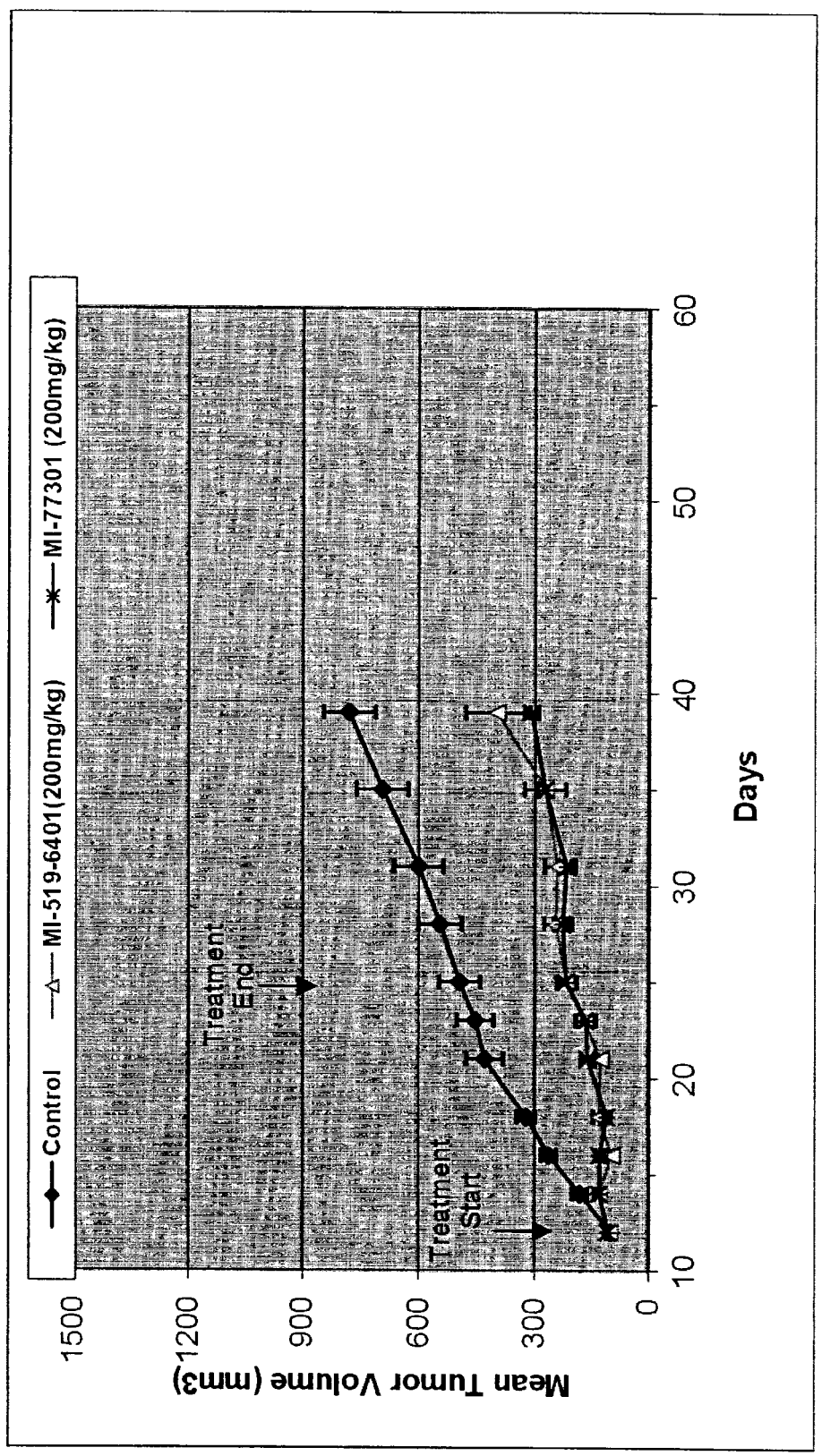
FIG. 19 is a line graph showing in vivo antitumor activity of MI-519-6401 and MI-77301 in the 22Rv1 human prostate xenograft model in mice.
Figure 20:
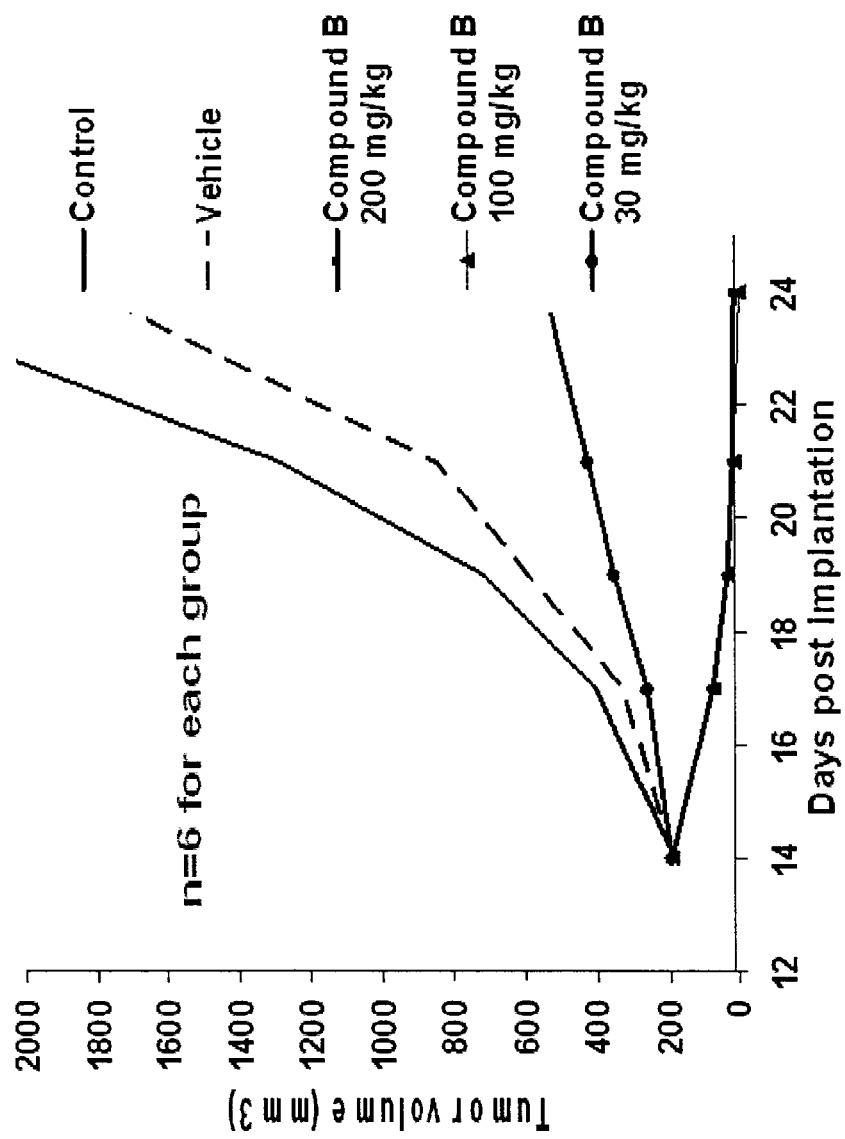
FIG. 20 is a line graph showing in vivo antitumor activity of MI-77301 in the SJSA-1 osteosarcoma xenograft model in mice (Cpd-B=MI-77301; treatment schedule=QD11).
Figure 31:
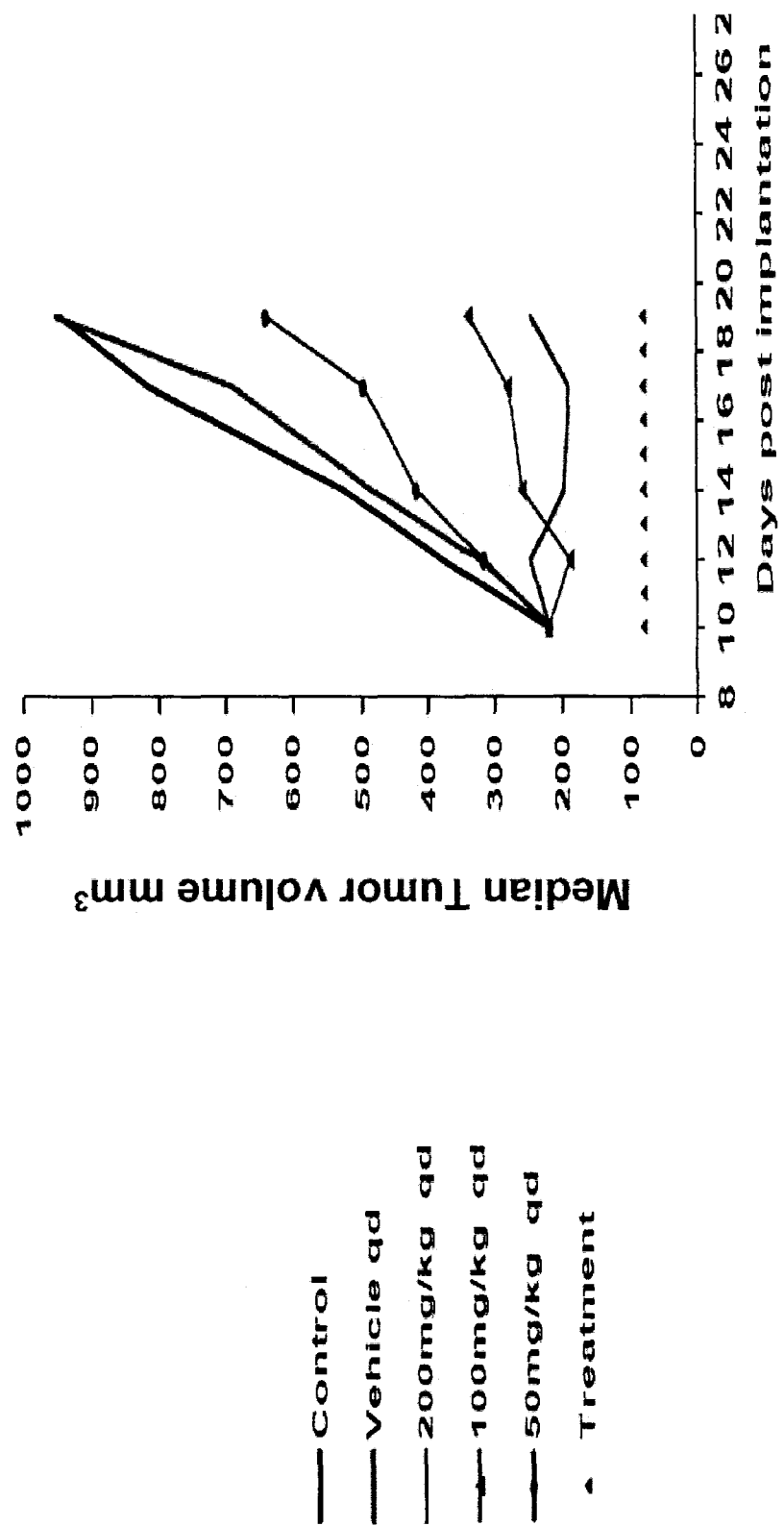
FIG. 31 is a line graph showing in vivo antitumor activity of MI-77301 in the HCT-116 human colorectal tumor xenograft model in mice.
Figure 32:
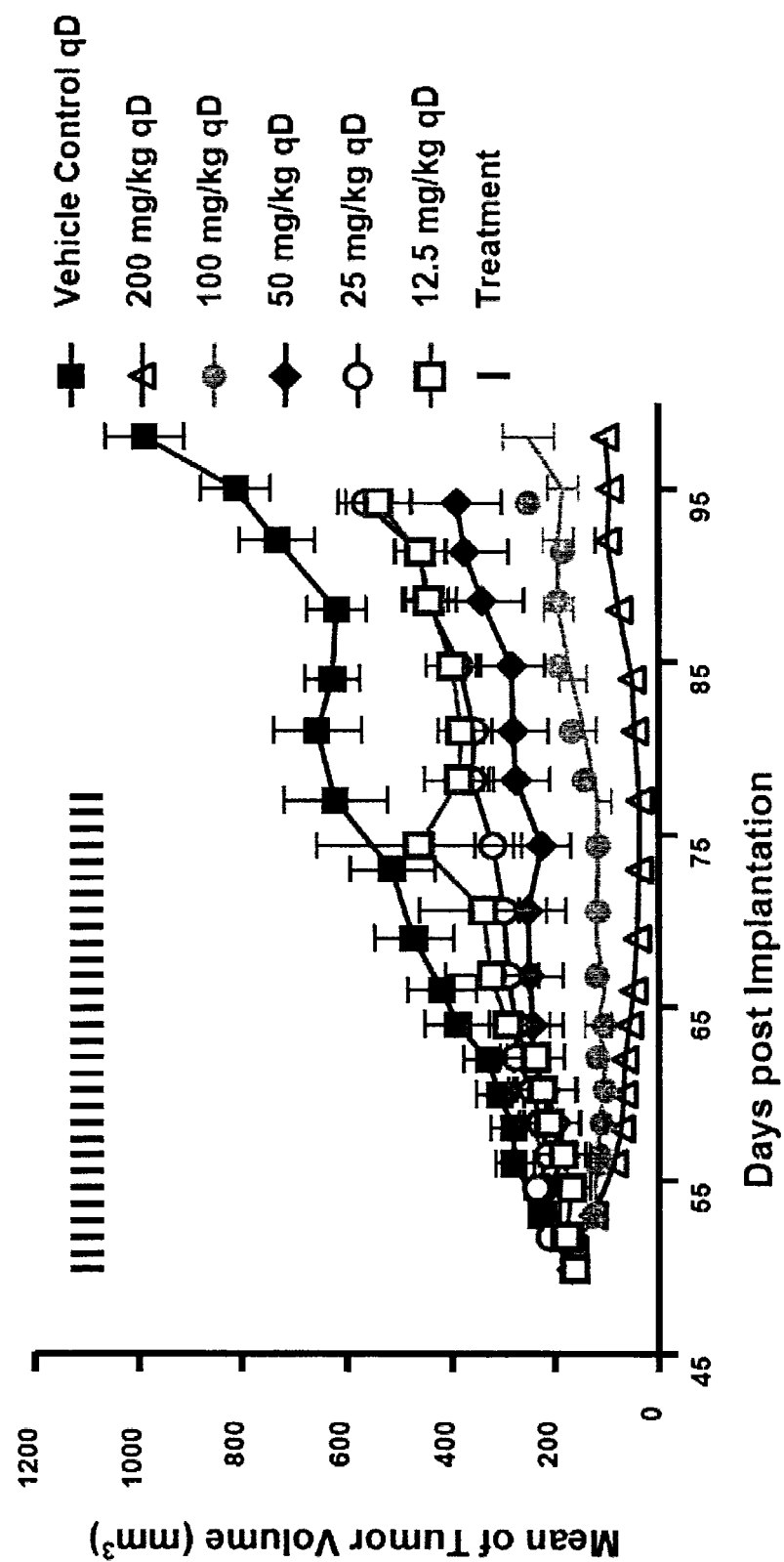
FIG. 32 is a line graph showing in vivo antitumor activity of MI-77301 in the LNCAP human prostate tumor xenograft model in mice.
Figure 33:
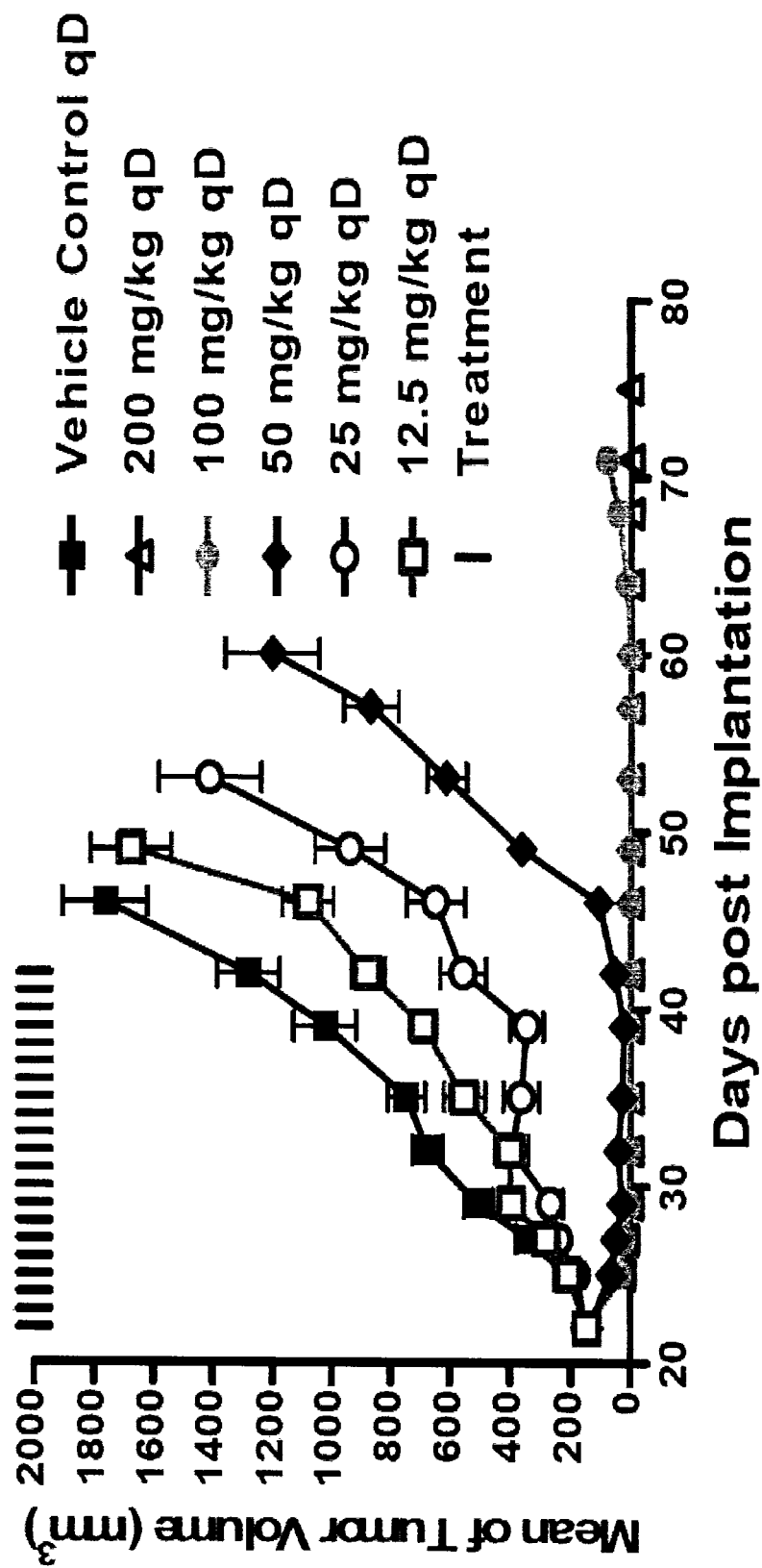
FIG. 33 is a line graph showing in vivo antitumor activity of MI-77301 in the RS4; 11 human acute lymphoblastic leukemia xenograft model in mice.

Using similar protocols, the antitumor activity of MI-519-6401 and MI-77301 was evaluated in the 22Rv1 prostate cancer model in mice (FIG. 19), and the antitumor activity of MI-77301 was evaluated in the HCT-116 human colorectal tumor model (FIG. 31), the LNCAP human prostate tumor model (FIG. 32), and the RS4;11 human ALL model (FIG. 33).

Example 8

Synthesis of MI-519-64 and MI-519-65

Step 1: benzyl 3-oxocyclobutanecarboxylate (2)

Referring to Scheme 6A, BnBr was added to the mixture of compound 1 and $K_2CO_3$ in acetonitrile 150 mL. The mixture was stirred at room temperature over 24 h and the solid was filtered. The solvent was removed and the residue was purified by column chromatography to give compound 2.

Step 2: benzyl 3-hydroxy-3-methylcyclobutanecarboxylates (3 and 4)

MeMgCl in THF was added dropwise to the solution of compound 2 in diethyl ether at −78° C. and the mixture was stirred at the same temperature for half an hour. After TLC monitoring showed the disappearance of the starting material, the reaction was quenched by adding aqueous $NH_4Cl$ solution. The aqueous phase was extracted with ethyl acetate three times and the combined organic phase was washed with brine and dried ($Na_2SO_4$). The solid was filtered and the solvent was removed. The residue was purified by column chromatography to give compounds 3 and 4 (5:1 based on TLC analysis).

Step 3: benzyl 3-(tert-butyldimethylsilyloxy)-3-methylcyclobutane carboxylates (5 and 6)

To the mixture of compounds 3 and 4 in DMF (10 mL) was added immidazole and TBSCl, and the resulting mixture was stirred at 80° C. for 30 h. After cooling to room temperature, water was added and the aqueous phase was extracted with ethyl acetate three times. The combined organic phase was washed with brine and dried ($Na_2SO_4$). The solid was filtered and the solvent was removed. The residue was purified by column chromatography to get compounds 5 and 6.

Step 4: 3-(tert-butyldimethylsilyloxy)-3-methylcyclobutanecarboxylic acids (7 and 8)

To the mixture of compounds 5 and 6 in isopropanol was added Pd/C. The resulting mixture was stirred under 1 atm hydrogen for 1 h. TLC showed the disappearance of the starting material and the solid was filtered. The solvent was removed to give compounds 7 and 8.

Step 5: benzyl-3-(tert-butyldimethylsilyloxy)-3-methylcyclobutylcarbamates 9 and 10

To a 0° C. stirring solution of compounds 7 and 8 and Et₃N in acetone was added ClCOOEt dropwise. The resulting mixture was stirred at 0° C. for 30 min.

A solution NaN₃ in water was added, and the resulting mixture was stirred at 0° C. for an additional 20 min. Water was added, and the aqueous phase was extracted with ethyl acetate three times. The combined organic phase was washed with brine and dried (Na₂SO₄). The solvent was removed and the residue was dissolved in toluene. Benzyl alcohol and NaHCO₃ were added. The resulting mixture was stirred at 80° C. for 2 h. All the solvent was removed and the residue was purified by column chromatography to obtain two isomers 9 and 10 in a 5:1 ratio.

Step 6: 3-(tert-butyldimethylsilyloxy)-3-methylcyclobutanamine (11)

To a mixture of the major isomer 9 and NaHCO₃ in isopropanol was added Pd/C and the resulting mixture was stirred under 1 atm hydrogen for 1 h. The solid was filtered and the solvent was removed to give compound 11.

Step 7: 3-(tert-butyldimethylsilyloxy)-3-methylcyclobutanamine (12)

To a mixture of the minor isomer 10 and NaHCO₃ in isopropanol was added Pd/C and the resulting mixture was stirred under 1 atm hydrogen for 1 h. The solid was filtered and the solvent was removed to give compound 12.

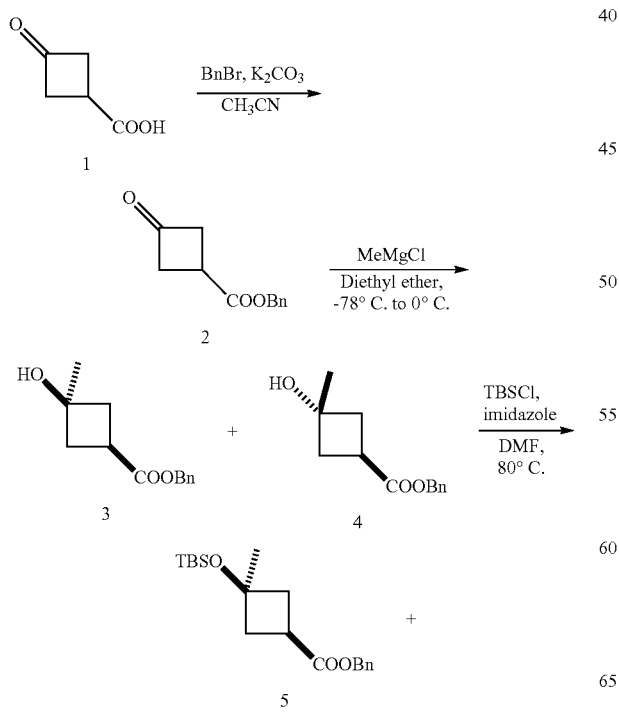

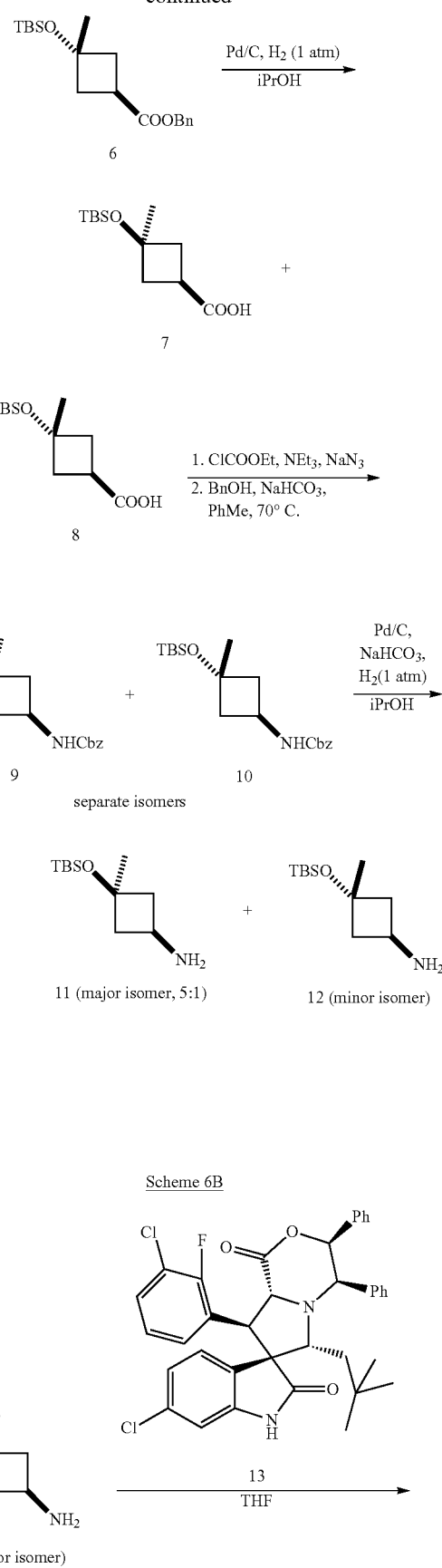

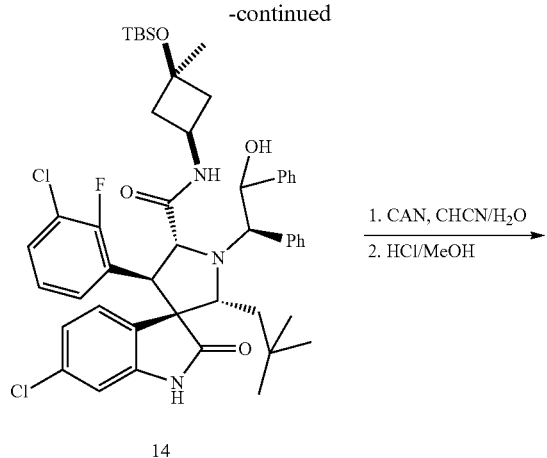

Step 8: MI-519-64

Referring to Scheme 6B, to a solution of compound 11 in THF was added compound 13 and the resulting solution was stirred overnight. The solvent was removed and the residue thus obtained was dissolved in CH$_3$CN/H$_2$O (1:1). CAN was added and the reaction mixture was stirred for 30 min. Water was added and the aqueous phase was extracted with ethyl acetate three times. The combined organic layers were dried (Na$_2$SO$_4$), filtered, and concentrated. The residue was purified by column chromatography on silica gel to give compound 14. Compound 14 was dissolved in methanol, 12M HCl in water was added, and the reaction mixture was stirred for 1 h at room temperature. The solvent was removed and the residue was purified by HPLC to give MI-519-64 as the TFA salt. $^1$H NMR (300 MHz, CD$_3$OD) δ 7.54-7.52 (m, 1H), 7.42-7.38 (m, 1H), 7.23-7.18 (m, 1H), 6.88-6.75 (m, 3H), 5.04 (d, J=9.9 Hz, 1H), 4.45 (d, J=9.9 Hz, 1H), 4.19-4.16 (m, 1H), 3.92-3.89 (m, 1H), 2.42-2.11 (m, 2H), 2.10-1.87 (m, 3H), 1.32-1.24 (m, 4H), 0.82 (s, 9H); MS (ESI) m/z 548 [M+H]$^+$.

Step 9: MI-519-65

To a solution of compound 12 in THF was added compound 13 and the resulting solution was stirred overnight. The solvent was removed and the residue was dissolved in CH$_3$CN/H$_2$O (1:1). CAN was added and the reaction mixture was stirred for 30 min. Water was added and the aqueous phase was extracted with ethyl acetate three times. The combined organic layers were dried (Na$_2$SO$_4$), filtered, and concentrated. The residue was purified by column chromatography on silica gel to give compound 15. Compound 15 was dissolved in methanol, 12M HCl in water was added, and the reaction mixture was stirred for 1 h at room temperature. The solvent was removed and the residue was purified by HPLC to give MI-519-65 as the TFA salt. $^1$H NMR (300 MHz, CD$_3$OD) δ 7.50 (m, 1H), 7.44-7.38 (m, 1H), 7.24-7.20 (m, 1H), 6.89-6.88 (m, 1H), 6.80 (m, 1H), 6.71 (m, 1H), 4.91-4.88 (m, 1H), 4.40-4.36 (m, 2H), 4.10-4.06 (m, 1H), 2.41-2.33 (m, 2H), 2.07-1.87 (m, 3H), 1.25-1.21 (m, 4H), 0.82 (s, 9H); MS (ESI) m/z 548 [M+H]$^+$.

Example 9

Synthesis of MI-519-6401

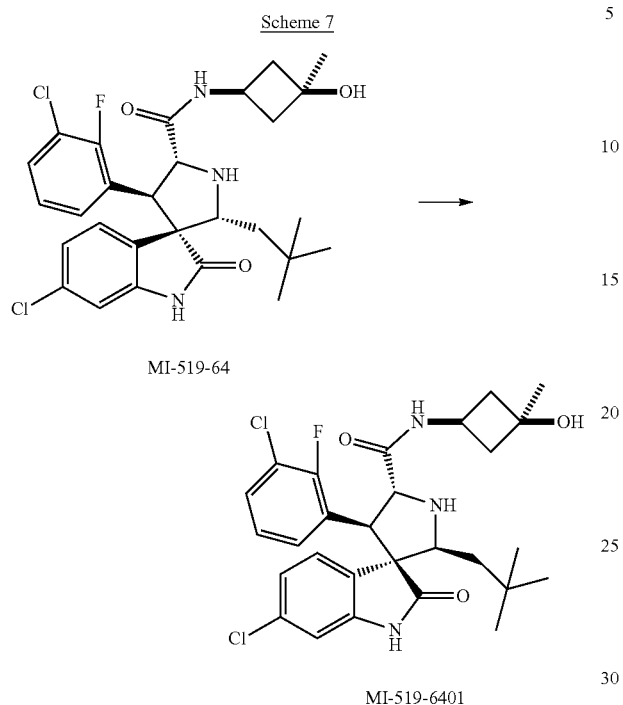

MI-519-64 (100 mg) purified by flash chromatography on silica gel was placed in a 50 mL round-bottom-flask equipped with magnetic stirring bar. Acetonitrile (20 mL) was added to fully dissolve the compound and deionized water (7 to 10 mL) was added. NaHCO$_3$ saturated aqueous solution (ca. 0.5 mL) was then added to adjust the pH value between 7 and 8. This solution was allowed to stir at room temperature for at least 12 h. TFA (0.1 mL) and another 10 mL of deionized water were added to the solution and the solution was purified by semi-preparative RP-HPLC immediately using acetonitrile and water as the eluents to give MI-519-6401 as the TFA salt. $^1$H NMR (300 MHz, MeOH-d$_4$): 7.62-7.53 (m, 2H), 7.45-7.35 (m, 1H), 7.20-7.10 (m, 2H), 6.80-6.85 (m, 1H), 5.11 (d, J=11.07 Hz, 1H), 4.57 (d, J=11.11 Hz, 1H), 4.40 (d, J=7.39 Hz, 1H), 4.00-3.80 (m, 1H), 2.50-2.35 (m, 1H), 2.35-2.20 (m, 1H), 2.10-1.90 (m, 1H), 1.90-1.60 (m, 2H), 1.30 (s, 3H), 1.20-1.05 (m, 1H), 0.88 (s, 9H); $^{13}$C NMR (75 MHz, MeOH-d$_4$): 177.8, 168.0, 157.6 (d, J$_{C-F}$=249 Hz), 144.9, 136.8, 132.2, 128.5, 126.5, 126.3 (d, J$_{C-F}$=4.76), 123.9, 123.7, 122.3 (d, J$_{C-F}$=18.97 Hz), 122.0 (d, J$_{C-F}$=13.1 Hz), 111.8, 67.1, 64.6, 64.5, 62.9, 49.0, 45.5, 45.4, 43.3, 38.0, 30.8, 29.5, 27.3; ESI-MS calculated for C$_{28}$H$_{33}$$^{35}$Cl$_2$FN$_3$O$_3$ [M+H]$^+$: 548.1883. Found: 548.25.

Figure 2:
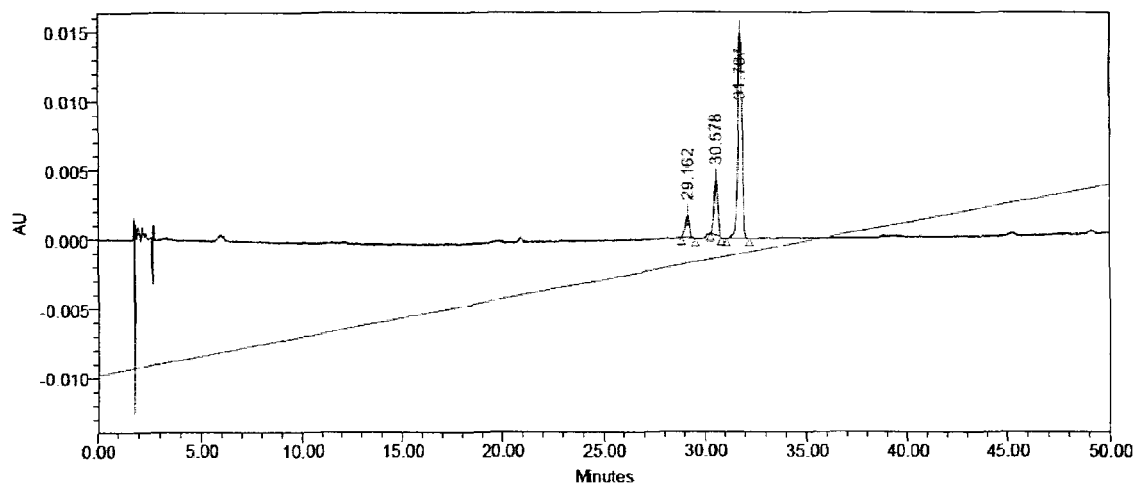
FIG. 2 is reverse phase HPLC chromatogram of MI-519-64 after treatment with acetonitrile/water for 12 h. Three isomers are present. MI-519-64 and MI-519-6401 correspond to RP-HPLC peaks at 30.578 minutes, and 31.787 minutes, respectively. The isomer eluting at 29.162 minutes is referred to as MI-519-6402.
Figure 3:
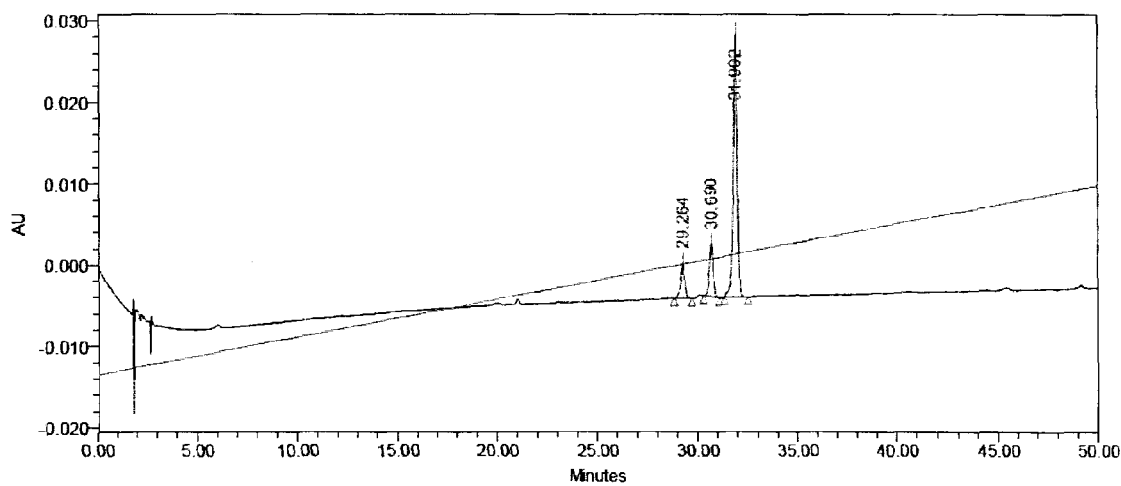
FIG. 3 is reverse phase HPLC chromatogram of MI-519-64 after treatment with acetonitrile/water for 3 days.
Figure 4:
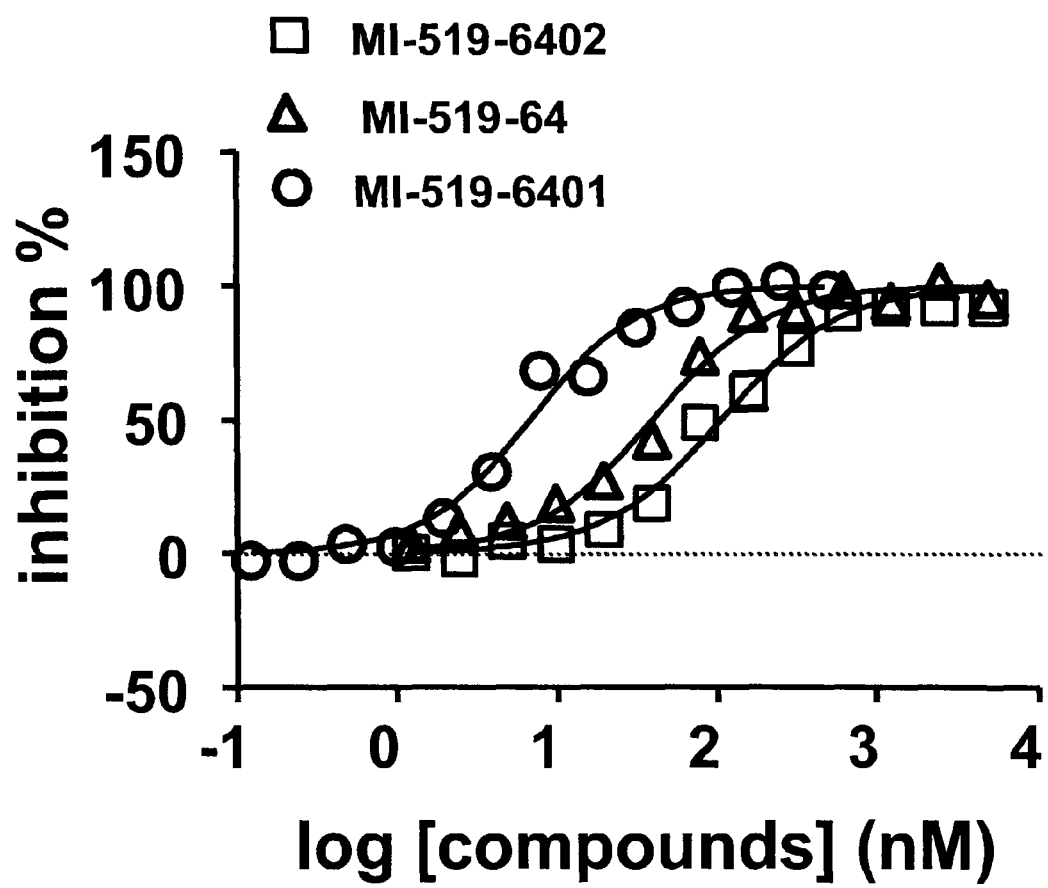
FIG. 4 is a line graph showing the binding affinities of MI-519-64, MI-519-6401, and MI-519-6402 to human MDM2 protein, as determined using a fluorescence-polarization binding assay. The purity of each isomer used in this experiment (as determined by RP-HPLC) are as follows: MI-519-6402: 90% (with 10% of MI-519-64); MI-519-64: 93% (with 3% of MI-519-64 and 4% of MI-519-6401); and MI-519-6401: >99%. The log $IC_{50}$ values for MI-519-6402, MI-519-64, and MI-519-6401 are 2.030 nM, 1.598 nM, and 0.8354 nM, respectively.
Figure 5:
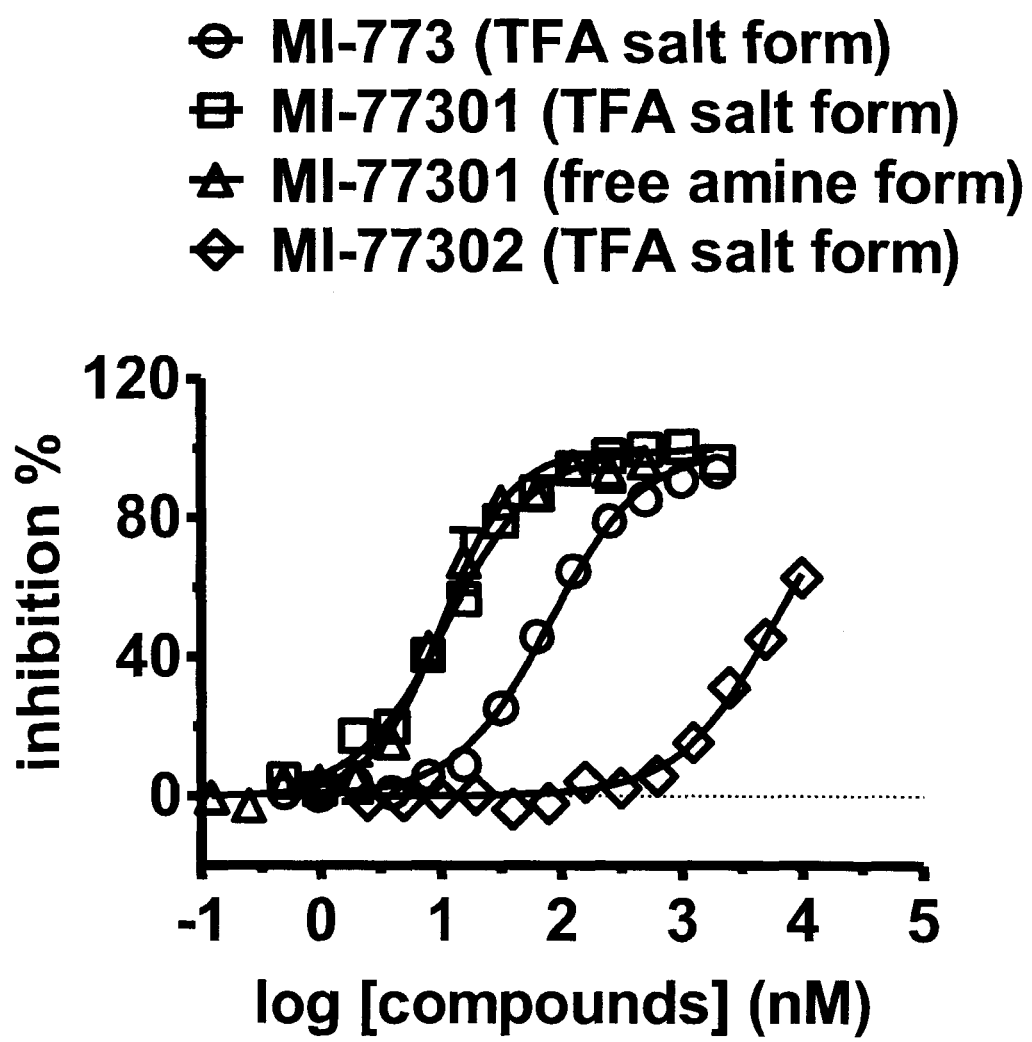
FIG. 5 is a line graph showing the binding affinities of MI-773 (TFA salt), MI-77301 (TFA salt), MI-77301 (free amine), and MI-77302 (TFA salt) to human MDM2 protein, as determined using a fluorescence-polarization binding assay.

Analytical RP-HPLC spectra are presented in FIGS. 1-3. Referring to

FIG. 3, MI-519-6401 corresponds to the RP-HPLC peak at 31.787 minutes.

In an alternate procedure, MI-519-64 (100 mg) purified by flash chromatography on silica gel was placed in a 50 mL round-bottom-flask equipped with magnetic stirring bar. Methanol (20 mL) was added to fully dissolve the compound and deionized water (10 to 20 mL) was added. NaHCO$_3$ saturated aqueous solution (ca. 0.5 mL) was then added to adjust the pH value between 7 and 8. This solution was allowed to stir at room temperature for at least 12 h. TFA (0.1 mL) and another 10 mL of deionized water were added to the solution and the solution was purified by semi-preparative RP-HPLC immediately using acetonitrile and water as the eluents to give MI-519-6401 as the TFA salt.

C02701, C02901, C03001, C03401, C03701, C03801, C04801, C08301, C08601, and C11701 of EXAMPLE 1 were prepared using procedures similar to that used to prepare MI-519-6401.

Example 10

Synthesis of MI-773

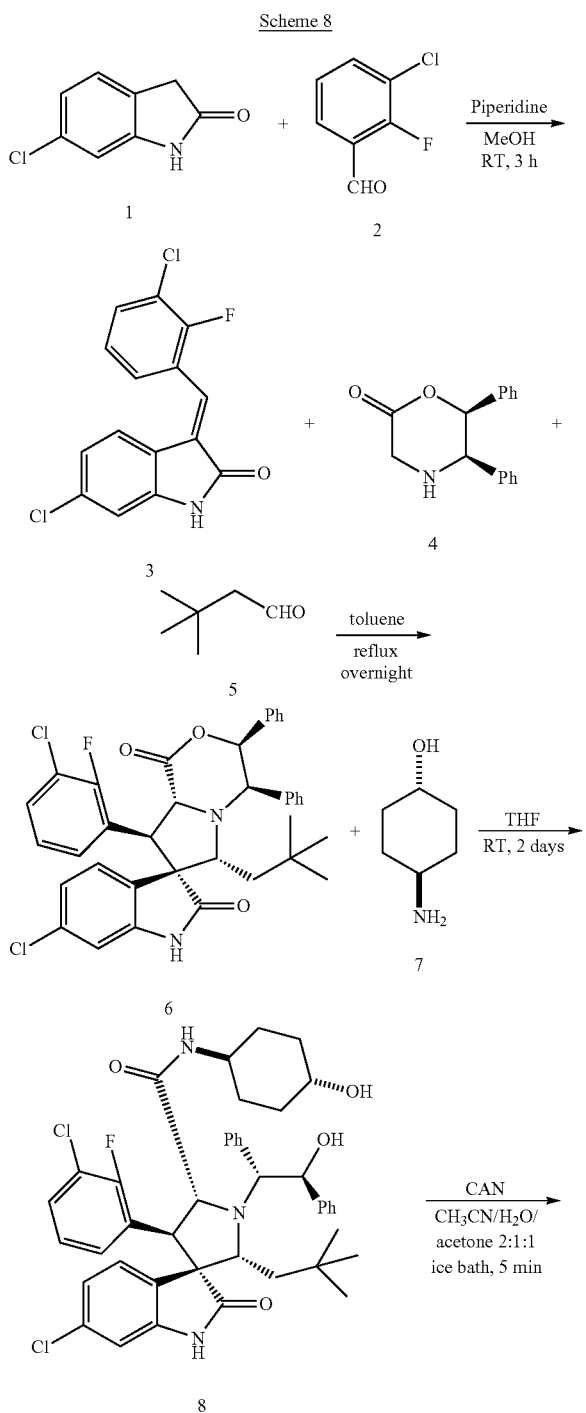

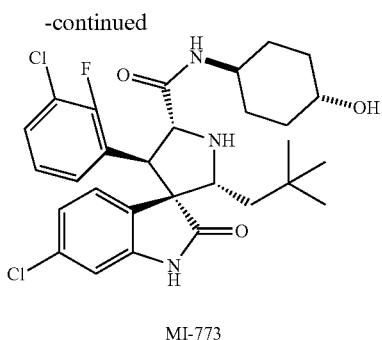

MI-773

Step 1

To a stirred solution of oxindole 1 (4.19 g, 25 mmol) in methanol (50 mL) was added aldehyde 2 (3.96 g, 25 mmol) and piperidine (2.45 mL, 25 mmol). The reaction mixture was stirred at room temperature for 3 h and the yellow precipitate was collected, washed successively with methanol, hexanes, and ethyl ether and dried to give compound 3 (6.25 g, 81% yield).

Step 2

To a solution of compound 3 (6.25 g, 21 mmol) in toluene (75 ml) was added compound 4 (5.43 g, 21 mmol), compound 5 (2.15 g, 21 mmol) and 4 Å molecular sieves (4 g). The reaction mixture was heated at reflux overnight and filtrated. The filtrate was evaporated and the residue was purified by silica gel flash column chromatography (n-hexane/ethyl acetate=9:1 to 5:1) to give compound 6 (8.78 g, 65% yield).

Step 3

The solution of compound 6 (965 mg, 1.5 mmol) and amine 7 (346 mg, 3 mmol) in 5 mL of THF was stirred at room temperature for 2 days and the solvent was removed under reduced pressure. The residue was purified by silica gel flash column chromatography (n-hexane/ethyl acetate=1:1 to 1:4) to give compound 8 (819 mg, 72% yield).

Step 4

Figure 35:
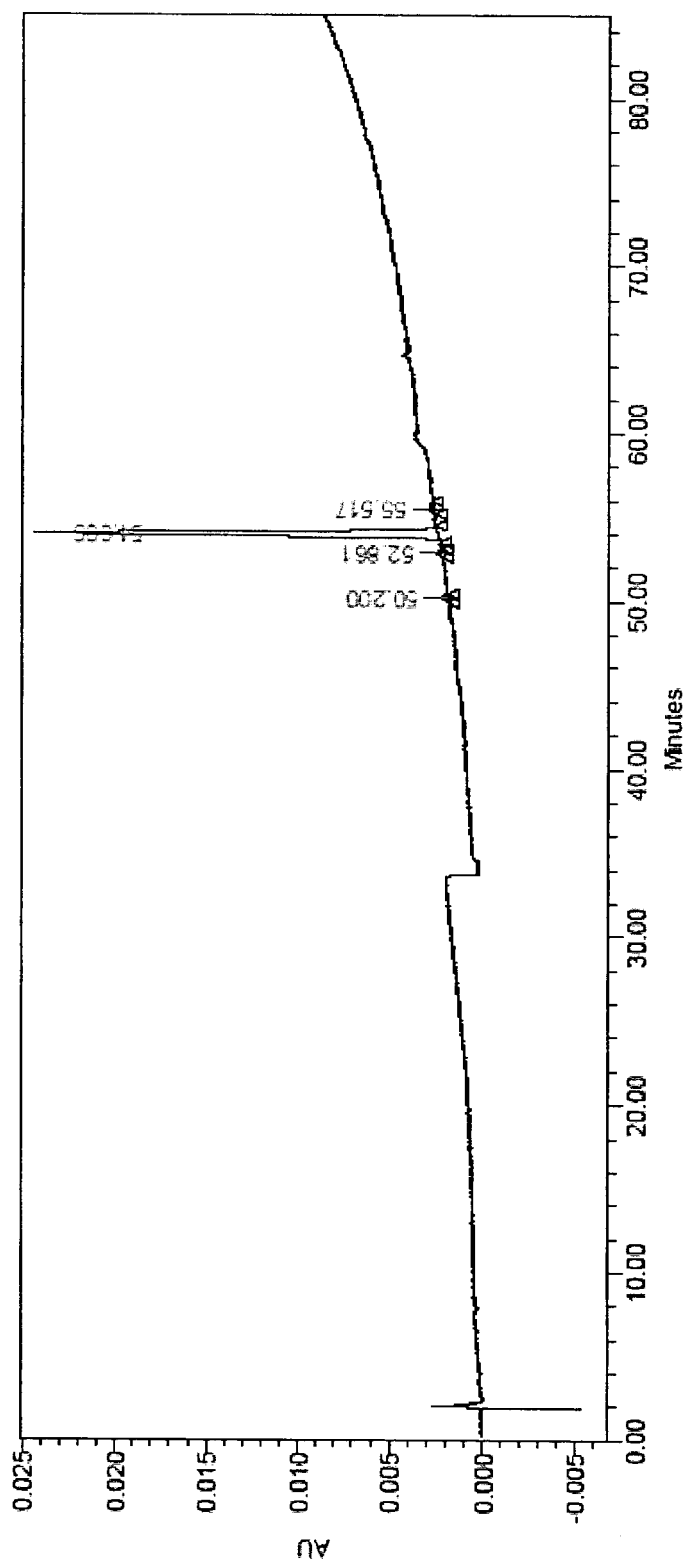
FIG. 35 is a reverse phase HPLC chromatogram of substantially pure MI-773 (eluent: MeOH/water with 0.1% TFA).

To an ice-bath cooled solution of compound 8 (800 mg, 1.05 mmol) in $CH_3CN$ (8 ml), $H_2O$ (4 ml) and acetone (4 ml) was added CAN (ammonium cerium) (1.15 g, 2.1 mmol). Progress of the reaction was monitored by TLC. When all the starting material disappeared (around 5 min), 100 mg of $NaHCO_3$ powder was added and the reaction mixture was diluted with 50 mL of ethyl acetate. The organic phase was dried over anhydrous $Na_2SO_4$, filtered, and concentrated. The residue was purified by silica gel flash column chromatography (methylene chloride/methanol/triethylamine=200:1:1 to 200:10:1) to give (2R,3S,4'S,5R)-6-chloro-4'-(3-chloro-2-fluorophenyl)-N-((trans-4-hydroxycyclohexyl)-2'-neopentyl-2-oxospiro[indoline-3,3'-pyrrolidine]-5'-carboxamide (MI-773) (402 mg, 68% yield, Purity (HPLC): >95% (FIG. 35)). The absolute stereochemical configuration of MI-773 was determined by x-ray analysis.

MI-773 was dissolved in DCM, TFA was added, and the solvent was removed by evaporation. The residue was further purified by chromatography on a C18 reverse phase semi-preparative HPLC column with solvent A (0.1% of TFA in water) and solvent B (0.1% of TFA in methanol) as eluents (gradient: 45% of solvent A and 55% of solvent B to 30% of solvent A and 70% of solvent B in 30 min) to give MI-773 as the TFA salt. NMR for MI-773 (TFA salt): $^1$H NMR (300 MHz, $CD_3OD$) δ 7.47 (t, J=7.0 Hz, 1H), 7.34 (t, J=7.4 Hz, 1H), 7.14 (t, J=7.9 Hz, 1H), 6.83 (s, 1H), 6.80 (s, 2H), 4.39 (d, J=10.0 Hz, 1H), 4.15-4.05 (m, 1H), 3.72-3.53 (m, 1H), 3.53-3.85 (m, 2H), 2.10-1.75 (m, 4H), 1.62 (d, J=12.2 Hz, 1H), 1.45-1.05 (m, 5H), 0.78 (s, 9H).

Figure 6:
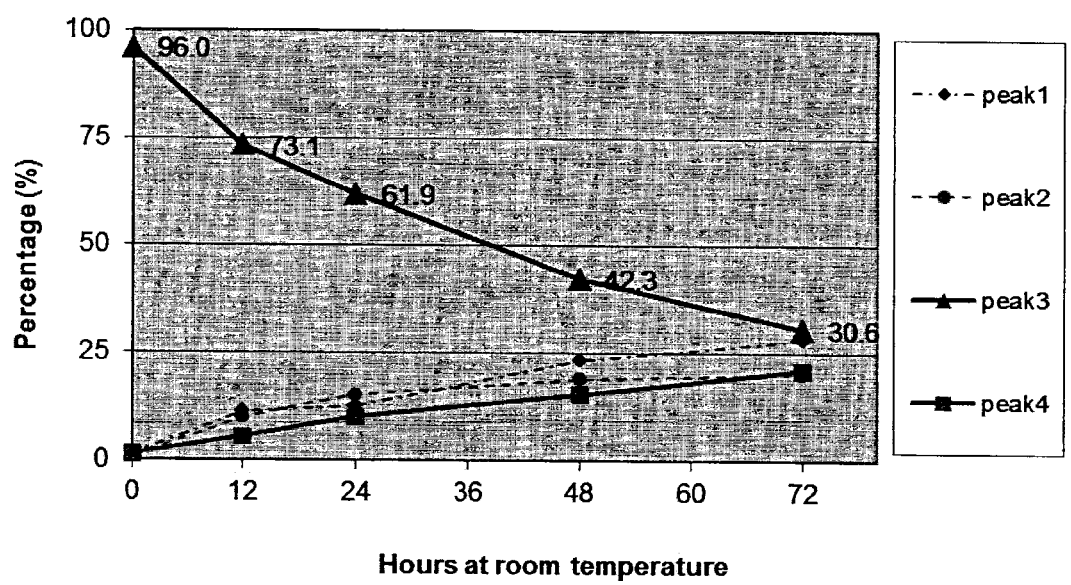
FIG. 6 is a line graph showing the stability of MI-773 (TFA salt) at various time points in water/methanol=1:1 with 0.1% of TFA, pH 2.1. The compound corresponding to peak 1 is MI-77302. The compound corresponding to peak 3 is MI-773. The compound corresponding to peak 4 is MI-77301.
Figure 37:
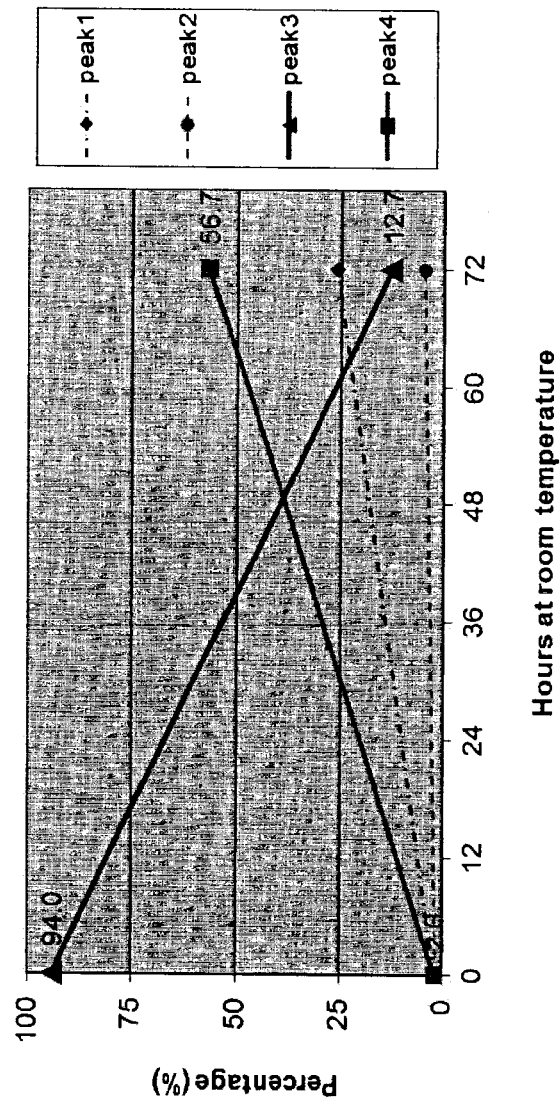
FIG. 37 is a line graph showing the stability of MI-773 (TFA salt) at various time points in water/methanol=1:1 with 0.1% of TEA, pH 10.8. The compound corresponding to peak 3 is MI-773. The compound corresponding to peak 4 is MI 77301.
Figure 38:
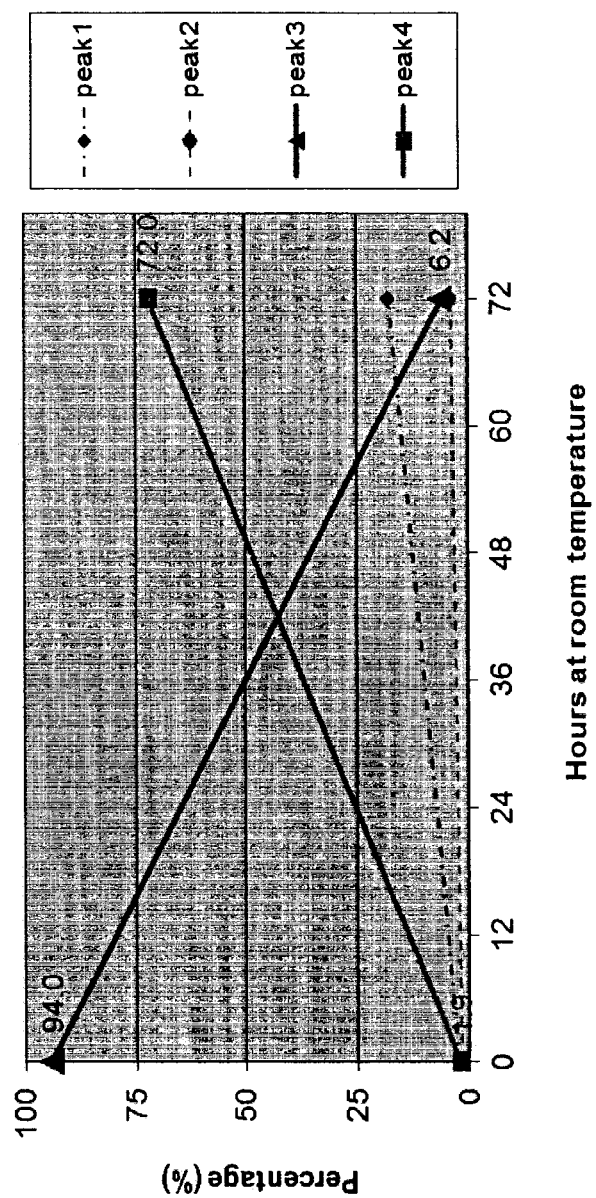
FIG. 38 is a line graph showing the stability of MI-773 (TFA salt) at various time points in water/methanol=1:1, pH 3.9. The compound corresponding to peak 3 is MI-773. The compound corresponding to peak 4 is MI-77301.
Figure 39:
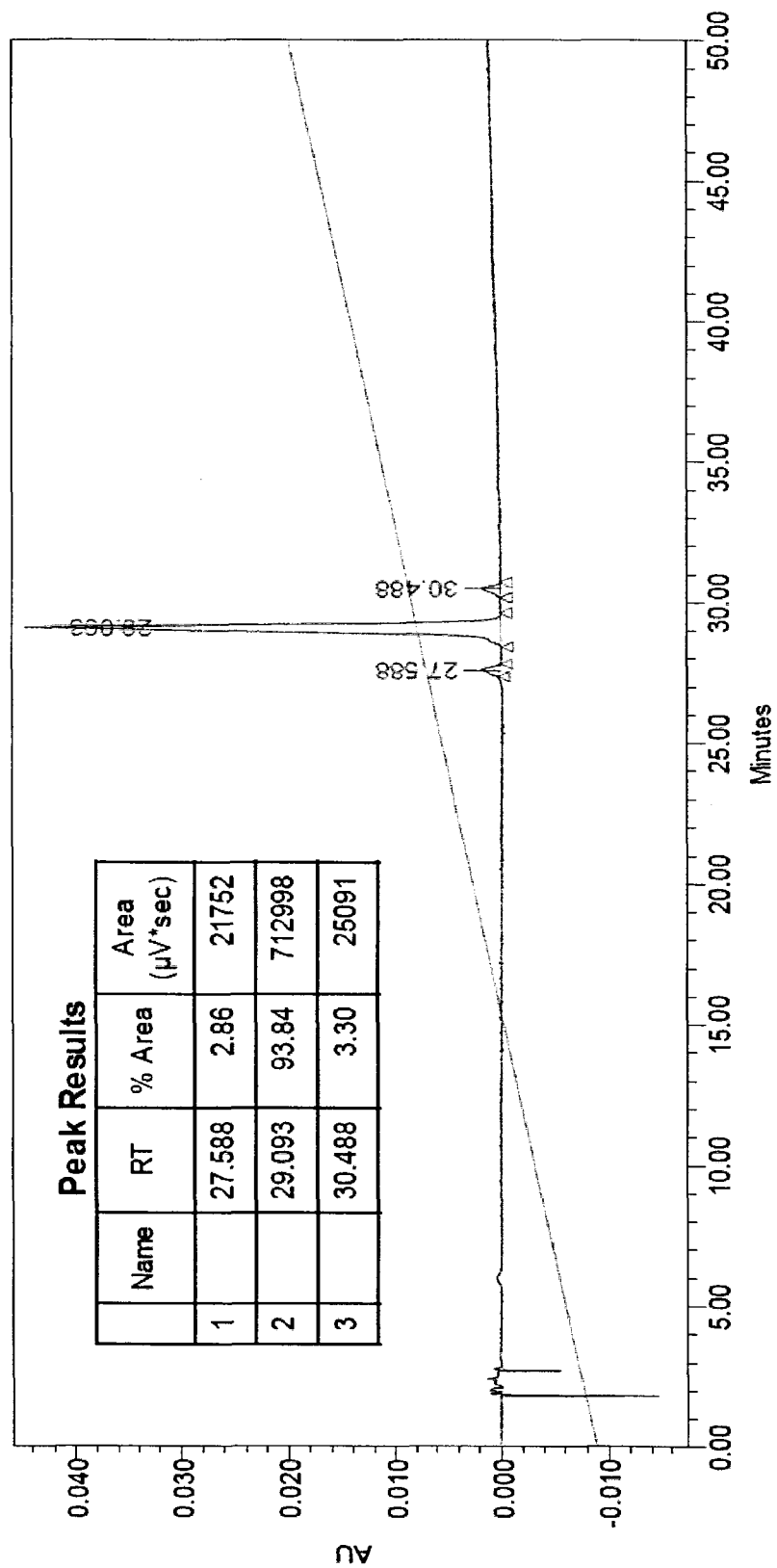
FIG. 39 is reverse phase HPLC chromatogram of substantially pure C027 (eluent: acetonitrile/$H_2O$ with 0.1% TFA).
Figure 40:
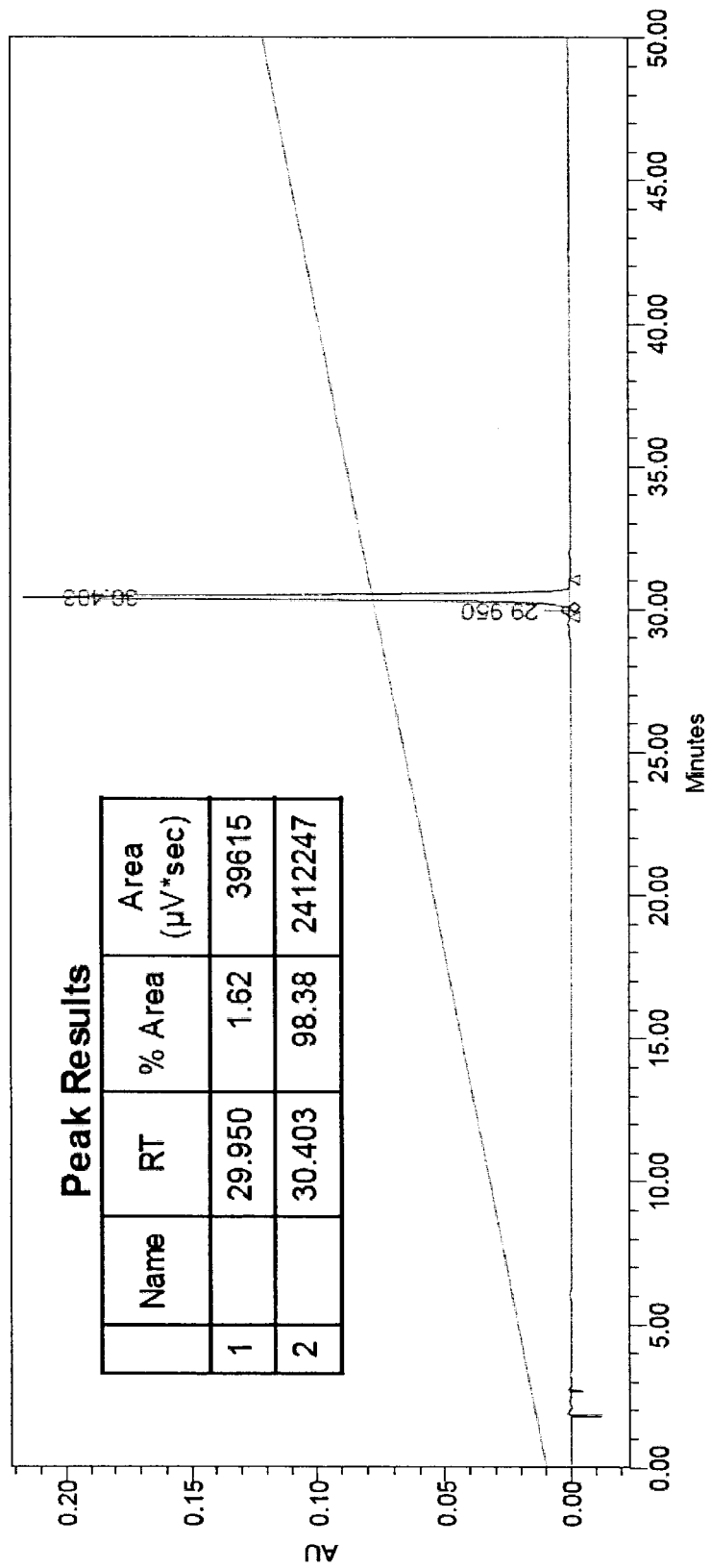
FIG. 40 is reverse phase HPLC chromatogram of substantially pure C02701 (eluent: acetonitrile/$H_2O$ with 0.1% TFA).
Figure 41:
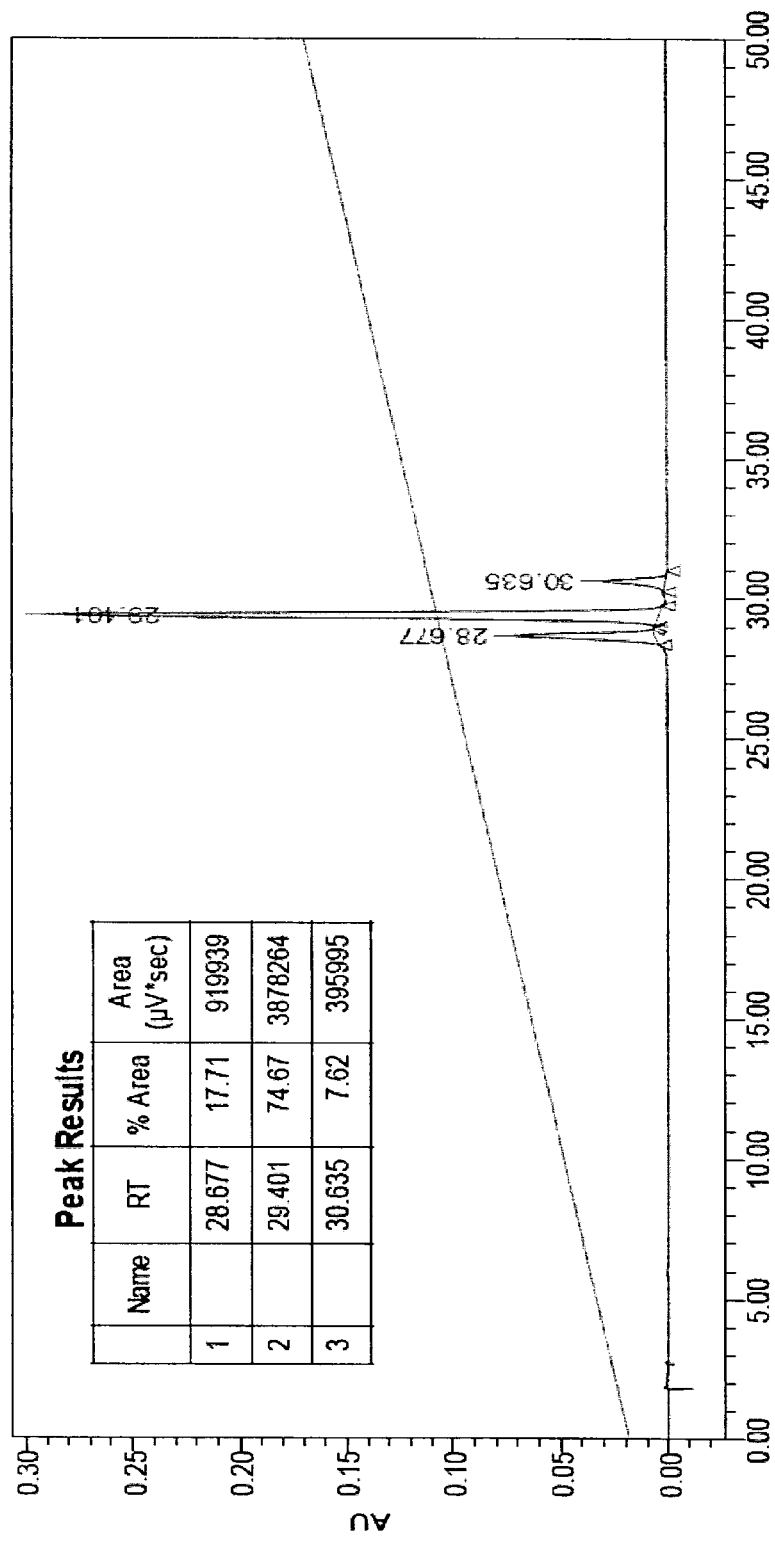
FIG. 41 is reverse phase HPLC chromatogram of C029 substantially free of other stereoisomers (eluent: acetonitrile/$H_2O$ with 0.1% TFA).
Figure 42:
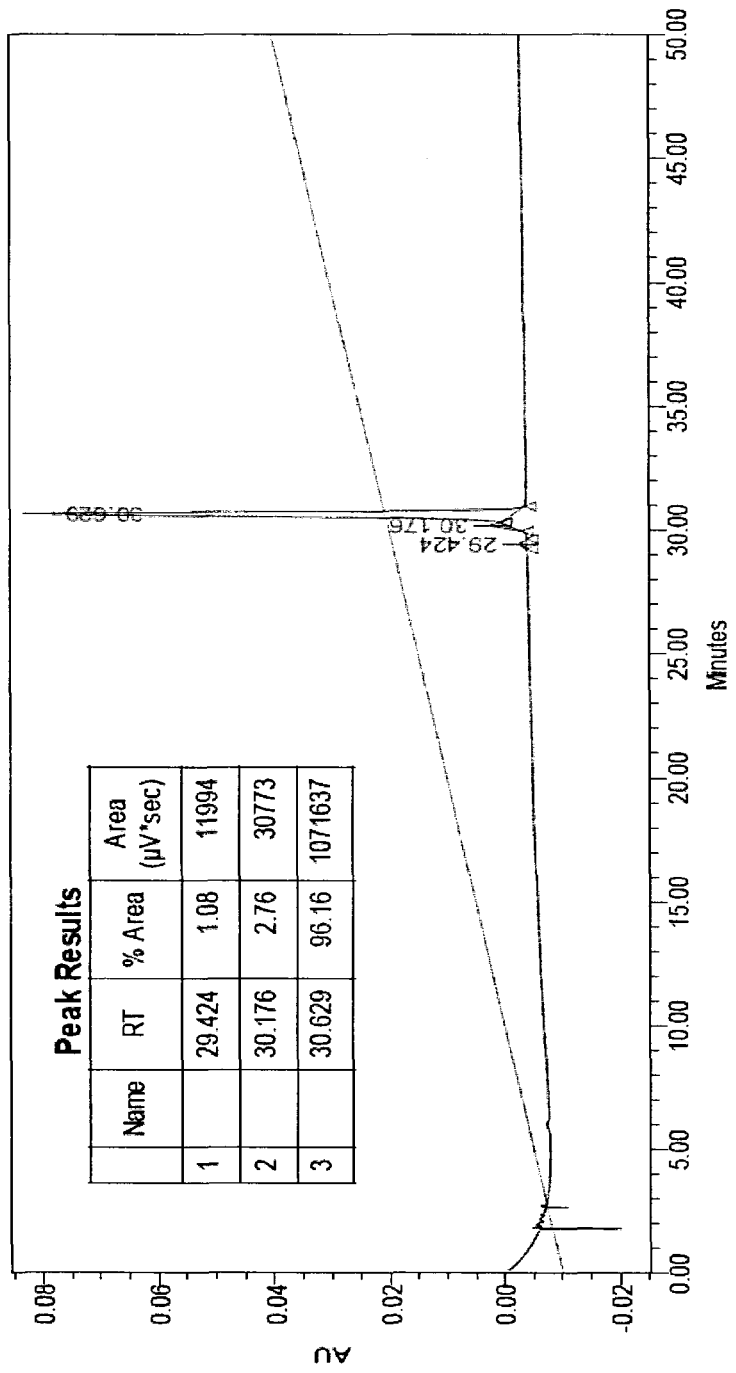
FIG. 42 is reverse phase HPLC chromatogram of substantially pure C02901 (eluent: acetonitrile/$H_2O$ with 0.1% TFA).

Stability of MI-773 (TFA salt): MI-773 (TFA salt) was dissolved in a water/methanol mixture: 1) water/methanol=1:1 with 0.1% of TFA, pH 2.1; 2) water/methanol=1:1 with 0.1% of TEA, pH 10.8; or 3) water/methanol=1:1, pH 3.9. The solution was allowed to stand at room temperature. The purity was tested using a C18 reverse phase analytical HPLC column at the time points of 0, 12 h, 24 h, 48 h, and 72 h. The results showed transformation of MI-773 (corresponding to peak 3) to MI-77302 (corresponding to peak 1), MI-77301 (corresponding to peak 4) and another compound (corresponding to peak 2) having the same molecular weight (FIGS. 6, 37, and 38). The purity of an identical sample solution stored at 4° C. was also tested at 0 and 36 h. The results showed comparably slow transformation of MI-773 at 4° C.

Example 11

Synthesis of MI-77301

Scheme 9

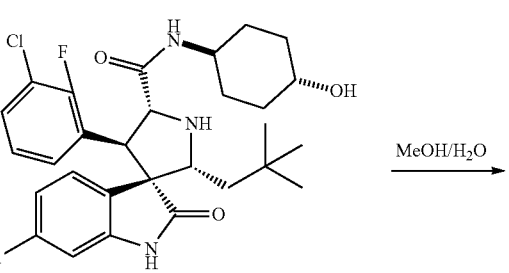

MI-773

MeOH/H₂O

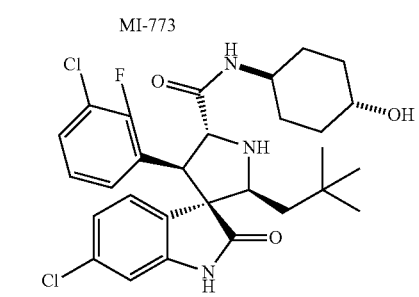

MI-77301

+

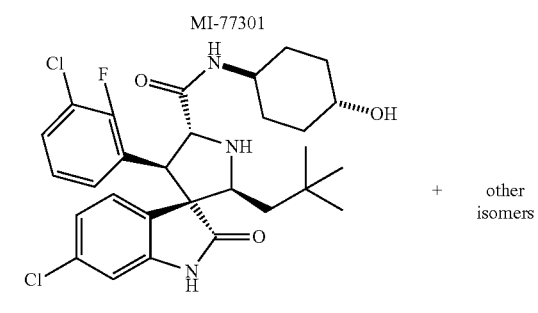

MI-77302

+ other isomers

Figure 36:
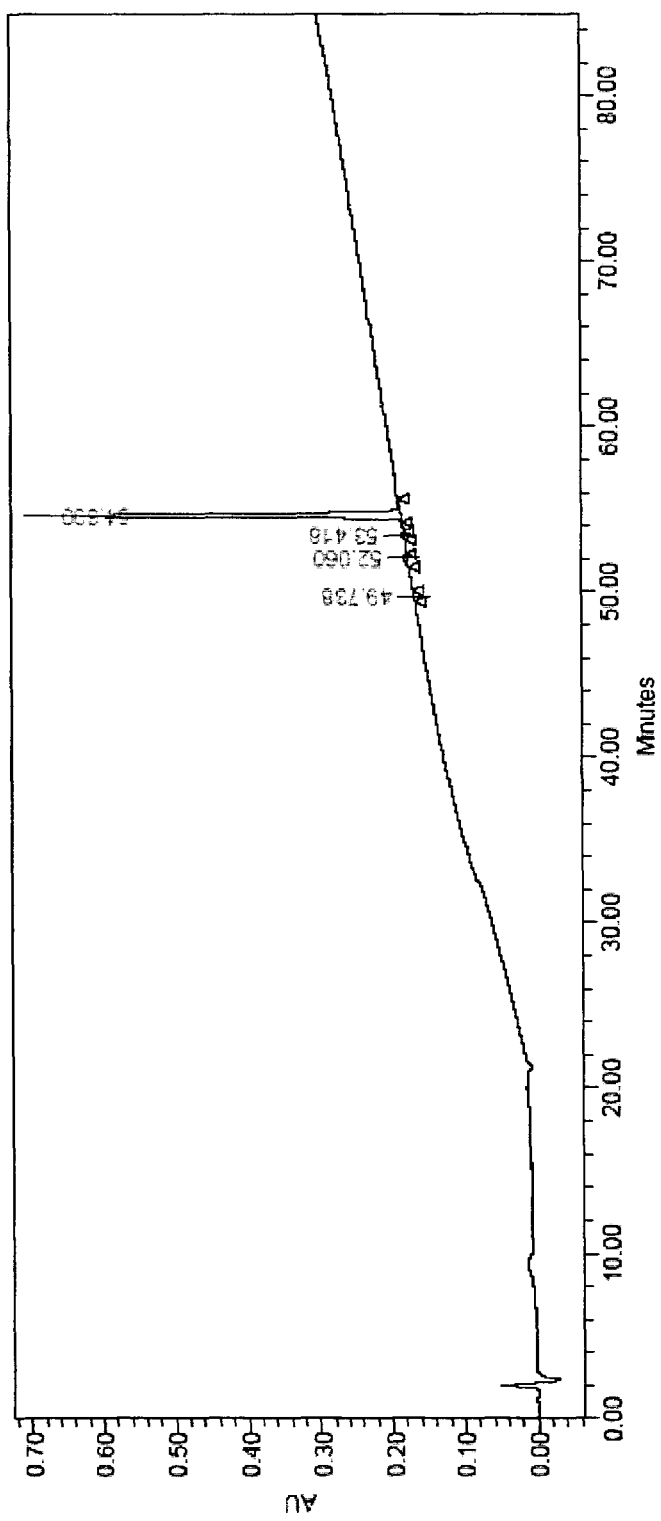
FIG. 36 is a reverse phase HPLC chromatogram of substantially pure MI-77301 (eluent: MeOH/water with 0.1% TFA).

MI-773 (as the TFA salt) was dissolved in MeOH/H₂O (1:1 v/v ratio) and allowed to stand at room temperature for 1-4 days. The solution was purified by chromatography on a C18 reverse phase semi-preparative HPLC column with solvent A (0.1% of TFA in water) and solvent B (0.1% of TFA in methanol) as eluents (gradient: 45% of solvent A and 55% of solvent B to 30% of solvent A and 70% of solvent B in 30 min) MI-77301 was isolated as the TFA salt. $^1$H NMR (300 MHz, MeOH-d$_4$): 8.35 (d, J=7.8 Hz, 1H), 7.54-7.62 (m, 2H), 7.37-7.43 (m, 1H), 7.12-7.20 (m, 2H), 6.80 (d, J=1.5 Hz, 1H), 5.20 (d, J=11.4 Hz, 1H), 4.58 (d, J=11.4 Hz, 1H), 4.51 (d, J=7.2 Hz, 1H), 3.50-3.75 (m, 1H), 3.30-3.50 (m, 1H), 1.82-2.00 (m, 3H), 1.76 (d, J=10.5 Hz, 1H), 1.52 (d, J=12.3 Hz, 1H), 1.05-1.42 (m, 4H), 0.88-1.00 (m, 1H), 0.88 (s, 9H); $^{13}$C NMR (75 MHz, MeOH-d$_4$): 177.7, 166.9, 157.6 (d, JC—F=248.0 Hz), 145.0, 137.0, 132.4, 128.6, 126.6, 126.4 (d, JC—F=4.9), 124.0, 123.4, 122.3 (d, JC—F=18.8 Hz), 121.5 (d, JC—F=12.8 Hz), 111.9, 69.9, 64.4, 64.0, 62.8, 49.7, 34.3, 34.2, 30.9, 30.82, 30.77, 29.4; ESI-MS calculated for C$_{29}$H$_{35}$Cl$_2$FN$_3$O$_3$ (M+H)+ requires 562.20. found 562.33; [α]$_D^{25}$=−27.2° (c=0.005 g/mL in MeOH); Purity (HPLC): >95% (See FIG. 36).

In an alternative procedure, MI-773 (77 mg) was dissolved in 15 mL MeOH/H$_2$O (v/v=1:1). After 3 days, the needle crystals that had formed were collected, washed with cold MeOH/H$_2$O (v/v=1:1) and dried in vacuum to give MI-77301 as the free amine (20 mg; >95% purity as determined by HPLC). $^1$H NMR (300 MHz, MeOH-d$_4$): 7.49-7.55 (m, 1H), 7.25-7.31 (m, 1H), 7.10-7.16 (m, 1H), 6.82 (d, J=1.8 Hz, 1H), 6.50-6.71 (m, 1H), 6.49 (d, J=8.4 Hz, 1H), 4.32 (d, J=9.0 Hz, 1H), 4.09 (d, J=8.7 Hz, 1H), 3.57-3.69 (m, 1H), 3.49 (d, J=9.2 Hz, 1H), 3.46-3.57 (m, 1H), 1.83-2.07 (m, 3H), 1.68-1.80 (m, 1H), 1.54 (dd, J=9.0, 14.3 Hz, 1H), 1.12-1.45 (m, 5H), 0.80 (s, 9H). The absolute stereochemical configuration of MI-77301 was determined by X-ray analysis.

Figure 7:
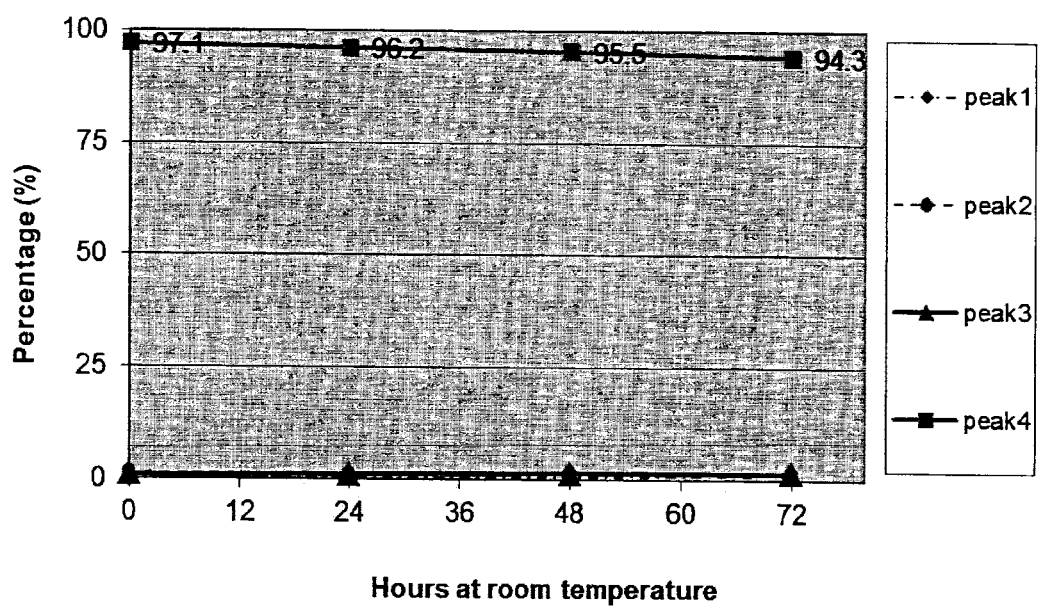
FIG. 7 is a line graph showing the stability of MI-77301 (TFA salt) at various time points in water/methanol=1:1 with 0.1% of TFA, pH 2.1. The compound corresponding to peak 1 is MI-77302. The compound corresponding to peak 3 is MI-773. The compound corresponding to peak 4 is MI-77301.
Figure 8:
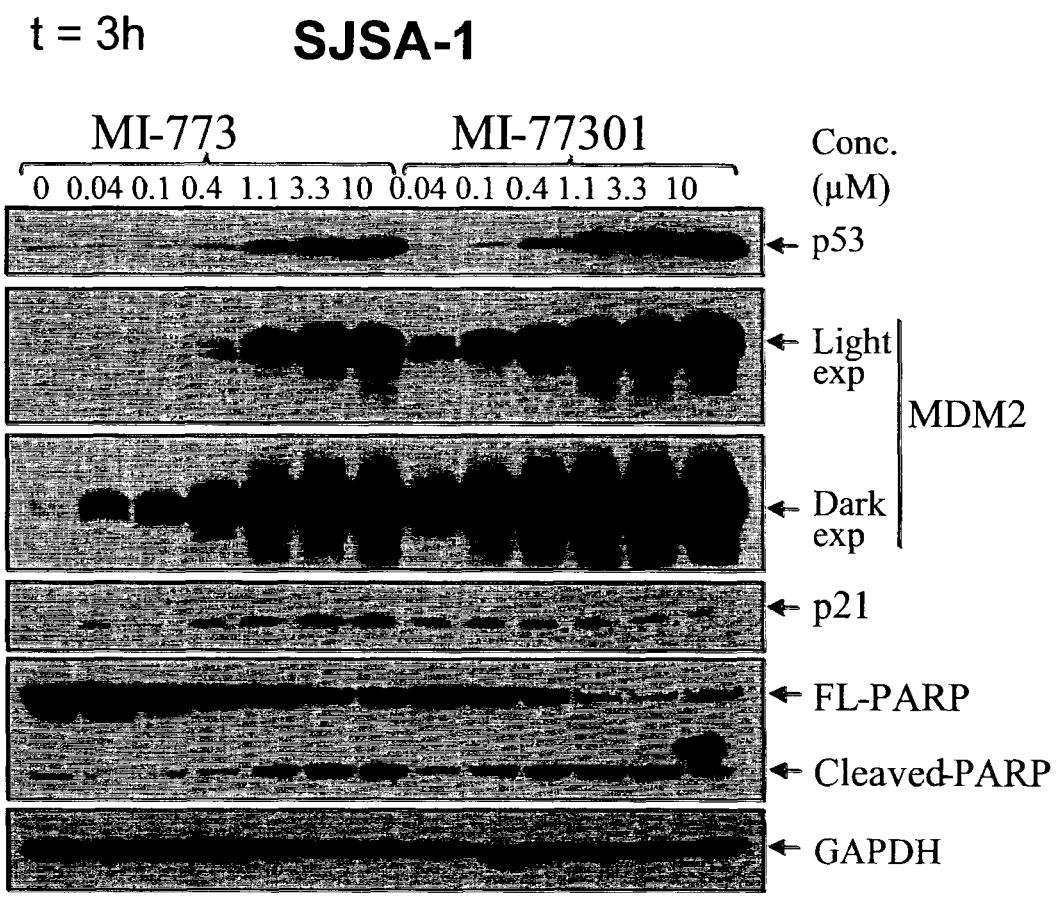
FIG. 8 is an illustration showing western blot analysis of p53 activation and apoptosis induced by MI-773 and MI-77301 in the SJSA-1 (osteosarcoma) cell line.
Figure 9:
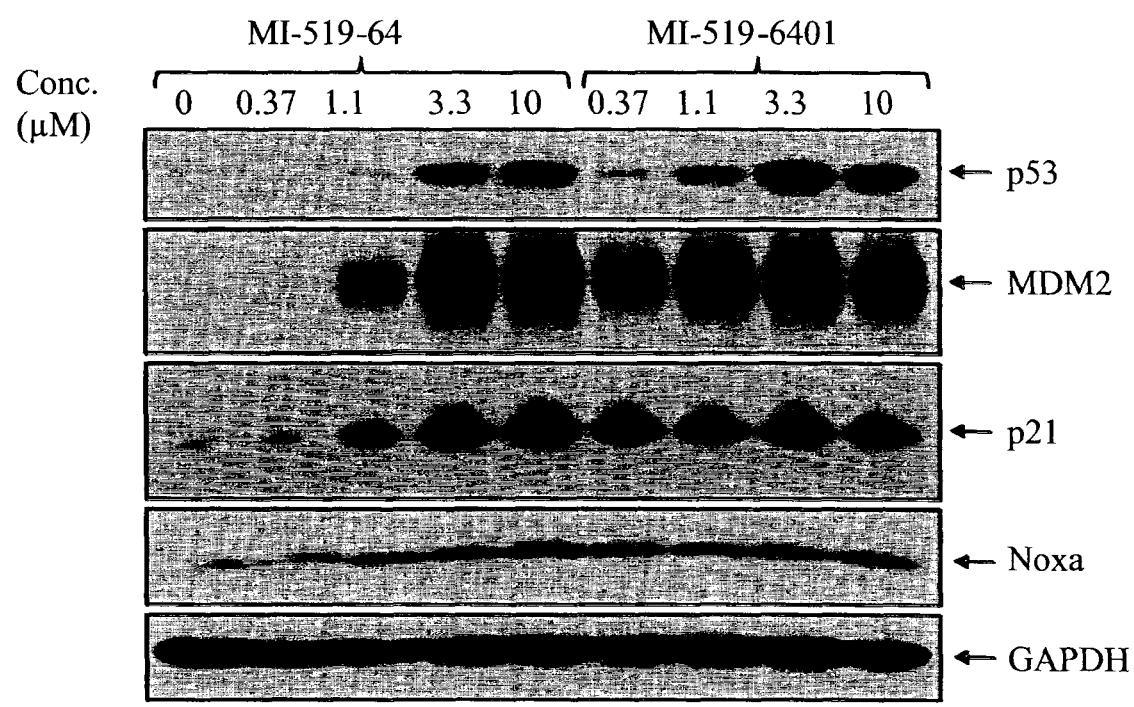
FIG. 9 is an illustration showing western blot analysis of p53 activation and apoptosis induced by MI-519-64 and MI-519-6401 in the SJSA-1 cell line.
Figure 10:
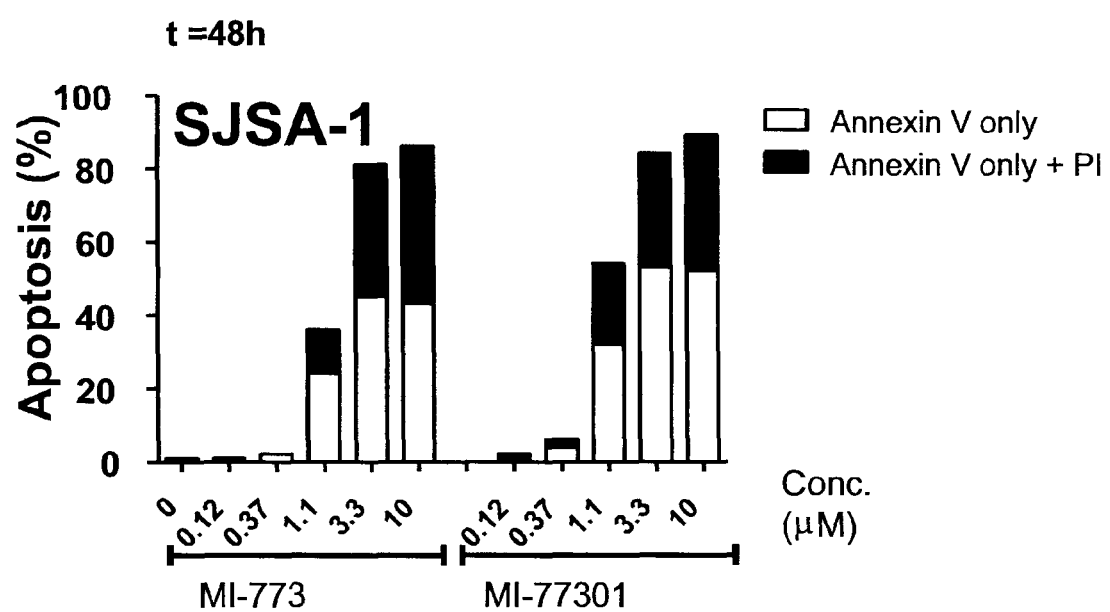
FIG. 10 is a bar graph showing apoptosis induced by MI-773 and MI-77301 in the SJSA-1 cell line.

Stability of MI-77301 (TFA salt): MI-77301 (TFA salt) was dissolved in a water/methanol mixture (water/methanol=1:1 with 0.1% of TFA). The solution was allowed to stand at room temperature. The purity was tested using a C18 reverse phase analytical HPLC column at the time points of 0, 12 h, 48 h, and 72 h. The results showed slow transformation of MI-77301 (corresponding to peak 4) to MI-77302 (corresponding to peak 1) and two other compounds (corresponding to peaks 2, and 3) having the same molecular weight (FIG. 7). The absolute stereochemistry of MI-77302 was determined by x-ray analysis.

MI-710201, MI-710401, MI-710501, MI-710601, MI-710801, and MI-710901 of EXAMPLE 1 were prepared using procedures similar to that used to prepare MI-77301.

Figure 34:
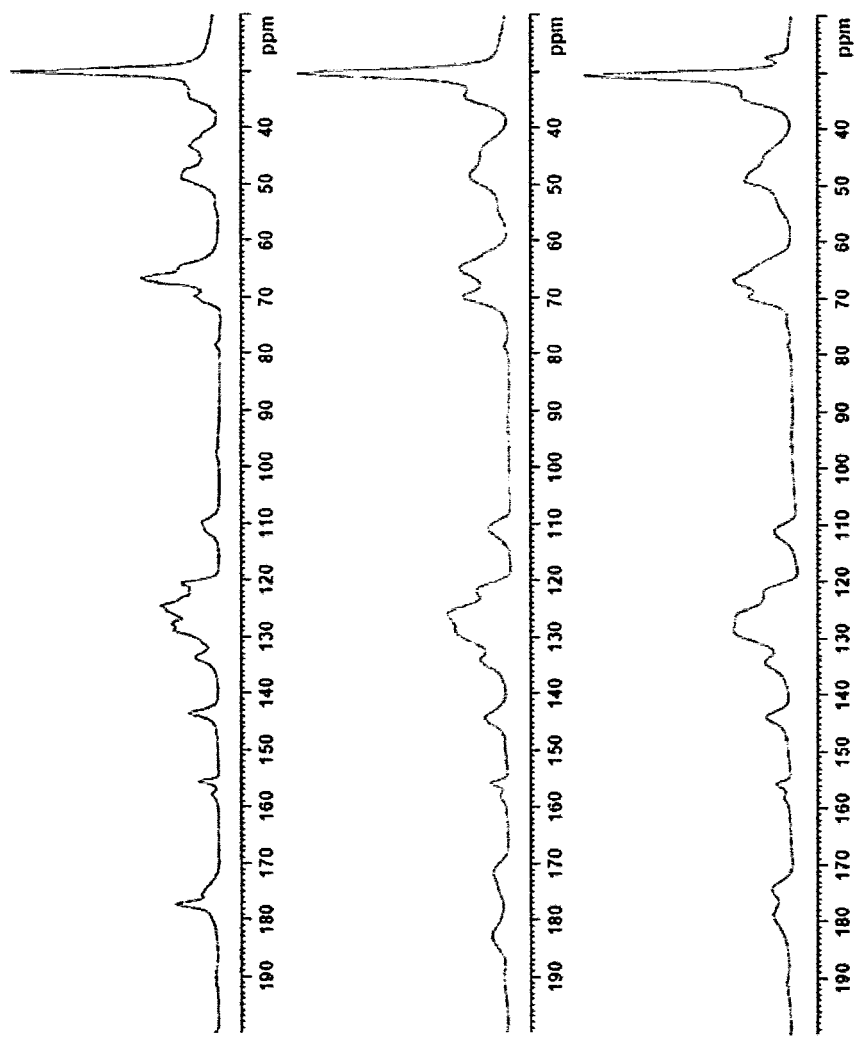
FIG. 34 is a series of three $^{13}$C CPMAS NMR spectrograms showing MI-77301 (top), MI-773 (middle), and MI-77302 (bottom).

$^{13}$C CPMAS NMR spectroscopy (400 MHz) of MI-77301 (top), MI-773 (middle), and MI-77302 (bottom) is presented in FIG. 34. Chemical shift differences are observed in the carbonyl region (170-185 ppm).

In an alternative procedure, MI-77301 was prepared as described in Scheme 9A.

Scheme 9A

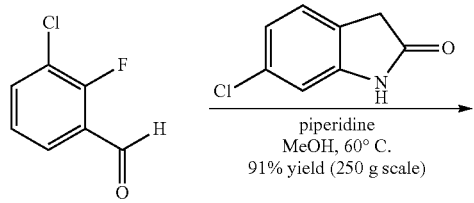

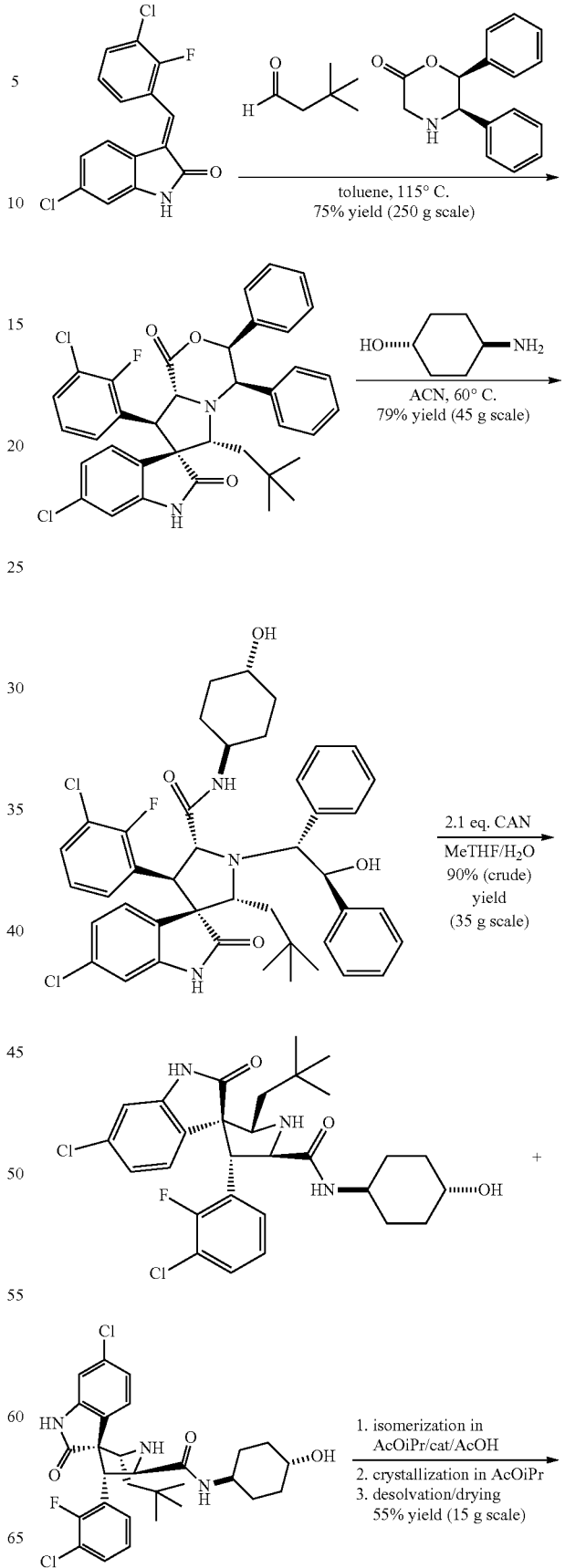

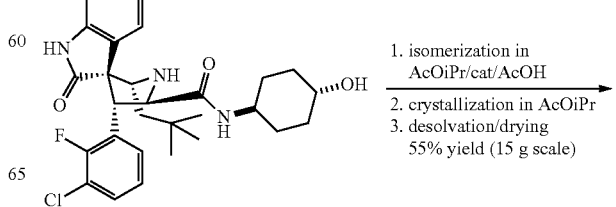

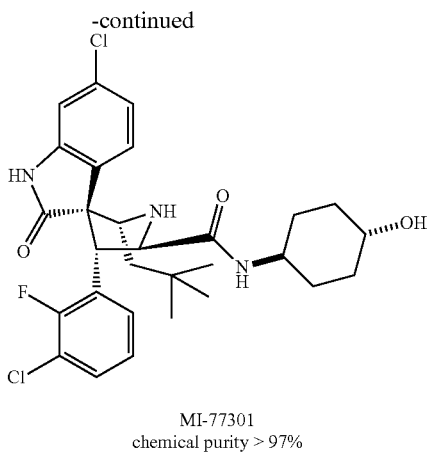

MI-77301
chemical purity > 97%

Example 12

Synthesis of: (2'S,3R,4'R,5'S)-6-chloro-4'-(3-chloro-2-fluorophenyl)-N-((trans)-4-hydroxycyclohexyl)-2'-neopentyl-2-oxospiro[indoline-3,3'-pyrrolidine]-5'-carboxamide; and (2'R,3S,4'R,5'S)-6-chloro-4'-(3-chloro-2-fluorophenyl)-N-((trans)-4-hydroxycyclohexyl)-2'-neopentyl-2-oxospiro[indoline-3,3'-pyrrolidine]-5'-carboxamide

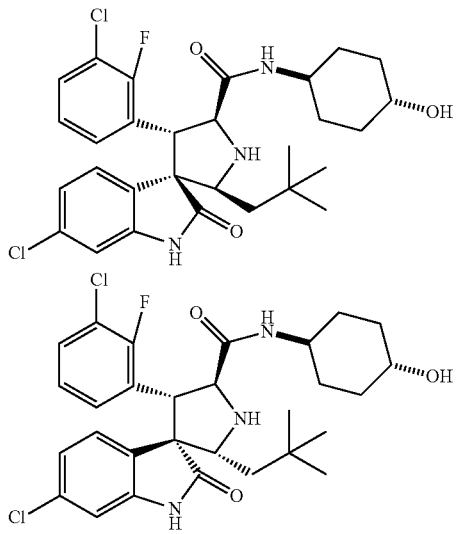

(5S,6R)-5,6-diphenylmorpholin-2-one was prepared according to *J. Org. Chem.* 2005, 70, 6653. mp: 139° C. (Kofler); LC-MS: $t_R$ (min)=0.96; [M+H]$^+$: m/z 254 (method C).

(3R,3'R,4'S,6'S,8'R,8a'S)-6-chloro-8'-(3-chloro-2-fluorophenyl)-6'-neopentyl-3',4'-diphenyl 3',4',8',8a'-tetrahydrospiro[indoline-3,7'-pyrrolo[2,1-c][1,4]oxazine]-1',2(6'H)-dione To a suspension of 496 mg (1.61 mmol) of (E)-6-chloro-3-(3-chloro-2-fluorobenzylidene)indolin-2-one in toluene under argon, were added 408 mg (1.61 mmol) of (5S,6R)-5,6-diphenylmorpholin-2-one and 213 µL (1.61 mmol) of 3,3-dimethyl-butyraldehyde. The reaction mixture was heated at reflux temperature for 6 hours, upon which it was cooled down to room temperature and concentrated to dryness under reduced pressure. The residue was purified by flash chromatography on a 70 g silica cartridge (15-40 µm silica gel; eluting solvent: cyclohexane/ethyl acetate 90/10 v/v; flow: 50 mL/min). 0.58 g of (3R,3'R,4'S,6'S,8'R,8a'S)-6-chloro-8'-(3-chloro-2-fluorophenyl)-6'-neopentyl-3',4'-diphenyl 3',4',8',8a'-tetrahydrospiro[indoline-3,7'-pyrrolo[2,1-c][1,4]oxazine]-1',2(6'H)-dione was obtained as an amorphous yellow solid. LC-MS: $t_R$ (min)=1.81; [M+H]$^+$: m/z 643; [M−H]$^-$: m/z 641 (WATERS UPLC-SQD apparatus; Ionization: electrospray in positive mode and/or negative mode (ES+/−); Chromatographic conditions: Column: ACQUITY BEH C18 1.7 µm-2.1×50 mm; Solvents: A: H2O (0.1% formic acid) B: CH$_3$CN (0.1% formic acid); Column temperature: 50° C.; Flow: 0.8 ml/min; Gradient (2.5 min): from 5 to 100% of B in 1.8 min; 2.4 min: 100% of B; 2.45 min: 100% of B; from 100 to 5% of B in 0.05 min; Retention time=$t_R$ (min); referred to herein as "Method C"); $^1$H NMR (400 MHz, DMSO-d$_6$): 0.39 (s, 9H); 1.30 (dd, J=4.0 and 15.2 Hz, 1H); 1.93 (dd, J=6.3 and 15.2 Hz, 1H); 3.49 (dd, J=4.0 and 6.3 Hz, 1H); 4.47 (d, J=11.2 Hz, 1H); 5.04 (d, J=4.2 Hz, 1H); 5.08 (d, J=11.2 Hz, 1H); 6.53 (d, J=8.1 Hz, 1H); 6.66 to 6.76 (m, 3H); 6.96 (m, 2H); 7.10 to 7.26 (m, 9H); 7.34 (t broad, J=7.9 Hz, 1H); 7.62 (t broad, J=7.9 Hz, 1H); 10.71 (s broad, 1H).

(2'S,3R,4'R,5'S)-6-chloro-4'-(3-chloro-2-fluorophenyl)-1'-((1S,2R)-2-hydroxy-1,2-diphenylethyl)-N-((trans)-4-hydroxycyclohexyl)-2'-neopentyl-2-oxospiro[indoline-3,3' pyrrolidine]-5'-carboxamide To a mixture of 112 mg (0.97 mmol) of trans-4-aminocyclohexanol in 2 mL of tetrahydrofuran under argon, was added 0.57 g (0.89 mmol) of (3R,3'R,4'S,6'S,8'R,8a'S)-6-chloro-8'-(3-chloro-2-fluorophenyl)-6'-neopentyl-3',4'-diphenyl 3',4',8',8a'-tetrahydrospiro[indoline-3,7'-pyrrolo[2,1-c][1,4]oxazine]-1',2(6'H)-dione in 8 mL of tetrahydrofuran. The resulting mixture was heated at 60° C. for 17 hours, upon which 136 µL (0.97 mmol) of triethylamine was added and heating was pursued.

After 24 hours, 13.6 mg (0.12 mmol) of trans-4-aminocyclohexanol and 2.5 mL of tetrahydrofuran were added. After 41 hours, the reaction mixture was cooled down to room temperature and concentrated to dryness under reduced pressure. The residue was diluted with a mixture of 20 mL of ethyl acetate and 6 mL of water and decanted. The aqueous phase was extracted with 6 mL of ethyl acetate. The combined organic phases were dried over magnesium sulfate and concentrated to dryness under reduced pressure. The residue was purified by flash chromatography on a 70 g silica cartridge (15-40 µm silica gel; eluting solvent: cyclohexane/ethyl acetate 50/50 v/v followed by 40/60 v/v; flow: 50 mL/min) 0.55 g of (2'S,3R,4'R,5'S)-6-chloro-4'-(3-chloro-2-fluorophenyl)-1'-((1S,2R)-2-hydroxy-1,2-diphenylethyl)-N-((trans)-4-hydroxycyclohexyl)-2'-neopentyl-2-oxospiro[indoline-3,3' pyrrolidine]-5'-carboxamide was obtained as a white meringue. mp: 190° C. (Kofler); LC-MS: $t_R$ (min)= 1.56; [M+H]$^+$: m/z 758; [M−H]$^-$: m/z 756 (method C); $^1$H NMR (400 MHz, DMSO-d$_6$): 0.51 (s, 9H); 0.62 (d, J=15.2 Hz, 1H); 0.81 (m, 1H); 1.02 to 1.35 (m, 4H); 1.60 (m, 1H); 1.79 (m, 2H); 2.36 (dd, J=9.3 and 15.2 Hz, 1H); 3.24 to 3.34 (m partially hidden, 2H); 3.48 (m, 1H); 3.69 (d, J=10.9 Hz, 1H); 3.94 (d, J=7.9 Hz, 1H); 4.13 (d, J=10.9 Hz, 1H); 4.45 (d, J=4.4 Hz, 1H); 5.05 (dd, J=4.4 and 7.9 Hz, 1H); 5.14 (d, J=4.4 Hz, 1H); 6.18 (d, J=8.2 Hz, 1H); 6.50 (d, J=2.0 Hz, 1H); 6.59

(t broad, J=7.9 Hz, 1H); 6.67 (dd, J=2.0 and 8.2 Hz, 1H); 6.73 (t broad, J=7.9 Hz, 1H); 7.20 (t, J=7.8 Hz, 1H); 7.24 (t broad, J=7.9 Hz, 1H); 7.28 (t, J=7.8 Hz, 2H); 7.35 (m, 2H); 7.39 to 7.45 (m, 3H); 7.49 (d, J=8.2 Hz, 1H); 7.57 (d, J=7.8 Hz, 2H); 10.32 (s broad, 1H).

(2'S,3R,4'R,5'S)-6-chloro-4'-(3-chloro-2-fluorophenyl)-N-((trans)-4-hydroxy-cyclohexyl)-2'-neopentyl-2-oxospiro[indoline-3,3'-pyrrolidine]-5'-carboxamide A mixture of 542 mg (0.71 mmol) of (2'S,3R,4'R,5'S)-6-chloro-4'-(3-chloro-2-fluorophenyl)-1'-((1S,2R)-2-hydroxy-1,2-diphenylethyl)-N-((trans)-4-hydroxycyclohexyl)-2'-neopentyl-2-oxospiro[indoline-3,3'-pyrrolidine]-5'-carboxamide in 10 mL of ethanol was cooled to 0° C. and 989 mg (1.79 mmol) of ceric ammonium nitrate was added slowly via spatula in 15 min. The reaction mixture was stirred at 0° C. for 1 hour, upon which it was treated with 4 mL of toluene, 2 mL of ethanol, 5 mL of saturated brine and 3 mL of ethyl acetate, and decanted. The organic phase was separated and the aqueous phase was extracted with 2×5 mL of ethyl acetate. The organic phases were combined and washed with 3 mL of 5% sodium carbonate. After decantation, the aqueous phase was diluted with water and reextracted with 10 mL of ethyl acetate. The organic phases were combined and successively washed with 2 mL of 11% sodium disulfite and 2 mL of saturated brine. It was then dried over magnesium sulfate and concentrated to dryness under reduced pressure. 222 mg of the residue was purified by flash chromatography on a 40 g silica cartridge (15 µm silica gel; eluting solvent: dichloromethane/acetone 75/25 v/v followed by 65/35 v/v; flow: 30 mL/min) 0.183 g of an off-white meringue was obtained, taken up twice in diisopropyl oxide and dried at 25° C. under reduced pressure. 157 mg of (2'S,3R,4'R,5'S)-6-chloro-4'-(3-chloro-2-fluorophenyl)-N-((trans)-4-hydroxy-cyclohexyl)-2'-neopentyl-2-oxospiro[indoline-3,3'-pyrrolidine]-5'-carboxamide were obtained as a white amorphous solid. mp: 176° C. (Kofler); LC-MS: $t_R$ (min)=1.13 (91%) and 1.03 (9%); [M+H]$^+$: m/z 562; [M−H]$^−$: m/z 560 (method C); $^1$H NMR (400 MHz, DMSO-d$_6$): 0.76 (s, 9H); 0.85 (dd, J=1.8 and 14.3 Hz, 1
H); 0.97 to 1.28 (m, 4H); 1.38 to 1.50 (m, 2H); 1.67 (m, 1H); 1.80 (m, 2H); 2.56 (t, J=12.1 Hz, 1H); 3.23 to 3.38 (m partially hidden, 2H); 3.45 (m, 1H); 3.93 (d, J=9.6 Hz, 1H); 4.22 (dd, J=9.6 and 12.1 Hz, 1H); 4.46 (d, J=4.4 Hz, 1H); 6.62 (d, J=8.1 Hz, 1H); 6.70 to 6.75 (m, 2H); 7.13 (t broad, J=7.9 Hz, 1H); 7.31 (t broad, J=7.9 Hz, 1H); 7.64 (t broad, J=7.9 Hz, 1H); 7.92 (d, J=7.7 Hz, 1H); 10.51 (s broad, 1H).

(2'R,3 S,4'R,5'S)-6-chloro-4'-(3-chloro-2-fluorophenyl)-N-((trans)-4-hydroxy-cyclohexyl)-2'-neopentyl-2-oxospiro[indoline-3,3'-pyrrolidine]-5'-carboxamide The rest of the crude compound (206 mg) was dissolved and stirred into 10 mL of ethyl acetate, treated with 41 µL (0.07 mmol) of glacial acetic acid and the reaction mixture was heated at 60° C. for 3 hours, upon which it was cooled down to room temperature and stirred for 16 hours. It was then washed with 5 mL of saturated sodium hydrogencarbonate and 3 mL of water. The organic phase was dried over magnesium sulfate and concentrated to dryness under reduced pressure. The residue was purified by flash chromatography on a 30 g silica cartridge (15-40 µm silica gel; eluting solvent: dichloromethane/acetone 75/25 v/v; flow: 20 mL/min) The isolated product was taken up twice in diisopropyl oxide. The solid was filtered and dried at 25° C. under reduced pressure. 106 mg of (2'R,3S,4'R,5'S)-6-chloro-4'-(3-chloro-2-fluorophenyl)-N-((trans)-4-hydroxycyclohexyl)-2'-neopentyl-2-oxospiro[indoline-3,3'pyrrolidine]-5'-carboxamide were obtained as a pinkish amorphous solid. mp: 193° C. (Kofler); LC-MS: $t_R$ (min)=1.03; [M+H]$^+$: m/z 562; [M−H]$^−$: m/z 560 (method C); $^1$H NMR (400 MHz, DMSO-d$_6$): 0.72 (dd, J=1.5 and 14.2 Hz, 1H); 0.80 (s, 9H); 1.08 to 1.30 (m, 5H); 1.68 to 1.91 (m, 4H); 3.28 to 3.49 (m, 3H); 3.58 (m, 1H); 4.29 (d, J=9.0 Hz, 1H); 4.39 (t, J=9.0 Hz, 1H); 4.50 (d, J=4.4 Hz, 1H); 6.68 (d, J=2.0 Hz, 1H); 7.05 (dd, J=2.0 and 8.1 Hz, 1H); 7.12 (t broad, J=7.9 Hz, 1H); 7.34 (t broad, J=7.9 Hz, 1H); 7.48 to 7.57 (m, 2H); 7.72 (d, J=8.1 Hz, 1H); 10.40 (s broad, 1H); α$_D$=+18.4°±/−0.9 (c=1.525 mg/0.5 mL MeOH).

Example 13

Synthesis of (2'S,3'R,4'S,5'R)-1'-acetyl-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (trans-4-hydroxy-cyclohexyl)-amide

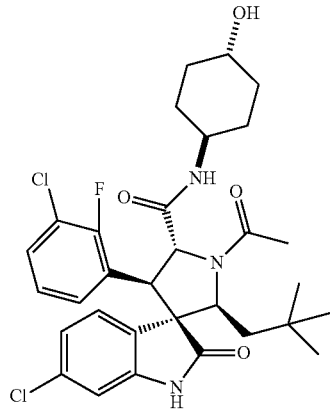 [SMILES: CC(=O)N1[C@@H](CC(C)(C)C)[C@@]2(C(=O)Nc3cc(Cl)ccc32)[C@@H](c2cccc(Cl)c2F)[C@@H]1C(=O)N[C@H]1CC[C@H](O)CC1]

Acetic acid 4-{[(2'S,3'R,4'S,5'R)-1,1'-diacetyl-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-cyclohexyl ester To a solution of 281 mg (0.50 mmol) of (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (trans-4-hydroxy-cyclohexyl)-amide in 5.0 mL of pyridine under argon, was added 178 µL (2.50 mmol) of acetyl chloride. The resulting mixture was stirred at room temperature for 4 days, upon which it was poured into a mixture of water and ethyl acetate. The organic phase was separated and the aqueous phase was extracted twice with ethyl acetate. The combined organic extracts were washed with brine, dried with magnesium sulfate and then concentrated to dryness under reduced pressure. The residue was purified by flash chromatography on a 50 g silica cartridge (15-40 µm silica gel; eluting solvent: dichloromethane/methanol 98/2 v/v; flow: 40 mL/min) followed by a second purification by flash chromatography on a 30 g silica cartridge (15-40 µm silica gel; eluting solvent: dichloromethane/methanol 98/2 v/v; flow: 20 mL/min) 123 mg of acetic acid 4-{[(2'S,3R,4'S,5'R)-1,1'-diacetyl-6-chloro-4'-(3-chloro-2-fluoro-phenyl)-2'-(2,2-dimethyl-propyl)-2-oxo-1,2-dihydrospiro [indole-3,3'-pyrrolidin]e-5'-carbonyl]-amino}-cyclohexyl ester were obtained as a white powder. LC-MS: $t_R$ (min)=1.19; [M+H]$^+$: m/z 688; [M−H]$^−$: m/z 686 (method A).

(2'S,3'R,4'S,5'R)-1'-Acetyl-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (trans-4-hydroxy-cyclohexyl)-amide To a solution of 117 mg (0.17 mmol) of acetic acid 4-{[(2'S,3'R,4'S,5'R)-1,1'-diacetyl-6-chloro-4'-(3-chloro-2-fluoro-phenyl)-2'-(2,2-dimethyl-propyl)-2-oxo-1,2-dihydro-spiro[indole-3,3'-pyrrolidine]-5'-carbonyl]-amino}-cyclohexyl ester in 10.0 mL of methanol under argon, was added 10 mL (81 mmol) of a saturated potassium carbonate solution. The resulting mixture was stirred at room temperature for 1 hour, upon which the methanol was evaporated under reduced pressure. The remaining aqueous phase was extracted 3 times with 20 mL of dichloromethane. The combined organic extracts were washed with 20 mL of brine, dried with magnesium sulfate and then concentrated to dryness under reduced pressure. 92 mg of (2'S,3'R,4'S,5'R)-1'-acetyl-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (trans-4-hydroxy-cyclohexyl)-amide were obtained as a white powder. mp: 220° C. (Kofler); LC-MS: $t_R$ (min)=0.97; [M+H]$^+$: m/z 604; [M−H]$^-$: m/z 602 (method A); $^1$H NMR (60° C., CHLOROFORM-d, 400 MHz): 0.68 (s, 9H); 0.75 to 2.62 (m partially hidden, 14H); 3.51 (m, 1H); 3.65 (m, 1H); 4.28 (m broad, 1H); 4.48 (dd, J=3.4 and 5.9 Hz, 1H); 4.98 (d, J=10.3 Hz, 1H); 6.65 (d, J=1.5 Hz, 1H); 6.99 (t, J=7.8 Hz, 1H); 7.05 to 7.48 (m, 5H).

Example 14

Synthesis of (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (trans-4-hydroxy-cyclohexylmethyl)-amide

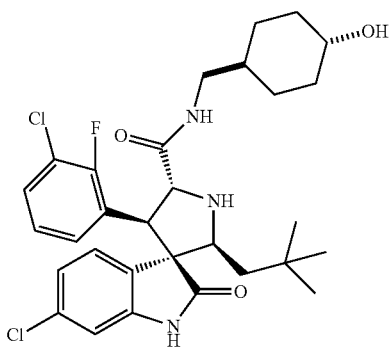 [SMILES: CC(C)(C)C[C@@H]1N[C@@H](C(=O)NC[C@H]2CC[C@H](O)CC2)[C@H](c2cccc(Cl)c2F)[C@]12C(=O)Nc1cc(Cl)ccc12]

(2'R,3'S,4'S,5'R)-6-Chloro-4'-(3-chloro-2-fluoro-phenyl)-2'-(2,2-dimethyl-propyl)-1'-((1R,2S)-2-hydroxy-1,2-diphenyl-ethyl)-2-oxo-1,2-dihydro-spiro[indole-3,3'-pyrrolidine]-5'-carboxylic acid (trans-4-hydroxy-cyclohexylmethyl)-amide To a solution of 0.28 g (1.71 mmol) of 4-aminomethyl-cyclohexanol hydrochloride in 12.0 mL of tetrahydrofuran, was added 0.46 mL (3.26 mmol) of triethylamine. The resulting mixture was stirred at room temperature for 30 minutes and 1 g (1.55 mmol) of:

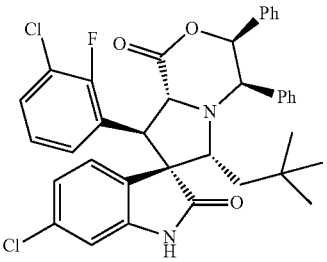 [SMILES: CC(C)(C)C[C@H]1N2[C@H](c3ccccc3)[C@H](c3ccccc3)OC(=O)[C@H]2[C@H](c2cccc(Cl)c2F)[C@@]12C(=O)Nc1cc(Cl)ccc12]

was added progressively via spatula, followed by 2 mL of tetrahydrofuran. The reaction mixture was heated at reflux temperature for 7 hours and then stirred at room temperature for 2.5 days, upon which it was diluted with 10 mL of water and 15 mL of ethyl acetate. The organic phase was separated and the aqueous phase was extracted with ethyl acetate. The combined organic extracts were dried with magnesium sulfate and then concentrated to dryness under reduced pressure. The residue was purified by flash chromatography on a 70 g silica cartridge (15-40 µm silica gel; eluting solvent: dichloromethane, then dichloromethane/methanol 98/2 v/v; flow: 50 mL/min). 0.40 g of (2'R,3'S,4'S,5'R)-6-chloro-4'-(3-chloro-2-fluoro-phenyl)-2'-(2,2-dimethyl-propyl)-1'-((1R,2S)-2-hydroxy-1,2-diphenyl-ethyl)-2-oxo-1,2-dihydro-spiro[indole-3,3'-pyrrolidine]-5'-carboxylic acid (trans-4-hydroxy-cyclohexylmethyl)-amide were obtained as a white solid. LC-MS: $t_R$ (min)=1.16; [M+H]$^+$: m/z 772; [M−H]$^-$: m/z 770 (method A); $^1$H NMR(CHLOROFORM-d, 400 MHz): 0.74 (s large, 9H); 0.83 (m, 2H); 1.13 (m, 2H); 1.20 (m, 1H); 1.25 (d, J=15.6 Hz, 1H); 1.35 (d, J=4.9 Hz, 1H); 1.42 (m, 1H); 1.55 (m partially hidden, 1H); 1.84 to 2.00 (m, 2H); 2.29 (d, J=2.9 Hz, 1H); 2.67 (dd, J=9.3 and 15.6 Hz, 1H); 2.86 (m, 1H); 3.38 (m, 1H); 3.48 (m, 2H); 4.11 (m, 2H); 4.36 (d, J=8.3 Hz, 1H); 5.20 (dd, J=2.9 and 8.3 Hz, 1H); 5.64 (d, J=8.1 Hz, 1H); 6.28 (m, 1H); 6.44 (t, J=7.8 Hz, 1H); 6.53 (d, J=2.2 Hz, 1H); 6.62 (dd, J=2.2 and 8.1 Hz, 1H); 6.67 (t, J=7.8 Hz, 1H); 7.09 (t, J=7.8 Hz, 1H); 7.25 (s, 1H); 7.30 to 7.45 (m, 5H); 7.54 to 7.67 (m, 5H).

(2'S,3'R,4'S,5'R)-6-Chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (trans-4-hydroxy-cyclohexylmethyl)-amide In a three-neck 50 mL flask were successively introduced 0.70 g (0.91 mmol) of (2'R,3'S,4'S,5'R)-6-chloro-4'-(3-chloro-2-fluoro-phenyl)-2'-(2,2-dimethyl-propyl)-1'-((1R,2S)-2-hydroxy-1,2-diphenyl-ethyl)-2-oxo-1,2-dihydro-spiro[indole-3,3'-pyrrolidine]-5'-carboxylic acid (trans-4-hydroxy-cyclohexylmethyl)-amide, 7.0 mL of acetonitrile, 3.5 mL of distilled water and 3.5 mL of acetone. The resulting mixture was stirred and cooled to 0° C. and 0.99 g (1.81 mmol) of cerium ammonium nitrate was added in small portions. The reaction mixture was stirred at 0° C. for 20 minutes, upon which 89 mg (1.06 mmol) of sodium hydrogencarbonate were added and stirring was maintained for 5 minutes. The mixture was diluted with 60 mL of ethyl acetate and decanted. The organic phase was separated and the aqueous phase was extracted twice with 10 mL of ethyl acetate. The combined organic extracts were washed with 20 mL of water, dried with magnesium sulfate and then concentrated to dryness under reduced pressure. The residue was purified by flash chromatography on a 30 g silica cartridge (15-40 µm silica gel; eluting solvent: dichloromethane; flow: 30 mL/min) followed by a second purification by flash chromatography on a 15 g silica cartridge (15-40 μm silica gel; eluting solvent: dichloromethane/methanol/28% ammonia 97/2/1 v/v/v; flow: 30 mL/min) 87 mg of (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (trans-4-hydroxy-cyclohexylmethyl)-amide were obtained as a white solid. mp: 192° C. (Kofler); LC-MS: $t_R$ (min)=0.84; [M+H]$^+$: m/z 576; [M–H]$^-$: m/z 574 (method A); $^1$H NMR (CHLOROFORM-d, 400 MHz): mixture of isomers: 0.90 (s, 9H); 0.99 to 2.09 (m partially hidden, 11H); 3.05 to 3.27 (m, 2H); 3.59 (m, 2H); 4.39 (d, J=8.8 Hz, 1H); 4.59 (m, 1H); 6.76 (s large, 1H); 6.99 (t, J=7.8 Hz, 1H); 7.06 to 7.56 (m, 6H); 7.82 (t broad, J=6.1 Hz, 1H).

Example 15

Synthesis of (2'S,3'R,4'S,5'R)-6-Chloro-4'-(3-chloro-2-fluoro-phenyl)-2'-(2,2-dimethyl-propyl)-1'-methyl-2-oxo-1,2-dihydro-spiro[indole-3,3'-pyrrolidine]-5'-carboxylic acid (trans-4-hydroxy-cyclohexyl)-amide

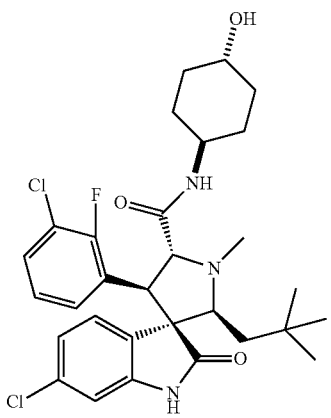 [SMILES: CN1[C@@H](CC(C)(C)C)[C@@]2(C(=O)Nc3cc(Cl)ccc32)[C@@H](c2cccc(Cl)c2F)[C@@H]1C(=O)N[C@H]1CC[C@H](O)CC1]

To a suspension of 0.50 g (0.89 mmol) of (2'S,3'R,4'S,5'R)-6-chloro-4'-(3-chloro-2-fluoro-phenyl)-2'-(2,2-dimethyl-propyl)-2-oxo-1,2-dihydro-spiro[indole-3,3'-pyrrolidine]-5'-carboxylic acid (trans-4-hydroxy-cyclohexyl)-amide in 18.0 mL of acetonitrile under argon, were added 0.89 mL (0.97 mmol) of a 36.5% solution of formaldehyde in water, followed by 65 mg (0.98 mmol) of sodium cyanoborohydride. The resulting solution was stirred at room temperature for 2 hours, upon which it was poured into 50 mL of ethyl acetate. The aqueous phase was separated and the organic phase was washed with a saturated solution of sodium hydrogencarbonate. The latter aqueous phase was reextracted with ethyl acetate. The combined organic extracts were washed with brine, dried with magnesium sulfate and then concentrated to dryness under reduced pressure. The residue (0.52 g) was purified by chiral HPLC chromatography on a Kromasil C18 column (1100 g batch 4680, 10 μm, 7.65×35 cm), eluting solvent: acetonitrile/water 40/60 v/v+0.1% trifluoroacetic acid; flow: 250 mL/min. The collected solution was treated with sodium hydrogencarbonate up to pH 8 and then extracted 3 times with 200 mL of ethyl acetate. The combined organic extracts were washed twice with 100 mL of water, dried with magnesium sulfate and then concentrated to dryness under reduced pressure. The residue was then dried in a dessicator under reduced pressure for 16 hours. 0.17 g of (2'S,3'R,4'S,5'R)-6-chloro-4'-(3-chloro-2-fluoro-phenyl)-2'-(2,2-dimethyl-propyl)-1'-methyl-2-oxo-1,2-dihydro-spiro[indole-3,3'-pyrrolidine]-5'-carboxylic acid (4-hydroxy-cyclohexyl)-amide was obtained as a white solid. mp: 188° C. (Kofler); LC-MS:
$t_R$ (min)=0.85-0.97 (mixture of isomers); [M+H]$^+$: m/z 576; [M–H]$^-$: m/z 574 (method A); $^1$H NMR (400 MHz, CHLOROFORM-d): 0.73 (d, J=15.6 Hz, 1H); 0.79 (s, 9H); 1.15 to 1.48 (m, 4H); 1.85 to 2.12 (m, 5H); 2.75 (s, 3H); 3.60 to 3.77 (m, 3H); 4.17 (d, J=9.8 Hz, 1H); 4.33 (d broad, J=9.8 Hz, 1H); 6.69 (d, J=1.5 Hz, 1H); 6.99 (t, J=7.8 Hz, 1H); 7.05 (dd, J=1.5 and 8.3 Hz, 1H); 7.10 to 7.25 (m, 3H); 7.37 (m broad, 1H); 7.56 (t, J=7.8 Hz, 1H).

Similar methodology was used to prepare C29701 and C30201.

Example 16

Isomerization Studies

General Information

Experiments involving moisture and/or air sensitive components were performed in oven-dried glassware under an atmosphere of nitrogen. Commercial solvents and reagents were used without further purification with the following exception: THF was freshly distilled from sodium wire.

Flash chromatography was performed using silica gel (type H) from TM chemicals, Inc. Columns were typically packed as slurry and equilibrated with hexane prior to use. Analytical thin layer chromatography (TLC) was performed using Merck 60 F254 precoated silica gel plate (0.2 mm thickness). Subjected to elution, plates were visualized using UV radiation. Further visualization was possible by staining with basic solution of potassium permanganate or acidic solution of phosphomolybdic acid, followed by heating with heating gun.

Compounds were purified by HPLC using a Waters Sunfire C18 reverse phase semipreparative HPLC column (19 mm×150 mm) using solvent A (water, 0.1% of TFA) and solvent B (CH$_3$CN, 0.1% of TFA or MeOH, 0.1% of TFA) as eluents with a flow rate of 10 mL/min on a Waters Delta 600 instrument. Analytical reverse phase HPLC was conducted using Waters 2795 Separation module.

Proton nuclear magnetic resonance ($^1$H NMR) and carbon nuclear magnetic resonance ($^{13}$C NMR) spectroscopy were performed on a Bruker Advance 300 NMR spectrometer. Chemical shifts of $^1$H NMR spectra are reported as δ in units of parts per million (ppm) downfield from SiMe$_4$ (δ 0.0) or relative to the signal of chloroform-d (δ=7.26, singlet), methanol-d$_4$ (δ=3.31, quintuplet) and DMSO-d$_6$ (δ=2.50, quintuplet). Multiplicities were given as: s (singlet); d (doublet); t (triplet); q (quartet); dd (doublet of doublets); ddd (doublet of doublets of doublets); dt (doublet of triplets); m (multiplets) and etc. The number of protons for a given resonance is indicated by nH. Coupling constants are reported as J values in Hz. Carbon nuclear magnetic resonance spectra ($^{13}$C NMR) are reported as δ in units of parts per million (ppm) downfield from SiMe$_4$ (δ0.0) or relative to the signal of chloroform-d (δ=77.23, triplet), MeOH-d$_4$ (δ=49.20, septuplet) and DMSO-d$_6$ (δ=39.52, septuplet).

Low resolution ESI mass spectrum analysis was performed on Thermo-Scientific LCQ Fleet mass spectrometer.

Compounds 1-10 were prepared according to Scheme 10 and Table 4 using methods previous described (See, e.g., Ding, K. et al., *J. Am. Chem. Soc.* 127:10130-10131 (2005); Ding, K. et al., *J. Med. Chem.* 49:3432-3435 (2006); Yu, S. et al., *J. Med. Chem.* 52:7970-7973 (2009); Shangary, S., *Proc. Natl. Acad. Sci.* 105:3933-3938 (2008); U.S. Pat. No. 7,759, 383) as a mixture of isomers. Isomer A was identified as the predominant isomer following CAN oxidation in most cases. Applicants have found that dissolving the mixture of isomers obtained from CAN oxidation in a solvent or a mixture of solvents and allowing the reaction mixture to mature for a period of time under various conditions provides a mixture of isomers having Isomer B as the predominant isomer. In some cases, Isomers C and D were isolated in pure or substantially pure form. Likewise, compounds 11 and 12 were prepared according to Scheme 11 and Table 5.

The procedure for isomerization used in this study was as follows: approximately 30 mg product obtained from CAN oxidation (pre-purified by flash column chromatography) was placed in a round bottom flask equipped with magnetic stirring bar. Acetonitrile (2.4 mL) was added to dissolve the product. To the acetonitrile solution was added water (2.0 mL) and 0.5 mL NaHCO$_3$ (saturated) solution to give a pH of approximately 8. The reaction mixture was allowed to stir at room temperature for approximately 3 days. The percentage of isomers was determined using analytical HPLC. Further purification was performed on semi-preparative or preparative reverse phase HPLC using MeOH (0.1% TFA) and water (0.1% TFA) as mobile phase.

Isomerization of Isomer A to Isomer B can also be carried out under acidic conditions, e.g., MeCN—H$_2$O, CF$_3$CO$_2$H (pH<1), room temperature, 3 days; ethyl acetate, acetic acid, 60° C., 3 h, or neutral conditions e.g., MeOH or MeOH—H$_2$O.

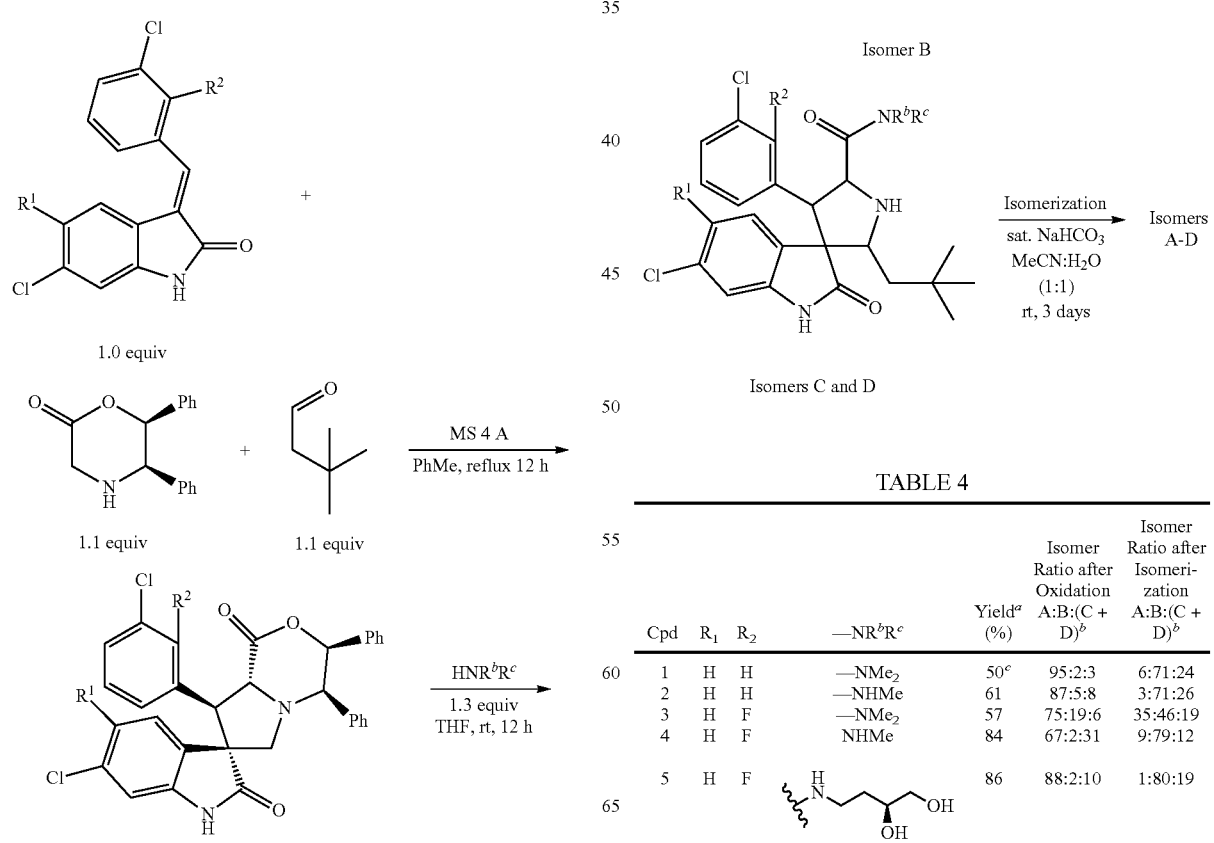

TABLE 4

| Cpd | R$_1$ | R$_2$ | —NR$^b$R$^c$ | Yield$^a$ (%) | Isomer Ratio after Oxidation A:B:(C + D)$^b$ | Isomer Ratio after Isomerization A:B:(C + D)$^b$ |
|---|---|---|---|---|---|---|
| 1 | H | H | —NMe$_2$ | 50$^c$ | 95:2:3 | 6:71:24 |
| 2 | H | H | —NHMe | 61 | 87:5:8 | 3:71:26 |
| 3 | H | F | —NMe$_2$ | 57 | 75:19:6 | 35:46:19 |
| 4 | H | F | NHMe | 84 | 67:2:31 | 9:79:12 |
| 5 | H | F | ⸺N(H)CH$_2$CH(OH)CH$_2$OH | 86 | 88:2:10 | 1:80:19 |

TABLE 4-continued

| Cpd | R₁ | R₂ | —NR$^b$R$^c$ | Yield$^a$ (%) | Isomer Ratio after Oxidation A:B:(C + D)$^b$ | Isomer Ratio after Isomerization A:B:(C + D)$^b$ |
|---|---|---|---|---|---|---|
| 6 | H | F | 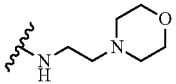 [SMILES: *NCCN1CCOCC1] | 79 | 89:10:1 | 12:61:27 |
| 7 | H | F | —NH₂ | 56 | 0:44:56 | 0:96:4 |
| 8 | F | H | —NMe₂ | 60 | 56:25:19 | 10:71:19$^d$ 2:88:8 |
| 9 | F | H | —NHMe | 87 | 19:52:27 | 1:74:25 |
| 10$^e$ | F | H | 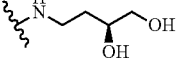 | 81 | 30:32:38 | 3:58:37 |

$^a$Yield after oxidation;
$^b$Ratio was determined by HPLC analysis;
$^c$Yield after HPLC separation;
$^d$Ratio determined by HPLC analysis after allowing oxidation product to stand in MeOH for two hours;
$^e$Compound 10 Isomer A and Compound 10 Isomer B are referred to as MI-219 and MI-21901, respectively, in Table 2A.

Scheme 11

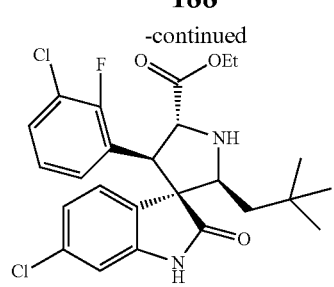

Compound 11 Isomer B

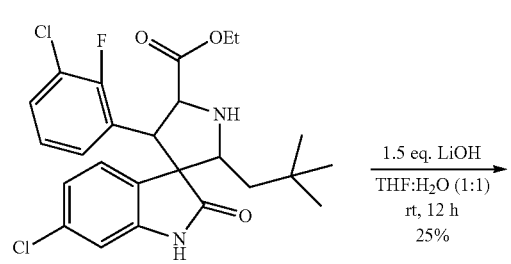

Compound 11 Isomers C and D

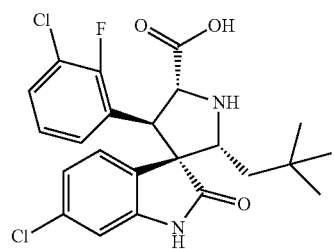

Compound 12 Isomer A

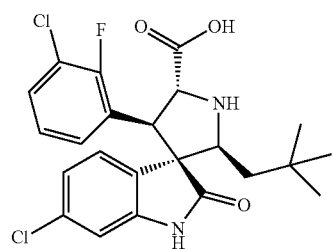

Compound 12 Isomer B

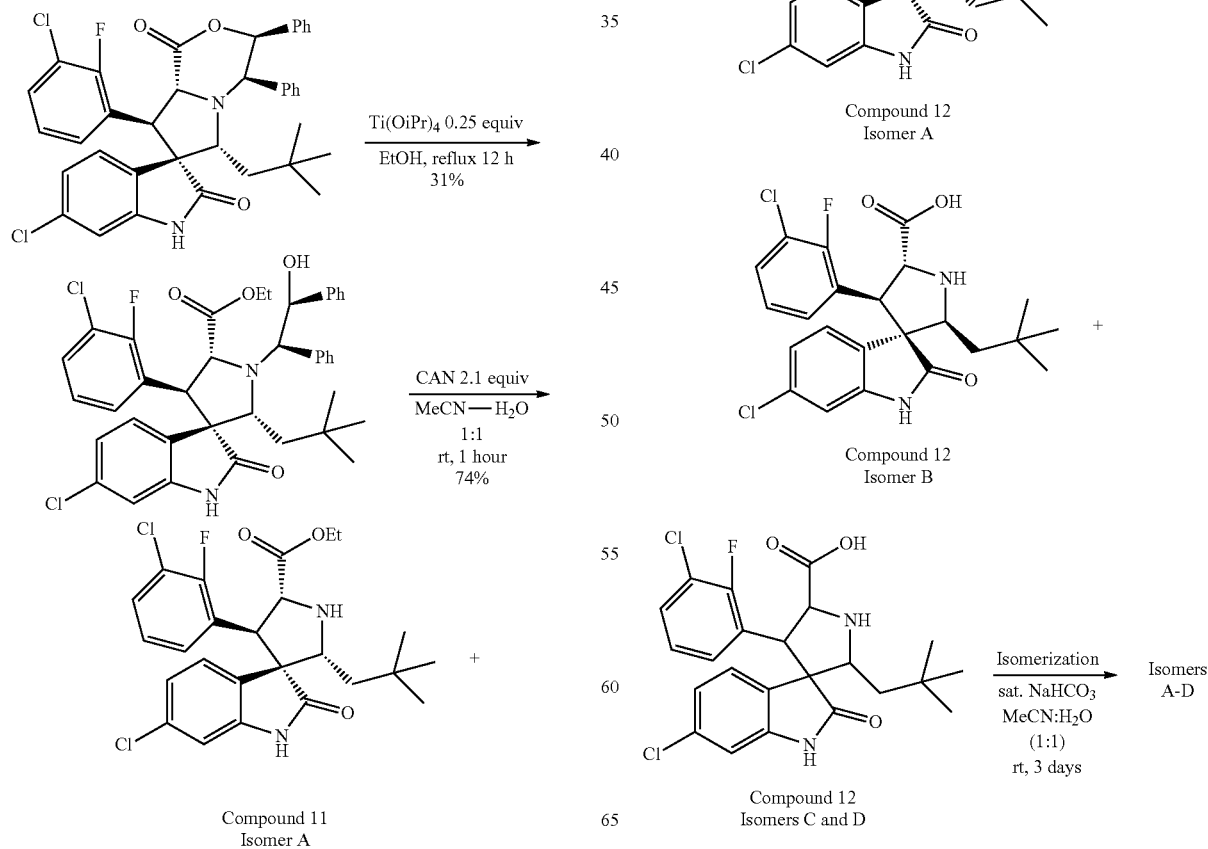

Compound 12 Isomers C and D

TABLE 5

| Cpd | Yield (%) | Isomer Ratio after Oxidation a:b:(c + d)[b] | Isomer Ratio after Equilibration a:b:(c + d)[b] |
|---|---|---|---|
| 11 | 74[a] | 89:6:3 | 44:50:6 |
| 12 | 25[c] | — | 41:34:25[d] |

[a]Yield after oxidation;
[b]Ratio was determined by HPLC analysis;
[c]Hydrolysis yield;
[d]Starting with pure Compound 12-Isomer A.

Analytical Data

Compound 1—Isomer A (TFA salt): ESI: Calculated for $C_{25}H_{30}{}^{35}Cl_2N_3O_2$ [M+H]$^+$=474.17. Found: 474.50.

Compound 1—Isomer B (TFA salt): ESI: Calculated for $C_{25}H_{30}{}^{35}Cl_2N_3O_2$ [M+H]$^+$=474.17. Found: 474.68.

Compound 1—Isomer D (TFA salt): $^1$H NMR (300 MHz, CD$_3$OD): 7.72 (d, J=8.08 Hz, 1H), 7.28-7.22 (m, 1H), 7.20-7.12 (m, 2H), 7.12-7.08 (m, 1H), 7.04 (d, J=7.65 Hz, 1H), 6.81 (d, J=1.79 Hz, 1H), 5.54 (d, J=10.87 Hz, 1H), 4.37 (dd, J=6.54, 4.52 Hz, 1H), 4.15 (d, J=10.85 Hz, 1H), 2.98 (s, 3H), 2.81 (s, 3H), 1.70 (dd, J=15.24, 6.67 Hz, 1H), 1.20 (dd, J=15.26, 4.43 Hz, 1H), 0.91 (s, 9H); ESI: Calculated for $C_{25}H_{30}{}^{35}Cl_2N_3O_2$ [M+H]$^+$=474.17. Found: 474.50.

Compound 2—Isomer A (TFA salt): $^1$H NMR (300 MHz, CD$_3$OD): 7.28-7.16 (m, 3H), 7.16-7.06 (m, 1H), 6.92-6.82 (m, 2H), 6.80-6.76 (m, 1H), 4.92 (d, J=10.23, 4.20-4.10 (m, 2H), 2.73 (s, 3H), 1.99 (s, J=15.32, 6.75 Hz, 1H), 1.47 (dd, J=15.54, 3.49 Hz, 1H), 0.80 (s, 9H); ESI: Calculated for $C_{24}H_{28}{}^{35}Cl_2N_3O_2$ [M+H]$^+$=460.16. Found: 460.52.

Compound 2—Isomer B (TFA salt): $^1$H NMR (300 MHz, CD$_3$OD): 7.63 (d, J=8.06 Hz, 1H), 7.30-7.14 (m, 4H), 7.12-7.00 (m, 1H), 6.82-6.76 (m, 1H), 5.29 (d, J=11.24 Hz, 1H), 4.47 (d, J=6.68 Hz, 1H), 4.16 (d, J=11.22 Hz, 1H), 2.73 (s, 3H), 1.92 (dd, J=15.40, 8.39 Hz, 1H), 1.17 (d, J=16.85 Hz, 1H), 0.90 (s, 9H); $^{13}$C (75 MHz, CD$_3$OD): 177.78, 168.54, 145.38, 137.07, 135.77, 134.60, 131.40, 130.29, 129.48, 128.29, 126.32, 124.24, 124.16, 112.18, 65.11, 64.18, 62.85, 56.95, 43.42, 30.97, 29.66, 26.98; ESI: Calculated for $C_{24}H_{28}{}^{35}Cl_2N_3O_2$ [M+H]$^+$=460.16. Found: 460.48.

Compound 2—Isomer D (TFA salt): $^1$H NMR (300 MHz, CD$_3$OD): 7.57 (d, J=8.12 Hz, 1H), 7.24-7.08 (m, 3H), 7.04-6.98 (m, 1H), 6.92 (d, J=7.62 Hz, 1H), 6.76 (d, J=1.78 Hz, 1H), 5.02 (d, J=12.47 Hz, 1H), 4.42 (dd, J=7.06, 4.40 Hz, 1H), 4.13 (d, J=12.47 Hz, 1H), 2.70 (s, 3H), 1.74 (dd, J=15.35, 7.14 Hz, 1H), 1.17 (dd, J=15.37, 4.38 Hz, 1H), 0.88 (s, 9H); $^{13}$C (75 MHz, CD$_3$OD): 176.72, 167.32, 144.88, 137.13, 135.62, 133.98, 131.17, 130.24, 129.73, 128.41, 127.88, 123.91, 123.53, 112.57, 65.42, 64.33, 62.97, 59.03, 44.86, 31.01, 29.57, 27.03; ESI: Calculated for $C_{24}H_{28}{}^{35}Cl_2N_3O_2$ [M+H]$^+$=460.16. Found: 460.50.

Compound 3—Isomer A (TFA salt): $^1$H NMR (300 MHz, CD$_3$OD): 7.80-7.70 (m, 1H), 7.50-7.40 (m, 1H), 7.32-7.22 (m, 1H), 6.92-6.88 (m, 1H), 6.74 (dd, J=8.15, 1.75 Hz, 1H), 6.48 (d, J=8.11 Hz, 1H), 5.58 (d, J=7.94 Hz, 1H), 4.38 (d, J=7.94 Hz, 1H), 4.26 (d, J=7.55 Hz, 1H), 2.99 (s, 3H), 2.84 (s, 3H), 2.06 (dd, J=15.42, 7.72 Hz, 1H), 1.13 (d, J=15.37 Hz, 1H), 0.89 (s, 9H); $^{13}$C (75 MHz, CD$_3$OD): 180.07, 166.93, 157.51 (d, $J_{C-F}$=243.98 Hz), 145.59, 137.11, 132.54, 128.77, 127.66, 126.74 (d, $J_{C-F}$=4.55 Hz), 125.89 (d, $J_{C-F}$=13.40 Hz), 123.68, 122.85 (d, $J_{C-F}$=10.19 Hz), 123.10 (d, $J_{C-F}$=18.37 Hz), 112.07, 63.03, 62.05, 61.76, 42.09, 37.70, 36.89, 30.77, 29.34; ESI: Calculated for $C_{25}H_{29}{}^{35}Cl_2FN_3O_2$ [M+H]$^+$=492.16. Found: 492.44.

Compound 3—Isomer B (TFA salt): $^1$H NMR (300 MHz, CD$_3$OD): 7.68-7.57 (m, 2H), 7.45-7.35 (m, 1H), 7.22-7.10 (m, 2H), 6.84-6.77 (m 1H), 5.68 (d, J=10.24 Hz, 1H), 4.64 (d, J=10.24 Hz, 1H), 4.48 (dd, J=8.20, 1.70 Hz, 1H), 2.98 (s, 3H), 2.80 (s, 3H), 1.89 (dd, J=15.48, 8.26 Hz, 1H), 1.14 (dd, J=15.48, 1.67 Hz, 1H), 0.89 (s, 9H); $^{13}$C (75 MHz, CD$_3$OD): 177.96, 168.37, 152.99 (d, $J_{C-F}$=253.32 Hz), 145.26, 137.39, 132.82, 128.82, 126.95, 126.70 (d, $J_{C-F}$=4.79 Hz), 124.28, 122.09 (d, $J_{C-F}$=13.13 Hz), 118.90, 115.11, 112.24, 64.69, 59.97, 42.64, 37.96, 37.03, 31.03, 29.62; ESI: Calculated for $C_{25}H_{29}{}^{35}Cl_2FN_3O_2$ [M+H]$^+$=492.16. Found: 492.46.

Compound 3—Isomer C (TFA salt): $^1$H NMR (300 MHz, CD$_3$OD) (TFA salt): 7.63 (d, J=8.13 Hz, 1H), 7.52-7.38 (m, 2H), 7.24-7.12 (m, 2H), 6.83 (d, J=1.80 Hz, 1H), 5.47 (d, J=11.16 Hz, 1H), 4.42 (d, J=11.31 Hz, 1H), 4.35 (t, J=5.66 Hz, 1H), 2.95 (s, 3H), 2.93 (s, 3H), 1.91 (dd, J=15.39, 5.80 Hz, 1H), 1.71 (dd, J=15.24, 5.43 Hz, 1H), 0.84 (s, 9H); ESI: Calculated for $C_{25}H_{29}{}^{35}Cl_2FN_3O_2$ [M+H]$^+$=492.16. Found: 494.20.

Compound 3—Isomer D (TFA salt): $^1$H NMR (300 MHz, CD$_3$OD) (TFA salt): 7.60 (d, J=8.07 Hz, 1H), 7.40-7.30 (m, 1H), 7.22-7.12 (m, 1H), 7.07 (dd, J=8.16, 1.87 Hz, 1H), 7.04-6.95 (m, 1H), 6.80 (d, J=1.87 Hz, 1H), 5.58 (d, J=9.80 Hz, 1H), 4.51 (d, J=9.84 Hz, 1H), 4.43 (dd, J=6.69, 4.15 Hz, 1H), 2.99 (s, 3H), 2.80 (s, 3H), 1.68 (dd, J=15.41, 6.81 Hz, 1H), 1.42 (dd, J=15.41, 4.26 Hz, 1H), 0.90 (s, 9H); ESI: Calculated for $C_{25}H_{29}{}^{35}Cl_2FN_3O_2$ [M+H]$^+$=492.16. Found: 492.28.

Compound 4—Isomer A (TFA salt): $^1$H NMR (300 MHz, CD$_3$OD): 7.66-7.54 (m, 1H), 7.38-7.28 (m, 1H), 7.22-7.10 (m, 1H), 6.87 (s, 1H), 6.82-6.72 (m, 2H), 5.21 (d, J=10.00 Hz, 1H), 4.50 (d, J=9.93 Hz, 1H), 4.30-4.24 (m, 1H), 2.75 (s, 3H), 2.07 (dd, J=15.35, 7.35 Hz, 1H), 1.8 (d, J=14.57 Hz, 1H), 0.80 (s, 9H); $^{13}$C (75 MHz, CD$_3$OD): 180.31, 167.24, 157.81 (d, $J_{C-F}$=247.78 Hz), 145.44, 136.94, 132.11, 128.66, 127.94, 126.47 (d, $J_{C-F}$=4.45 Hz), 125.29, 125.01 (d, $J_{C-F}$=13.96 Hz), 123.37, 122.64 (d, $J_{C-F}$=18.03 Hz), 122.04, 64.35, 63.69, 61.74, 49.51, 42.34, 30.92, 29.55, 27.10; ESI: Calculated for $C_{24}H_{27}{}^{35}Cl_2FN_3O_2$ [M+H]$^+$=478.15. Found: 478.92.

Compound 4—Isomer B (TFA salt): $^1$H NMR (300 MHz, CD$_3$OD): 7.65-7.55 (m, 2H), 7.40-7.34 (m, 1H), 7.20-7.10 (m, 2H), 6.84-6.80 (m, 1H), 5.26 (d, J=11.15 Hz, 1H), 4.64 (d, J=11.19 Hz, 1H), 4.45 (d, J=7.86 Hz, 1H), 2.74 (s, 3H), 1.87 (dd, J=15.19, 8.58 Hz, 1H), 1.11 (d, J=15.21 Hz, 1H), 0.90 (s, 9H); $^{13}$C (75 MHz, CD$_3$OD): 177.75, 168.20, 159.53 (d, $J_{C-F}$=248.25 Hz), 145.22, 137.24, 132.59, 128.58, 126.63 (d, $J_{C-F}$=5.25 Hz), 124.16, 123.43, 126.66, 122.59 (d, $J_{C-F}$=4.05 Hz), 121.54 (d, $J_{C-F}$=12.75 Hz), 112.13, 64.49, 64.40, 62.73, 55.34, 43.33, 31.01, 29.58, 27.06; ESI: Calculated for $C_{24}H_{27}{}^{35}Cl_2FN_3O_2$ [M+H]$^+$=478.15. Found: 478.25.

Compound 4—Isomer C (TFA salt): $^1$H NMR (300 MHz, CD$_3$OD): 7.62 (d, J=8.17 Hz, 1H), 7.46-7.36 (m, 2H), 7.22 (dd, J=8.13, 1.89 Hz, 1H), 7.15 (t, J=8.08 Hz, 1H), 6.80 (d, J=1.85 Hz, 1H), 4.84 (d, J=12.32 Hz, 1H), 4.35 (d, J=12.32 Hz, 1H), 4.24 (t, J=5.62 Hz, 1H), 2.67 (s, 3H), 1.87 (dd, J=5.44, 2.53 Hz, 2H), 0.77 (s, 9H); ESI: Calculated for $C_{24}H_{27}{}^{35}Cl_2FN_3O_2$ [M+H]$^+$=478.15. Found: 478.52.

Compound 4—Isomer D (TFA salt): $^1$H NMR (300 MHz, CD$_3$OD): 7.53 (d, J=8.11 Hz, 1H), 7.36-7.26 (m, 1H), 7.11 (dd, J=8.08, 1.88 Hz, 1H), 6.98-6.90 (m, 2H), 6.77 (d, J=1.85 Hz, 1H), 5.03 (d, J=11.95 Hz, 1H), 4.51 (d, J=11.87 Hz, 1H), 4.50-4.42 (m, 1H), 2.72 (s, 3H), 1.72 (d, J=15.36, 7.30 Hz, 1H), 1.16 (dd, J=15.37, 4.09 Hz, 1H), 0.89 (s, 9H); ESI: Calculated for $C_{24}H_{27}{}^{35}Cl_2FN_3O_2$ [M+H]$^+$=478.15. Found: 478.38.

Compound 5—Isomer A (TFA salt): $^1$H NMR (300 MHz, CD$_3$OD): 7.63-7.53 (m, 1H), 7.40-7.30 (m, 1H), 7.23-7.13

(m, 1H), 6.87 (d, J=1.36 Hz, 1H), 6.86-6.74 (m, 2H), 5.19 (d, J=10.22 Hz, 1H), 4.49 (d, J=10.22 Hz, 1H), 4.25 (dd, J=7.35, 2.71 Hz, 1H), 3.56-3.43 (m, 1H), 3.42-3.30 (m, 4H), 2.07 (dd, J=15.43, 7.44 Hz, 1H), 1.72-1.58 (m, 1H), 1.56-1.40 (m, 1H), 1.30 (dd, J=15.43, 2.62 Hz, 1H), 0.80 (s, 9H); $^{13}$C (75 MHz, CD$_3$OD): 180.26, 166.78, 157.81 (d, $J_{C-F}$=247.93 Hz), 145.43, 136.90, 132.16, 128.82, 127.96, 126.48 (d, $J_{C-F}$=4.49 Hz), 125.43, 124.94 (d, $J_{C-F}$=14.00 Hz), 123.37, 122.63 (d, $J_{C-F}$=18.23 Hz), 112.00, 71.01, 67.25, 64.38, 63.80, 61.69, 50.06, 42.36, 38.30, 33.80, 30.94, 29.55; ESI: Calculated for C$_{27}$H$_{33}$$^{35}$Cl$_2$FN$_3$O$_4$ [M+H]$^+$=552.18. Found: 552.92.

Compound 5—Isomer B (TFA salt): $^1$H NMR (300 MHz, CD$_3$OD): 7.60 (d, J=8.15 Hz, 1H), 7.55 (t, J=7.12 Hz, 1H), 7.38 (t, J=7.57 Hz, 1H), 7.20-7.10 (m, 2H), 6.78 (d, J=1.70 Hz, 1H), 5.27 (d, J=11.40 Hz, 1H), 4.62 (d, J=11.40 Hz, 1H), 4.52 (dd, J=8.33, 1.29 Hz, 1H), 3.45-3.25 (m, 5H), 1.90 (dd, J=15.46, 8.38 Hz, 1H), 1.64-1.48 (m, 1H), 1.46-1.32 (m, 1H), 1.14 (dd, J=15.46, 1.34 Hz, 1H), 0.87 (s, 9H); $^{13}$C (75 MHz, CD$_3$OD): 177.77, 167.67, 157.90 (d, $J_{C-F}$=251.2 Hz), 145.21, 137.26, 132.67, 128.64, 126.89 (d, $J_{C-F}$=1.88 Hz), 126.65 (d, $J_{C-F}$=4.89 Hz), 124.17, 123.43, 122.60 (d, $J_{C-F}$=19.0 Hz), 121.52 (d, $J_{C-F}$=13.0 Hz), 112.14, 79.99, 67.25, 64.45, 62.873, 48.8, 43.39, 38.26, 33.78, 31.02, 29.57; ESI: Calculated for C$_{27}$H$_{33}$$^{35}$Cl$_2$FN$_3$O$_4$ [M+H]$^+$=552.18. Found: 552.42;

Compound 5—Isomer C (TFA salt): $^1$H NMR (300 MHz, CD$_3$OD): 8.37 (s, broad, NH), 7.62 (d, J=8.11 Hz, 1H), 7.50-7.34 (m, 2H), 7.36-7.10 (m, 2H), 6.83 (d, J=1.83 Hz, 1H), 4.32 (d, J=12.09 Hz, 1H), 4.24-4.14 (m, 1H), 3.50-3.10 (m, 5H), 1.86-1.72 (m, 2H), 1.58-1.44 (m, 1H), 1.44-1.26 (m, 1H), 0.80 (s, 9H); ESI: Calculated for C$_{27}$H$_{33}$$^{35}$Cl$_2$FN$_3$O$_4$ [M+H]$^+$=552.18. Found: 552.42.

Compound 5—Isomer D (TFA salt): $^1$H NMR (300 MHz, CD$_3$OD): 7.49 (d, J=8.02 Hz, 1H), 7.36-7.24 (m, 1H), 7.11 (dd, J=8.09, 1.89 Hz, 1H), 7.06-6.96 (m, 1H), 6.96-6.88 (m, 1H), 6.80 (d, J=1.88 Hz, 1H), 4.89 (d, J=11.57 Hz, 1H), 4.46 (d, J=11.57 Hz, 1H), 4.35-4.25 (m, 1H), 3.56-3.40 (m, 1H), 3.40-3.20 (m, 4H), 1.70-1.40 (m, 3H), 1.10 (dd, J=14.59, 3.06 Hz, 1H), 0.91 (s, 9H); ESI: Calculated for C$_{27}$H$_{33}$$^{35}$Cl$_2$FN$_3$O$_4$ [M+H]$^+$=552.18. Found: 552.40.

Compound 6—Isomer A (TFA salt): $^1$H NMR (300 MHz, CD$_3$OD): 7.59 (t, J=6.93 Hz, 1H), 7.41 (td, J=7.55, 0.97 Hz, 1H), 7.22 (t, J=7.90 Hz, 1H), 6.90 (d, J=1.79 Hz, 1H), 6.77 (dd, J=8.14, 1.79 Hz, 1H), 6.48 (d, J=8.15 Hz, 1H), 5.21 (d, J=8.22 Hz, 1H), 4.50 (d, J=8.19 Hz, 1H), 4.17 (dd, J=7.63, 2.23 Hz, 1H), 4.10-3.80 (m, 4H), 3.75-3.45 (m, 4H), 3.40-3.00 (m, 4H), 2.08-1.96 (m, 1H), 1.19 (dd, J=15.32, 2.23 Hz, 1H), 0.81 (s, 9H); $^{13}$C (75 MHz, CD$_3$OD): 180.28, 168.91, 157.75 (d, $J_{C-F}$=248.38 Hz), 145.50, 137.13, 132.29, 128.63, 127.67, 126.63 (d, $J_{C-F}$=4.50 Hz), 125.74 (d, $J_{C-F}$=13.69 Hz), 124.72, 123.44, 122.83 (d, $J_{C-F}$=18.25 Hz), 112.20, 65.16, 64.25, 63.84, 62.22, 58.01, 53.84, 50.05, 42.39, 35.72, 30.95, 29.52; ESI: Calculated for C$_{29}$H$_{36}$$^{35}$Cl$_2$FN$_4$O$_3$ [M+H]$^+$=577.21. Found: 577.48.

Compound 6—Isomer B (TFA salt): $^1$H NMR (300 MHz, CD$_3$OD): 7.66-7.48 (m, 2H), 7.42-7.32 (m, 1H), 7.20-7.10 (m, 2H), 6.78 (d, J=1.68 Hz, 1H), 5.38 (d, J=11.48 Hz, 1H), 4.65 (d, J=11.48 Hz, 1H), 4.52 (d, J=7.59 Hz, 1H), 4.00-3.70 (m, 4H), 3.70-3.60 (m, 2H), 3.50-3.40 (m, 2H), 3.40-3.10 (m, 4H), 1.97 (dd, J=15.40, 8.62 Hz, 1H), 1.12 (d, J=15.40 Hz, 1H), 0.88 (s, 9H); $^{13}$C (75 MHz, CD$_3$OD): 177.73, 169.20, 145.19, 137.15, 132.54, 128.69, 126.84, 126.64 (d, $J_{C-F}$=4.80 Hz), 124.11, 123.72, 122.57 (d, $J_{C-F}$=13.19 Hz), 121.77 (d, $J_{C-F}$=13.19 Hz), 112.06, 65.08, 64.59, 64.32, 62.69, 57.41, 53.70, 48.47, 43.55, 35.61, 31.06, 29.56; ESI: Calculated for C$_{29}$H$_{36}$$^{35}$Cl$_2$FN$_4$O$_3$ [M+H]$^+$=577.21. Found: 577.48.

Compound 7—Isomer B (TFA salt): $^1$H NMR (300 MHz, CD$_3$OD): 7.54-7.44 (m, 2H), 7.36-7.26 (m, 1H), 7.14-7.00 (m, 2H), 6.70 (d, J=1.76 Hz, 1H), 5.22 (d, J=11.36 Hz, 1H), 4.50 (d, J=11.36 Hz, 1H), 4.41 (d, J=8.23, 1.85 Hz, 1H), 1.81 (dd, J=15.46, 8.31 Hz, 1H), 1.06 (dd, J=15.46, 1.90 Hz, 1H), 0.78 (s, 9H); ESI: Calculated for C$_{23}$H$_{25}$$^{35}$Cl$_2$FN$_3$O$_2$ [M+H]$^+$=464.13. Found: 464.60.

Compound 7—Isomer D (TFA salt): $^1$H NMR (300 MHz, CD$_3$OD): 7.64 (d, J=8.01 Hz, 1H), 7.54-7.40 (m, 2H), 7.28-7.12 (m, 2H), 6.83 (d, J=1.68 Hz, 1H), 4.96 (d, J=12.33 Hz, 1H), 4.36 (d, J=12.33 Hz, 1H), 4.28 (t, J=5.60 Hz, 1H), 1.93-1.86 (m, 2H), 0.80 (s, 9H); ESI: Calculated for C$_{23}$H$_{25}$$^{35}$Cl$_2$FN$_3$O$_2$ [M+H]$^+$=464.13. Found: 464.42.

Compound 8—Isomer B (TFA salt): $^1$H NMR (300 MHz, CD$_3$OD): 7.66 (d, J=8.49 HZ, 1H), 7.35-7.12 (m, 4H), 6.86 (d, J=6.02 Hz, 1H), 5.67 (d, J=10.03 Hz, 1H), 4.41 (dd, J=8.20, 1.79 Hz, 1H), 4.13 (d, J=10.03 Hz, 1H), 2.97 (s, 3H), 2.74 (s, 3H), 1.91 (dd, J=15.46, 8.20 Hz, 1H) 1.17 (dd, J=15.46, 1.82 Hz, 1H), 0.91 (s, 9H); $^{13}$C (75 MHz, CD$_3$OD): 177.80, 168.54, 156.04 (d, $J_{C-F}$=243.74 Hz), 141.04, 136.12, 135.16, 131.81, 130.66, 129.73, 128.52, 125.50 (d, $J_{C-F}$=7.37 Hz), 123.70 (d, $J_{C-F}$=19.58 Hz), 114.43 (d, $J_{C-F}$=25.50 Hz), 113.62, 65.81, 64.45, 60.58, 57.31, 42.59, 38.04, 37.00, 31.04, 29.63; ESI: Calculated for C$_{25}$H$_{29}$$^{35}$Cl$_2$FN$_3$O$_2$ [M+H]$^+$=492.16. Found: 492.50.

Compound 8—Isomer D (TFA salt): $^1$H NMR (300 MHz, CD$_3$OD): 7.73 (d, J=8.75 Hz, 1H), 7.30-7.18 (m, 1H), 7.18-7.12 (m, 1H), 7.12-7.06 (m, 1H), 6.89 (d, J=6.12 Hz, 1H), 5.52 (d, J=10.56 Hz, 1H), 4.37 (dd, J=6.56, 4.48 Hz, 1H), 4.18 (d, J=10.62 Hz, 1H), 2.99 (s, 3H), 2.80 (s, 3H), 1.69 (dd, J=15.35, 6.58 Hz, 1H), 1.21 (dd, J=15.35, 4.37 Hz, 1H), 0.93 (s, 9H); ESI: Calculated for C$_{25}$H$_{29}$$^{35}$Cl$_2$FN$_3$O$_2$ [M+H]$^+$=492.16. Found: 492.62.

Compound 9—Isomer A (TFA salt): $^1$H NMR (300 MHz, CD$_3$OD): 7.25-7.20 (m, 3H), 7.10-7.00 (m, 1H), 6.85 (d, J=6.00 Hz, 1H), 5.13 (d, J=11.10 Hz, 1H), 4.30-4.10 (m, 2H), 2.72 (s, 3H), 2.02 (dd, J=15.30, 7.20 Hz, 1H), 1.52 (dd, J=15.30, 3.90 Hz, 1H), 0.79 (s, 9H); ESI: Calculated for C$_{24}$H$_{27}$$^{35}$Cl$_2$FN$_3$O$_2$ [M+H]$^+$=478.15. Found: 478.46.

Compound 9—Isomer B (TFA salt): $^1$H NMR (300 MHz, CD$_3$OD): 7.68 (d, J=8.47 Hz, 1H), 7.32-7.16 (m, 3H), 7.04 (d, J=7.63 Hz, 1H), 6.85 (d, J=6.01 Hz, 1H), 5.23 (d, J=11.21 Hz, 1H), 4.46 (dd, J=8.23, 1.76 Hz, 1H), 4.13 (d, J=11.21 Hz, 1H), 2.71 (S, 3H), 1.90 (dd, J=15.46, 8.23 Hz, 1H), 1.17 (dd, J=15.48, 1.75 Hz, 1H), 0.89 (s, 9H) $^{13}$C (75 MHz, CD$_3$OD): 177.57, 168.31, 159.98 (d, $J_{C-F}$=244.73 Hz), 140.90, 135.98, 134.31, 131.59, 130.56, 129.45, 128.47, 125.84 (d, $J_{C-F}$=7.48 Hz), 123.61 (d, $J_{C-F}$=19.45 Hz), 114.33 (d, $J_{C-F}$=25.29 Hz), 113.57, 65.62, 64.15, 62.93, 57.04, 63.42, 31.01, 29.60, 27.02; ESI: Calculated for C$_{24}$H$_{27}$$^{35}$Cl$_2$FN$_3$O$_2$ [M+H]$^+$=478.15. Found: 478.46.

Compound 9—Isomer C (TFA salt): $^1$H NMR (300 MHz, CD$_3$OD): 7.66 (d, J=8.70 Hz, 1H), 7.32 (d, J=8.20 Hz, 1H), 7.23 (t, J=7.89 Hz, 1H), 7.09 (t, J=1.70 Hz, 1H), 6.93 (d, J=7.66 Hz, 1H), 6.89 (, J=6.13 Hz, 1H), 4.22 (t, J=5.73 Hz, 1H), 3.91 (d, J=12.36 Hz, 1H), 2.70 (s, 3H), 1.90-1.84 (m, 2H), 0.83 (s, 9H); ESI: Calculated for C$_{24}$H$_{27}$$^{35}$Cl$_2$FN$_3$O$_2$ [M+H]$^+$=478.15. Found: 478.58.

Compound 9—Isomer D (TFA salt): $^1$H NMR (300 MHz, CD$_3$OD): 7.51 (d, J=8.79 Hz, 1H), 7.24-7.12 (m, 2H), 7.08 (s, 1H), 7.25 (d, J=7.13 Hz, 1H), 6.85 (d, J=6.13 Hz, 1H), 4.80 (d, J=11.25 Hz, 1H), 4.25-4.15 (m, 1H), 4.09 (d, J=11.25 Hz, 1H), 2.76 (s, 3H), 1.44 (dd, J=15.26, 7.62 Hz, 1H), 1.08 (dd, J=15.26, 3.19 Hz, 1H), 0.92 (s, 9H); ESI: Calculated for $C_{24}H_{27}{}^{35}Cl_2FN_3O_2$ [M+H]$^+$=478.15. Found: 478.56.

Compound 10—Isomer A (TFA salt) (MI-219—TFA Salt): $^1$H NMR (300 MHz, CD$_3$OD): 7.32-7.22 (m, 3H), 7.18-7.10 (m, 1H), 7.06 (d, J=8.74 Hz, 1H), 6.88 (d, J=6.08 Hz, 1H), 4.97 (d, J=10.79 Hz, 1H), 4.22 (d, J=10.79 Hz, 1H), 4.26-4.18 (m, 1H), 3.50-3.20 (m, 5H), 2.03 (dd, J=15.35, 6.56 Hz, 1H), 1.68-1.52 (m, 2H), 1.50-1.40 (m, 1H), 0.84 (s, 9H); $^{13}$C (75 MHz, CD$_3$OD): 179.64, 166.47, 140.40 (d, $J_{P-C}$=2.94 Hz), 136.54, 136.06, 131.64, 130.16, 130.02, 128.14, 127.27 (d, $J_{P-C}$=40.14 Hz), 123.05 (d, $J_{P-C}$=19.44 Hz), 115.94 (d, $J_{P-C}$=25.54 Hz), 113.09, 70.91, 67.24, 64.19, 64.10, 62.73, 57.52, 42.66, 38.14, 33.85, 30.99, 29.57; ESI: Calculated for $C_{27}H_{33}{}^{35}Cl_2FN_3O_4$ [M+H]$^+$=552.18. Found: 552.75; HPLC Purity=82%.

Compound 10—Isomer B, (TFA salt) (MI-21901—TFA salt): $^1$H NMR (300 MHz, CD$_3$OD): 7.68 (d, J=8.47 Hz, 1H), 7.32-7.17 (m, 3H), 7.12-7.02 (m, 1H), 6.85 (d, J=6.00 Hz, 1H), 5.23 (d, J=11.28 Hz, 1H), 4.46 (dd, J=8.41, 1.91 Hz, 1H), 4.10 (d, J=11.28 Hz, 1H), 3.50-3.20 (m, 5H), 1.90 (dd, J=15.18, 8.62 Hz, 1H), 1.65-1.47 (m, 1H), 1.47-1.33 (m, 1H), 1.18 (d, J=15.18 Hz, 1H), 0.89 (s, 9H); $^{13}$C (75 MHz, CD$_3$OD): 177.56, 167.81, 155.99 (d, $J_{P-C}$=243.27 Hz), 140.87, 135.98, 134.28, 131.63, 130.60, 129.51, 128.60, 125.82 (d, $J_{P-C}$=7.39 Hz), 123.58 (d, $J_{P-C}$=19.68 Hz), 114.30 (d, $J_{P-C}$=25.32 Hz), 113.55, 70.86, 67.23, 65.53, 64.16, 63.07, 57.35, 43.43, 38.15, 33.78, 31.01, 29.57; ESI: Calculated for $C_{27}H_{33}{}^{35}Cl_2FN_3O_4$ [M+H]$^+$=552.18. Found: 552.38; HPLC Purity=95%.

Compound 10—Isomer D (TFA salt): $^1$H NMR (300 MHz, CD$_3$OD): 7.60-7.53 (m, 1H), 7.30-7.10 (m, 2H), 7.08-7.02 (m, 1H), 7.00-6.92 (m, 1H), 6.84 (d, J=6.13 Hz, 1H), 4.96 (d, J=12.25 Hz, 1H), 4.39 (dd, J=7.22, 4.31 Hz, 1H), 4.10 (d, J=12.27 Hz, 1H), 3.50-3.20 (m, 5H), 1.68 (dd, J=15.29, 7.23 Hz, 1H), 1.62-1.48 (m, 1H), 1.48-1.32 (m, 1H), 1.17 (dd, J=15.29, 4.16 Hz, 1H), 0.90 (s, 9H); ESI: Calculated for $C_{27}H_{33}{}^{35}Cl_2FN_3O_4$ [M+H]$^+$=552.18. Found: 552.40.

Compound 11—Isomer A (TFA salt): $^1$H NMR (300 MHz, CD$_3$OD): 7.50-7.40 (m, 2H), 7.28-7.18 (m, 1H), 6.91 (d, J=1.81 Hz, 1H), 6.78 (dd, J=8.13, 1.87 Hz, 1H), 6.46 (d, J=8.14 Hz, 1H), 5.30 (d, J=8.52 Hz, 1H), 4.43 (d, J=8.52 Hz, 1H), 4.40-4.20 (m, 2H), 4.08 (dd, J=7.47, 2.43 Hz, 1H), 2.00 (dd, J=15.32, 7.53 Hz, 1H), 1.22 (t, J=7.12 Hz, 3H), 1.19 (dd, J=15.32, 2.55 Hz, 1H), 0.81 (s, 9H); $^{13}$C (75 MHz, CD$_3$Cl, note free amine): 181.33, 171.91, 156.54 (d, $J_{C-F}$=248.02 Hz), 142.85, 134.15, 129.91, 128.37 (d, $J_{C-F}$=14.61 Hz), 127.19 (d, $J_{C-F}$=3.19 Hz), 125.94, 124.94, 124.63 (d, $J_{C-F}$=4.50 Hz), 122.10, 121.69 (d, $J_{C-F}$=18.50 Hz), 110.72, 67.16, 65.70, 63.19, 61.74, 51.17, 43.45, 30.33, 29.97, 14.32; ESI: Calculated for $C_{25}H_{28}{}^{35}Cl_2FN_2O_3$ [M+H]$^+$=493.15. Found: 493.44.

Compound 11—Isomer B (TFA salt): $^1$H NMR (300 MHz, CD$_3$OD): 7.59 (d, J=7.41 Hz, 1H), 7.50-7.42 (m, 1H), 7.40-7.32 (m, 1H), 7.17-7.07 (m, 2H), 6.78 (d, J=1.65 Hz, 1H), 5.61 (d, J=12.25 Hz, 1H), 4.56 (d, J=12.25 Hz, 1H), 4.47 (dd, J=8.50, 1.50 Hz, 1H), 4.25 (dq, J=10.77, 7.12 Hz, 1H), 4.13 (dq, J=10.77, 7.12 Hz, 1H), 1.93 (dd, J=15.39, 8.67 Hz, 1H), 1.34 (dd, J=15.39, 1.57 Hz, 1H), 1.10 (t, J=7.12 Hz, 3H), 0.87 (s, 9H); ESI: Calculated for $C_{25}H_{28}{}^{35}Cl_2FN_2O_3$ [M+H]$^+$=493.15. Found: 493.44.

Compound 12—Isomer A (TFA salt): $^1$H NMR (300 MHz, CD$_3$OD): 7.56-7.46 (m, 1H), 7.46-7.36 (m, 1H), 7.26-7.18 (m, 1H), 6.91 (d, J=1.61 Hz, 1H), 6.76 (dd, J=8.10, 1.50 Hz, 1H), 6.47 (d, J=8.14 Hz, 1H), 5.29 (d, J=8.67 Hz, 1H), 4.43 (d, J=8.67 Hz, 1H), 4.11 (d, J=7.47, 2.13 Hz, 1H), 2.02 (dd, J=15.36, 7.50 Hz, 1H), 1.16 (dd, J=15.36, 2.24 Hz, 1H), 0.81 (s, 9H); ESI: Calculated for $C_{23}H_{24}{}^{35}Cl_2FN_2O_3$ [M+H]$^+$=465.11. Found: 465.42.

Compound 12—Isomer B (TFA salt): $^1$H NMR (300 MHz, CD$_3$OD): 7.58-7.42 (m, 2H), 7.36-7.26 (m, 1H), 7.14-7.02 (m, 1H), 6.75 (s, 1H), 5.43 (d, J=12.00 Hz, 1H), 4.58 (d, J=11.97 Hz, 1H), 4.35 (d, J=8.53 Hz, 1H), 1.87 (dd, J=15.08, 9.31 Hz, 1H), 1.09 (d, J=15.31 Hz, 1H), 0.85 (s, 9H); ESI: Calculated for $C_{23}H_{24}{}^{35}Cl_2FN_2O_3$ [M+H]$^+$=465.11. Found: 465.38.

Compound 12—Isomer D (TFA salt): $^1$H NMR (300 MHz, CD$_3$OD): 7.49 (d, J=8.10 Hz, 1H), 7.36-7.26 (m, 1H), 7.13 (dd, J=8.10, 1.85 Hz, 1H), 7.08-7.00 (m, 1H), 6.96-6.86 (m, 1H), 6.78 (d, J=1.80 Hz, 1H), 5.32 (d, J=12.69 Hz, 1H), 4.56 (d, J=12.69 Hz, 1H), 4.42 (dd, J=7.27, 3.88 Hz, 1H), 1.69 (dd, J=15.44, 7.64 Hz, 1H), 1.13 (d, J=15.44, 3.76 Hz, 1H), 0.90 (s, 9H); ESI: Calculated for $C_{23}H_{24}{}^{35}Cl_2FN_2O_3$ [M+H]$^+$=465.11. Found: 465.54.

Example 17

Synthesis of CB061—Isomer B (TFA Salt)

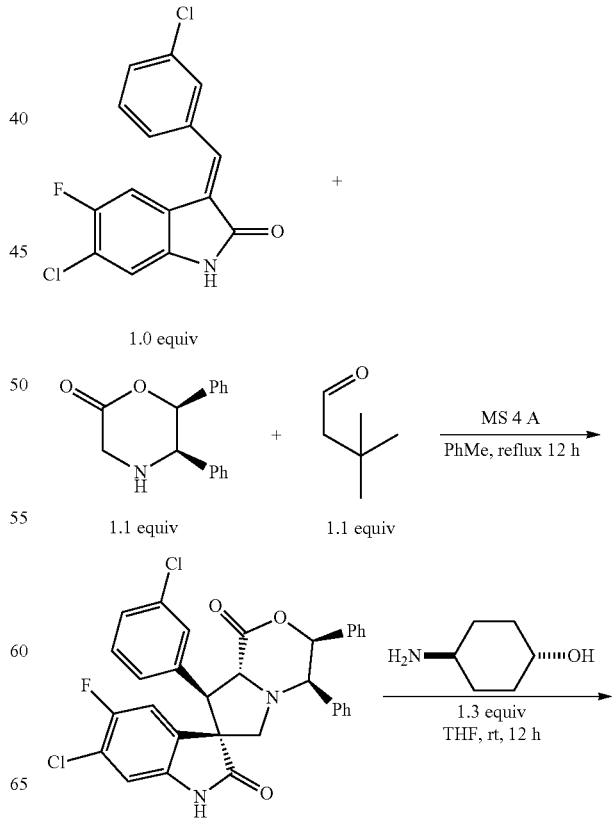

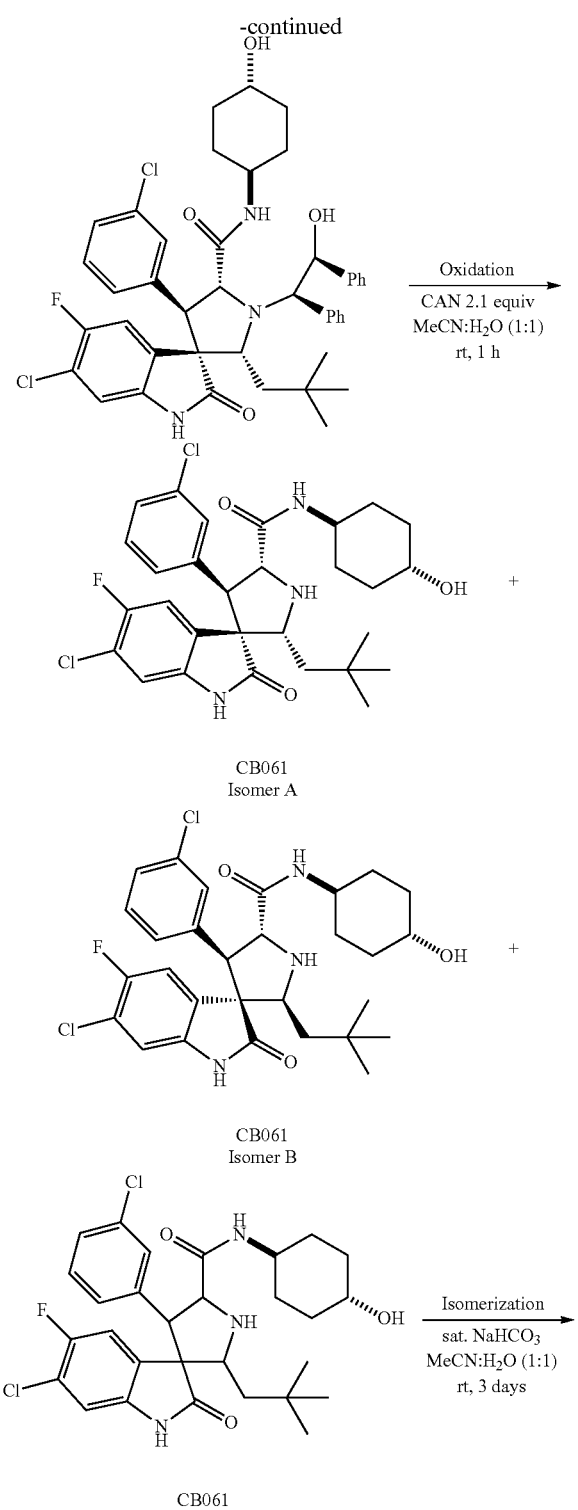

Figure 30:
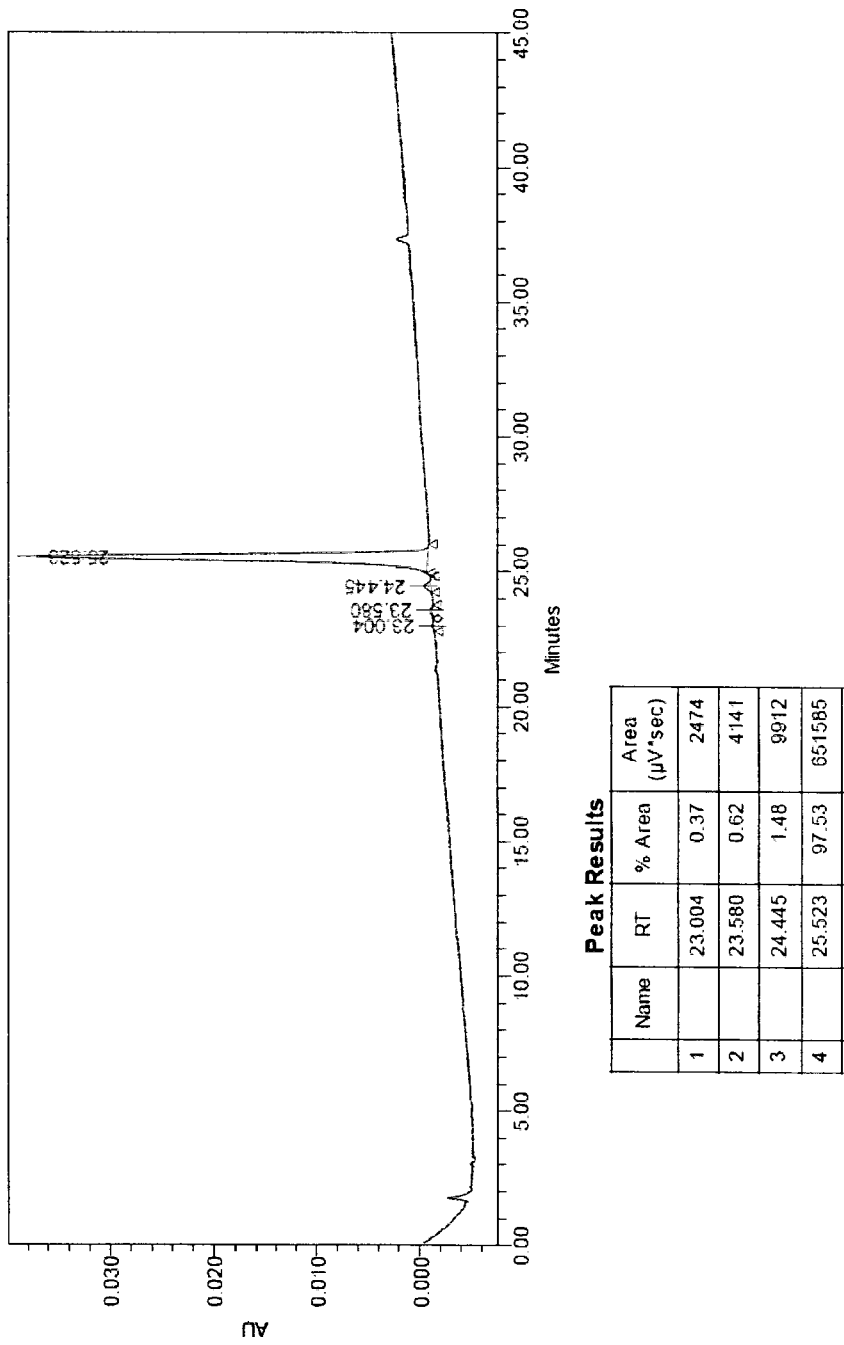
FIG. 30 is reverse phase HPLC chromatogram of substantially pure CB061—Isomer B.

CB061 was prepared according to Scheme 12 using methodology described in EXAMPLE 16 to give an A:B:(C+D) isomer ratio after oxidation of 15:67:18, an A:B:(C+D) isomer ratio after isomerization of 2:74:24, and substantially pure CB061—Isomer B (as the TFA salt) after chromatography (FIG. 30).

Analytical data for CB061—Isomer B (TFA salt): $^1$H NMR (300 MHz, CD$_3$OD): 7.66 (d, J=8.45 Hz, 1H), 7.30-7.16 (m, 3H), 7.10-7.03 (m, 1H), 6.85 (d, J=5.98 Hz, 1H), 5.22 (d, J=11.37 Hz, 1H), 4.46 (dd, J=8.31, 1.68 Hz, 1H), 4.09 (d, J=11.37 Hz, 1H), 3.70-3.50 (m, 1H), 3.50-3.39 (m, 1H), 2.00-1.84 (m, 3H), 1.82-1.70 (m, 1H), 1.58-1.46 (m, 1H), 1.40-1.12 (m, 4H), 1.08-0.90 (m, 1H), 0.88 (s, 9H); $^{13}$C NMR (75 MHz, CD$_3$OD): 177.42, 166.80, 155.82 (d, $J_{C-F}$=243.61 Hz), 140.67 (d, $J_{C-F}$=2.77 Hz), 135.73, 134.18, 131.36, 130.33, 129.44, 128.37, 125.77 (d, $J_{C-F}$=7.38 Hz), 123.38 (d, $J_{C-F}$=19.54 Hz), 114.06 (d, $J_{C-F}$=25.18 Hz), 113.39, 69.97, 65.12, 64.06, 62.94, 57.41, 49.88, 43.37, 34.38, 34.29, 30.98, 30.82, 29.39; ESI: Calculated for C$_{29}$H$_{35}$Cl$_2$FN$_3$O$_3$ [M+H]$^+$=562.20. Found: 562.36. The absolute stereochemistry of CB061—Isomer B was determined by single crystal x-ray crystallography.

Example 18

Synthesis of CB087—Isomer B (TFA Salt)

Scheme 13

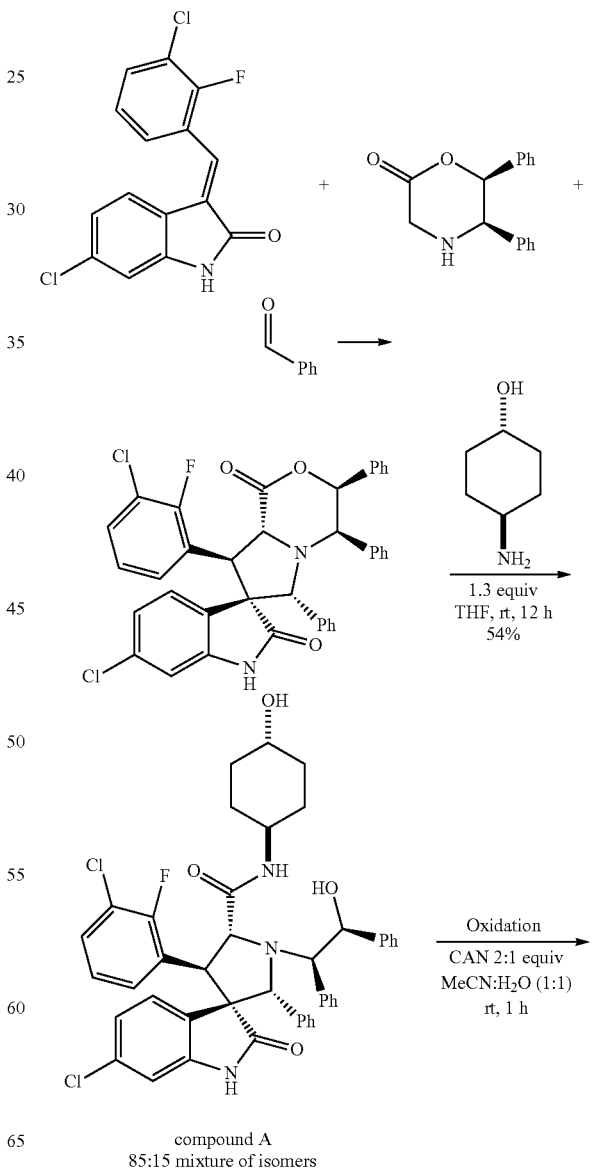

compound A
85:15 mixture of isomers

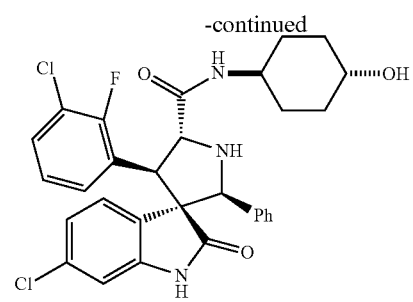

CB087
Isomer B

+

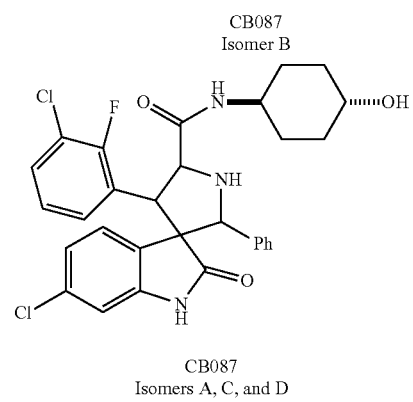

CB087
Isomers A, C, and D

Isomerization
———————→
TFA (pH < 1)
MeCN—H₂O
3 days

CB087
Isomers A-D

CB087 was prepared according to Scheme 13 using methodology described in EXAMPLE 16 to give an (A+C+D):B isomer ratio after oxidation of 65:35, an (A+C+D):B isomer ratio after isomerization of 18:82 (in acetonitrile-water in the presence of TFA), and substantially pure CB087—Isomer B (as the TFA salt) after chromatography. In this study, intermediate A was isolated as an 85:15 mixture of isomers based on ¹H NMR analysis. This mixture was used in the oxidation step. The major isomer was characterized by ¹H NMR and ESI. Also, little isomerization was observed in MeOH or in MeOH-water at a pH of 8 after 3 days at room temperature.

Analytical data for compound A major isomer: ¹H NMR (300 MHz, CD₃OD): 7.40 (s, 6H), 7.10 (s, 9H), 7.20 (t, J=7.12 Hz, 1H), 6.74 (t, J=7.86 Hz, 1H), 6.48 (s, 1H), 6.44 (d, J=8.20 Hz, 1H), 6.08 (t, J=7.02 Hz, 1H), 5.51 (d, J=8.22 Hz, 1H), 5.35 (d, J=4.67 Hz, 1H), 4.55 (d, J=4.45 Hz, 1H), 4.18 (s, 1H), 4.15-3.90 (m, 3H), 3.70-3.55 (m, 1H), 2.30-2.00 (m, 4H), 1.60-1.30 (m, 4H); ¹³C (75 MHz, CD₃OD): 179.68, 175.39, 155.86 (d, $J_{C-F}$=247.63 Hz), 142.81, 134.49, 134.21, 132.34, 132.09, 129.46, 129.28 (d, $J_{C-F}$=12.91 Hz), 128.45, 128.09, 127.78, 127.16, 126.90, 126.67, 125.20, 124.90, 124.08 (d, $J_{C-F}$=3.27 Hz), 121.32 (d, $J_{C-F}$=8.18 Hz), 121.17, 110.01, 76.10, 75.35, 69.39, 67.82, 66.89, 61.60, 49.60, 48.14, 33.60, 33.48, 30.12, 29.82; ESI: Calculated for $C_{44}H_{41}Cl_2FN_3O_4$ [M+H]⁺=764.25. Found: 764.26.

Analytical data for CB087—Isomer B (TFA salt): ¹H NMR (300 MHz, CD₃OD): 8.34 (d, J=7.70 Hz, 1H), 7.70 (d, J=8.11 Hz, 1H), 7.70 (t, J=7.02 Hz, 1H), 7.42 (t, J=7.61 Hz, 1H), 7.40-7.30 (m, 5H), 7.22 (d, J=7.90 Hz, 1H), 7.16 (dd, J=8.17, 1.85 Hz, 1H), 6.61 (d, J=1.74 Hz, 1H), 5.58 (s, 1H), 5.34 (d, J=10.97 Hz, 1H), 4.83 (d, J=11.04 Hz, 1H), 3.78-3.60 (m, 1H), 3.50-3.40 (m, 1H), 2.00-1.86 (m, 2H), 1.86-1.78 (m, 1H), 1.70-1.60 (m, 1H), 1.42-1.20 (m, 3H), 1.02 (qd, J=12.68, 3.30 Hz, 1H); ¹³C (75 MHz, CD₃OD): 177.29, 167.33, 154.20 (d, $J_{C-F}$=284.04 Hz), 144.70, 136.97, 132.50, 131.26, 130.24, 130.03, 128.83, 128.70, 126.61, 126.54, 123.98, 122.91, 122.35 (d, $J_{C-F}$=18.95 Hz), 121.70 (d, $J_{C-F}$=12.66 Hz), 111.78, 70.44, 69.95, 64.89, 62.47, 49.98, 49.87, 34.33, 34.28, 30.91, 30.80; ESI: Calculated for $C_{30}H_{29}Cl_2FN_3O_3$ [M+H]⁺=568.16. Found: 568.54.

Example 19

Synthesis of CB083—Isomer B (TFA Salt)

Scheme 14

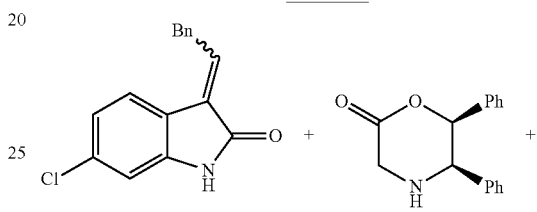

1.0 equiv    1.1 equiv

MS 4 A
————→
PhMe,
reflux 12 h 1.1 equiv

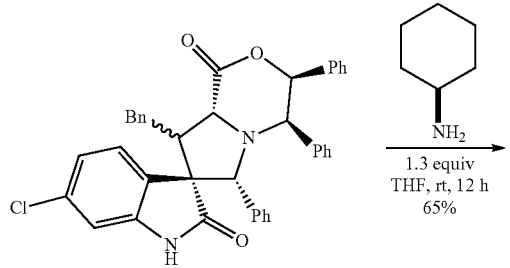

mixture of isomers

NH₂
————→
1.3 equiv
THF, rt, 12 h
65%

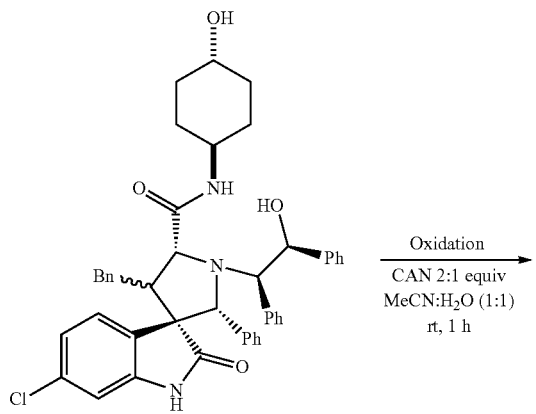

compound A
Isomer Ratio:
84:16

Oxidation
————→
CAN 2:1 equiv
MeCN:H₂O (1:1)
rt, 1 h

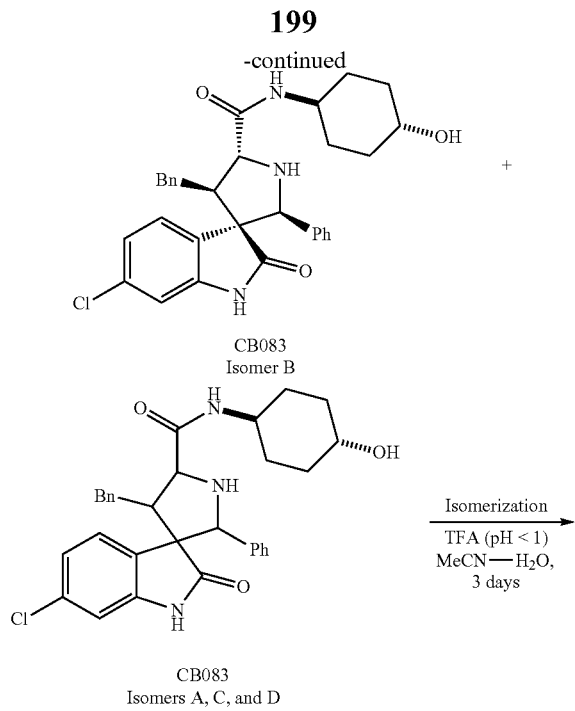

CB083
Isomer B

Isomerization
TFA (pH < 1)
MeCN—H₂O,
3 days

CB083
Isomers A, C, and D

CB083
Isomers A-D

CB083 was prepared according to Scheme 14 using methodology described in EXAMPLE 16 to give an (A+C+D):B isomer ratio after oxidation of 41:59, an (A+C+D):B isomer ratio after isomerization of 10:90 (in acetonitrile-water in the presence of TFA), and substantially pure CB083—Isomer B (as the TFA salt) after chromatography. In this study, intermediate A was isolated as an 84:16 mixture of isomers, and the major isomer was used in the oxidation step. Also, little isomerization was observed in MeOH or in MeOH-water at a pH of 8 after 3 days at room temperature.

Analytical data for compound A major isomer: $^1$H NMR (300 MHz, CD$_3$OD): 8.42 (d, J=7.49 Hz, NH, 1H), 7.40-7.25 (m, 5H), 7.25-7.10 (m, 9H), 7.20-6.98 (m, 3H), 6.94 (dd, J=8.06, 1.88 Hz, 1H), 6.82 (d, J=8.07 Hz, 1H), 6.63-6.55 (m, 2H), 6.53 (d, J=1.84 Hz, 1H), 5.18 (d, J=5.70 Hz, 1H), 4.32 (s, 1H), 3.97 (d, J=5.70 Hz, 1H), 3.70 (d, J=7.57 Hz, 1H), 3.70-3.55 (m, 2H), 3.25-3.10 (m, 1H), 2.64 (dd, J=14.03, 6.91 Hz, 1H), 2.45 (dd, J=13.97, 9.24 Hz, 1H), 2.15-1.90 (m, 4H), 1.55-1.30 (m, 4H); $^{13}$C (75 MHz, CD$_3$OD): 181.03, 176.38, 144.79, 144.55, 139.09, 138.54, 135.17, 134.94, 133.16, 130.13, 130.07, 129.77, 129.26, 129.11, 129.03, 128.95, 128.80, 128.18, 127.66, 127.35, 122.68, 111.27, 79.40, 76.05, 72.19, 70.6, 70.56, 62.05, 53.09, 49.63, 37.84, 34.88, 34.77, 31.34, 31.07; ESI: Calculated for C$_{45}$H$_{45}$ClN$_3$O$_4$ [M+H]$^+$=726.31. Found: 726.44.

Analytical data for CB083—Isomer B (TFA salt): $^1$H NMR (300 MHz, DMSO-d$_6$): 10.28 (s, NH, 1H), 8.51 (d, J=6.67 Hz, NH, 1H), 7.59 (d, J=8.03 Hz, 1H), 7.25-7.00 (m, 9H), 6.60-6.50 (m, 3H), 4.82 (s, 1H), 4.42 (d, J=9.65 Hz, 1H), 3.64-3.50 (m, 1H), 3.46-3.32 (m, 1H), 3.30-3.16 (m, 1H), 2.85 (dd, J=13.83, 4.77 Hz, 1H), 2.28 (dd, J=13.83, 10.20 Hz, 1H), 1.90-1.66 (m, 4H), 1.38-1.10 (m, 4H); $^{13}$C (75 MHz, DMSO-d$_6$): 178.36, 166.47, 143.95, 136.55, 133.32, 131.90, 128.69, 128.46, 128.09, 127.88, 127.18, 126.83, 126.52, 123.21, 120.72, 109.97, 70.38, 67.78, 63.18, 62.17, 52.83, 47.76, 34.54, 33.57, 29.82, 29.78; ESI: Calculated for C$_{31}$H$_{33}$ClN$_3$O$_3$ [M+H]$^+$=530.22. Found: 530.40.

Example 20

Synthesis of Synthesis of CB084—Isomer B (TFA Salt)

CB084 was prepared according to Scheme 15 using methodology described in EXAMPLE 16 to give an A:B:(C+D) isomer ratio after oxidation of 97:1:2, an A:B:(C+D) isomer ratio after isomerization of 46:52:2 in acetonitrile-water in the presence of TFA after 3 days, an A:B:(C+D) isomer ratio after isomerization of 9:49:42 in acetonitrile-water at pH 8 after 3 days, and substantially pure CB084—Isomer B (as the TFA salt) after chromatography.

Analytical data for CB084—Isomer A (free amine): $^1$H NMR (300 MHz, DMSO-d6): 10.02 (s, NH, 1H), 7.86 (d, J=7.60 Hz, NH, 1H), 7.31 (d, J=7.91 Hz, 1H), 7.05 (d, J=7.91 Hz, 1H), 6.97 (s, 3H), 6.54 (s, 1H), 6.46 (d, J=3.65 Hz, 2H), 4.50 (d, J=4.08 Hz, NH, 1H), 3.60-3.40 (m, 2H), 3.40-3.30 (m, 1H), 3.25-3.10 (m, 1H), 2.80-2.70 (m, 2H), 2.60-2.40 (m, 1H), 1.90-1.60 (m, 4H), 1.34 (dd, J=13.86, 10.33 Hz, 1H), 1.30-1.05 (m, 4H), 0.90-0.70 (m, 1H), 0.71 (s, 9H); $^{13}$C (75 MHz, DMSO-d6): 180.50, 169.86, 143.83, 138.61, 131.88, 129.53, 127.91, 127.64, 125.83, 125.55, 120.61, 108.90, 68.15, 68.08, 68.03, 61.27, 55.94, 47.20, 43.56, 34.36, 33.83, 33.77, 30.30, 30.02, 29.80, 29.67; ESI: Calculated for C$_{30}$H$_{39}$$^{35}$ClN$_3$O$_3$ [M+H]$^+$=524.27. Found: 524.55.

Scheme 15

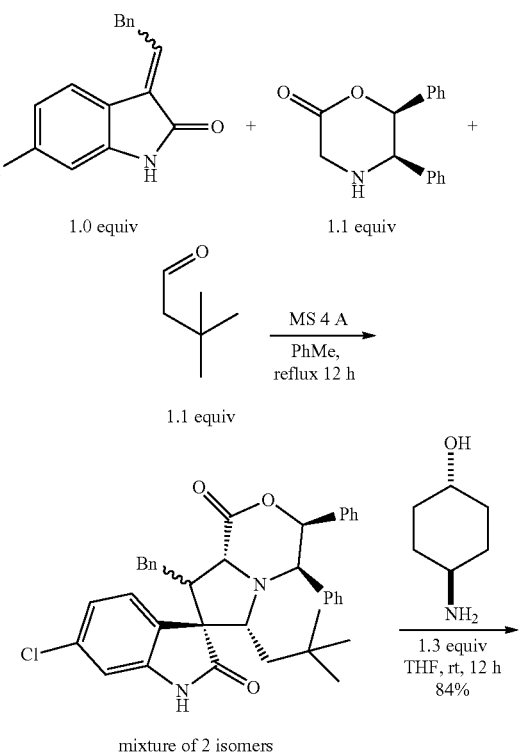

mixture of 2 isomers

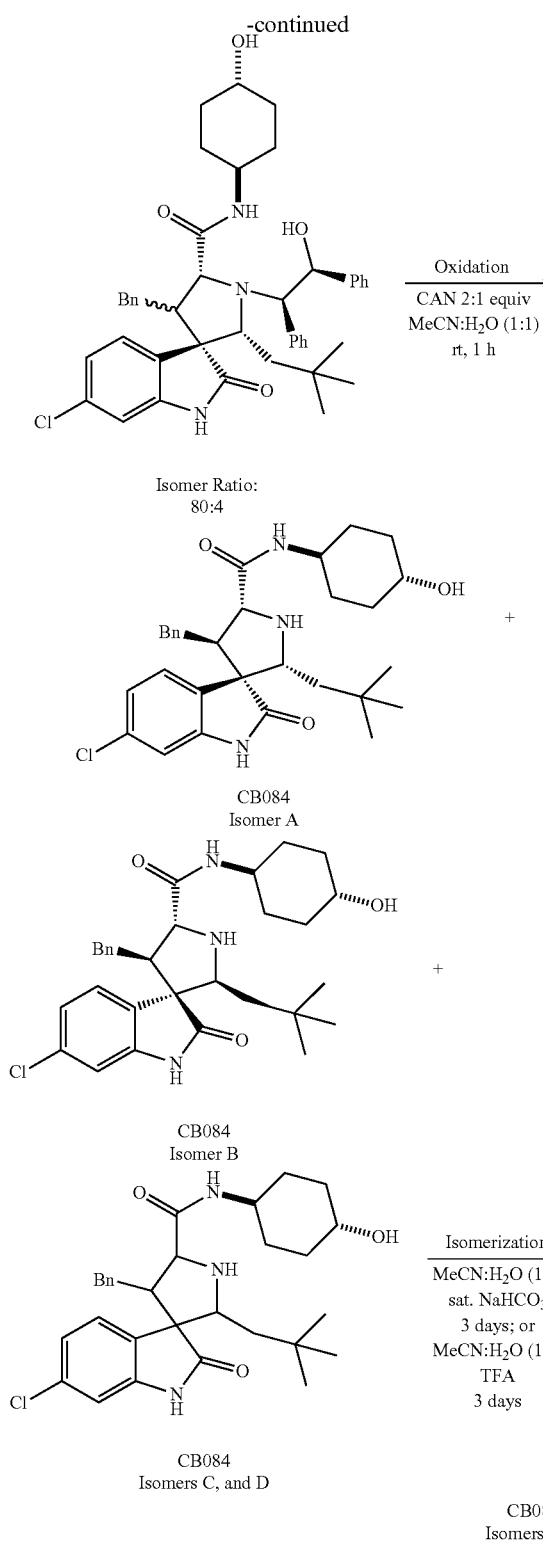

Analytical data for CB084—Isomer B (TFA salt): $^1$H NMR (300 MHz, CD$_3$OD): 8.54 (d, J=7.42 Hz, NH, 1H), 7.48 (d, J=8.06 Hz, 1H), 7.23 (d, J=8.06 Hz, 1H), 7.20-7.08 (m, 3H), 6.90 (s, 1H), 6.67 (d, J=6.94 Hz, 1H), 4.49 (d, J=11.08 Hz, 1H), 4.17 (dd, J=7.91, 1.68 Hz, 1H), 3.75-3.60 (m, 1H), 3.60-3.45 (m, 1H), 3.40-3.30 (m, 1H), 2.79 (dd, J=14.10, 6.05 Hz, 1H), 2.36 (dd, J=14.10, 10.21 Hz, 1H), 2.10-1.80 (m, 4H), 1.49 (dd, J=15.58, 8.30 Hz, 1H), 1.45-1.20 (m, 4H), 1.00-0.80 (m, 1H), 0.87 (s, 9H); $^{13}$C (75 MHz, DMSO-d6): 175.40, 144.42, 136.34, 133.82, 128.42, 127.93, 127.02, 126.60, 123.34, 121.24, 110.53, 67.72, 63.74, 63.35, 61.30, 51.75, 47.89, 42.56, 33.47, 33.44, 32.92, 29.78, 29.66, 29.52, 28.85; ESI: Calculated for C$_{30}$H$_{39}$$^{35}$ClN$_3$O$_3$ [M+H]$^+$=524.27. Found: 524.44.

Example 21

Synthesis of C144

Scheme 16

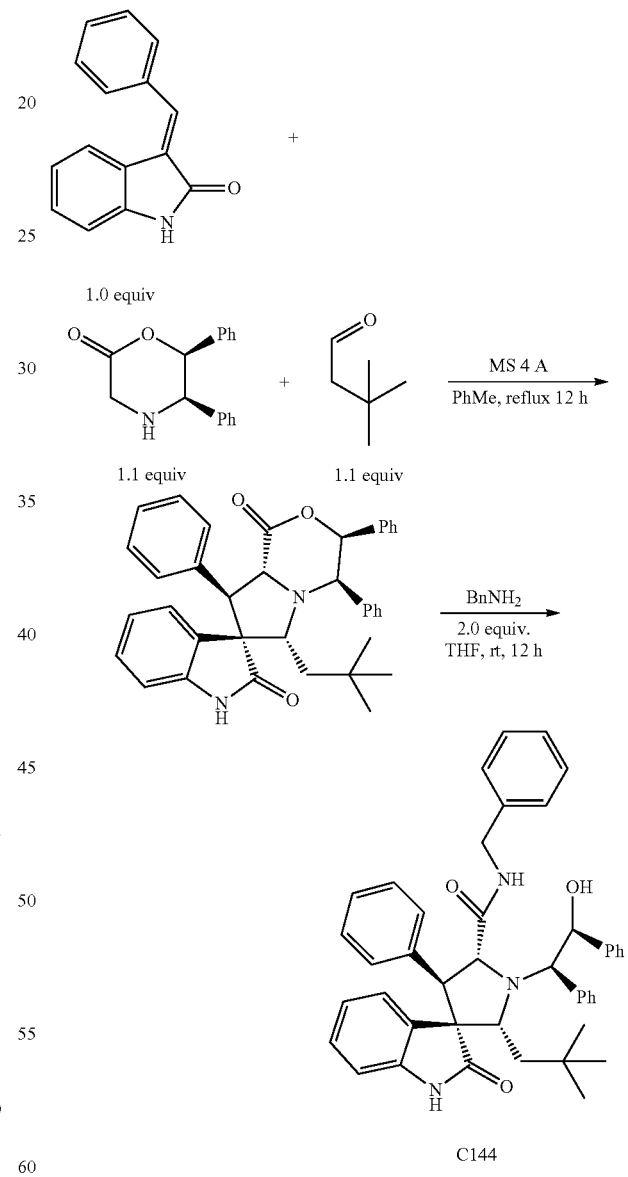

C144 was prepared using methodology described above. The absolute stereochemistry of C144 determined by single crystal x-ray crystallography.

Analytical data for C144: $^1$H NMR (300 MHz, CD$_3$Cl): 7.70-7.40 (m, 5H), 7.50-7.00 (m, 9H), 7.00-6.80 (m, 5H), 6.80-6.60 (m, 2H), 6.43 (d, J=7.68 Hz, 1H), 6.11 (t, J=5.79

Hz, 1H), 5.99 (d, J=7.56 Hz, 1H), 5.27 (d, J=6.91 Hz, 1H), 4.48 (dd, J=14.79, 6.31 Hz, 1H), 4.34 (d, J=6.91 Hz, 1H), 4.21 (dd, J=14.79, 5.41 Hz, 1H), 4.13 (d, J=11.24 Hz, 1H), 3.80 (d, J=11.24 Hz, 1H), 3.51 (d, J=9.46 Hz, 1H), 2.83 (dd, J=15.40, 9.46 Hz, 1H), 1.32 (d, J=15.40 Hz, 1H), 0.76 (s, 9H); $^{13}$C (75 MHz, CD$_3$Cl): 178.42, 173.63, 142.12, 139.27, 137.97, 134.54, 133.23, 132.49, 131.78, 129.21, 128.88, 128.74, 128.48, 128.21, 127.92, 127.86, 127.77, 127.52, 127.29, 124.63, 122.27, 109.35, 75.06, 72.14, 70.40, 66.08, 60.65, 60.51, 43.62, 43.56, 30.11, 29.91; ESI: Calculated for $C_{44}H_{46}N_3O_3$ $[M+H]^+$=664.35. Found: 664.36.

Example 22

Cellular Activity of MI-77301

The activity of MI-773001 in a variety of tumor cell lines is presented in Table 6. The cytotoxic concentration is the first concentration where cell death corresponding to the cytotoxic index is observed. Cytotoxicity was quantified by blue trypan exclusion at 96 h except for CCF-STTG1 at 192 hours (medium 20-50% cell death and high >50% cell death). The anti-proliferative IC$_{50}$ was determined by ATP assay.

Example 23

Cell Growth Inhibition and Cytoxic Effects on 22Rv1 Cell Lines

MI-519-6401 and MI-77301 were evaluated for their cell growth inhibition and cytotoxic effects on a prostate cancer cell line 22Rv1 (from The DSMZ—Deutsche Sammlung von Mikroorganismen and Zellkulturen GmbH, reference DSMZ ACC438). For growth inhibition assays, cells were incubated in the presence of MI-519-6401 or MI-77301 for 96 h in 96-well format. Cell seeding conditions were adapted to get significant cell growth in this assay format. Growth inhibition assays were performed using the Celltiter-Glo Luminescent kit (Promega). The IC$_{50}$ values (concentration where the growth inhibition percentage is equal to half of the maximum inhibitory effect of the tested compound) were calculated and ranged between 100 nM and 500 nM in this prostate cancer cell line for both compounds.

For cytotoxicity assays, cells were incubated with MI-519-6401 or MI-77301 for 96 h in 6-well format. Cell seeding conditions were adapted to get significant cell growth in this assay format. Cytotoxic effects were measured using trypan blue staining. Both the floating and adherent cells were

TABLE 6

| tumor cell line | origin | p53 | BM | Cytotox | Cytotox* (µM) | IC$_{50}$ (nM) |
|---|---|---|---|---|---|---|
| H1299 | lung | —/— | — | — | — | >10,000 |
| U2OS | bone | WT/WT | — | — | — | >10,000 |
| SJSA1 | bone | WT/WT | MDM2 amplified | high | 1 | 145 |
| HCT116 | colon | WT/WT | — | — | — | 229 |
| RKO | colon | WT/WT | — | — | — | 480 |
| 22RV1 | prostate | WT/MUT | — | medium | 3 | 399 |
| LnCap | prostate | WT/WT | — | high | 3 | 50 |
| JAR | placenta | WT/WT | MDM2 amplified | high | 3 | 169 |
| CCF-STTG1 | CNS | WT/WT | MDM2 amplified | medium | 1 | 162 |
| Capan2 | pancreas | —/— | — | — | — | >10,000 |
| MCF7 | breast | WT/WT | — | — | — | 201 |
| Y79 | retinoblastome | WT/WT | Rb mutated | medium | 1 | 430 |
| Weri-RB1 | retinoblastome | WT/WT | Rb mutated | high | 0.3 | not determined |
| SNU-1 | gastric | WT/WT | KRAS mut | high | 10 | 77 |
| MKN45 | gastric | WT/WT | Met amplified | — | — | >10,000 |
| Hs746T | gastric | | Met amplified | — | — | 10,000 |
| SNU-5 | gastric | | Met amplified | — | — | >10,000 |
| MOLM13 | AML | WT/WT | FLT3-ITD | high | 0.1 | 14.7 |
| MV4; 11 | AML | WT/WT | FLT3-ITD | medium | 0.3 | 45.4 |
| RS4; 11 | ALL | WT/WT | — | high | 0.1 | 28 |
| LY3 | ABC-DLBCL | WT/WT | — | medium | 0.3 | 280 |
| Ly10 | ABC-DLBCL | WT/WT | — | medium/high | 0.3 | 0.9 |
| Ly7 | GCB-DLBCL | WT/MUT | — | — | — | >10,000 |
| DoHH2 | GCB-DLBCL | WT/WT | BCL2 overexpression | high | 0.3 | 39.3 |
| Rec1 | MCL | WT/WT | — | high | 10 | 738 |
| SR | lymphoma | WT/WT | — | medium | 0.3 | 14.9 |
| H929 | MM | WT/WT | — | high | 1 | 114 |
| Ku812 | CML-BC | WT/WT | — | medium | 3 | >10,000 |
| EHEB | CLL | WT/WT | — | medium | 0.3 | 70 | stained with trypan blue. Quantification was performed by Vi-CELL® Cell Viability Analyzer (Beckmann-Coulter) which determines both cell concentration and percentage of viable cells. For both compounds at concentrations which were close to $IC_{90}$ concentrations (concentration where the growth inhibition percentage is equal to 90 percent of the maximum inhibitory effect of the tested compound), the percentages of viable cells were significantly decreased compared to untreated cells and were at best between 50 and 70% in the 22Rv1 cell line.

Example 24

Apoptosis Assay

Figure 27:
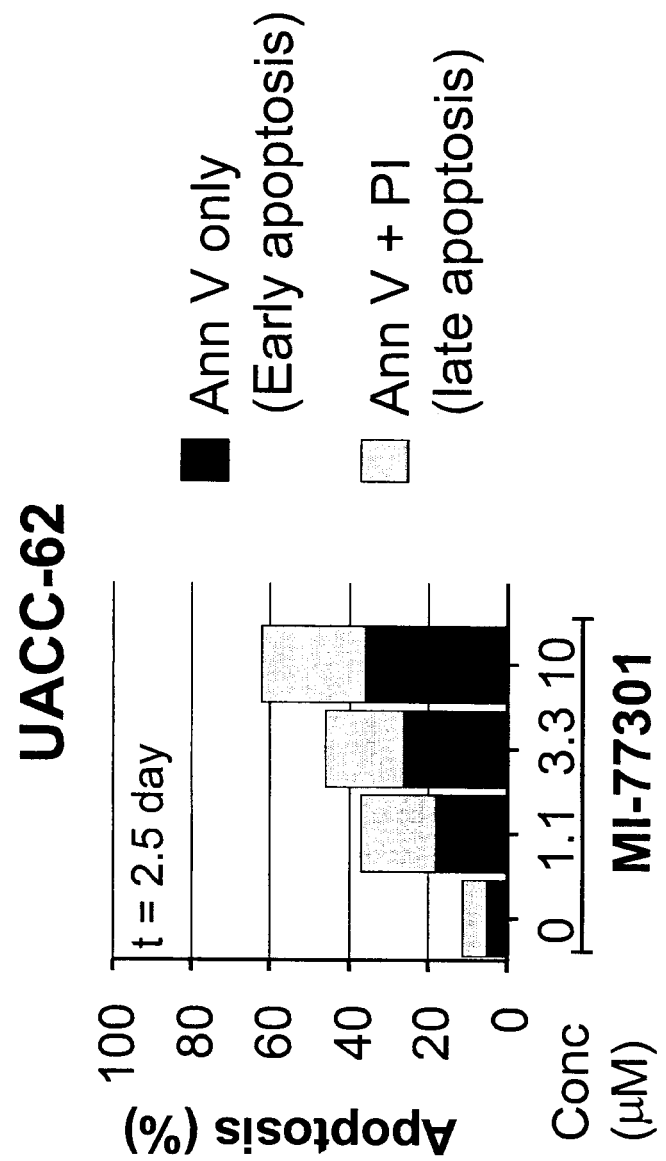
FIG. 27 is a bar graph showing apoptosis induced by MI-77301 in the UACC-62 cell line.

Apoptosis was determined using Annexin-V-FLUOS/propidium iodide staining kit (Roche Applied Science) by modifications of the manufacturer's instructions. Early stage apoptotic cells display translocation of phosphatidylserine from inner to outer surface of plasma membrane which can be detected by Annexin V fluorescein staining. Propidium iodide (PI) staining determines the late stage apoptotic cells or necrotic cells. A total of 0.25×106 cells were plated overnight in a 6-well tissue culture. Next day, adherent cells were treated in the presence or absence of MI-77301 and incubated at 37° C. for 2.5 days. Cells were harvested using 0.05% trypsin-EDTA (Invitrogen) by pooling the floating and the adherent cell populations, and were washed with PBS. Next, cells were stained with Annexin-V-FLUOS and PI in the incubation buffer at room temperature for 10 minutes in the dark. Modifications were made by using 0.5 µl each of Annexin-V-FLUOS and PI (instead of 2 µl each, mentioned in the instruction manual) for staining. These modifications were found to decrease the background noise, especially of fluorescein, in the assay. Cells were acquired and analyzed in a flow cytometer. Annexin V+/PI− cells were scored as early apoptotic cells and Annexin V+/PI+ cells as late apoptotic cells. The results of this assay are presented in FIG. 27.

Example 25

In Vivo Efficacy in the SK-Mel-103 Xenograft Model in Mice

Drug Preparation

MI-77301 was dissolved in 10% PEG400 (polyethylene glycol, mol wt 400, Sigma # P3265) 3% Cremophor EL (Sigma # C5135) and 87% 1×PBS (GIBCO™, Invitrogen Corp.) at the desired concentration (prepared fresh each day and dosed orally within 1 hour). The pH of the drug solutions were checked before use and required to be between pH 3.0 and 9.0 for PO (oral gavage) and between pH 4.5 and 9.0 for IV (intravenous) administration. The pH of a solution was adjusted with 0.5N NaOH when necessary.

Cell Culture

Human melanoma cells SK-MEL-103 were maintained at 37° C., 95% air, 5% carbon dioxide in HyQ® RPMI-1640 medium (with 2.05 mM L-glutamine, 0.1 µM sterile filtered, Hyclone®, QB Perbio) supplemented with 10% FBS and penicillin/streptomycin and passaged twice weekly.

Xenograft Tumor Cell Injection

Tumor cells for xenografts were harvested with Trypsin (0.05%)-EDTA (0.53 mM) (GIBCO™, Invitrogen Corp.), growth medium added and cells placed on ice. A cell sample was mixed 1:1 with Trypan Blue (GIBCO™, Invitrogen Corp.) and counted on a hemocytometer to determine the number of live/dead cells. Cells were washed once with 1×PBS (GIBCO™, Invitrogen Corp.) and resuspended in PBS. Cells in 0.1 ml were injected subcutaneously (s.c.) into the flank region of each mouse using a 27 gauge needle. For Matrigel injections, after washing in PBS, cells were resuspended in an ice cold mixture of 1:1 PBS and Matrigel (BD Biosciences, Invitrogen Corp.) for a final Matrigel protein concentration of 5 mg/ml. SK-MEL-103 tumors were inoculated into SCID mice (UM breeding strain: 236 C.B-17 SCID, Charles River) at $5 \times 10^6$ cells in 0.1 ml with Matrigel. Treatment was started on day 4-5 after tumor injection.

Xenograft Tumor Growth and Weight Monitoring

The size of tumors growing in the mice was measured in two dimensions using calipers. Tumor volume $(mm^3) = (A \times B^2)/2$ where A and B are the tumor length and width (in mm), respectively. During treatment, tumor volume and body weight were measured three times a week. After the treatment was stopped, tumor volume and body weight was measured at least once a week and mice were kept for additional 60 days for further observation of tumor growth and toxicity.

Assessment of Toxicity and End Point

Tumors were not allowed to exceed 10% of the animal's total body weight. If an animal had two or more tumors the total weight of all tumors were not allowed to exceed 10% of the animal's total body weight. At the end of the experimental period or when tumor size approached 10% of the total body weight, the animal was euthanized. Animals that showed profound morbidity or a weight loss of over 20% of body weight were euthanized.

Figure 29:
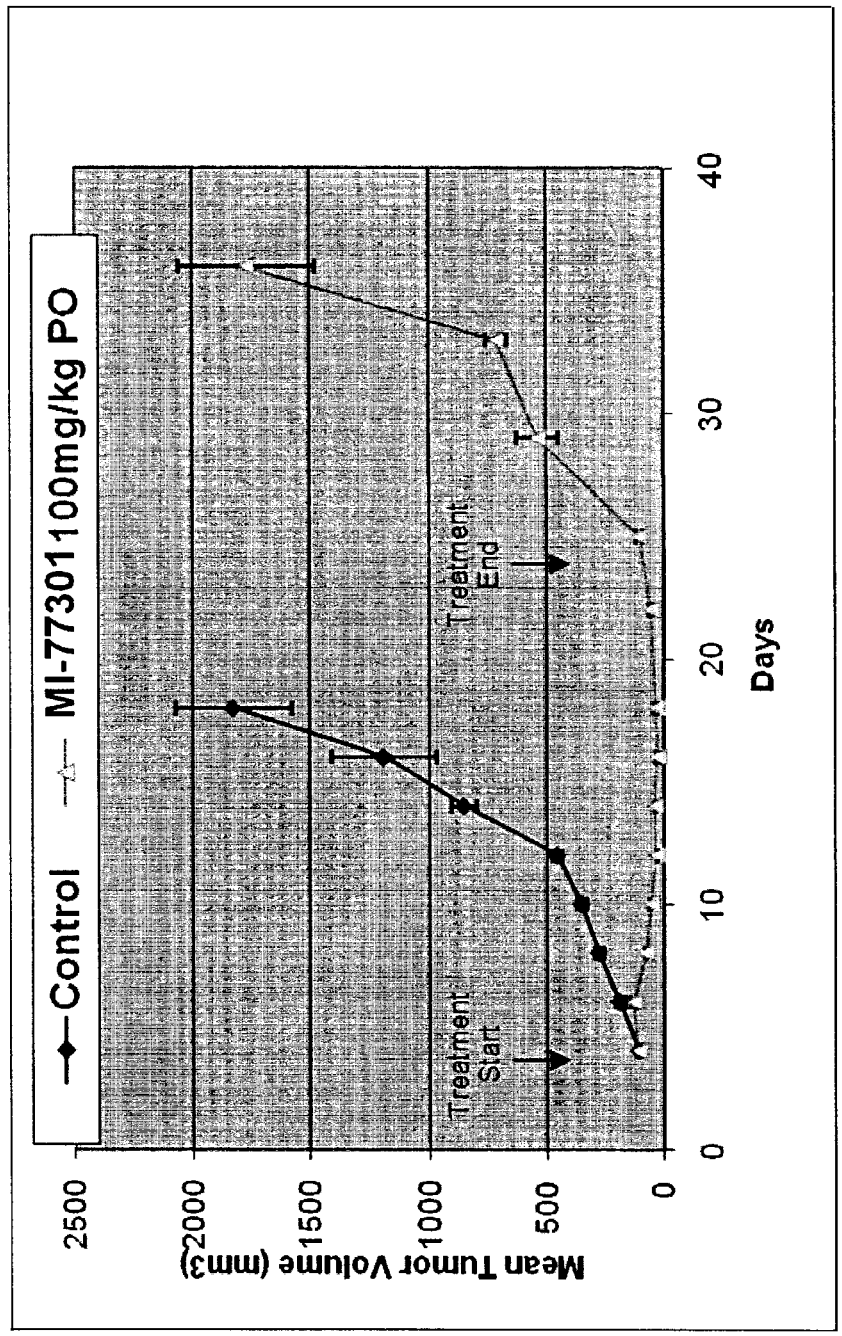
FIG. 29 is a line graph showing in vivo antitumor activity of MI-77301 in the SK-Mel-103 melanoma xenograft model in mice.

The efficacy of MI-77301 at 100 mg/kg PO in this assay is presented in FIG. 29.

Having now fully described the methods, compounds, and compositions of matter provided herein, it will be understood by those of skill in the art that the same can be performed within a wide and equivalent range of conditions, formulations, and other parameters without affecting the scope of the methods, compounds, and compositions provided herein or any embodiment thereof. All patents, patent applications and publications cited herein are fully incorporated by reference herein in their entirety.

What is claimed is:

1. A method of preparing:

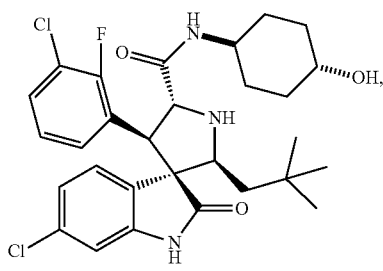

the method comprising:
(a) dissolving:

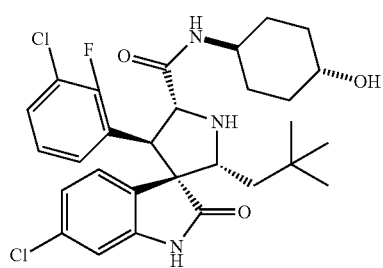 [SMILES: CC(C)(C)C[C@H]1N[C@@H](C(=O)N[C@H]2CC[C@H](O)CC2)[C@H](c2cccc(Cl)c2F)[C@@]12C(=O)Nc1cc(Cl)ccc12]

in a solvent or a mixture of solvents; and (b) allowing

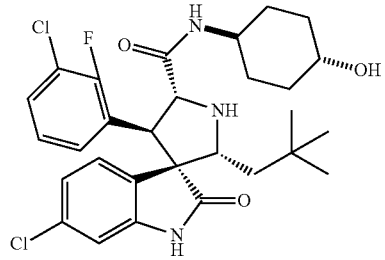 [SMILES: CC(C)(C)C[C@H]1N[C@@H](C(=O)N[C@H]2CC[C@H](O)CC2)[C@H](c2cccc(Cl)c2F)[C@@]12C(=O)Nc1cc(Cl)ccc12]

to isomerize to

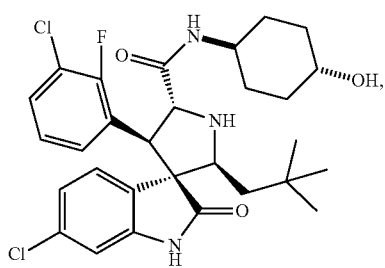

wherein the isomerization involves the formation of:
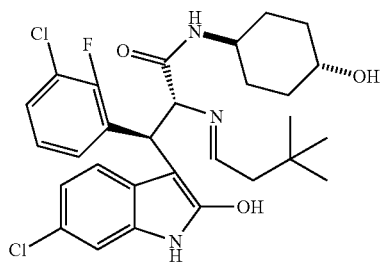 [SMILES: CC(C)(C)C/C=N/[C@@H](C(=O)N[C@H]1CC[C@H](O)CC1)[C@H](c1cccc(Cl)c1F)c1c(O)[nH]c2cc(Cl)ccc12]
as an intermediate.
2. The method of claim 1 further comprising isolating
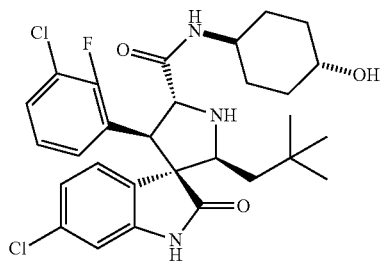 [SMILES: CC(C)(C)C[C@@H]1N[C@@H](C(=O)N[C@H]2CC[C@H](O)CC2)[C@H](c2cccc(Cl)c2F)[C@]12C(=O)Nc1cc(Cl)ccc12]
substantially free of one or more other stereoisomers.
3. The method of claim 1, wherein the solvent or mixture of solvents is methanol/water in a 1:1 v/v ratio.
* * * * *